United States Patent
Schaeper

(10) Patent No.: US 12,076,335 B2
(45) Date of Patent: Sep. 3, 2024

(54) NUCLEIC ACIDS FOR INHIBITING EXPRESSION OF TMPRSS6 AND IRON CHELATORS

(71) Applicant: SILENCE THERAPEUTICS GMBH, Berlin (DE)

(72) Inventor: Ute Schaeper, Berlin (DE)

(73) Assignee: SILENCE THERAPEUTICS GMBH, Berlin (DE)

(*) Notice: Subject to any disclaimer, the term of this patent is extended or adjusted under 35 U.S.C. 154(b) by 451 days.

(21) Appl. No.: 17/263,090

(22) PCT Filed: Jul. 26, 2019

(86) PCT No.: PCT/EP2019/070270
§ 371 (c)(1),
(2) Date: Jan. 25, 2021

(87) PCT Pub. No.: WO2020/021108
PCT Pub. Date: Jan. 30, 2020

(65) Prior Publication Data
US 2022/0331351 A1 Oct. 20, 2022

(30) Foreign Application Priority Data
Jul. 26, 2018 (EP) .................................. 18185879

(51) Int. Cl.
| | | |
|---|---|---|
| *A61K 31/713* | (2006.01) | |
| *A61K 31/4412* | (2006.01) | |
| *A61P 3/02* | (2006.01) | |
| *A61P 7/06* | (2006.01) | |
| *C12N 15/113* | (2010.01) | |

(52) U.S. Cl.
CPC ........ *A61K 31/713* (2013.01); *A61K 31/4412* (2013.01); *A61P 3/02* (2018.01); *A61P 7/06* (2018.01); *C12N 15/1137* (2013.01); *C12N 2310/14* (2013.01); *C12N 2310/315* (2013.01); *C12N 2310/321* (2013.01); *C12N 2310/322* (2013.01); *C12N 2310/3231* (2013.01); *C12N 2310/351* (2013.01); *C12N 2320/31* (2013.01)

(58) Field of Classification Search
CPC ..... A61K 31/713; A61K 31/4412; A61P 7/06; A61P 3/02; C12N 15/1137; C12N 2310/14; C12N 2310/315; C12N 2310/321; C12N 2310/322; C12N 2310/3231; C12N 2310/351; C12N 2320/31
USPC ................. 435/6.1, 91.1, 91.31, 455, 458; 514/44 A; 536/23.1, 24.5
See application file for complete search history.

(56) References Cited

U.S. PATENT DOCUMENTS

| | | | | |
|---|---|---|---|---|
| 11,015,198 | B2 * | 5/2021 | Hauptmann | A61K 47/549 |
| 2005/0255487 | A1 * | 11/2005 | Khvorova | A61P 13/12 |
| | | | | 435/6.16 |
| 2016/0145629 | A1 * | 5/2016 | Butler | A61P 25/28 |
| | | | | 435/375 |
| 2020/0208158 | A1 * | 7/2020 | Dames et al. | A61K 31/713 |

FOREIGN PATENT DOCUMENTS

| | | |
|---|---|---|
| EP | 3385380 A1 | 10/2018 |
| WO | 2012/135246 A2 | 10/2012 |
| WO | 2014/190157 A1 | 11/2014 |
| WO | 2016/085852 A1 | 6/2016 |
| WO | 2016/161429 A1 | 10/2016 |
| WO | 2018/185239 A1 | 10/2018 |
| WO | 2018/185240 A1 | 10/2018 |

OTHER PUBLICATIONS

Springer AD, Dowdy SF. GalNAc-siRNA Conjugates: Leading the Way for Delivery of RNAi Therapeutics. Nucleic Acid Ther. Jun. 2018;28(3):109-118. doi: 10.1089/nat.2018.0736. Epub May 24, 2018. PMID: 29792572; PMCID: PMC5994659. (Year: 2018).*
Casu et al., Combination of Tmprss6-ASO and the iron chelator deferiprone improves erythropoiesis and reduces iron overload in a mouse model of beta-thalassemia intermedia, Hem., 101(1):e8-e11 (2016).
International Application No. PCT/EP2019/070270, International Preliminary Report on Patentability, mailed Feb. 4, 2021.
International Application No. PCT/EP2019/070270, International Search Report and Written Opinion, mailed Mar. 19, 2020.
Schmidt et al., Combination therapy with a Tmprss6 RNAi-therapeutic and the oral iron chelator deferiprone additively diminishes secondary iron overload in a mouse model of Beta-thalassemia intermedia, Amer. J. Hemat., 90(4):310-313 (2015).
Sohail et al., A simple and cost-effective method for producing small interfering RNAs with high efficacy, Nucl. Aci. Res., 31(7):E38-1 (2003).

* cited by examiner

*Primary Examiner* — Jane J Zara
(74) *Attorney, Agent, or Firm* — MARSHALL, GERSTEIN & BORUN LLP

(57) ABSTRACT

The present invention relates to products and compositions and their uses. In particular the invention relates to nucleic acid products that interfere with the TMPRSS6 gene expression or inhibits its expression in combination with one or more iron chelators and possibly other active agents, as well as therapeutic uses such as for the treatment of hemochromatosis, porphyria and blood disorders such as beta-thalassemia, sickle cell disease and transfusional iron overload or myelodysplastic syndrome, and infections and non-relapse related mortality associated with bone marrow transplantation.

12 Claims, 37 Drawing Sheets

Specification includes a Sequence Listing.

| siRNA conjugate (duplex) | Sequence (single strands) | Modifications (single strands) | SEQ ID NO of oligonucleotide |
|---|---|---|---|
| GN-TMPRSS6-hcm9 (STS012) | 5' a(ps)a(ps)ccagaagagcaggu(ps)g(ps)a 3' | 6(ps)2(ps)7364628264728 45(ps)4(ps)6 | 17 |
| | 5' GN-ucaccugcuucuucugg(ps)u(ps)u 3' | GN-1727354715351718 4(ps)5(ps)1 | 18 |
| GN-TTR-hc | 5' u(ps)c(ps)ucgguuacaugaaucc(ps)c(ps)a 3' | 5(ps)3(ps)518451636182625 37(ps)3(ps)6 | 107 |
| | 5' GN-ugggauuucauguaaccaa(ps)g(ps)a 3' | GN 18482515361827362(ps)8(ps)2 | 108 |
| GN2-TMPRSS6-hcm9 (STS12009L4) | 5' a(ps)a(ps)ccagaagagcaggu(ps)g(ps)a 3' | 6(ps)2(ps)7364628264728 45(ps)4(ps)6 | 17 |
| | 5' GN2-ucaccugcuucuucugg(ps)u(ps)u 3' | GN2-1727354715351718 4(ps)5(ps)1 | 18 |
| GN2-Luc-siRNA 1 | 5' u(ps)c(ps)gaaguauccgcgua(ps)c(ps)g 3' | 5(ps)3(ps)826452517383816(ps)3(ps)8 | 109 |
| | 5' GN2-cguacgcggauauacuuc(ps)g(ps)a 3' | GN2-38163839462527153(ps)8(ps)2 | 110 |

Figure 7: Sequences and modification pattern of GalNAc siRNA conjugates that were tested for inhibition of TMPRSS6 expression. 1=2'F-dU, 2=F'-dA, 3=2'F-dC, 4=2'F-dC, 5=2'-OMe-rU; 6=2'-OMe-rA; 7=2'-OMe-rC; 8=2'-OMe-rG; ps=phosphorothioate. siRNAs are conjugated to GalNAc linker GN or to GalNAc linker GN2, respectively.

| duplex ID | sequence and chemistry (5'-3') | | SEQ ID NO of sequence |
|---|---|---|---|
| STS012 | a(ps)a(ps)ccagaagaagcaggu(ps)g(ps)a | 6(ps)2(ps)7364628264472845(ps)4(ps)6 | 111 |
| | GN-ucaccugcuucuucugg(ps)u(ps)u | GN-1727354715 3517184(ps)5(ps)1 | 112 |
| STS012-1 | a(ps)a(ps)ccagaagaagcaggu(ps)g(ps)a | 6(ps)2(ps)7364628264472845(ps)4(ps)6 | 113 |
| | GN-ucaccugcuucuucugg(ps)u(ps)u | GN-5767754715 3517588(ps)5(ps)5 | 114 |
| STS012-2 | a(ps)a(ps)ccagaagaagcaggu(ps)g(ps)a | 6(ps)2(ps)7364628264472845(ps)4(ps)6 | 115 |
| | GN-ucaccugcuucuucugg(ps)u(ps)u | GN-5767354315 7557588(ps)5(ps)5 | 116 |
| STS012-3 | a(ps)a(ps)ccagaagaagcaggu(ps)g(ps)a | 6(ps)2(ps)7364628264472845(ps)4(ps)6 | 117 |
| | GN-ucAccugcuucuucTgG(ps)u(ps)T | GN-57A7C54715 3517T8G(ps)5(ps)T | 118 |
| STS012-4 | a(ps)a(ps)ccagaagaagcaggu(ps)g(ps)a | 6(ps)2(ps)7764624668724845(ps)8(ps)6 | 119 |
| | GN-ucaccugcuucuucugg(ps)u(ps)u | GN-5767354315 7557588(ps)5(ps)5 | 120 |
| STS012-5 | a(ps)a(ps)ccagaagaagcaggu(ps)g(ps)a | 6(ps)2(ps)7364624264472845(ps)4(ps)6 | 121 |
| | GN-ucaccugcuucuucugg(ps)u(ps)u | GN-1727354315 3517184(ps)5(ps)1 | 122 |
| STS012-6 | a(ps)a(ps)ccagaagaagcagguga(ps)c(ps)c | 6(ps)2(ps)7364624264728454 6(ps)7(ps)7 | 123 |
| | GN-ucaccugcuucuucugg(ps)u(ps)u | GN-1727354315 3517184(ps)5(ps)1 | 124 |
| STS012-7 | a(ps)a(ps)ccagaagaagcaggu(ps)g(ps)a | 6(ps)2(ps)7768668664472885(ps)8(ps)6 | 125 |
| | GN-ucaccugcuucuucugg(ps)u(ps)u | GN-5767754715 3517588(ps)5(ps)5 | 126 |
| STS012-8 | a(ps)a(ps)ccagaagaagcaggu(ps)g(ps)a | 6(ps)2(ps)7768668664472885(ps)8(ps)6 | 127 |
| | GN-ucaccugcuucuucugg(ps)u(ps)u | GN-5767354315 7557588(ps)5(ps)5 | 128 |
| STS012-9 | a(ps)a(ps)ccagaagaagcaggu(ps)g(ps)a | 2(ps)2(ps)7724224242472445(ps)4(ps)2 | 129 |
| | GN-ucaccugcuucuucugg(ps)u(ps)u | GN-5727754715 7557544(ps)5(ps)5 | 130 |
| control siRNA | u(ps)u(ps)aguaaaccuuuugag(ps)a(ps)c | 5(ps)1(ps)6452627351151828(ps)2(ps)7 | 131 |
| | GN-gucucaaaagguuuacu(ps)a(ps)a | GN-4535362628 4515271(ps)6(ps)2 | 132 |

Figure 12

| | % max inhibition | IC50 [nM] | IC50 95% CI |
|---|---|---|---|
| GN3-TMPRSS6-hcm9 | 85 | 3,0 | 0,8-12,4 |
| GN3-TMPRSS6-hcm12 | 49 | 6,9 | 0,7-357 |
| GN3-TMPRSS6-hc17 | 49 | 3,8 | 1,8-8,0 |
| GN3-TMPRSS6-hc18 | 71 | 2,2 | 0,2-23,7 |
| GN3-TMPRSS6-hc23 | 69 | 3,3 | 0,2-133 |
| GN3-TMPRSS6-hc25 | 51 | 6,4 | 1,9-25,8 |
| GN3-TMPRSS6-hc26 | 62 | 16,9 | very wide |

| Duplex ID | Sequence ID number | Sequence name | Sequence | modifications |
|---|---|---|---|---|
| GN3-TMPRSS6-hcm9 | 17 | TMPRSS6-hcm-9A | 5' a(ps)a(ps)ccagaagaagcaggu(ps)g(ps)a 3' | 6(ps)2(ps)736462826472845(ps)4(ps)6 |
| | 18 | TMPRSS6-hcm-9B | 5' GN3-ucaccugcuucucugg(ps)u(ps)u 3' | GN3-17273547153517184(ps)5(ps)1 |
| GN3-TMPRSS6-hcm12 | 23 | TMPRSS6-hcm-12A | 5' g(ps)c(ps)aucucucuggcuuug(ps)g(ps)c 3' | 8(ps)3(ps)617153548471518(ps)4(ps)7 |
| | 24 | TMPRSS6-hcm-12B | 5' GN3-gccaaagcccagagau(ps)g(ps)c 3' | GN3-47362647372826461(ps)8(ps)3 |
| GN3-TMPRSS6-hc17 | 197 | TMPRSS6-hc-17A | 5' a(ps)u(ps)cuucuggcuuuggc(ps)g(ps)g 3' | 6(ps)1(ps)715354847151847(ps)4(ps)8 |
| | 198 | TMPRSS6-hc-17B | 5' GN3-ccgccaaagcccagaag(ps)a(ps)u 3' | GN3-37473626473728264(ps)6(ps)1 |
| GN3-TMPRSS6-hc18 | 199 | TMPRSS6-hc-18A | 5' u(ps)u(ps)uucuccuuggagucccu(ps)c(ps)a 3' | 5(ps)1(ps)517171548281735(ps)3(ps)6 |
| | 200 | TMPRSS6-hc-18B | 5' GN3-ugaggaccuccaagagaa(ps)a(ps)a 3' | GN3-18284635372646462(ps)6(ps)2 |
| GN3-TMPRSS6-hc23 | 207 | TMPRSS6-hc-23A | 5' c(ps)u(ps)gnucuggaucggucca(ps)c(ps)u 3' | 7(ps)1(ps)815354825381736(ps)3(ps)5 |
| | 208 | TMPRSS6-hc-23B | 5' GN3-aguggacgauccagaac(ps)a(ps)g 3' | GN3-28184638253728263(ps)6(ps)4 |
| GN3-TMPRSS6-hc25 | 211 | TMPRSS6-hcmr-25A | 5' a(ps)g(ps)uuucucucauccagg(ps)c(ps)c 3' | 6(ps)4(ps)515353536173648(ps)3(ps)7 |
| | 212 | TMPRSS6-hcmr-25B | 5' GN3-ggccuggaugagagaaa(ps)c(ps)u 3' | GN3-48371846182828262(ps)7(ps)1 |
| GN3-TMPRSS6-hc26 | 213 | TMPRSS6-hcm-26A | 5' g(ps)u(ps)acccuaggaaauacc(ps)a(ps)g 3' | 8(ps)1(ps)637352846261637(ps)2(ps)8 |
| | 214 | TMPRSS6-hcm-26B | 5' GN3-cugguauuuccuagggu(ps)a(ps)c 3' | GN3-35481615173528481(ps)6(ps)3 |

1=2'F-dU, 2=F'-dA, 3=2'F-dC, 4=2'F-dC, 5=2'-OMe-rU; 6=2'-OMe-rA; 7=2'-OMe-rC; 8=2'-OMe-rG; ps=phosphorothioate. siRNAs are conjugated GalNAc linker GN3.

Figure 47

| duplex ID | sequence and chemistry (top: first strand, bottom: second strand, both 5'-3') | |
|---|---|---|
| STS12009L4 | mA(ps)fA(ps)mCfCmAfGmAfGmAfAmGfAmGfGmcfAmGfGmU(ps)fG(ps)mA<br>GN2-fUmCfAmCfCmUfGmCfCmUfCmUfGmCfUmGfG(ps)mU(ps)fU | (SEQ ID NO: 217)<br>(SEQ ID NO: 218) |
| STS12009V54L50 | mA(ps)fA(ps)mCfCmAfGmAfGmAfAmGfAmGfGmCfAmGfGmUfG(ps2)mA<br>GNo-fU(ps2)mCfAmCfCmUfGmCfCmUfCmUfGmCfUmGfGmU(ps2)fU | (SEQ ID NO: 309)<br>(SEQ ID NO: 310) |
| STS12009V55L50 | mA(ps)fA(ps)mCfCmAfGmAfGmAfAmGfAmGfGmCfAmGfGmUfG(ps2)mA<br>GNo-fUmCfAmCfCmUfGmCfCmUfCmUfGmCfUmGfGmU(ps2)fU | (SEQ ID NO: 311)<br>(SEQ ID NO: 312) |
| STS12009V56L50 | mAfAmCfCmAfGmAfGmAfAmGfAmGfGmCfAmGfGmUfGmA<br>GNo-fUmCfAmCfCmUfGmCfCmUfCmUfGmCfUmGfGmU(ps2)fU | (SEQ ID NO: 313)<br>(SEQ ID NO: 314) |
| STS12009V57L50 | mAfAmCfCmAfGmAfGmAfAmGfAmGfGmCfAmGfGmUfG(ps2)mA<br>GNo-fUmCfAmCfCmUfGmCfCmUfCmUfGmCfUmGfGmU(ps2)fU | (SEQ ID NO: 315)<br>(SEQ ID NO: 316) | mA, mU, mC, mG – 2'-OMe RNA
fA, fU, fC, fG – 2'-F RNA
(ps) – phosphorothioate
(ps2) – phosphorodithioate
GN2 – GalNAc
GNo – GN2 with phosphodiesters instead of (ps)

Figure 48

NUCLEIC ACIDS FOR INHIBITING EXPRESSION OF TMPRSS6 AND IRON CHELATORS

The present invention relates to products and compositions and their uses. In particular the invention relates to nucleic acid products that interfere with the TMPRSS6 gene expression or inhibits its expression, in combination with other active agents, and therapeutic uses such as for the treatment of hemochromatosis, porphyria and blood disorders such as β-thalassemia, sickle cell disease and transfusional iron overload, and infections and non-relapse related mortality associated with bone marrow transplantation.

BACKGROUND

Double-stranded RNA (dsRNA) able to complementarily bind expressed mRNA has been shown to be able to block gene expression (Fire et al, 1998, Nature. 1998 Feb. 19; 391(6669):806-11 and Elbashir et al., 2001, Nature. 2001 May 24; 411(6836):494-8) by a mechanism that has been termed RNA interference (RNAi). Short dsRNAs direct gene-specific, post-transcriptional silencing in many organisms, including vertebrates, and have become a useful tool for studying gene function. RNAi is mediated by the RNA-induced silencing complex (RISC), a sequence-specific, multi-component nuclease that destroys messenger RNAs homologous to the silencing trigger loaded into the RISC complex. Interfering RNA (IRNA) such as siRNAs, anti-sense RNA, and micro-RNA are oligonucleotides that prevent the formation of proteins by gene-silencing i.e. inhibiting gene translation of the protein through degradation of mRNA molecules. Gene-silencing agents are becoming increasingly important for therapeutic applications in medicine.

According to Watts and Corey in the Journal of Pathology (2012; Vol 226, p 365-379) there are algorithms that can be used to design nucleic acid silencing triggers, but all of these have severe limitations. It may take various experimental methods to identify potent siRNAs, as algorithms do not take into account factors such as tertiary structure of the target mRNA or the involvement of RNA binding proteins. Therefore the discovery of a potent nucleic acid silencing trigger with minimal off-target effects is a complex process. For the pharmaceutical development of these highly charged molecules it is necessary that they can be synthesised economically, distributed to target tissues, enter cells and function within acceptable limits of toxicity.

Matriptase-2 (MT-2) is the product of the TMPRSS6 gene. MT-2 is a type II transmembrane serine protease that plays a critical role in the regulation of iron homeostasis. MT-2 is a negative regulator for gene expression of the peptide hormone hepcidin. Hepcidin is predominantly produced and secreted by the liver. Hepcidin regulates iron balance in the body by acting as a negative regulator of gastro-intestinal iron absorption and release of iron from cellular stores. Upregulation of hepcidin leads to a reduction in iron availability within the body (McDonald et al, American Journal of Physiology, 2015, vol 08 no. 7, C539-C547). Hepcidin levels are low in patients with iron overload. Therefore a possible target for reducing iron overload is to increase Hepcidin by silencing TMPRSS6 gene expression in the liver.

TMPRSS6 is primarily expressed in the liver, although high levels of TMPRSS6 mRNA are also found in the kidney, with lower levels in the uterus and much smaller amounts detected in many other tissues (Ramsay et al, *Haematologica* (2009), 94(*6), 84-849).

Various disorders are associated with iron overload, a condition characterised by increased blood and tissue iron levels, such as hereditary hemochromatosis, porphyria cutanea tarda, and blood disorders, like β-thalassemia, congenital sideroblastic anemia (CSA), congenital dyserythropoietic anemia (CDA), marrow failure syndromes, myelodysplasia and sickle cell disease (SCD). In addition all patient populations, that receive regular blood transfusions are at risk of developing transfusional iron overload (Coates, Free Rad Biol Med 2014, Vol 72, 23-40, Bulaj et al., Blood 2000, Vol 95, 1565-71). Both a paper by Nai et al (Blood, 2012, Vol 119, No. 21, p 5021-5027) and Guo et al (The Journal of Clinical Investigation, 2013, Vol 123, No. 4, p 1531-1541) show how a deletion or reduction of TMPRSS6 expression was effective in treating β-thalassemia in mice. A paper by Schmidt (2013, Blood, Vol 121, 7, p 1200-1208) explores the use of TMPRSS6 nucleic acid to decrease iron overload in mouse models of hereditary hemochromatosis and β-thalassemia. In both models the authors determined that lipid nanoparticles—TMPRSS6 nucleic acid treatment induced hepcidin and diminished tissue and serum iron levels for up to 21 days. Furthermore a paper by Schmidt et al (American Journal of Hematology, 2015, Vol 90, No. 4, p 310-313) demonstrated that LNP-TMPRSS6 nucleic acid plus oral iron chelator deferiprone therapy reduced secondary iron overload in mouse model of β-thalassemia. Further, there is evidence that patients with iron overload that undergo bone marrow transplantation experience an enhanced risk for infection and non-relapse related mortality. Enhanced systemic iron levels increase the risk of infections due to impairment of immunity and by heightened microbial virulence. Patients receiving bone marrow transplantations are particularly vulnerable to infections as the cytotoxic conditioning required to prepare the patients for transplantation ablates their bone marrow and increases also systemic iron levels as erythropoiesis is impaired. Furthermore, high systemic iron levels may have a negative impact on the implantation and outgrowth of the grafted donor stem cells.

Reducing iron overload and systemic iron levels before and during conditioning of patients receiving bone marrow transplantation may reduce the risk of infections and non-relapse related mortality (Wermke et al., 2018, Lancet Haematol. May; 5 (5):e201-e210).

Accordingly, methods for effective treatment of disorders associated with iron overload are currently needed and the present invention addresses this need.

The invention relates to a nucleic acid or conjugated nucleic acid according to any aspect of the disclosure, in combination with one or more iron chelators.

Nucleic Acids and Conjugated Nucleic Acids

A first aspect disclosed herein relates to a nucleic acid for inhibiting expression of TMPRSS6, comprising at least one duplex region that comprises at least a portion of a first strand and at least a portion of a second strand that is at least partially complementary to the first strand, wherein said first strand is at least partially complementary to at least a portion of a RNA transcribed from the TMPRSS6 gene, wherein said first strand comprises a nucleotide sequence selected from the following sequences: SEQ ID NOs: 317, 319, 321, 323, 325, 327, 329, 331, 333, 335, 337, 339, 341, 343, 345, 353, 356, 358, 360, 362, 364, 366, 368, 370, 372, 374, 376, 378, 380, 382, 384, 386, 388, 390, 392, 394, 396, 398, 400, 402, 404, 406, 407, 410, 412, 414, 416, 418, 420, 422, 424, 426, 428, 430, 432, 434, 436, 438, 440, or 442, or the first strand comprises a sequence selected from SEQ ID NOs 1, 3, 5, 7, 9, 11, 13, 15, 17, 19, 21, 23, 25, 27, 29, 67, 69, 71, 73, 74, 76, 77, 78, 79, 80, 81, 82, 83, 85, 87, 88, 90, 91, 92, 93, 94, 95, 96, 97, 98, 99, 111, 113, 115, 117, 119, 121, 123, 125, 127, 129, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 225, 227, 229, 231, 233, 235, 237, 239, 241, 243, 245, 247, 249, 251, 253, 255, 257, 259, 261, 263, 265, 267, 269, 270, 271, 273, 275, 277, 279, 281, 283, 285, 287, 289, 291, 293, 295, 297, 299, 301, 309, 311, 312, 313, 314, or 315, such as SEQ ID NOs:1, 3, 5, 7, 9, 11, 13, 15, 17, 19, 21, 23, 25, 27, 29, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, or 215.

A further related aspect is a nucleic acid for inhibiting expression of TMPRSS6, comprising at least one duplex region that comprises at least a portion of a first strand and at least a portion of a second strand that is at least partially complementary to the first strand, wherein said first strand is at least partially complementary to at least a portion of a RNA transcribed from the TMPRSS6 gene, wherein said second strand comprises a nucleotide sequence selected from the following sequences: SEQ ID NOs 318, 320, 322, 324, 326, 328, 330, 332, 334, 336, 338, 340, 342, 344, 346, 357, 359, 361, 363, 365, 367, 369, 371, 373, 375, 377, 379, 381, 383, 385, 387, 389, 391, 393, 395, 397, 399, 401, 403, 405, 407, 409, 411, 413, 415, 417, 419, 421, 423, 425, 427, 429, 431, 433, 435, 437, 439, 441, or 443, or the second strand comprises a nucleotide sequence selected from the following sequences: SEQ ID NOs 2, 4, 6, 8, 10, 12, 14, 16, 18, 20, 22, 24, 26, 28, 30, 68, 70, 72, 75, 84, 86, 89, 100, 101, 102, 103, 104, 105, 106, 112, 114, 116, 118, 120, 122, 124, 126, 128, 130, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 226, 228, 230, 232, 234, 236, 238, 240, 242, 246, 248, 250, 252, 254, 256, 258, 260, 262, 264, 266, 268, 270, 272, 274, 276, 278, 280, 282, 284, 286, 288, 290, 292, 294, 296, 298, 300, 302, 310, 312, 314, or 316, such as a sequence selected from the following: SEQ ID NO:2, 4, 6, 8, 10, 12, 14, 16, 18, 20, 22, 24, 26, 28, 30, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, or 216.

Certain nucleic acids are preferred in all of the aspects of the invention. In particular:

The first strand may comprise the nucleotide sequence of SEQ ID NO:333 and/or the second strand may comprise the nucleotide sequence of SEQ ID NO:334.

| 333 | TMPRSS6-hcm-9A | aaccagaagaagcagguga |
| 334 | TMPRSS6-hcm-9B | ucaccugcuucuucgguu |

The first strand may comprise the nucleotide sequence of SEQ ID NO:17 and/or the second strand may comprise the nucleotide sequence of SEQ ID NO:18, namely:

| SEQ ID 17 | TMPRSS6-hcm-9A | 6273646282647284546 |

| SEQ ID 18 | TMPRSS6-hcm-9B | 1727354715351718451 |

The first strand may comprise the nucleotide sequence of SEQ ID NO:422 and/or the second strand may comprise the nucleotide sequence of SEQ ID NO:423.

| TMPRSS6-hc-18A | UUUUCUCUUGGAGUCCUCA |
| TMPRSS6-hc-18B | UGAGGACUCCAAGAGAAAA |

The first strand may comprise the nucleotide sequence of SEQ ID NO:199 and/or the second strand may comprise the nucleotide sequence of SEQ ID NO:200.

TMPRSS6-hc-18A
mU (ps) fU (ps) mUfUmCfUmCfUmUfGmGfAmGfUmCfCmU (ps) fC (ps) mA

TMPRSS6-hc-18B
fUmGfAmGfGmAfCmUfCmCfAmAfGmAfGmAfA (ps) mA (ps) fA

The first strand may comprise the nucleotide sequence of SEQ ID NO:429 and/or the second strand may comprise the nucleotide sequence of SEQ ID NO:430.

| TMPRSS6-hc-23A | CUGUUCUGGAUCGUCCACU |
| TMPRSS6-hc-23B | AGUGGACGAUCCAGAACAG |

The first strand may comprise the nucleotide sequence of SEQ ID NO:207 and/or the second strand may comprise the nucleotide sequence of SEQ ID NO:208.

TMPRSS6-hc-23A
mC (ps) fU (ps) mGfUmUfCmUfCmGfAmUfCmGfUmCfCmA (ps) fC (ps) mU

TMPRSS6-hc-23B
fAmGfUmGfGmAfCmGfAmUfCmCfAmGfAmAfC (ps) mA (ps) fG

A nucleic acid may be disclosed herein in a sequence listing association with a particular linker and/or ligand, but any reference to the linker or ligand in the context of the sequence listing is optional, although these features are preferred. Certain preferred linkers are disclosed in combination with certain nucleic acid sequences.

The first strand and/or said second strand may each be from 17-35 nucleotides in length and at least one duplex region may be from 10-25 nucleotides in length. The duplex may comprise two separate strands or it may comprise a single strand which comprises the first strand and the second strand.

The nucleic acid may: a) be blunt ended at both ends; b) have an overhang at one end and a blunt end at the other; or c) have an overhang at both ends.

One or more nucleotides on the first and/or second strand may be modified, to form modified nucleotides. One or more of the odd numbered nucleotides of the first strand may be modified. One or more of the even numbered nucleotides of the first strand may be modified by at least a second modification, wherein the at least second modification is different from the modification on the one or more odd numbered nucleotides. At least one of the one or more modified even numbered nucleotides may be adjacent to at least one of the one or more modified odd numbered nucleotides.

A plurality of odd numbered nucleotides in the first strand may be modified in the nucleic acid disclosed herein. A plurality of even numbered nucleotides in the first strand may be modified by a second modification. The first strand may comprise adjacent nucleotides that are modified by a common modification. The first strand may also comprise adjacent nucleotides that are modified by a second different modification.

One or more of the odd numbered nucleotides of the second strand may be modified by a modification that is different to the modification of the odd numbered nucleotides on the first strand and/or one or more of the even numbered nucleotides of the second strand may be modified by the same modification of the odd numbered nucleotides of the first strand. At least one of the one or more modified even numbered nucleotides of the second strand may be adjacent to the one or more modified odd numbered nucleotides. A plurality of odd numbered nucleotides of the second strand may be modified by a common modification and/or a plurality of even numbered nucleotides may be modified by the same modification that is present on the first strand odd numbered nucleotides. A plurality of odd numbered nucleotides on the second strand may be modified by a second modification, wherein the second modification is different from the modification of the first strand odd numbered nucleotides.

The second strand may comprise adjacent nucleotides that are modified by a common modification, which may be a second modification that is different from the modification of the odd numbered nucleotides of the first strand.

In the nucleic acid disclosed herein, each of the odd numbered nucleotides in the first strand and each of the even numbered nucleotides in the second strand may be modified with a common modification and, each of the even numbered nucleotides may be modified in the first strand with a second modification and each of the odd numbered nucleotides may be modified in the second strand with a second different modification.

The nucleic acid disclosed herein may have the modified nucleotides of the first strand shifted by at least one nucleotide relative to the unmodified or differently modified nucleotides of the second strand.

The modification and/or modifications may each and individually be selected from the group consisting of 3'-terminal deoxy-thymine, 2'-O-methyl, a 2'-deoxy-modification, a 2'-amino-modification, a 2'-alkyl-modification, a morpholino modification, a phosphoramidate modification, 5'-phosphorothioate group modification, a 5' phosphate or 5' phosphate mimic modification and a cholesteryl derivative or a dodecanoic acid bisdecylamide group modification and/or the modified nucleotide may be any one of a locked nucleotide, an abasic nucleotide or a non-natural base comprising nucleotide.

At least one modification may be 2'-O-methyl and/or at least one modification may be 2'-F.

The disclosure further provides, as a second aspect, a nucleic acid for inhibiting expression of TMPRSS6, comprising at least one duplex region that comprises at least a portion of a first strand and at least a portion of a second strand that is at least partially complementary to the first strand, wherein said first strand is at least partially complementary to at least a portion of an RNA transcribed from the TMPRSS6 gene, wherein said first strand comprises a nucleotide sequence selected from the following sequences: SEQ ID Nos:
  317, 319, 321, 323, 325, 327, 329, 331, 333, 335, 337, 339, 341, 343, 345, 353, 356, 358, 360, 362, 364, 366, 368, 370, 372, 374, 376, 378, 380, 382, 384, 386, 388, 390, 392, 394, 396, 398, 400, 402, 404, 406, 407, 410, 412, 414, 416, 418, 420, 422, 424, 426, 428, 430, 432, 434, 436, 438, 440, or 442;
or selected from
  SEQ ID NOs 1, 3, 5, 7, 9, 11, 13, 15, 17, 19, 21, 23, 25, 27, 29, 67, 69, 71, 73, 74, 76, 77, 78, 79, 80, 81, 82, 83, 85, 87, 88, 90, 91, 92, 93, 94, 95, 96, 97, 98, 99, 111, 113, 115, 117, 119, 121, 123, 125, 127, 129,133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 225, 227, 229, 231, 233, 235, 237, 239, 241, 243, 245, 247, 249, 251, 253, 255, 257, 259, 261, 263, 265, 267, 269, 270, 271, 273, 275, 277, 279, 281, 283, 285, 287, 289, 291, 293, 295, 297, 299, 301, 309, 311, 312, 313, 314, or 315,
such as SEQ ID NOs:1, 3, 5, 7, 9, 11, 13, 15, 17, 19, 21, 23, 25, 27, 29, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, or 215,
wherein the nucleotides of first strand are modified by first modification on the odd numbered nucleotides, and modified by a second modification on the even numbered nucleotides, and nucleotides of the second strand are modified by a third modification on the even numbered nucleotides and modified by a fourth modification the odd numbered nucleotides, wherein at least the first modification is different to the second modification and the third modification is different to the fourth modification.

The disclosure further provides, as a related second aspect, a nucleic acid for inhibiting expression of TMPRSS6, comprising at least one duplex region that comprises at least a portion of a first strand and at least a portion of a second strand that is at least partially complementary to the first strand, wherein said first strand is at least partially complementary to at least a portion of an RNA transcribed from the TMPRSS6 gene, wherein said second strand may comprise a nucleotide sequence selected from the following sequences: SEQ ID no's 318, 320, 322, 324, 326, 328, 330, 332, 334, 336, 338, 340, 342, 344, 346, 357, 359, 361, 363, 365, 367, 369, 371, 373, 375, 377, 379, 381, 383, 385, 387, 389, 391, 393, 395, 397, 399, 401, 403, 405, 407, 409, 411, 413, 415, 417, 419, 421, 423, 425, 427, 429, 431, 433, 435,437, 439, 441, or 443,
  or selected from SEQ ID no's 2, 4, 6, 8, 10, 12, 14, 16, 18, 20, 22, 24, 26, 28, 30, 68, 70, 72, 75, 84, 86, 89, 100, 101, 102, 103, 104, 105, 106, 112, 114, 116, 118, 120, 122, 124, 126, 128, 130, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 226, 228, 230, 232, 234, 236, 238, 240, 242, 246, 248, 250, 252, 254, 256, 258, 260, 262, 264, 266, 268, 270, 272, 274, 276, 278, 280, 282, 284, 286, 288, 290, 292, 294, 296, 298, 300, 302, 310, 312, 314, or 316, such as a sequence selected from the following: SEQ ID NO:2, 4, 6, 8, 10, 12, 14, 16, 18, 20, 22, 24, 26, 28, 30, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, or 216, wherein the nucleotides of first strand are modified by first modification on the odd numbered nucleotides, and modified by a second modification on the even numbered nucleotides, and nucleotides of the second strand are modified by a third modification on the even numbered nucleotides and modified by a fourth modification the odd numbered nucleotides, wherein at least the first modification is different to the second modification and the third modification is different to the fourth modification.

The third modification and the first modification may be the same and/or the second modification and the fourth modification may be the same.

The first modification may be 2'OMe and the second modification may be 2'F.

In the nucleic acid of any aspect, e.g. the second aspect, the first strand may comprise the nucleotide sequence of SEQ ID NO:17 and the second strand may comprise the nucleotide sequence of SEQ ID NO:18. The sequence and modifications may be as shown in the table below:

| SEQ ID NO: 17 | 5'aaccagaagaag cagguga 3' | 6273646282647284546 |
|---|---|---|
| SEQ ID NO: 18 | 5'ucaccugcuucu ucugguu 3' | 1727354715351718451 | wherein the specific modifications are depicted by the following numbers 1=2'F-dU, 2=2'F-dA, 3=2'F-dC, 4=2'F-dG, 5=2'-OMe-rU;
6=2'-OMe-rA;
7=2'-OMe-rC;
8=2'-OMe-rG.

As taught above, these are preferred sequences, along with the other preferred sequences.

A nucleic acid disclosed herein may comprise a phosphorothioate linkage between the terminal one, two or three 3' nucleotides and/or one two or three 5' nucleotides of the first and/or the second strand. It may comprise two phosphorothioate linkages between each of the three terminal 3' and between each of the three terminal 5' nucleotides on the first strand, and two phosphorothioate linkages between the three terminal nucleotides of the 3' end of the second strand.

Such a nucleic acid may be conjugated to a ligand.

The disclosure further provides, as a third aspect, a nucleic acid for inhibiting expression of TMPRSS6, comprising at least one duplex region that comprises at least a portion of a first strand and at least a portion of a second strand that is at least partially complementary to the first strand, wherein said first strand is at least partially complementary to at least a portion of a RNA transcribed from the TMPRSS6 gene, wherein said first strand comprises a nucleotide sequence selected from the following sequences, SEQ ID Nos:

317, 319, 321, 323, 325, 327, 329, 331, 333, 335, 337, 339, 341, 343, 353 345, 353, 356, 358, 360, 362, 364, 366, 368, 370, 372, 374, 376, 378, 380, 382, 384, 386, 388, 390, 392, 394, 396, 398, 400, 402, 404, 406, 407, 410, 412, 414, 416, 418, 420, 422, 424, 426, 428, 430, 432, 434, 436, 438, 440, or 442;

or selected from

SEQ ID NOs 1, 3, 5, 7, 9, 11, 13, 15, 17, 19, 21, 23, 25, 27, 29, 67, 69, 71, 73, 74, 76, 77, 78, 79, 80, 81, 82, 83, 85, 87, 88, 90, 91, 92, 93, 94, 95, 96, 97, 98, 99, 111, 113, 115, 117, 119, 121, 123, 125, 127, 129, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 225, 227, 229, 231, 233, 235, 237, 239, 241, 243, 245, 247, 249, 251, 253, 255, 257, 259, 261, 263, 265, 267, 269, 270, 271, 273, 275, 277, 279, 281, 283, 285, 287, 289, 291, 293, 295, 297, 299, 301, 309, 311, 312, 313, 314, or 315, such as SEQ ID NOs:1, 3, 5, 7, 9, 11, 13, 15, 17, 19, 21, 23, 25, 27, 29, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, or 215, and wherein the nucleic acid is conjugated to a ligand.

The disclosure further provides, as a further related aspect, a nucleic acid for inhibiting expression of TMPRSS6, comprising at least one duplex region that comprises at least a portion of a first strand and at least a portion of a second strand that is at least partially complementary to the first strand, wherein said first strand is at least partially complementary to at least a portion of a RNA transcribed from the TMPRSS6 gene, wherein the second strand comprises a nucleotide sequence selected from the following sequences, SEQ ID Nos 318, 320, 322, 324, 326, 328, 330, 332, 334, 336, 338, 340, 342, 344, 346, 357, 359, 361, 363, 365, 367, 369, 371, 373, 375, 377, 379, 381, 383, 385, 387, 389, 391, 393, 395, 397, 399, 401, 403, 405, 407, 409, 411, 413, 415, 417, 419, 421, 423, 425, 427, 429, 431, 433, 435,437, 439, 441, or 443, or the second strand comprises a nucleotide sequence selected from the following sequences: SEQ ID nos 2, 4, 6, 8, 10, 12, 14, 16, 18, 20, 22, 24, 26, 28, 30, 68, 70, 72, 75, 84, 86, 89, 100, 101, 102, 103, 104, 105, 106, 112, 114, 116, 118, 120, 122, 124, 126, 128, 130, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 226, 228, 230, 232, 234, 236, 238, 240, 242, 246, 248, 250, 252, 254, 256, 258, 260, 262, 264, 266, 268, 270, 272, 274, 276, 278, 280, 282, 284, 286, 288, 290, 292, 294, 296, 298, 300, 302, 310, 312, 314, or 316, such as a sequence selected from the following: SEQ ID NO:2, 4, 6, 8, 10, 12, 14, 16, 18, 20, 22, 24, 26, 28, 30, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, or 216, and wherein the nucleic acid is conjugated to a ligand.

The ligand may comprise (i) one or more N-acetyl galactosamine (GalNAc) moieties and derivatives thereof, and (ii) a linker, wherein the linker conjugates the GalNAc moieties to a sequence as defined in any preceding aspects. The linker may be a bivalent or trivalent or tetravalent branched structure. The nucleotides may be modified as defined herein.

The ligand may comprise the formula I:

[S-X$^1$-P-X$^2$]$_3$-A-linker- (I)

wherein:
S represents a saccharide, wherein the saccharide is N-acetyl galactosamine;
X$^1$ represents C$_3$-C$_6$ alkylene or (—CH$_2$—CH$_2$—O)$_m$(—CH$_2$)$_2$— wherein m is 1, 2, or 3;
P is a phosphate or modified phosphate (preferably a thiophosphate);
X$^2$ is alkylene or an alkylene ether of the formula (—CH$_2$)$_n$—O—CH$_2$— where n=1-6;
A is a branching unit;
X$^3$ represents a bridging unit;
wherein a nucleic acid disclosed herein is conjugated to X$^3$ via a phosphate or modified phosphate (preferably a thiophosphate).

The present disclosure therefore additionally provides a conjugated nucleic acid having one of the following structures

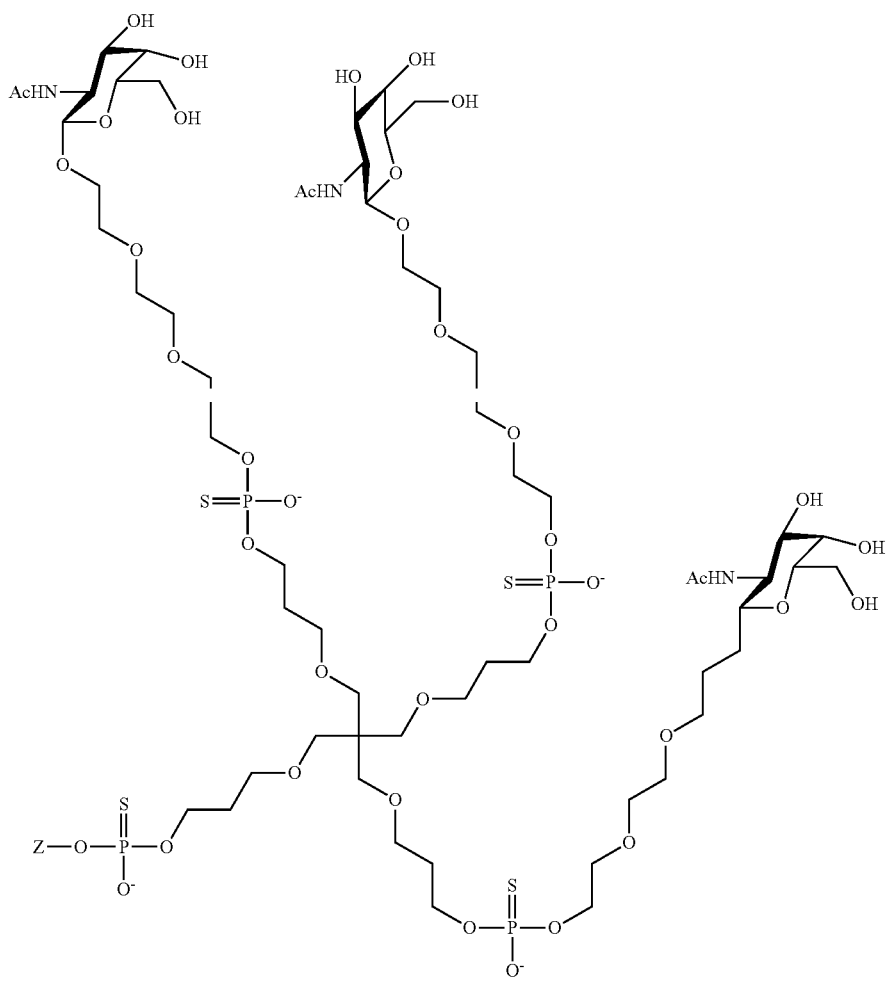

-continued
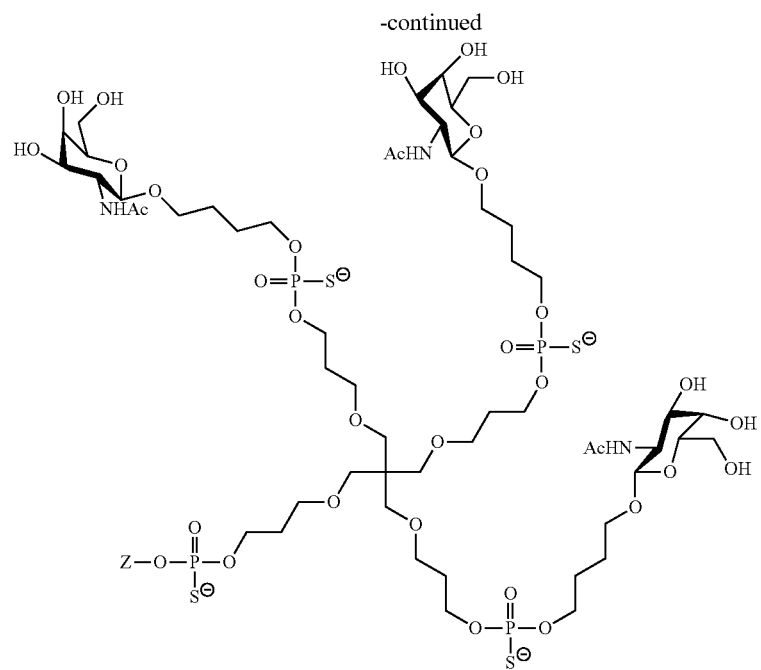
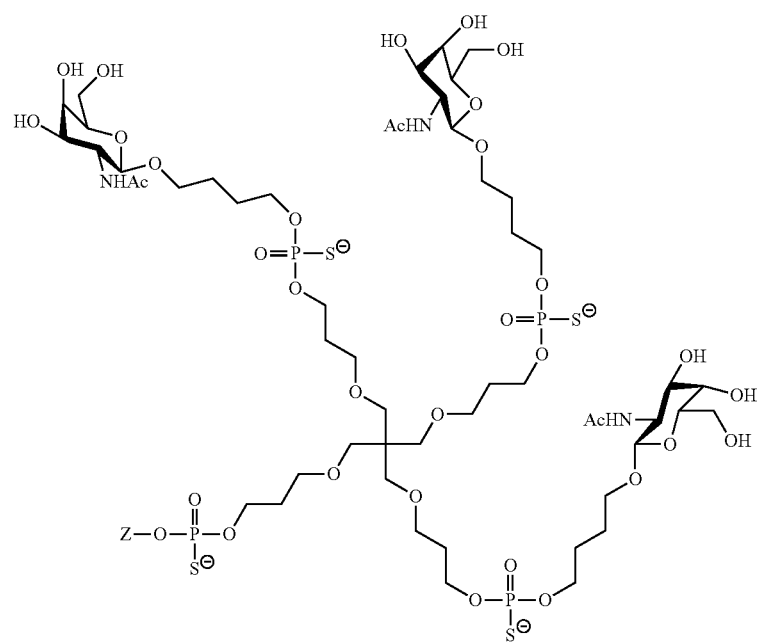

-continued
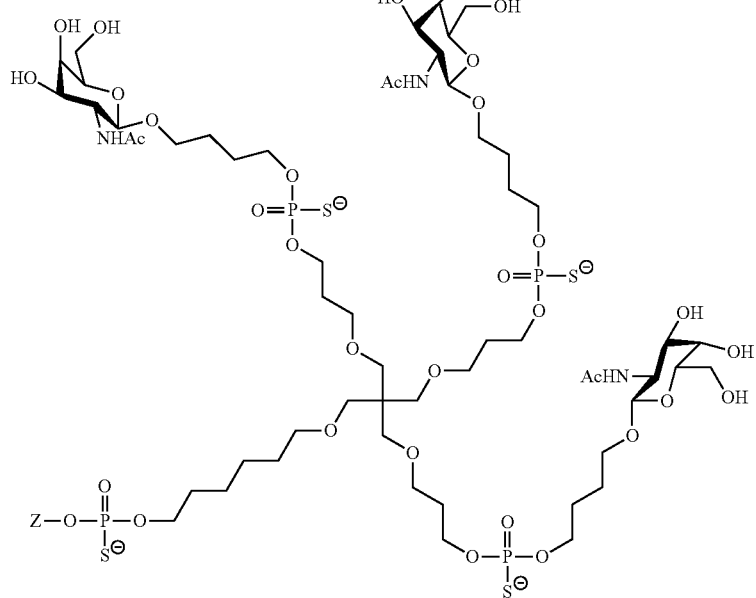
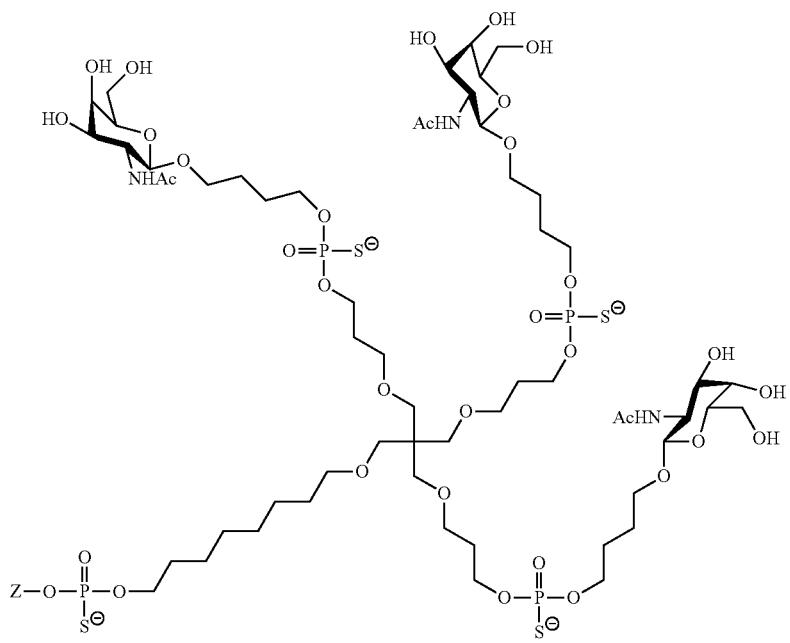

-continued
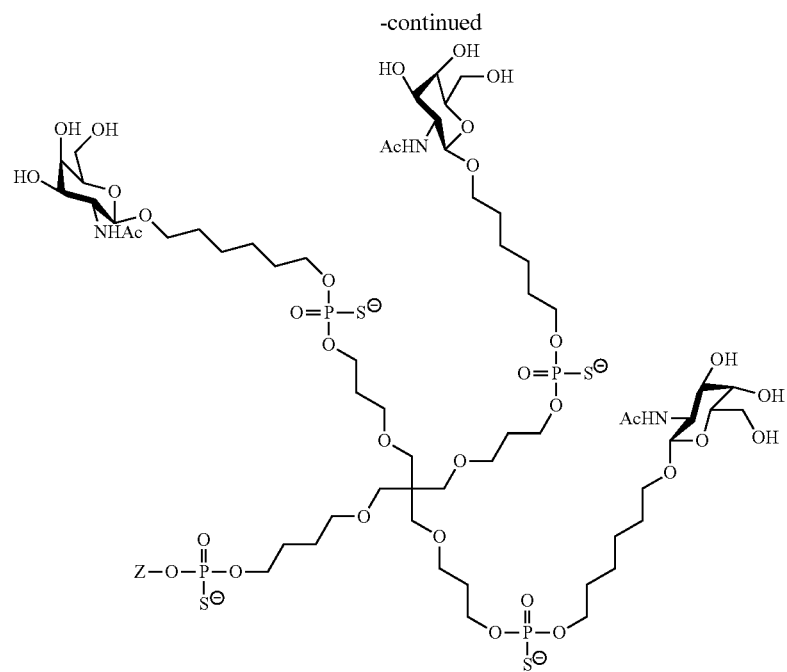
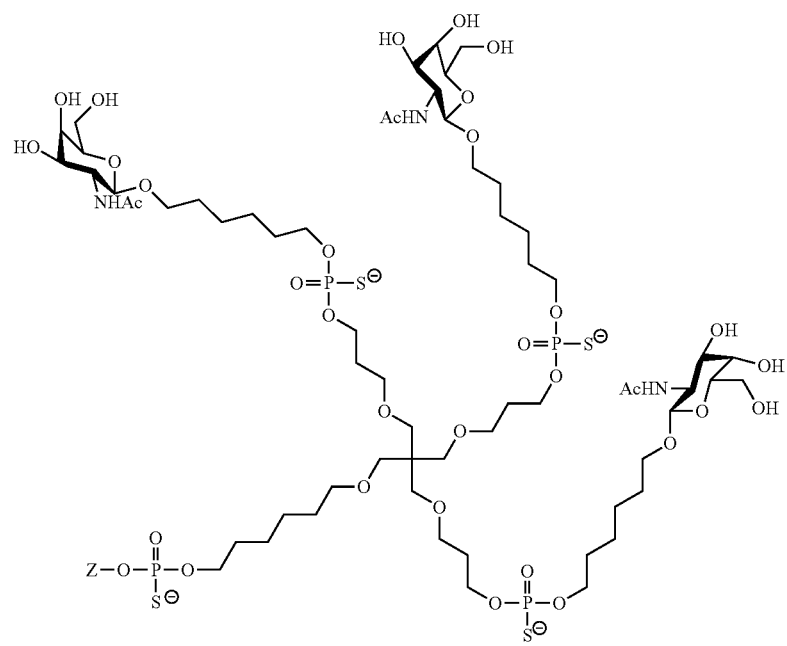

-continued

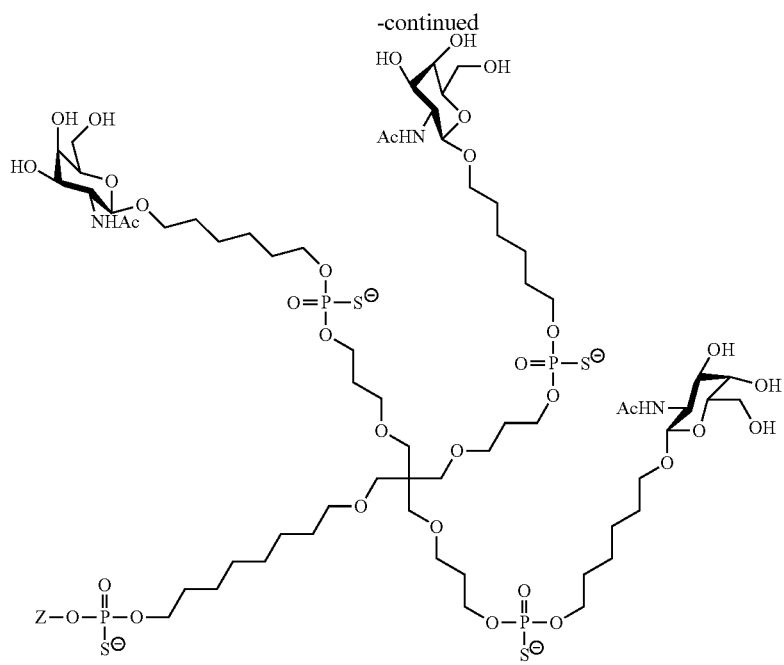

wherein Z represents a nucleic acid as defined herein before.

Alternatively, a nucleic acid disclosed herein may be conjugated to a ligand of the following structure

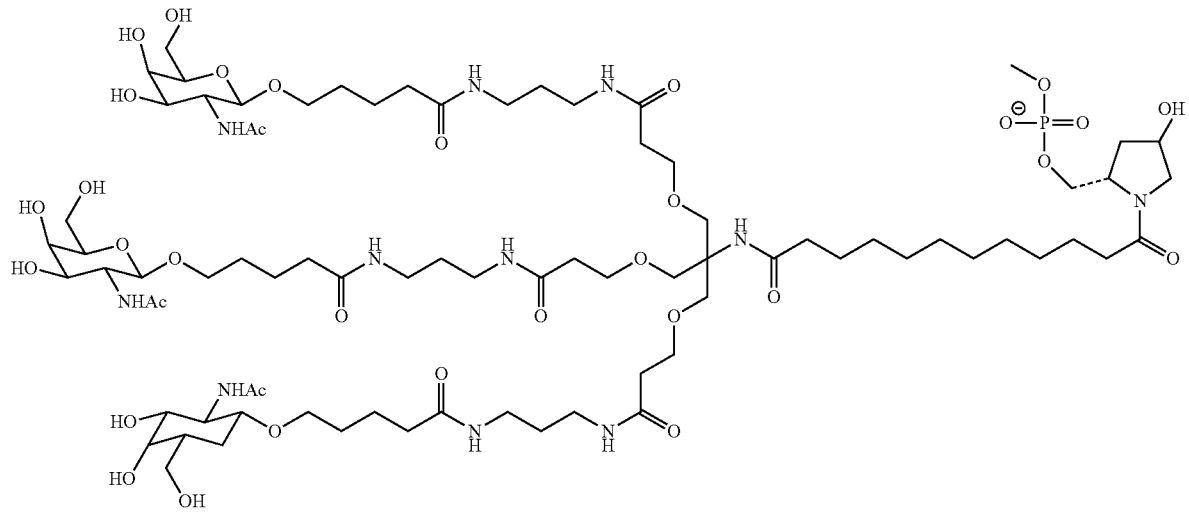 [SMILES: COP(=O)([O-])OC[C@@H]1CC(O)CN1C(=O)CCCCCCCCCCC(=O)NC(COCCC(=O)NCCCNC(=O)CCCCOC1CC(CO)C(O)C(O)C1NC(C)=O)(COCCC(=O)NCCCNC(=O)CCCCOC1OC(CO)C(O)C(O)C1NC(C)=O)COCCC(=O)NCCCNC(=O)CCCCOC1OC(CO)C(O)C(O)C1NC(C)=O]

The invention also provides a composition comprising a nucleic acid as defined herein in combination with one or more iron chelators and a formulation comprising:
  i) a cationic lipid, or a pharmaceutically acceptable salt thereof;
  ii) a steroid;
  iii) a phosphatidylethanolamine phospholipid;
  iv) a PEGylated lipid.

The content of the cationic lipid component in the formulation may be from about 55 mol % to about 65 mol % of the overall lipid content of the lipid formulation, preferably about 59 mol % of the overall lipid content of the lipid formulation.

The formulation may comprise a cationic lipid having the structure

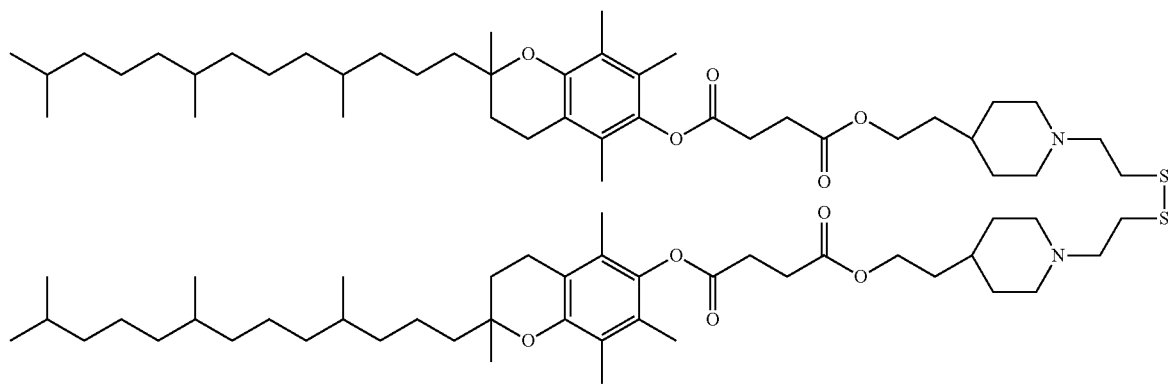 [SMILES: Cc1c(C)c2c(c(C)c1OC(=O)CCC(=O)OCCC1CCN(CCSSCCN3CCC(CCOC(=O)CCC(=O)Oc4c(C)c(C)c5c(c4C)CCC(C)(CCCC(C)CCCC(C)CCCC(C)C)O5)CC3)CC1)CCC(C)(CCCC(C)CCCC(C)CCCC(C)C)O2]

a steroid having the structure

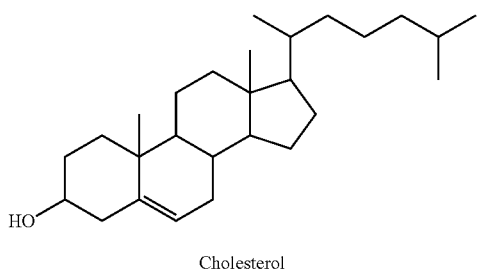 [SMILES: CC(C)CCCC(C)C1CCC2C3CC=C4CC(O)CCC4(C)C3CCC12C]

Cholesterol a phosphatidylethanolamine phospholipid having the structure

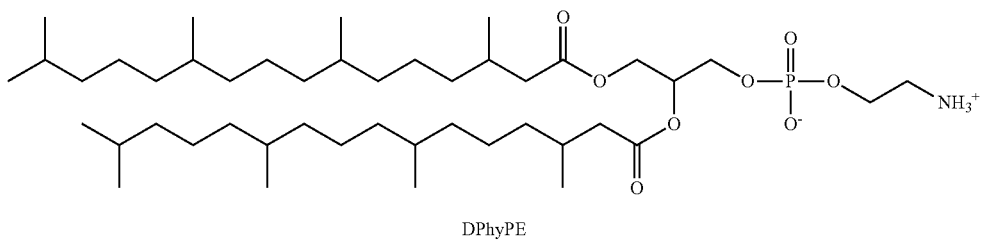 [SMILES: CC(C)CCCC(C)CCCC(C)CCCC(C)CC(=O)OCC(COP(=O)([O-])OCC[NH3+])OC(=O)CC(C)CCCC(C)CCCC(C)CCCC(C)C]

DPhyPE

And a PEGylated lipid having the structure

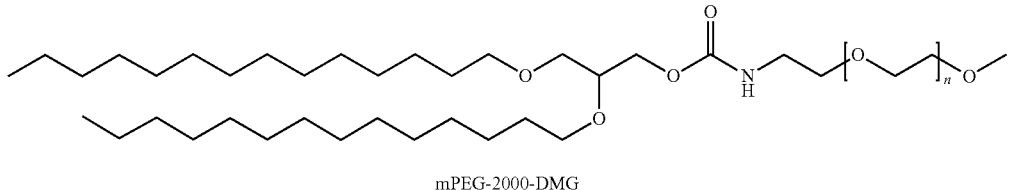

mPEG-2000-DMG

Iron Chelators

An iron chelator is any molecule capable of binding to metal iron ions in the body, and removing or decreasing excess iron from the body, thereby alleviating iron-mediated toxicity.

The one or more iron chelators may be selected from, for example, deferoxamine, deferiprone, deferasirox (Exjade) and deferairox (Jadenu), preferably deferiprone.

The invention also provides a composition comprising a nucleic acid or a conjugated nucleic acid of any aspect of the disclosure, in combination with one or more iron chelators, and a physiologically acceptable excipient.

Also provided is a nucleic acid or a conjugated nucleic acid according to any aspect of the disclosure, in combination with one or more iron chelators, for use in the treatment of a disease or disorder and/or in the manufacture of a medicament for treating a disease or disorder.

The invention provides a method of treating or preventing a disease or disorder comprising administration of a composition comprising a nucleic acid or a conjugated nucleic acid according to any aspect of the disclosure, in combination with one or more iron chelators, to an individual in need of treatment.

The nucleic acid or conjugated nucleic acid may be administered to the subject subcutaneously, intravenously or using any other application routes such as oral, rectal or intraperitoneal.

The iron chelator may be administered to the subject subcutaneously, intravenously or using any other application routes such as oral, rectal or intraperitoneal.

The nucleic acid or conjugated nucleic acid may be administered simultaneously, separately or sequentially with one or more iron chelators.

It will therefore be appreciated that the nucleic acid or conjugated nucleic acid may be delivered in combination with an iron chelator, (such as a fixed dose composition) or the combination may be delivered as separate pharmaceutical compositions.

The disease or disorder may be selected from the group comprising hemochromatosis, porphyria cutanea tarda and blood disorders, such as β-thalassemia or sickle cell disease, congenital dyserythropoietic anemia, marrow failure syndromes, myelodysplasia and transfusional iron overload. The disorder may be associated with iron overload and the disorder associated with iron overload may be Parkinson's Disease, Alzheimer's Disease or Friedreich's Ataxia. The disease or disorder may also be selected from infections and non-relapse related mortality associated with bone marrow transplantation. A preferred disease or disorder to be treated with a nucleic acid as disclosed herein and one or more iron chelators is hemochromatosis.

A method of making a nucleic acid or a conjugated nucleic acid according to the disclosure, in combination with one or more iron chelators, is also included.

DETAILED DESCRIPTION OF INVENTION

The present invention relates to a nucleic acid which is double stranded and directed to an expressed RNA transcript of TMPRSS6 in combination with one or more iron chelators and compositions thereof. These nucleic acids can be used in the treatment of a variety of diseases and disorders where reduced expression of TMPRSS6 gene product is desirable.

The present invention provides a nucleic acid or conjugated nucleic acid according to any aspect disclosed herein in combination with one or more iron chelators.

A first aspect disclosed herein relates to a nucleic acid for inhibiting expression of TMPRSS6 in a cell, comprising at least one duplex region that comprises at least a portion of a first strand and at least a portion of a second strand that is at least partially complementary to the first strand, wherein said first strand is at least partially complementary to at least a portion of a RNA transcribed from the TMPRSS6 gene, wherein said first strand comprises a nucleotide sequence selected from the following sequences:

SEQ ID Nos: 317, 319, 321, 323, 325, 327, 329, 331, 333, 335, 337, 339, 341, 343, 345, 353, 356, 358, 360, 362, 364, 366, 368, 370, 372, 374, 376, 378, 380, 382, 384, 386, 388, 390, 392, 394, 396, 398, 400, 402, 404, 406, 407, 410, 412, 414, 416, 418, 420, 422, 424, 426, 428, 430, 432, 434, 436, 438, 440, or 442, or selected from SEQ ID NOs 1, 3, 5, 7, 9, 11, 13, 15, 17, 19, 21, 23, 25, 27, 29, 67, 69, 71, 73, 74, 76, 77, 78, 79, 80, 81, 82, 83, 85, 87, 88, 90, 91, 92, 93, 94, 95, 96, 97, 98, 99, 111, 113, 115, 117, 119, 121, 123, 125, 127, 129, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 225, 227, 229, 231, 233, 235, 237, 239, 241, 243, 245, 247, 249, 251, 253, 255, 257, 259, 261, 263, 265, 267, 269, 270, 271, 273, 275, 277, 279, 281, 283, 285, 287, 289, 291, 293, 295, 297, 299, 301, 309, 311, 312, 313, 314, or 315, such as SEQ ID NOs:1, 3, 5, 7, 9, 11, 13, 15, 17, 19, 21, 23, 25, 27, 29, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, or 215.

By nucleic acid it is meant a nucleic acid comprising two strands comprising nucleotides, that is able to interfere with gene expression. Inhibition may be complete or partial and results in down regulation of gene expression in a targeted manner. The nucleic acid comprises two separate polynucleotide strands; the first strand, which may also be a guide strand; and a second strand, which may also be a passenger strand. The first strand and the second strand may be part of the same polynucleotide molecule that is self complementary which 'folds' to form a double stranded molecule. The nucleic acid may be an siRNA molecule.

The nucleic acid may comprise ribonucleotides, modified ribonucleotides, deoxynucleotides, deoxyribonucleotides, or nucleotide analogues. The nucleic acid may further comprise a double-stranded nucleic acid portion or duplex region formed by all or a portion of the first strand (also known in the art as a guide strand) and all or a portion of the second strand (also known in the art as a passenger strand). The duplex region is defined as beginning with the first base pair formed between the first strand and the second strand and ending with the last base pair formed between the first strand and the second strand, inclusive.

By duplex region it is meant the region in two complementary or substantially complementary oligonucleotides that form base pairs with one another, either by Watson-Crick base pairing or any other manner that allows for the formation of a duplex between oligonucleotide strands that are complementary or substantially complementary. For example, an oligonucleotide strand having 21 nucleotide units can base pair with another oligonucleotide of 21 nucleotide units, yet only 19 nucleotides on each strand are complementary or substantially complementary, such that the "duplex region" consists of 19 base pairs. The remaining base pairs may exist as 5' and 3' overhangs, or as single stranded regions. Further, within the duplex region, 100% complementarity is not required; substantial complementarity is allowable within a duplex region. Substantial complementarity refers to complementarity between the strands such that they are capable of annealing under biological conditions. Techniques to empirically determine if two strands are capable of annealing under biological conditions are well known in the art. Alternatively, two strands can be synthesised and added together under biological conditions to determine if they anneal to one another.

The portion of the first strand and second strand that form at least one duplex region may be fully complementary and are at least partially complementary to each other.

Depending on the length of a nucleic acid, a perfect match in terms of base complementarity between the first strand and second strand is not necessarily required. However, the first and second strands must be able to hybridise under physiological conditions.

The complementarity between the first strand and second strand in the at least one duplex region may be perfect in that there are no nucleotide mismatches or additional/deleted nucleotides in either strand. Alternatively, the complementarity may not be perfect. The complementarity may be at least 70%, 75%, 80%, 85%, 90% or 95%.

The first strand and the second strand may each comprise a region of complementarity which comprises at least 15 contiguous nucleotides differing by no more than 3 nucleotides from any one of the sequences listed in Table 1.

A related aspect of the disclosure relates to a nucleic acid for inhibiting expression of TMPRSS6 in a cell, comprising at least one duplex region that comprises at least a portion of a first strand and at least a portion of a second strand that is at least partially complementary to the first strand, wherein said first strand is at least partially complementary to at least a portion of a RNA transcribed from the TMPRSS6 gene, wherein said second strand comprises a nucleotide sequence selected from the following sequences:

SEQ ID no's 318, 320, 322, 324, 326, 328, 330, 332, 334, 336, 338, 340, 342, 344, 346, 357, 359, 361, 363, 365, 367, 369, 371, 373, 375, 377, 379, 381, 383, 385, 387, 389, 391, 393, 395, 397, 399, 401, 403, 405, 407, 409, 411, 413, 415, 417, 419, 421, 423, 425, 427, 429, 431, 433, 435, 437, 439, 441, or 443, or selected from SEQ ID no's 2, 4, 6, 8, 10, 12, 14, 16, 18, 20, 22, 24, 26, 28, 30, 68, 70, 72, 75, 84, 86, 89, 100, 101, 102, 103, 104, 105, 106, 112, 114, 116, 118, 120, 122, 124, 126, 128, 130, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 226, 228, 230, 232, 234, 236, 238, 240, 242, 246, 248, 250, 252, 254, 256, 258, 260, 262, 264, 266, 268, 270, 272, 274, 276, 278, 280, 282, 284, 286, 288, 290, 292, 294, 296, 298, 300, 302, 310, 312, 314, or 316, such as a sequence selected from the following: SEQ ID NO:2, 4, 6, 8, 10, 12, 14, 16, 18, 20, 22, 24, 26, 28, 30, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, or 216.

Suitably, in any aspect of the disclosure, the second and first stand together are any of the complementary pairs of nucleic acids disclosed herein, such as those of SEQ ID 1 and 2, 3 and 4 etc.

The combination of nucleic acids consisting of SEQ ID 17 and 18 is a preferred combination, as is SEQ 199 with 200 and SEQ ID 207 with 208.

The nucleic acid involves the formation of a duplex region between all or a portion of the first strand and a portion of the target nucleic acid, TMPRSS6. The portion of the target nucleic acid that forms a duplex region with the first strand, defined as beginning with the first base pair formed between the first strand and the target sequence and ending with the last base pair formed between the first strand and the target sequence, inclusive, is the target nucleic acid sequence or simply, target sequence. The duplex region formed between the first strand and the second strand need not be the same as the duplex region formed between the first strand and the target sequence. That is, the second strand may have a sequence different from the target sequence however, the first strand must be able to form a duplex structure with both the second strand and the target sequence.

The complementarity between the first strand and target sequence may be perfect (no nucleotide mismatches or additional/deleted nucleotides in either nucleic acid).

The complementarity between the first strand and the target sequence may not be perfect. The complementarity may be from about 70% to about 100%. More specifically, the complementarity may be at least 70%, 80%, 85%, 90% or 95%, or an intermediate value.

The identity between the first strand and the complementary sequence of the target sequence may be from about 75% to about 100%. More specifically, the complementarity may be at least 75%, 80%, 85%, 90% or 95%, or an intermediate value, provided a nucleic acid is capable of reducing or inhibiting the expression of TMPRSS6.

A nucleic acid with less than 100% complementarity between the first strand and the target sequence may be able to reduce the expression of TMPRSS6 to the same level as a nucleic acid with perfect complementarity between the first strand and the target sequence. Alternatively, it may be able to reduce expression of TMPRSS6 to a level that is 15%, 20%, 30%, 40%, 50%, 60%, 70%, 80%, 90% or 100% of the level of expression achieved by the nucleic acid with perfect complementarity.

The nucleic acid may comprise a first strand and a second strand that are each from 19-25 nucleotides in length. The first strand and the second strand may be of different lengths.

The nucleic acid may be 15-25 nucleotide pairs in length.
The nucleic acid may be 17-23 nucleotide pairs in length.
The nucleic acid may be 17-25 nucleotide pairs in length.
The nucleic acid may be 23-24 nucleotide pairs in length.
The nucleic acid may be 19-21 nucleotide pairs in length.
The nucleic acid may be 21-23 nucleotide pairs in length.

The nucleic acid may comprise a duplex region that consists of 19-25 nucleotide base pairs. The duplex region may consist of 17, 18, 19, 20, 21, 22, 23, 24 or 25 base pairs which may be contiguous.

The nucleic acid may comprise a first strand sequence of SEQ ID NO:17. The nucleic acid may comprise a second strand sequence of SEQ ID NO:18. The nucleic acid disclosed herein may comprise SEQ ID NO:17 and SEQ ID NO:18.

In a further aspect the nucleic acid as described herein may reduce the expression of TMPRSS6 in a cell by at least 15% compared to the level observed in the absence of an inhibitor, which may be the nucleic acid. All preferred features of any of the previous aspects also apply to this aspect. In particular, the expression of TMPRSS6 in a cell may be reduced to 90%, 80%, 70%, 60%, 50%, 40%, 30%, 20%, 15% or less, and intermediate values, than that observed in the absence of an inhibitor (which may be the nucleic acid).

The disclosure also relates to any first strand or any second strand of nucleic acid as disclosed herein, which comprises no more than 2 base changes when compared to the specific sequence ID provided. For example, one base may be changed within any sequence.

In one embodiment, the change may be made to the 5' most nucleotide of the antisense (first) strand. In one embodiment, the change may be made to the 3' most nucleotide of the antisense (first) strand. In one embodiment, the change may be made to the 5' most nucleotide of the sense (second) strand. In one embodiment, the change may be made to the 3' most nucleotide of the sense (second) strand.

In one embodiment, the change is made to the 5' most nucleotide of the antisense (first) strand. The base of the 5' nucleotide may be changed to any other nucleotide. An A or a U at the 5' end are preferred, and an A or a U are taught herein as the potential 5' terminal base for all of the antisense (first strand) sequences disclosed herein Overhangs The nucleic acid may be blunt ended at both ends; have an overhang at one end and a blunt end at the other end; or have an overhang at both ends.

An "overhang" as used herein has its normal and customary meaning in the art, i.e. a single stranded portion of a nucleic acid that extends beyond the terminal nucleotide of a complementary strand in a double strand nucleic acid. The term "blunt end" includes double stranded nucleic acid whereby both strands terminate at the same position, regardless of whether the terminal nucleotide(s) are base paired. The terminal nucleotide of a first strand and a second strand at a blunt end may be base paired. The terminal nucleotide of a first strand and a second strand at a blunt end may not be paired. The terminal two nucleotides of a first strand and a second strand at a blunt end may be base paired. The terminal two nucleotides of a first strand and a second strand at a blunt end may not be paired.

The nucleic acid may have an overhang at one end and a blunt end at the other. The nucleic acid may have an overhang at both ends. The nucleic acid may be blunt ended at both ends. The nucleic acid may be blunt ended at the end with the 5'-end of the first strand and the 3'-end of the second strand or at the 3'-end of the first strand and the 5'-end of the second strand.

The nucleic acid may comprise an overhang at a 3'- or 5'-end. The nucleic acid may have a 3'-overhang on the first strand. The nucleic acid may have a 3'-overhang on the second strand. The nucleic acid may have a 5'-overhang on the first strand. The nucleic acid may have a 5'-overhang on the second strand. The nucleic acid may have an overhang at both the 5'-end and 3'-end of the first strand. The nucleic acid may have an overhang at both the 5'-end and 3'-end of the second strand. The nucleic acid may have a 5' overhang on the first strand and a 3' overhang on the second strand. The nucleic acid may have a 3' overhang on the first strand and a 5' overhang on the second strand. The nucleic acid may have a 3' overhang on the first strand and a 3' overhang on the second strand. The nucleic acid may have a 5' overhang on the first strand and a 5' overhang on the second strand.

An overhang at the 3'-end or 5' end of the second strand or the first strand may be selected from consisting of 1, 2, 3, 4 and 5 nucleotides in length. Optionally, an overhang may consist of 1 or 2 nucleotides, which may or may not be modified.

Modifications

Unmodified polynucleotides, particularly ribonucleotides, may be prone to degradation by cellular nucleases, and, as such, modifications/modified nucleotides may be included in the nucleic acid disclosed herein.

One or more nucleotides on the second and/or first strand of the nucleic acid disclosed herein may be modified.

Modifications of the nucleic acid disclosed herein generally provide a powerful tool in overcoming potential limitations including, but not limited to, in vitro and in vivo stability and bioavailability inherent to native RNA molecules. The nucleic acid according disclosed herein may be modified by chemical modifications. Modified nucleic acid can also minimise the possibility of inducing interferon activity in humans. Modification can further enhance the functional delivery of a nucleic acid to a target cell. The modified nucleic acid disclosed herein may comprise one or more chemically modified ribonucleotides of either or both of the first strand or the second strand. A ribonucleotide may comprise a chemical modification of the base, sugar or phosphate moieties. The ribonucleic acid may be modified by substitution or insertion with analogues of nucleic acids or bases.

It will be appreciated that the disclosure of a modified nucleic acid, in particular such as an modified RNA, provides both a disclosure of the "primary" nucleic acid sequence, and also the modifications of that sequence. A sequence listing thus provides both the information on the primary nucleic acid sequence and also a modified sequence. For the avoidance of doubt, and the disclosure relates to both to unmodified nucleic acid sequences, partially modified and any sequences for which the modifications have been fully defined.

One or more nucleotides of a nucleic acid disclosed herein may be modified. The nucleic acid may comprise at least one modified nucleotide. The modified nucleotide may be on the first strand. The modified nucleotide may be in the second strand. The modified nucleotide may be in the duplex region. The modified nucleotide may be outside the duplex region, i.e., in a single stranded region. The modified nucleotide may be on the first strand and may be outside the duplex region. The modified nucleotide may be on the second strand and may be outside the duplex region. The 3'-terminal nucleotide of the first strand may be a modified nucleotide. The 3'-terminal nucleotide of the second strand may be a modified nucleotide. The 5'-terminal nucleotide of the first strand may be a modified nucleotide. The 5'-terminal nucleotide of the second strand may be a modified nucleotide.

A nucleic acid disclosed herein may have 1 modified nucleotide or a nucleic acid disclosed herein may have about 2-4 modified nucleotides, or a nucleic acid may have about 4-6 modified nucleotides, about 6-8 modified nucleotides, about 8-10 modified nucleotides, about 10-12 modified nucleotides, about 12-14 modified nucleotides, about 14-16 modified nucleotides about 16-18 modified nucleotides, about 18-20 modified nucleotides, about 20-22 modified nucleotides, about 22-24 modified nucleotides, 24-26 modified nucleotides or about 26-28 modified nucleotides. In each case the nucleic acid comprising said modified nucleotides retains at least 50% of its activity as compared to the same nucleic acid but without said modified nucleotides. The nucleic acid may retain 55%, 60%, 65%, 70%, 75%, 80%, 85%, 90%, 95% or 100% or an intermediate value of its activity as compared to the same nucleic acid but without said modified nucleotides, or may have more than 100% of the activity of the same nucleotide without said modified nucleotides.

The modified nucleotide may be a purine or a pyrimidine. At least half of the purines may be modified. At least half of the pyrimidines may be modified. All of the purines may be modified. All of the pyrimidines may be modified. The modified nucleotides may be selected from the group consisting of a 3'-terminal deoxy-thymine (dT) nucleotide, a 2'-O-methyl modified nucleotide, a 2' modified nucleotide, a 2'-deoxy-modified nucleotide, a locked nucleotide, an abasic nucleotide, a 2'-amino-modified nucleotide, a 2'-alkyl-modified nucleotide, a morpholino nucleotide, a phosphoramidate, a non-natural base comprising nucleotide, a nucleotide comprising a 5'-phosphorothioate group, a nucleotide comprising a 5' phosphate or 5' phosphate mimic and a terminal nucleotide linked to a cholesteryl derivative or a dodecanoic acid bisdecylamide group.

The nucleic acid may comprise a nucleotide comprising a modified nucleotide, wherein the base is selected from 2-aminoadenosine, 2,6-diaminopurine, inosine, pyridin-4-one, pyridin-2-one, phenyl, pseudouracil, 2,4,6-trimethoxy benzene, 3-methyl uracil, dihydrouridine, naphthyl, amino-phenyl, 5-alkylcytidine (e.g., 5-methylcytidine), 5-alkyluridine (e.g., ribothymidine), 5-halouridine (e.g., 5-bromouridine), 6-azapyrimidine, 6-alkylpyrimidine (e.g. 6-methyluridine), propyne, quesosine, 2-thiouridine, 4-thiouridine, wybutosine, wybutoxosine, 4-acetylcytidine, 5-(carboxyhydroxymethyl)uridine, 5'-carboxymethylaminomethyl-2-thiouridine, 5-carboxymethylaminomethyluridine, beta-D-galactosylqueosine, 1-methyladenosine, 1-methylinosine, 2,2-dimethylguanosine, 3-methylcytidine, 2-methyladenosine, 2-methylguanosine, N6-methyladenosine, 7-methylguanosine, 5-methoxyaminomethyl-2-thiouridine, 5-methylaminomethyluridine, 5-methylcarbonylmethyluridine, 5-methyloxyuridine, 5-methyl-2-thiouridine, 2-methylthio-N6-isopentenyladenosine, beta-D-mannosylqueosine, uridine-5-oxyacetic acid and 2-thiocytidine.

Nucleic acids discussed herein include unmodified RNA as well as RNA which has been modified, e.g., to improve efficacy, and polymers of nucleoside surrogates. Unmodified RNA refers to a molecule in which the components of the nucleic acid, namely sugars, bases, and phosphate moieties, are the same or essentially the same as that which occur in nature, for example as occur naturally in the human body. Modified nucleotide as used herein refers to a nucleotide in which one or more of the components of the nucleic acid, namely sugars, bases, and phosphate moieties, are different from that which occur in nature. While they are referred to as modified nucleotides they will of course, because of the modification, include molecules which are not nucleotides, for example a polynucleotide molecules in which the ribophosphate backbone is replaced with a non-ribophosphate construct that allows hybridisation between strands i.e. the modified nucleotides mimic the ribophosphate backbone.

Many of the modifications described below that occur within a nucleic acid will be repeated within a polynucleotide molecule, such as a modification of a base, or a phosphate moiety, or the a non-linking O of a phosphate moiety. In some cases the modification will occur at all of the possible positions/nucleotides in the polynucleotide but in many cases it will not. A modification may only occur at a 3' or 5' terminal position, may only occur in a terminal regions, such as at a position on a terminal nucleotide or in the last 2, 3, 4, 5, or 10 nucleotides of a strand. A modification may occur in a double strand region, a single strand region, or in both. A modification may occur only in the double strand region of a nucleic acid disclosed herein or may only occur in a single strand region of an nucleic acid disclosed herein. A phosphorothioate modification at a non-linking O position may only occur at one or both termini, may only occur in a terminal region, e.g., at a position on a terminal nucleotide or in the last 2, 3, 4 or 5 nucleotides of a strand, or may occur in duplex and/or in single strand regions, particularly at termini. The 5' end or 3' ends may be phosphorylated.

Stability of a nucleic acid disclosed herein may be increased by including particular bases in overhangs, or by including modified nucleotides, in single strand overhangs, e.g., in a 5' or 3' overhang, or in both. Purine nucleotides may be included in overhangs. All or some of the bases in a 3' or 5' overhang may be modified. Modifications can include the use of modifications at the 2' OH group of the ribose sugar, the use of deoxyribonucleotides, instead of ribonucleotides, and modifications in the phosphate group, such as phosphorothioate modifications. Overhangs need not be homologous with the target sequence.

The 5'- or 3'-overhangs at the sense strand, antisense strand or both strands of the dsRNA agent disclosed herein may be phosphorylated. In some embodiments, the overhang region contains two nucleotides having a phosphorothioate between the two nucleotides, where the two nucleotides can be the same or different. In one embodiment, the overhang is present at the 3'-end of the sense strand, antisense strand or both strands. In one embodiment, this 3'-overhang is present in the antisense strand. In one embodiment, this 3'-overhang is present in the sense strand.

Nucleases can hydrolyze nucleic acid phosphodiester bonds. However, chemical modifications to nucleic acids can confer improved properties, and, can render oligoribonucleotides more stable to nucleases.

Modified nucleic acids, as used herein, can include one or more of:
(i) alteration, e.g., replacement, of one or both of the non-linking phosphate oxygens and/or of one or more of the linking phosphate oxygens (referred to as linking even if at the 5' and 3' terminus of the nucleic acid disclosed herein);
(ii) alteration, e.g., replacement, of a constituent of the ribose sugar, e.g., of the 2' hydroxyl on the ribose sugar;
(iii) replacement of the phosphate moiety with "dephospho" linkers;
(iv) modification or replacement of a naturally occurring base;
(v) replacement or modification of the ribose-phosphate backbone;
(vi) modification of the 3' end or 5' end of the RNA, e.g., removal, modification or replacement of a terminal phosphate group or conjugation of a moiety, e.g., a fluorescently labeled moiety, to either the 3' or 5' end of RNA.

The terms replacement, modification, alteration, indicate a difference from a naturally occurring molecule.

Specific modifications are discussed in more detail below.

Examples of modified phosphate groups include phosphorothioate, phosphoroselenates, borano phosphates, borano phosphate esters, hydrogen phosphonates, phosphoroamidates, alkyl or aryl phosphonates and phosphotriesters. Phosphorodithioates have both non-linking oxygens replaced by sulphur. One, each or both non-linking oxygens in the phosphate group can be independently any one of S, Se, B, C, H, N, or OR (R is alkyl or aryl).

The phosphate linker can also be modified by replacement of a linking oxygen with nitrogen (bridged phosphoroamidates), sulfur (bridged phosphorothioates) and carbon (bridged methylenephosphonates). The replacement can occur at a terminal oxygen. Replacement of the non-linking oxygens with nitrogen is possible.

A modified nucleotide can include modification of the sugar groups. The 2' hydroxyl group (OH) can be modified or replaced with a number of different "oxy" or "deoxy" substituents.

Examples of "oxy"-2' hydroxyl group modifications include alkoxy or aryloxy (OR, e.g., R=H, alkyl, cycloalkyl, aryl, aralkyl, heteroaryl or sugar); polyethyleneglycols (PEG), O(CH2CH2O)nCH2CH2OR; "locked" nucleic acids (LNA) in which the 2' hydroxyl is connected, e.g., by a methylene bridge, to the 4' carbon of the same ribose sugar; O-AMINE (AMINE=$NH_2$; alkylamino, dialkylamino, heterocyclyl, arylamino, diaryl amino, heteroaryl amino, or diheteroaryl amino, ethylene diamine, polyamino) and aminoalkoxy, O($CH_2$)nAMINE, (e.g., AMINE=$NH_2$; alkylamino, dialkylamino, heterocyclyl, arylamino, diaryl amino, heteroaryl amino, or diheteroaryl amino, ethylene diamine, polyamino).

"Deoxy" modifications include hydrogen halo; amino (e.g., $NH_2$; alkylamino, dialkylamino, heterocyclyl, arylamino, diaryl amino, heteroaryl amino, diheteroaryl amino, or amino acid); NH(CH$_2$CH$_2$NH)$_n$CH$_2$CH$_2$-AMINE (AMINE=NH$_2$); alkylamino, dialkylamino, heterocyclyl, arylamino, diaryl amino, heteroaryl amino, or diheteroaryl amino), —NHC(O)R (R=alkyl, cycloalkyl, aryl, aralkyl, heteroaryl or sugar), cyano; mercapto; alkyl-thio-alkyl; thioalkoxy; and alkyl, cycloalkyl, aryl, alkenyl and alkynyl, which may be optionally substituted with e.g., an amino functionality. Other substituents of certain embodiments include 2'-methoxyethyl, 2'-OCH$_3$, 2'-O-allyl, 2'-C-allyl, and 2'-fluoro.

The sugar group can also contain one or more carbons that possess the opposite stereochemical configuration than that of the corresponding carbon in ribose. Thus, a modified nucleotides may contain a sugar such as arabinose.

Modified nucleotides can also include "abasic" sugars, which lack a nucleobase at C-I'. These abasic sugars can further contain modifications at one or more of the constituent sugar atoms.

The 2' modifications may be used in combination with one or more phosphate linker modifications (e.g., phosphorothioate).

The phosphate group can be replaced by non-phosphorus containing connectors.

Examples of moieties which can replace the phosphate group include siloxane, carbonate, carboxymethyl, carbamate, amide, thioether, ethylene oxide linker, sulfonate, sulfonamide, thioformacetal, formacetal, oxime, methyleneimino, methylenemethylimino, methylenehydrazo, methylenedimethylhydrazo and methyleneoxymethylimino. In certain embodiments, replacements may include the methylenecarbonylamino and methylenemethylimino groups.

The phosphate linker and ribose sugar may be replaced by nuclease resistant nucleotides.

Examples include the morpholino, cyclobutyl, pyrrolidine and peptide nucleic acid (PNA) nucleoside surrogates. In certain embodiments, PNA surrogates may be used.

The 3' and 5' ends of an oligonucleotide can be modified. Such modifications can be at the 3' end or the 5' end or both ends of the molecule. They can include modification or replacement of an entire terminal phosphate or of one or more of the atoms of the phosphate group. For example, the 3' and 5' ends of an oligonucleotide can be conjugated to other functional molecular entities such as labeling moieties, e.g., fluorophores (e.g., pyrene, TAMRA, fluorescein, Cy3 or Cy5 dyes) or protecting groups (based e.g., on sulfur, silicon, boron or ester). The functional molecular entities can be attached to the sugar through a phosphate group and/or a linker. The terminal atom of the linker can connect to or replace the linking atom of the phosphate group or the C-3' or C-5' O, N, S or C group of the sugar. Alternatively, the linker can connect to or replace the terminal atom of a nucleotide surrogate (e.g., PNAs). These spacers or linkers can include e.g., —(CH$_2$)$_n$—, —(CH$_2$)$_n$N—, —(CH$_2$)$_n$O—, —(CH$_2$)$_n$S—, O(CH$_2$CH$_2$O)$_n$CH$_2$CH$_2$OH (e.g., n=3 or 6), abasic sugars, amide, carboxy, amine, oxyamine, oxyimine, thioether, disulfide, thiourea, sulfonamide, or morpholino, or biotin and fluorescein reagents. The 3' end can be an —OH group.

Other examples of terminal modifications include dyes, intercalating agents (e.g., acridines), cross-linkers (e.g., psoralene, mitomycin C), porphyrins (TPPC4, texaphyrin, Sapphyrin), polycyclic aromatic hydrocarbons (e.g., phenazine, dihydrophenazine), artificial endonucleases (e.g., EDTA), lipophilic carriers (e.g., cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, 03-(oleoyl) lithocholic acid, 03-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]2, polyamino, alkyl, substituted alkyl, radiolabeled markers, enzymes, haptens (e.g., biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu$^{3+}$ complexes of tetraazamacrocycles).

Terminal modifications can be added for a number of reasons, including to modulate activity or to modulate resistance to degradation. Terminal modifications useful for modulating activity include modification of the 5' end with phosphate or phosphate analogs. Nucleic acids disclosed herein, on the first or second strand, may be 5' phosphorylated or include a phosphoryl analog at the 5' prime terminus. 5'-phosphate modifications include those which are compatible with RISC mediated gene silencing. Suitable modifications include: 5'-monophosphate ((HO)$_2$(O)P—O-5'); 5'-diphosphate ((HO)$_2$(O)P—O—P(HO)(O)—O-5'); 5'-triphosphate ((HO)$_2$(O)P—O—(HO)(O)P—O—P(HO)(O)—O-5'); 5'-guanosine cap (7-methylated or non-methylated) (7m-G-O-5'-(HO)(O)P—O—(HO)(O)P—O—P(HO)(O)—O-5'); 5'-adenosine cap (Appp), and any modified or unmodified nucleotide cap structure (N—O-5'-(HO)(O)P—O—(HO)(O)P—O—P(HO)(O)—O-5'); 5'-monothiophosphate (phosphorothioate; (HO)$_2$(S)P—O-5'); 5'-monodithiophosphate (phosphorodithioate; (HO)(HS)(S)P—O-5'), 5'-phosphorothiolate ((HO)$_2$(O)P—S-5'); any additional combination of oxygen/sulfur replaced monophosphate, diphosphate and triphosphates (e.g., 5'-alpha-thiotriphosphate, 5'-gamma-thiotriphosphate, etc.), 5'-phosphoramidates ((HO)$_2$(O)P—NH-5', (HO)(NH$_2$)(O)P—O-5'), 5'-alkylphosphonates (R=alkyl=methyl, ethyl, isopropyl, propyl, etc., e.g., RP(OH)(O)—O-5'-, (OH)$_2$(O)P-5'-CH$_2$—), 5'vinylphosphonate, 5'-alkyletherphosphonates (R=alkylether=methoxymethyl (MeOCH$_2$—), ethoxymethyl, etc., e.g., RP(OH)(O)—O-5'-).

The nucleic acid of the present disclosure may include one or more phosphorothioate modifications on one or more of the terminal ends of the first and/or the second strand. Optionally, each or either end of the first strand may comprise one or two or three phosphorothioate modified nucleotides. Optionally, each or either end of the second strand may comprise one or two or three phosphorothioate modified nucleotides. Optionally, both ends of the first strand and the 5' end of the second strand may comprise two phosphorothioate modified nucleotides. By phosphorothioate modified nucleotide it is meant that the linkage between the nucleotide and the adjacent nucleotide comprises a phosphorothioate group instead of a standard phosphate group.

Terminal modifications can also be useful for monitoring distribution, and in such cases the groups to be added may include fluorophores, e.g., fluorescein or an Alexa dye. Terminal modifications can also be useful for enhancing uptake, useful modifications for this include cholesterol. Terminal modifications can also be useful for cross-linking an RNA agent to another moiety.

Nucleotides

Adenine, guanine, cytosine and uracil are the most common bases found in RNA. These bases can be modified or replaced to provide RNA's having improved properties.

E.g., nuclease resistant oligoribonucleotides can be prepared with these bases or with synthetic and natural nucleobases (e.g., inosine, thymine, xanthine, hypoxanthine, nubularine, isoguanisine, or tubercidine) and any one of the above modifications. Alternatively, substituted or modified analogs of any of the above bases and "universal bases" can be employed. Examples include 2-aminoadenine, 6-methyl and other alkyl derivatives of adenine and guanine, 2-propyl and other alkyl derivatives of adenine and guanine, 5-halouracil and cytosine, 5-propynyl uracil and cytosine, 6-azo uracil, cytosine and thymine, 5-uracil (pseudouracil), 4-thiouracil, 5-halouracil, 5-(2-aminopropyl)uracil, 5-amino allyl uracil, 8-halo, amino, thiol, thioalkyl, hydroxyl and other 8-substituted adenines and guanines, 5-trifluoromethyl and other 5-substituted uracils and cytosines, 7-methylguanine, 5-substituted pyrimidines, 6-azapyrimidines and N-2, N-6 and O-6 substituted purines, including 2-aminopropyladenine, 5-propynyluracil and 5-propynylcytosine, dihydrouracil, 3-deaza-5-azacytosine, 2-aminopurine, 5-alkyluracil, 7-alkylguanine, 5-alkyl cytosine, 7-deazaadenine, N6,N6-dimethyladenine, 2,6-diaminopurine, 5-amino-allyl-uracil, N3-methyluracil, substituted 1,2,4-triazoles, 2-pyridinone, 5-nitroindole, 3-nitropyrrole, 5-methoxyuracil, uracil-5-oxyacetic acid, 5-methoxycarbonylmethyluracil, 5-methyl-2-thiouracil, 5-methoxycarbonylmethyl-2-thiouracil, 5-methylaminomethyl-2-thiouracil, 3-(3-amino-3-carboxypropyl)uracil, 3-methylcytosine, 5-methylcytosine, N<4>-acetyl cytosine, 2-thiocytosine, N6-methyladenine, N6-isopentyladenine, 2-methylthio-N6-isopentenyladenine, N-methylguanines, or O-alkylated bases.

As used herein, the terms "non-pairing nucleotide analogue" means a nucleotide analogue which includes a non-base pairing moiety including but not limited to: 6 des amino adenosine (Nebularine), 4-Me-indole, 3-nitropyrrole, 5-nitroindole, Ds, Pa, N3-Me ribo U, N3-Me riboT, N3-Me dC, N3-Me-dT, N1-Me-dG, N1-Me-dA, N3-ethyl-dC, N3-Me dC. In some embodiments the non-base pairing nucleotide analog is a ribonucleotide. In other embodiments it is a deoxyribonucleotide.

As used herein, the term, "terminal functional group" includes without limitation a halogen, alcohol, amine, carboxylic, ester, amide, aldehyde, ketone, ether groups.

Certain moieties may be linked to the 5' terminus of the first strand or the second strand and includes abasic ribose moiety, abasic deoxyribose moiety, modifications abasic ribose and abasic deoxyribose moieties including 2' O alkyl modifications; inverted abasic ribose and abasic deoxyribose moieties and modifications thereof, C6-imino-Pi; a mirror nucleotide including L-DNA and L-RNA; 5'OMe nucleotide; and nucleotide analogs including 4',5'-methylene nucleotide; 1-(β-D-erythrofuranosyl)nucleotide; 4'-thio nucleotide, carbocyclic nucleotide; 5'-amino-alkyl phosphate; 1,3-diamino-2-propyl phosphate, 3-aminopropyl phosphate; 6-aminohexyl phosphate; 12-aminododecyl phosphate; hydroxypropyl phosphate; 1,5-anhydrohexitol nucleotide; alpha-nucleotide; threo-pentofuranosyl nucleotide; acyclic 3',4'-seco nucleotide; 3,4-dihydroxybutyl nucleotide; 3,5-dihydroxypentyl nucleotide, 5'-5'-inverted abasic moiety; 1,4-butanediol phosphate; 5'-amino; and bridging or non bridging methylphosphonate and 5'-mercapto moieties.

The nucleic acids disclosed herein may be included one or more inverted nucleotides, for example inverted thymidine or inverted adenine (for example see Takei, et al., 2002. JBC 277 (26):23800-06).

As used herein, the term "inhibit", "down-regulate", or "reduce" with respect to gene expression means the expression of the gene, or level of RNA molecules or equivalent RNA molecules encoding one or more proteins or protein subunits (e.g., mRNA), or activity of one or more proteins, protein subunits or peptides, is reduced below that observed in the absence of a nucleic acid disclosed herein or in reference to an siRNA molecule with no known homology to human transcripts (herein termed non-silencing control). Such control may be conjugated and modified in an analogous manner to the molecule disclosed herein and delivered into the target cell by the same route; for example the expression may be reduced to 90%, 80%, 70%, 60%, 50%, 40%, 30%, 20%, 15% or an intermediate value, in the absence of the nucleic acid or conjugated nucleic acid disclosed herein, or in the presence of a non-silencing control.

The nucleic acid of the present disclosure may comprise an abasic nucleotide. The term "abasic" as used herein, refers to moieties lacking a base or having other chemical groups in place of a base at the 1' position, for example a 3',3'-linked or 5',5'-linked deoxyabasic ribose derivative.

The nucleic acid may comprise one or more nucleotides on the second and/or first strands that are modified. Alternating nucleotides may be modified, to form modified nucleotides.

Alternating as described herein means to occur one after another in a regular way. In other words, alternating means to occur in turn repeatedly. For example if one nucleotide is modified, the next contiguous nucleotide is not modified and the following contiguous nucleotide is modified and so on. One nucleotide may be modified with a first modification, the next contiguous nucleotide may be modified with a second modification and the following contiguous nucleotide is modified with the first modification and so on, where the first and second modifications are different.

One or more of the odd numbered nucleotides of the first strand of the nucleic acid disclosed herein may be modified wherein the first strand is numbered 5' to 3'. The term "odd numbered" as described herein means a number not divisible by two. Examples of odd numbers are 1, 3, 5, 7, 9, 11 and so on. One or more of the even numbered nucleotides of the first strand of the nucleic acid disclosed herein may be modified, wherein the first strand is numbered 5' to 3'. The term "even numbered" as described herein means a number which is evenly divisible by two. Examples of even numbers are 2, 4, 6, 8, 10, 12, 14 and so on. One or more of the odd numbered nucleotides of the second strand of the nucleic acid disclosed herein may be modified wherein the second strand is numbered 3' to 5'. One or more of the even numbered nucleotides of the second strand of the nucleic acid disclosed herein may be modified, wherein the second strand is numbered 3' to 5'.

One or more nucleotides on the first and/or second strand may be modified, to form modified nucleotides. One or more of the odd numbered nucleotides of the first strand may be modified. One or more of the even numbered nucleotides of the first strand may be modified by at least a second modification, wherein the at least second modification is different from the modification on the one or more add nucleotides. At least one of the one or more modified even numbered nucleotides may be adjacent to at least one of the one or more modified odd numbered nucleotides.

A plurality of odd numbered nucleotides in the first strand may be modified in the nucleic acid disclosed herein. A plurality of even numbered nucleotides in the first strand may be modified by a second modification. The first strand may comprise adjacent nucleotides that are modified by a common modification. The first strand may also comprise adjacent nucleotides that are modified by a second different modification.

One or more of the odd numbered nucleotides of the second strand may be modified by a modification that is different to the modification of the odd numbered nucleotides on the first strand and/or one or more of the even numbered nucleotides of the second strand may be by the same modification of the odd numbered nucleotides of the first strand. At least one of the one or more modified even numbered nucleotides of the second strand may be adjacent to the one or more modified odd numbered nucleotides. A plurality of odd numbered nucleotides of the second strand may be modified by a common modification and/or a plurality of even numbered nucleotides may be modified by the same modification that is present on the first stand odd numbered nucleotides. A plurality of odd numbered nucleotides on the second strand may be modified by a second modification, wherein the second modification is different from the modification of the first strand odd numbered nucleotides.

The second strand may comprise adjacent nucleotides that are modified by a common modification, which may be a second modification that is different from the modification of the odd numbered nucleotides of the first strand.

In the nucleic acid disclosed herein, each of the odd numbered nucleotides in the first strand and each of the even numbered nucleotides in the second strand may be modified with a common modification and, each of the even numbered nucleotides may be modified in the first strand with a second modification and each of the odd numbered nucleotides may be modified in the second strand with the second modification.

The nucleic acid disclosed herein may have the modified nucleotides of the first strand shifted by at least one nucleotide relative to the unmodified or differently modified nucleotides of the second strand.

One or more or each of the odd numbered nucleotides may be modified in the first strand and one or more or each of the even numbered nucleotides may be modified in the second strand. One or more or each of the alternating nucleotides on either or both strands may be modified by a second modification. One or more or each of the even numbered nucleotides may be modified in the first strand and one or more or each of the even numbered nucleotides may be modified in the second strand. One or more or each of the alternating nucleotides on either or both strands may be modified by a second modification. One or more or each of the odd numbered nucleotides may be modified in the first strand and one or more of the odd numbered nucleotides may be modified in the second strand by a common modification. One or more or each of the alternating nucleotides on either or both strands may be modified by a second modification. One or more or each of the even numbered nucleotides may be modified in the first strand and one or more or each of the odd numbered nucleotides may be modified in the second strand by a common modification. One or more or each of the alternating nucleotides on either or both strands may be modified by a second modification.

The nucleic acid disclosed herein may comprise single or double stranded constructs that comprise at least two regions of alternating modifications in one or both of the strands. These alternating regions can comprise up to about 12 nucleotides but preferably comprise from about 3 to about 10 nucleotides. The regions of alternating nucleotides may be located at the termini of one or both strands of the nucleic acid disclosed herein. The nucleic acid may comprise from 4 to about 10 nucleotides of alternating nucleotides at each termini (3' and 5') and these regions may be separated by from about 5 to about 12 contiguous unmodified or differently or commonly modified nucleotides.

The odd numbered nucleotides of the first strand may be modified and the even numbered nucleotides may be modified with a second modification. The second strand may comprise adjacent nucleotides that are modified with a common modification, which may be the same as the modification of the odd numbered nucleotides of the first strand. One or more nucleotides of second strand may also be modified with the second modification. One or more nucleotides with the second modification may be adjacent to each other and to nucleotides having a modification that is the same as the modification of the odd numbered nucleotides of the first strand. The first strand may also comprise phosphorothioate linkages between the two nucleotides at the 3' end and at the 5' end. The second strand may comprise a phosphorothioate linkage between the two nucleotides at 5' end. The second strand may also be conjugated to a ligand at the 5' end.

The nucleic acid disclosed herein may comprise a first strand comprising adjacent nucleotides that are modified with a common modification. One or more of such nucleotides may be adjacent to one or more nucleotides which may be modified with a second modification. One or more nucleotides with the second modification may be adjacent. The second strand may comprise adjacent nucleotides that are modified with a common modification, which may be the same as one of the modifications of one or more nucleotides of the first strand. One or more nucleotides of second strand may also be modified with the second modification. One or more nucleotides with the second modification may be adjacent. The first strand may also comprise phosphorothioate linkages between the two nucleotides at the 5' end and at the 3' end. The second strand may comprise a phosphorothioate linkage between the two nucleotides at 3' end. The second strand may also be conjugated to a ligand at the 5' end.

The nucleotides numbered from 5' to 3' on the first strand and 3' and 5' on the second strand, 1, 3, 5, 7, 9, 11, 13, 15, 17, 19, 21, 23 and 25 may be modified by a modification on the first strand. The nucleotides numbered 2, 4, 6, 8, 10, 12, 14, 16, 18, 20, 22 and 24 may be modified by a second modification on the first strand. The nucleotides numbered 1, 3, 5, 7, 9, 11, 13, 15, 17, 19, 21, 23 may be modified by a modification on the second strand. The nucleotides numbered 2, 4, 6, 8, 10, 12, 14, 16, 18, 20, 22 and 24 may be modified by a second modification on the second strand. Nucleotides are numbered for the sake of the nucleic acid of the present disclosure from 5' to 3' on the first strand and 3' and 5' on the second strand The nucleotides numbered 2, 4, 6, 8, 10, 12, 14, 16, 18, 20, 22 and 24 may be modified by a modification on the first strand. The nucleotides numbered 1, 3, 5, 7, 9, 11, 13, 15, 17, 19, 21, 23 may be modified by a second modification on the first strand. The nucleotides numbered 1, 3, 5, 7, 9, 11, 13, 15, 17, 19, 21, 23 may be modified by a modification on the second strand. The nucleotides numbered 2, 4, 6, 8, 10, 12, 14, 16, 18, 20, 22 and 24 may be modified by a second modification on the second strand.

Clearly, if the first and/or the second strand are shorter than 25 nucleotides in length, such as 19 nucleotides in length, there are no nucleotides numbered 20, 21, 22, 23, 24 and 25 to be modified. The skilled person understands the description above to apply to shorter strands, accordingly.

One or more modified nucleotides on the first strand may be paired with modified nucleotides on the second strand having a common modification. One or more modified nucleotides on the first strand may be paired with modified nucleotides on the second strand having a different modification. One or more modified nucleotides on the first strand may be paired with unmodified nucleotides on the second strand. One or more modified nucleotides on the second strand may be paired with unmodified nucleotides on the first strand. In other words, the alternating nucleotides can be aligned on the two strands such as, for example, all the modifications in the alternating regions of the second strand are paired with identical modifications in the first strand or alternatively the modifications can be offset by one nucleotide with the common modifications in the alternating regions of one strand pairing with dissimilar modifications (i.e. a second or further modification) in the other strand. Another option is to have dissimilar modifications in each of the strands.

The modifications on the first strand may be shifted by one nucleotide relative to the modified nucleotides on the second strand, such that common modified nucleotides are not paired with each other.

The modification and/or modifications may each and individually be selected from the group consisting of 3'-terminal deoxy-thymine, 2'-O-methyl, a 2'-deoxy-modification, a 2'-amino-modification, a 2'-alkyl-modification, a morpholino modification, a phosphoramidate modification, 5'-phosphorothioate group modification, a 5' phosphate or 5' phosphate mimic modification and a cholesteryl derivative or a dodecanoic acid bisdecylamide group modification and/or the modified nucleotide may be any one of a locked nucleotide, an abasic nucleotide or a non-natural base comprising nucleotide.

At least one modification may be 2'-O-methyl and/or at least one modification may be 2'-F.

Further modifications as described herein may be present on the first and/or second strand.

Throughout the description of the invention and disclosure, "same or common modification" means the same modification to any nucleotide, be that A, G, C or U modified with a group such as such as a methyl group or a fluoro group. Is it not taken to mean the same addition on the same nucleotide. For example, 2'F-dU, 2'F-dA, 2'F-dC, 2'F-dG are all considered to be the same or common modification, as are 2'-OMe-rU, 2'-OMe-rA; 2'-OMe-rC; 2'-OMe-rG. A 2'F modification is a different modification to a 2'OMe modification.

Some representative modified nucleic acid sequences of the present disclosure are shown in the examples. These examples are meant to be representative and not limiting.

Preferably, the nucleic acid may comprise a modification and the second or further modification which are each and individually selected from the group comprising 2'-O-methyl modification and 2'-F modification. The nucleic acid may comprise a modification that is 2'-O-methyl (2'OMe) that may be a first modification, and a second modification that is 2'-F. The nucleic acid disclosed herein may also include a phosphorothioate modification and/or a deoxy modification which may be present in or between the terminal 1, 2 or 3 nucleotides of each or any end of each or both strands.

The disclosure provides as a further aspect, a nucleic acid for inhibiting expression of TMPRSS6, comprising a nucleotide sequence of SEQ ID 317, 319, 321, 323, 325, 327, 329, 331, 333, 335, 337, 339, 341, 343, 345, 353, 356, 358, 360, 362, 364, 366, 368, 370, 372, 374, 376, 378, 380, 382, 384, 386, 388, 390, 392, 394, 396, 398, 400, 402, 404, 406, 407, 410, 412, 414, 416, 418, 420, 422, 424, 426, 428, 430, 432, 434, 436, 438, 440, or 442, or SEQ ID 1, 3, 5, 7, 9, 11, 13, 15, 17, 19, 21, 23, 25, 27, 29, 67, 69, 71, 73, 74, 76, 77, 78, 79, 80, 81, 82, 83, 85, 87, 88, 90, 91, 92, 93, 94, 95, 96, 97, 98, 99, 111, 113, 115, 117, 119, 121, 123, 125, 127, 129, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 225, 227, 229, 231, 233, 235, 237, 239, 241, 243, 245, 247, 249, 251, 253, 255, 257, 259, 261, 263, 265, 267, 269, 270, 271, 273, 275, 277, 279, 281, 283, 285, 287, 289, 291, 293, 295, 297, 299, 301, 309, 311, 312, 313, 314, or 315, such as SEQ ID NO:1, 3, 5, 7, 9, 11, 13, 15, 17, 19, 21, 23, 25, 27, 29, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, or 215, wherein the nucleotides of first strand are modified by a first modification on the odd numbered nucleotides, and modified by a second modification on the even numbered nucleotides, and nucleotides of the second strand are modified by a third modification on the even numbered nucleotides and modified by a fourth modification the odd numbered nucleotides, wherein at least the first modification is different to the second modification and the third modification is different to the fourth modification. The third and first modifications may be the same or different, the second and fourth modifications may be the same or different. The first and second modifications may be different to each other and the third and fourth modifications may be different to each other.

In a further aspect is provided a nucleic acid for inhibiting expression of TMPRSS6, wherein the second strand comprises a nucleotide sequence of SEQ ID NO 318, 320, 322, 324, 326, 328, 330, 332, 334, 336, 338, 340, 342, 344, 346, 357, 359, 361, 363, 365, 367, 369, 371, 373, 375, 377, 379, 381, 383, 385, 387, 389, 391, 393, 395, 397, 399, 401, 403, 405, 407, 409, 411, 413, 415, 417, 419, 421, 423, 425, 427, 429, 431, 433, 435,437, 439, 441, or 443, or a nucleotide sequence of SEQ ID no 2, 4, 6, 8, 10, 12, 14, 16, 18, 20, 22, 24, 26, 28, 30, 68, 70, 72, 75, 84, 86, 89, 100, 101, 102, 103, 104, 105, 106, 112, 114, 116, 118, 120, 122, 124, 126, 128, 130, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 226, 228, 230, 232, 234, 236, 238, 240, 242, 246, 248, 250, 252, 254, 256, 258, 260, 262, 264, 266, 268, 270, 272, 274, 276, 278, 280, 282, 284, 286, 288, 290, 292, 294, 296, 298, 300, 302, 310, 312, 314, or 316, such as a nucleotide sequence of SEQ ID NO2, 4, 6, 8, 10, 12, 14, 16, 18, 20, 22, 24, 26, 28, 30, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, or 216 wherein the nucleotides of first strand are modified by a first modification on the odd numbered nucleotides, and modified by a second modification on the even numbered nucleotides, and nucleotides of the second strand are modified by a third modification on the even numbered nucleotides and modified by a fourth modification the odd numbered nucleotides, wherein at least the first modification is different to the second modification and the third modification is different to the fourth modification. The third and first modifications may be the same or different, the second and fourth modifications may be the same or different. The first and second modifications may be different to each other and the third and fourth modifications may be different to each other. Suitably the nucleotide sequence of the second strand is complementary to the first strand. The nucleotides of first strand may be modified by first modification on the odd numbered nucleotides, and modified with a second modification on the even numbered nucleotides, and the second strand may be modified on the odd numbered nucleotides with the second modification and modified with the first modification the even numbered nucleotides. The first modification may be 2'OMe and the second modification may be 2'F. The first strand may comprise the nucleotide sequence of SEQ ID NO: 17 and/or the second strand may comprise the nucleotide sequence of SEQ ID NO: 18. The modifications may be those as set out in table 1.

In one aspect all the even-numbered nucleotides of the first strand of the nucleic acid are modified by a first modification, all the odd-numbered nucleotides of the first strand are modified by a second modification, all the nucleotides of the second strand in positions corresponding to nucleotides 11-13 of the first strand are modified by a fourth modification, all the nucleotides of the second strand other than the nucleotides corresponding to nucleotides 11-13 of the first strand are modified by a third modification, wherein the first and fourth modification are preferably 2'-F and the second and third modification are preferably 2'-OMe.

The nucleic acid disclosed herein may be conjugated to a ligand.

Some ligands can have endosomolytic properties. The endosomolytic ligands promote the lysis of the endosome and/or transport of the composition of the invention, or its components, from the endosome to the cytoplasm of the cell. The endosomolytic ligand may be a polyanionic peptide or peptidomimetic which shows pH-dependent membrane activity and fusogenicity. The endosomolytic component may contain a chemical group which undergoes a change in charge or protonation in response to a change in pH. The endosomolytic component may be linear or branched.

Ligands can include therapeutic modifiers, e.g., for enhancing uptake; diagnostic compounds or reporter groups e.g., for monitoring distribution; cross-linking agents; and nuclease-resistance conferring moieties. General examples include lipids, steroids, vitamins, sugars, proteins, peptides, polyamines, and peptide mimics. Ligands can include a naturally occurring substance, such as a protein, carbohydrate, or lipid. The ligand may be a recombinant or synthetic molecule.

Ligands can also include targeting groups, e.g. a cell or tissue targeting agent. The targeting ligand may be a lectin, glycoprotein, lipid or protein.

Other examples of ligands include dyes, intercalating agents, cross-linkers, porphyrins, polycyclic aromatic hydrocarbons, artificial endonucleases or a chelator, lipophilic molecules, alkylating agents, phosphate, amino, mercapto, PEG, MPEG, alkyl, substituted alkyl, radiolabelled markers, enzymes, haptens, transport/absorption facilitators, synthetic ribonucleases, or imidazole clusters.

Ligands can be proteins, e.g. glycoproteins or peptides. Ligands may also be hormones or hormone receptors. They may also include non-peptidic species, such as lipids, lectins, carbohydrates, vitamins, or cofactors.

The ligand may be a substance such as a drug which can increase the uptake of the nucleic acid into a cell, for example, by disrupting the cell's cytoskeleton.

The ligand may increase uptake of the nucleic acid into the cell by activating an inflammatory response. Such ligands include tumour necrosis factor alpha (TNF-alpha), interleukin-1 beta, or gamma interferon.

The ligand may be a lipid or lipid-based molecule. The lipid or lipid-based molecule preferably binds a serum protein. Preferably, the lipid-based ligand binds human serum albumin (HSA). A lipid or lipid-based molecule can increase resistance to degradation of the conjugate, increase targeting or transport into target cell, and/or can adjust binding to a serum protein. A lipid-based ligand can be used to modulate binding of the conjugate to a target tissue.

The ligand may be a steroid. Preferably, the ligand is cholesterol or a cholesterol derivative.

The ligand may be a moiety e.g. a vitamin, which is taken up by a target cell. Exemplary vitamins include vitamin A, E, K, and the B vitamins. Vitamins may be taken up by a proliferating cell, which may be useful for delivering the nucleic acid to cells such as malignant or non-malignant tumour cells.

The ligand may be a cell-permeation agent, such as a helical cell-permeation agent. Preferably such an agent is amphipathic.

The ligand may be a peptide or peptidomimetic. A peptidomimetic is a molecule capable of folding into a defined three-dimensional structure similar to a natural peptide. The peptide or peptidomimetic ligand may include naturally occurring or modified peptides, or both. A peptide or peptidomimetic can be a cell permeation peptide, cationic peptide, amphipathic peptide, or hydrophobic peptide. The peptide moiety can be a dendrimer peptide, constrained peptide, or crosslinked peptide. The peptide moiety can include a hydrophobic membrane translocation sequence. The peptide moiety can be a peptide capable of carrying large polar molecules such as peptides, oligonucleotides, and proteins across cell membranes, e.g. sequences from the HIV Tat protein (GRKKRRQRRRPPQ; SEQ ID NO: 450) and the *Drosophila* Antennapedia protein (RQIKIWFQNRRMKWKK; SEQ ID NO: 451). Preferably the peptide or peptidomimetic is a cell targeting peptide, e.g. arginine-glycine-aspartic acid (RGD)-peptide.

The ligand may be a cell permeation peptide that is capable of permeating, for example, a microbial cell or a mammalian cell.

The ligand may be a pharmacokinetic modulator. The pharmacokinetic modulator may be lipophiles, bile acids, steroids, phospholipid analogues, peptides, protein binding agents, PEG, vitamins, etc.

When two or more ligands are present, the ligands can all have the same properties, all have different properties, or some ligands have the same properties while others have different properties. For example, a ligand can have targeting properties, have endosomolytic activity or have PK modulating properties. In a preferred embodiment, all the ligands have different properties.

Ligands can be coupled to the nucleic acid at the 3'-end, 5'-end, and/or at an internal position. Preferably the ligand is coupled to the nucleic acid via an intervening tether or linker.

In some embodiments the nucleic acid is a double-stranded nucleic acid. In a double-stranded nucleic acid the ligand may be attached to one or both strands. In some embodiments, a double-stranded nucleic acid contains a ligand conjugated to the sense strand. In other embodiments, a double-stranded nucleic acid contains a ligand conjugated to the antisense strand.

Ligands can be conjugated to nucleobases, sugar moieties, or internucleosidic linkages of nucleic acid molecules. Conjugation to purine nucleobases or derivatives thereof can occur at any position including endocyclic and exocyclic atoms. Conjugation to pyrimidine nucleotides or derivatives thereof can also occur at any position. Conjugation to sugar moieties of nucleosides can occur at any carbon atom. Conjugation to internucleosidic linkages may occur at the phosphorus atom of a phosphorus-containing linkage or at an oxygen, nitrogen, or sulphur atom bonded to the phosphorus atom. For amine- or amide-containing internucleosidic linkages, conjugation may occur at the nitrogen atom of the amine or amide or to an adjacent carbon atom.

The ligand is typically a carbohydrate, e.g. a monosaccharide, disaccharide, trisaccharide, tetrasaccharide or polysaccharide. The ligand may be conjugated to the nucleic acid by a linker. The linker may be a monovalent, bivalent, or trivalent branched linker.

Efficient delivery of oligonucleotides, in particular double stranded nucleic acids disclosed herein, to cells in vivo is important and requires specific targeting and substantial protection from the extracellular environment, particularly serum proteins. One method of achieving specific targeting is to conjugate a ligand to the nucleic acid. The ligand helps in targeting the nucleic acid to the required target site. There is a need to conjugate appropriate ligands for the desired receptor molecules in order for the conjugated molecules to be taken up by the target cells by mechanisms such as different receptor-mediated endocytosis pathways or functionally analogous processes. The targeting moiety or ligand can be any moiety or ligand that is capable of targeting a specific receptor.

For example, the Asialoglycoprotein receptor (ASGP-R) is a high capacity receptor, which is highly abundant on hepatocytes. One of the first disclosures of triantennary cluster glycosides was in U.S. Pat. No. 5,885,968. Conjugates having three GalNAc ligands and comprising phosphate groups are known and are described in Dubber et al. (2003, Bioconjug. Chem. 2003 January-February; 14(1): 239-46.). The ASGP-R shows a 50-fold higher affinity for N-Acetyl-D-Galactosylamine (GalNAc) than D-Gal.

Hepatocytes expressing the lectin (asialoglycoprotein receptor; ASGPR), which recognizes specifically terminal β-galactosyl subunits of glycosylated proteins or other oligosaccharides (Weigel, P. H. et. al., Biochim. Biophys. Acta. 2002 Sep. 19; 1572(2-3):341-63), can be used for targeting a drug to the liver by covalent coupling of galactose or galactoseamine to the drug substance (Ishibashi, S.; et. al., J Biol. Chem. 1994 Nov. 11; 269(45):27803-6)). Furthermore the binding affinity can be significantly increased by the multi-valency effect, which is achieved by the repetition of the targeting unit (E. A. L. Biessen et. al., 1995).

The ASGPR is a mediator for an active endosomal transport of terminal β-galactosyl containing glycoproteins, thus ASGPR is highly suitable for targeted delivery of drug candidates like nucleic acid, which have to be delivered into a cell (Akinc et al.).

The ligand may be attached to the nucleic acid disclosed herein via a linker, which may be a bivalent or trivalent or tetramer branched linker.

The saccharide, which can also be referred to as the ligand, may be selected to have an affinity for at least one type of receptor on a target cell. In particular, the receptor is on the surface of a mammalian liver cell, for example, the hepatic asialoglycoprotein receptor (ASGP-R).

The saccharide may be selected from N-acetyl galactosamine, mannose, galactose, glucose, glucosamine and fucose. The saccharide may be N-acetyl galactosamine (GalNAc).

A ligand for use in the present disclosure may therefore comprise (i) one or more N-acetyl galactosamine (GalNAc) moieties and derivatives thereof, and (ii) a linker, wherein the linker conjugates the GalNAc moieties to a sequence as defined in any preceding aspects. The linker may be a bivalent or trivalent or tetravalent branched structure. The nucleotides may be modified as defined herein.

"GalNAc" refers to 2-(Acetylamino)-2-deoxy-D-galactopyranose, commonly referred to in the literature as N-acetyl galactosamine. Reference to "GalNAc" or "N-acetyl galactosamine" includes both the β-form: 2-(Acetylamino)-2-deoxy-β-D-galactopyranose and the α-form: 2-(Acetylamino)-2-deoxy-α-D-galactopyranose. Both the β-form: 2-(Acetylamino)-2-deoxy-β-D-galactopyranose and α-form: 2-(Acetylamino)-2-deoxy-α-D-galactopyranose may be used interchangeably. Preferably, the compounds disclosed herein comprise the β-form, 2-(Acetylamino)-2-deoxy-β-D-galactopyranose.

The ligand may comprise GalNAc.

The ligand may comprise a compound of formula I:

$$[S-X^1-P-X^2]_3-A-X^3- \qquad (I)$$

wherein:
S represents a saccharide, wherein the saccharide is N-acetyl galactosamine;

$X^1$ represents $C_3$-$C_6$ alkylene or $(-CH_2-CH_2-O)_m(-CH_2)_2-$ wherein m is 1, 2, or 3;

P is a phosphate or modified phosphate (preferably a thiophosphate);

$X^2$ is alkylene or an alkylene ether of the formula $(-CH_2)_n-O-CH_2-$ where n=1-6;

A is a branching unit;

$X^3$ represents a bridging unit;

wherein a nucleic acid disclosed herein is conjugated to $X^3$ via a phosphate or modified phosphate (preferably a thiophosphate).

In formula I, branching unit "A" branches into three in order to accommodate the three saccharide moieties. The branching unit is covalently attached to the remaining tethered portions of the ligand and the nucleic acid. The branching unit may comprise a branched aliphatic group comprising groups selected from alkyl, amide, disulphide, polyethylene glycol, ether, thioether and hydroxyamino groups. The branching unit may comprise groups selected from alkyl and ether groups.

The branching unit A may have a structure selected from:

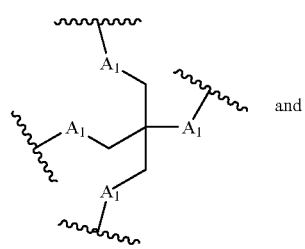 and

-continued

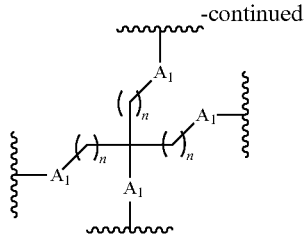

wherein each $A_1$ independently represents O, S, C=O or NH; and
each n independently represents an integer from 1 to 20.
The branching unit may have a structure selected from:

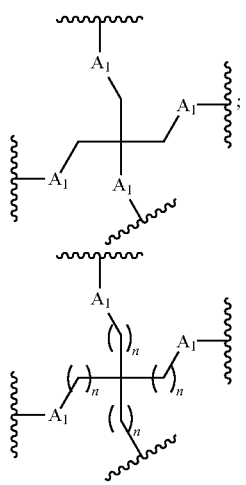

wherein each $A_1$ independently represents O, S, C=O or NH; and
each n independently represents an integer from 1 to 20.
The branching unit may have a structure selected from:

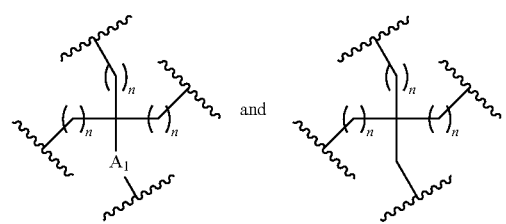

wherein $A_1$ is O, S, C=O or NH; and
each n independently represents an integer from 1 to 20.
The branching unit may have the structure:

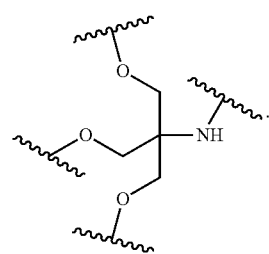 [SMILES: *NC(CO*)(CO*)CO*]

The branching unit may have the structure:

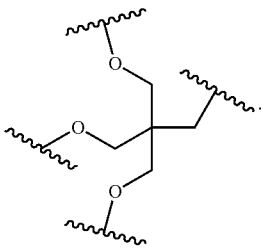 [SMILES: *CC(CO*)(CO*)CO*]

The branching unit may have the structure:

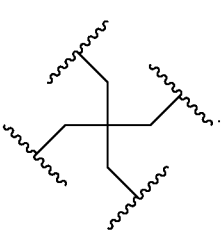 [SMILES: *CC(C*)(C*)C*]

Optionally, the branching unit consists of only a carbon atom.

The "$X^3$" portion of the compounds of formula I is a bridging unit. The bridging unit is linear and is covalently bound to the branching unit and the nucleic acid.

$X^3$ may be selected from —$C_1$-$C_{20}$ alkylene-, —$C_2$-$C_{20}$ alkenylene-, an alkylene ether of formula-($C_1$-$C_{20}$ alkylene)-O—($C_1$-$C_{20}$ alkylene)-, —C(O)—$C_1$-$C_{20}$ alkylene-, —$C_0$-$C_4$ alkylene(Cy)$C_0$-$C_4$ alkylene- wherein Cy represents a substituted or unsubstituted 5 or 6 membered cycloalkylene, arylene, heterocyclylene or heteroarylene ring, —$C_1$-$C_4$ alkylene-NHC(O)—$C_1$-$C_4$ alkylene-, —$C_1$-$C_4$ alkylene-C(O)NH—$C_1$-$C_4$ alkylene-, —$C_1$-$C_4$ alkylene-SC(O)—$C_1$-$C_4$ alkylene-, —$C_1$-$C_4$ alkylene-C(O)S—$C_1$-$C_4$ alkylene-, —$C_1$-$C_4$ alkylene-OC(O)—$C_1$-$C_4$ alkylene-, —$C_1$-$C_4$ alkylene-C(O)O—$C_1$-$C_4$ alkylene-, and —$C_1$-$C_6$ alkylene-S—S—$C_1$-$C_6$ alkylene-.

$X^3$ may be an alkylene ether of formula-($C_1$-$C_{20}$ alkylene)-O—($C_1$-$C_{20}$ alkylene)-. $X^3$ may be an alkylene ether of formula-($C_1$-$C_{20}$ alkylene)-O—($C_4$-$C_{20}$ alkylene)-, wherein said ($C_4$-$C_{20}$ alkylene) is linked to Z. $X^3$ may be selected from the group consisting of —$CH_2$—O—$C_3H_6$—, —$CH_2$—O—$C_4H_8$—, —$CH_2$—O—$C_6H_{12}$— and —$CH_2$—O—$C_8H_{16}$—, especially —$CH_2$—O—$C_4H_8$—, —$CH_2$—O—$C_6H_{12}$— and —$CH_2$—O—$C_8H_{16}$—, wherein in each case the —$CH_2$— group is linked to A.

The ligand may comprise a compound of formula (II):

$$[S-X^1-P-X^2]_3-A-X^3- \quad (II)$$

wherein:
S represents a saccharide;
$X^1$ represents $C_3$-$C_6$ alkylene or (—$CH_2$—$CH_2$—O)$_m$(—$CH_2$)$_2$— wherein m is 1, 2, or 3;
P is a phosphate or modified phosphate (preferably a thiophosphate);
$X^2$ is $C_1$-$C_8$ alkylene;

A is a branching unit selected from:

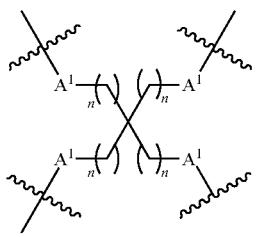

A¹ = O, NH
n = 1 to 4

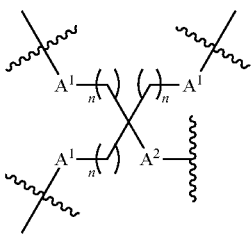

A¹ = O, NH
A² = NH, CH₂, O
n = 1 to 4

$X^3$ is a bridging unit;
wherein a nucleic acid disclosed herein is conjugated to $X^3$ via a phosphate or modified phosphate (preferably a thiophosphate).
Branching unit A may have the structure:

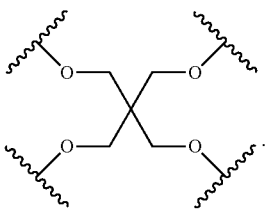 [SMILES: *OCC(CO*)(CO*)CO*]

Branching unit A may have the structure:

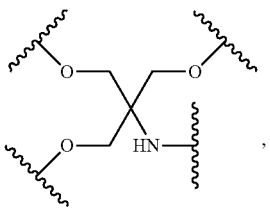

wherein $X^3$ is attached to the nitrogen atom.
$X^3$ may be $C_1$-$C_{20}$ alkylene. Preferably, $X^3$ is selected from the group consisting of —$C_3H_6$—, —$C_4H_8$—, —$C_6H_{12}$— and —$C_8H_{16}$—, especially —$C_8H_{16}$—, —$C_6H_{12}$— and —$C_8H_{16}$—.
The ligand may comprise a compound of formula (III):

[S-X¹-P-X²]₃-A-X³-     (III)

wherein:
 S represents a saccharide;
 $X^1$ represents $C_3$-$C_6$ alkylene or (—$CH_2$—$CH_2$—O)$_m$ (—$CH_2$)$_2$— wherein m is 1, 2, or 3;
 P is a phosphate or modified phosphate (preferably a thiophosphate);
 $X^2$ is an alkylene ether of formula -$C_3H_6$—O—$CH_2$—;
 A is a branching unit;
 $X^3$ is an alkylene ether of formula selected from the group consisting of —$CH_2$—O—$CH_2$—, —$CH_2$—O—$C_2H_4$—, —$CH_2$—O—$C_3H_6$—, —$CH_2$—O—$C_4H_8$—, —$CH_2$—O—$C_5H_{10}$—, —$CH_2$—O—$C_6H_{12}$—, —$CH_2$—O—$C_7H_{14}$—, and —$CH_2$—O—$C_8H_{16}$—, wherein in each case the —$CH_2$— group is linked to A,
 Z is the nucleic acid;
 and wherein the linkage between $X^3$ and Z is a phosphate or thiophosphate The branching unit may comprise carbon. Preferably, the branching unit is carbon.

$X^3$ may be selected from the group consisting of —$CH_2$—O—$C_4H_8$—, —$CH_2$—O—$C_5H_{10}$—, —$CH_2$—O—$C_6H_{12}$—, —$CH_2$—O—$C_7H_{14}$—, and —$CH_2$—O—$C_8H_{16}$—. Preferably, $X^3$ is selected from the group consisting of —$CH_2$—O—$C_4H_8$—, —$CH_2$—O—$C_6H_{12}$— and —$CH_2$—O—$C_8H_{16}$—.

For any of the above aspects, when P represents a modified phosphate group, P can be represented by:

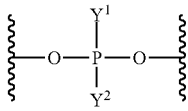

wherein $Y^1$ and $Y^2$ each independently represent =O, =S, —O, —OH, —SH, —BH₃, —OCH₂CO₂, —OCH₂CO₂R$^x$, —OCH₂C(S)OR$^x$, and —OR$^x$, wherein R$^x$ represents $C_1$-$C_6$ alkyl and wherein indicates attachment to the remainder of the compound.

By modified phosphate it is meant a phosphate group wherein one or more of oxygens is replaced. Examples of modified phosphate groups include phosphorothioate, phosphoroselenates, borano phosphates, borano phosphate esters, hydrogen phosphonates, phosphoroamidates, alkyl or aryl phosphonates and phosphotriesters. Phosphorodithioates have both non-linking oxygens replaced by sulphur. One, each or both non-linking oxygens in the phosphate group can be independently any one of S, Se, B, C, H, N, or OR (R is alkyl or aryl).

The phosphate linker can also be modified by replacement of a linking oxygen with nitrogen (bridged phosphoroamidates), sulfur (bridged phosphorothioates) and carbon (bridged methylenephosphonates). The replacement can occur at a terminal oxygen. Replacement of the non-linking oxygens with nitrogen is possible.

For example, $Y^1$ may represent —OH and $Y^2$ may represent =O or =S; or
 $Y^1$ may represent —O and $Y^2$ may represent =O or =S;
 $Y^1$ may represent =O and $Y^2$ may represent —CH₃, —SH, —OR$^x$, or —BH₃
 $Y^1$ may represent =S and $Y^2$ may represent —CH₃, OR$^x$ or —SH.

It will be understood by the skilled person that in certain instances there will be delocalisation between $Y^1$ and $Y^2$.

Preferably, the modified phosphate group is a thiophosphate group. Thiophosphate groups include bithiophosphate (i.e. where $Y^1$ represents =S and $Y^2$ represents —S⁻) and monothiophosphate (i.e. where $Y^1$ represents —O⁻ and $Y^2$ represents =S, or where $Y^1$ represents =O and $Y^2$ represents —S⁻). Preferably, P is a monothiophosphate. The inventors have found that conjugates having thiophosphate groups in replacement of phosphate groups have improved potency and duration of action in vivo.

P may also be an ethylphosphate (i.e. where $Y^1$ represents =O and $Y^2$ represents $OCH_2CH_3$).

The saccharide may be selected to have an affinity for at least one type of receptor on a target cell. In particular, the receptor is on the surface of a mammalian liver cell, for example, the hepatic asialoglycoprotein receptor (ASGP-R).

For any of the above aspects, the saccharide may be selected from N-acetyl with one or more of galactosamine, mannose, galactose, glucose, glucosamine and fructose. Preferably, the saccharide is two molecules of N-acetyl galactosamine (GalNAc). The compounds disclosed herein may have 3 ligands which are each preferably N-acetyl galactosamine.

"GalNAc" refers to 2-(Acetylamino)-2-deoxy-D-galactopyranose, commonly referred to in the literature as N-acetyl galactosamine. Reference to "GalNAc" or "N-acetyl galactosamine" includes both the β-form: 2-(Acetylamino)-2-deoxy-β-D-galactopyranose and the α-form: 2-(Acetylamino)-2-deoxy-α-D-galactopyranose. In certain embodiments, both the β-form: 2-(Acetylamino)-2-deoxy-β-D-galactopyranose and α-form: 2-(Acetylamino)-2-deoxy-α-D-galactopyranose may be used interchangeably. Preferably, the compounds disclosed herein comprise the β-form, 2-(Acetylamino)-2-deoxy-β-D-galactopyranose.

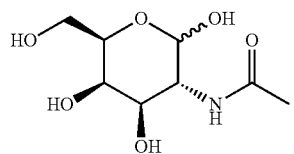

2-(Acetylamino)-2-deoxy-D-galactopyranose

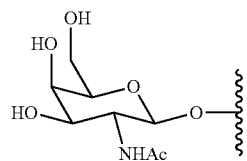 [SMILES: *OC1OC(CO)C(O)C(O)C1NC(C)=O]

2-(Acetylamino)-2-deoxy-β-D-galactopyranose

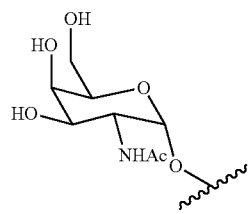 [SMILES: *OC1OC(CO)C(O)C(O)C1NC(C)=O]

2-(Acetylamino)-2-deoxy-α-D-galactopyranose

For any of the above compounds of formula (III), $X^1$ may be $(-CH_2-CH_2-O)(-CH_2)_2-$. $X^1$ may be $(-CH_2-CH_2-O)_2(-CH_2)_2-$. $X^1$ may be $(-CH_2-CH_2-O)_3(-CH_2)_2-$. Preferably, $X^1$ is $(-CH_2-CH_2-O)_2(-CH_2)_2-$. Alternatively, $X^1$ represents $C_3$-$C_6$ alkylene. $X^1$ may be propylene. $X^1$ may be butylene. $X^1$ may be pentylene. $X^1$ may be hexylene. Preferably the alkyl is a linear alkylene. In particular, $X^1$ may be butylene.

For compounds of formula (III), $X^2$ represents an alkylene ether of formula $-C_3H_6-O-CH_2-$ i.e. $C_3$ alkoxy methylene, or $-CH_2CH_2CH_2OCH_2-$.

The disclosure provides a conjugated nucleic acid having one of the following structures:

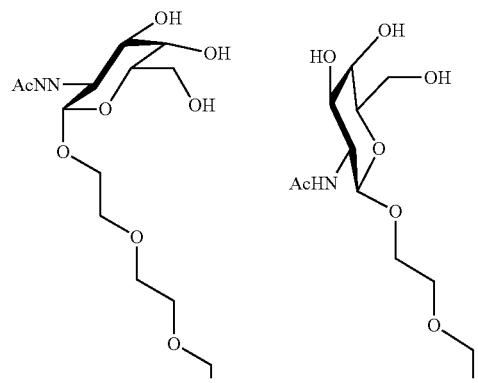

-continued
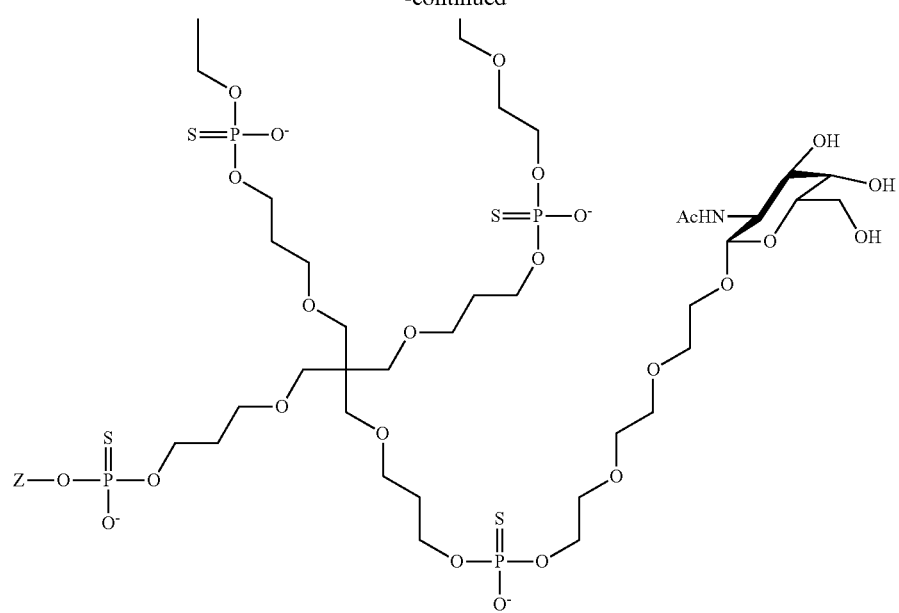
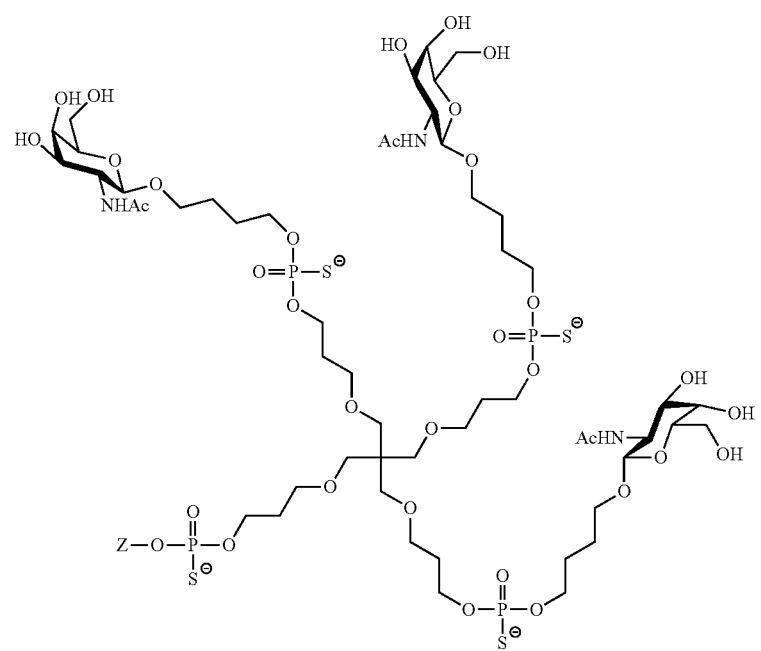

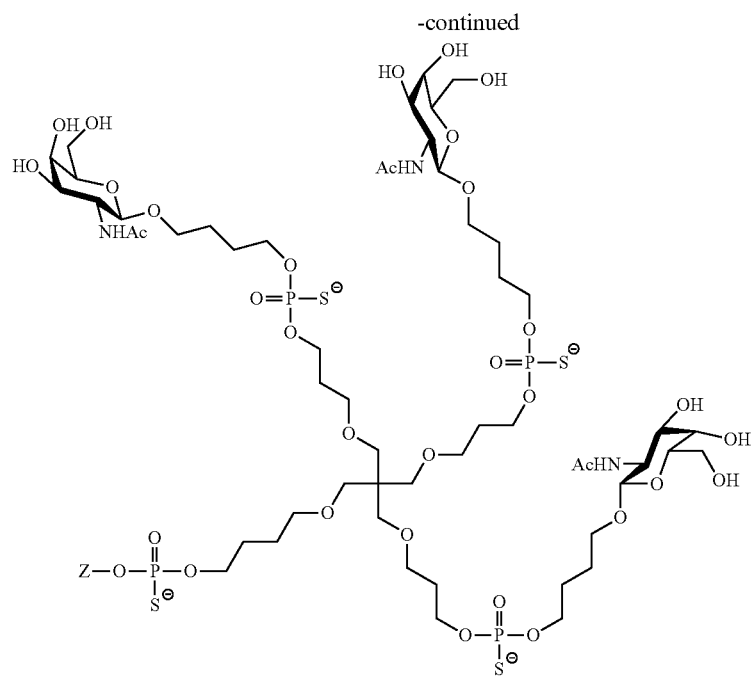
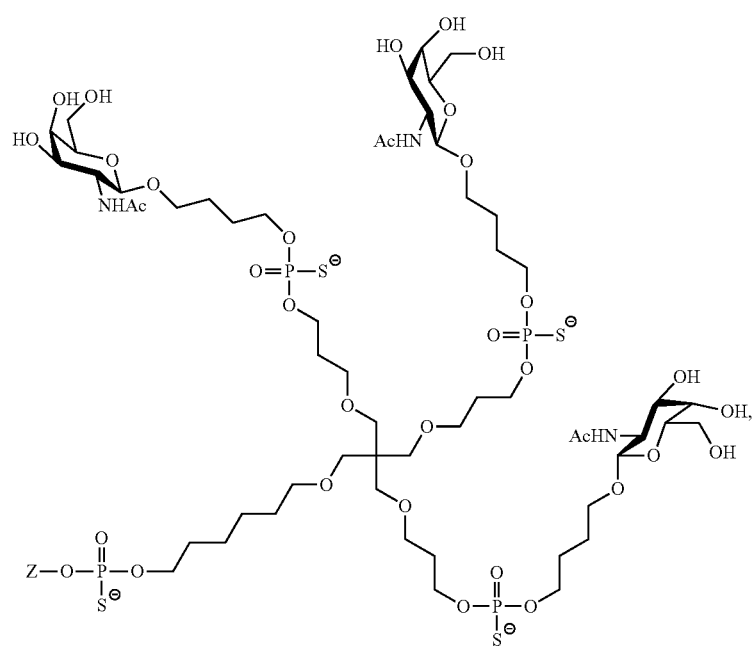

-continued
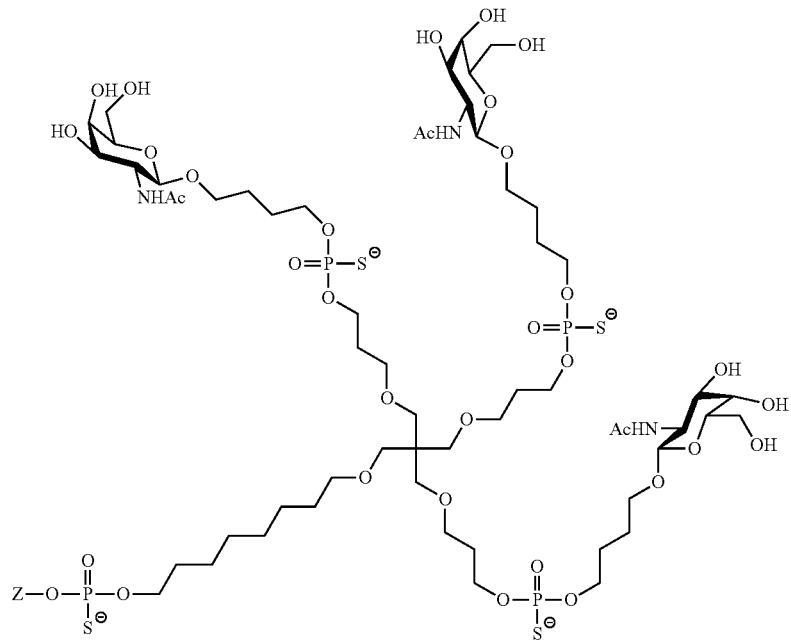
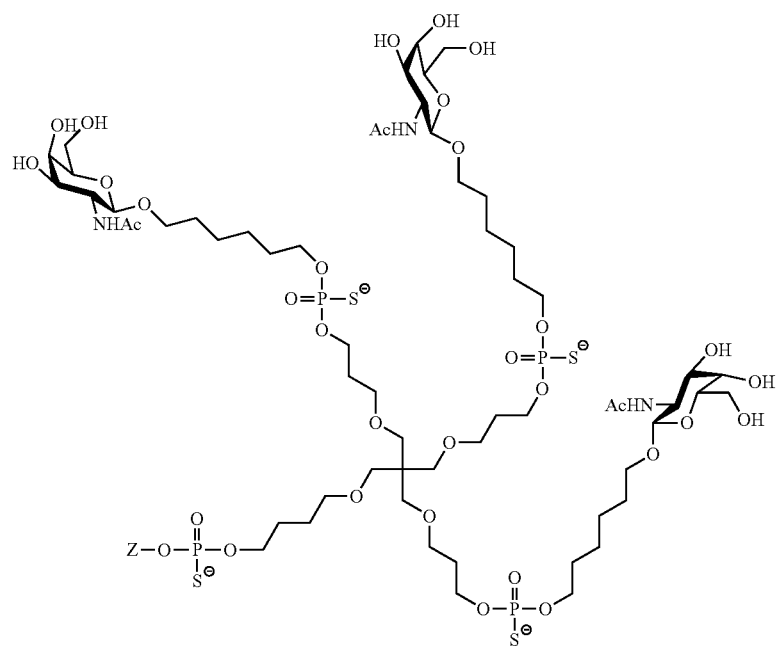

-continued
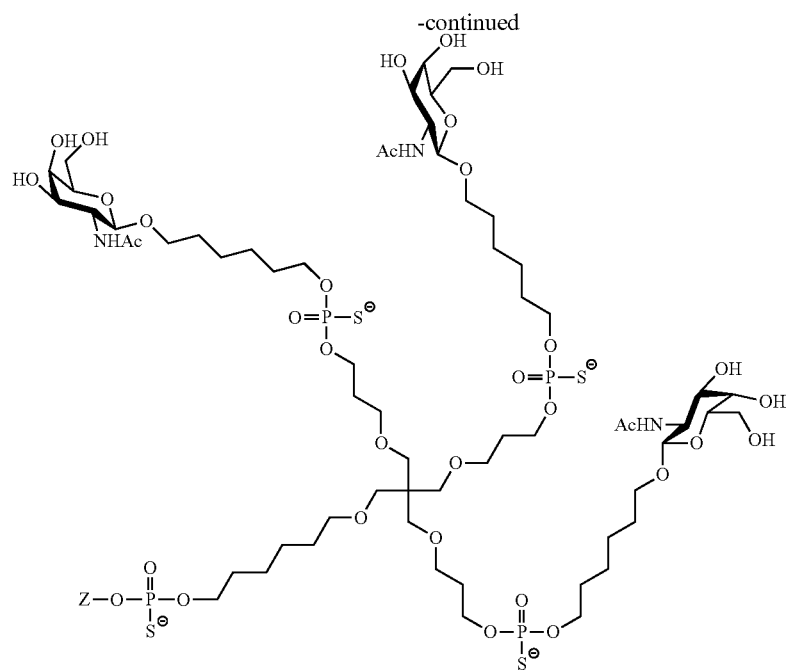
wherein Z is a nucleic acid as defined herein before or after.
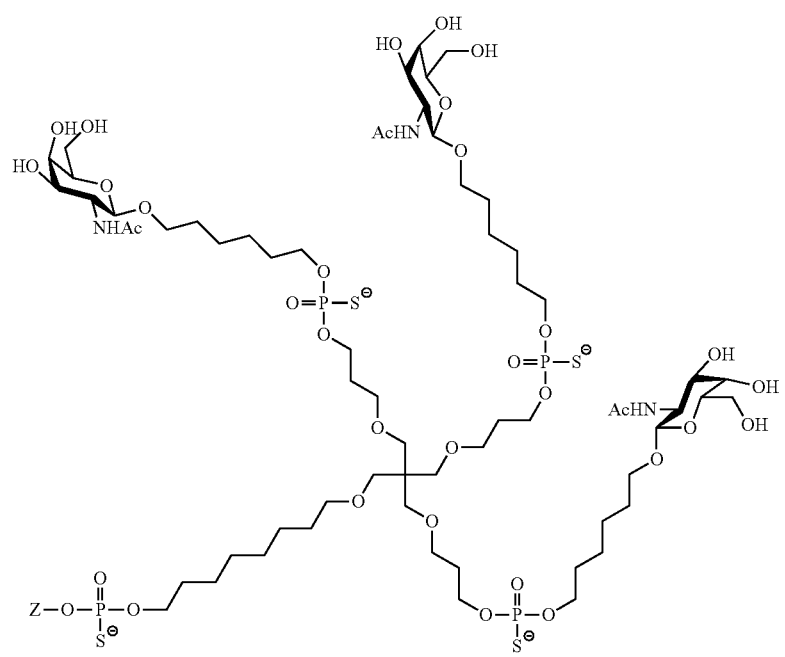
Preferred is a nucleic acid having one of the following structures

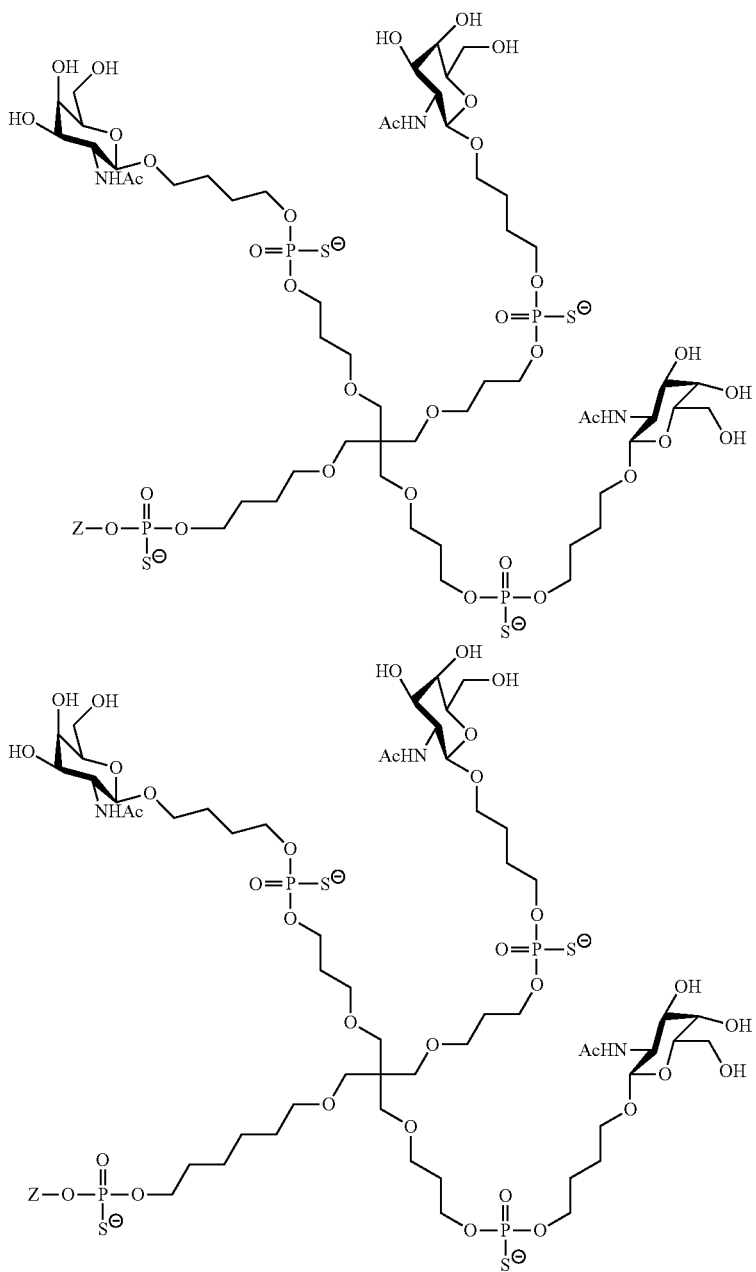

wherein Z is a nucleic acid as defined herein before or after, but a nucleic acid with the first of these two structures is particularly preferred.

The disclosure provides, as another aspect, a nucleic acid for inhibiting expression of TMPRSS6 in a cell, comprising at least one duplex region that comprises at least a portion of a first strand and at least a portion of a second strand that is at least partially complementary to the first strand, wherein said first strand is at least partially complementary to at least a portion of a RNA transcribed from the TMPRSS6 gene, wherein said first strand comprises a nucleotide sequence selected from the following sequences: SEQ ID NOs: 317, 319, 321, 323, 325, 327, 329, 331, 333, 335, 337, 339, 341, 343, 345, 353, 356, 358, 360, 362, 364, 366, 368, 370, 372, 374, 376, 378, 380, 382, 384, 386, 388, 390, 392, 394, 396, 398, 400, 402, 404, 406, 407, 410, 412, 414, 416, 418, 420, 422, 424, 426, 428, 430, 432, 434, 436, 438, 440, or 442, or selected from SEQ ID Nos 1, 3, 5, 7, 9, 11, 13, 15, 17, 19, 21, 23, 25, 27, 29, 67, 69, 71, 73, 74, 76, 77, 78, 79, 80, 81, 82, 83, 85, 87, 88, 90, 91, 92, 93, 94, 95, 96, 97, 98, 99, 111, 113, 115, 117, 119, 121, 123, 125, 127, 129, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 225, 227, 229, 231, 233, 235, 237, 239, 241, 243, 245, 247, 249, 251, 253, 255, 257, 259, 261, 263, 265, 267, 269, 270, 271, 273, 275, 277, 279, 281, 283, 285, 287, 289, 291, 293, 295, 297, 299, 301, 309, 311, 312, 313, 314, or 315, such as selected from SEQ ID nos 1, 3, 5, 7, 9, 11, 13, 15, 17, 19, 21, 23, 25, 27, 29, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, or 215, wherein the nucleic acid is conjugated indirectly or directly to a ligand via a linker.

The second strand may comprise a nucleotide sequence of SEQ ID NO 318, 320, 322, 324, 326, 328, 330, 332, 334, 336, 338, 340, 342, 344, 346, 357, 359, 361, 363, 365, 367, 369, 371, 373, 375, 377, 379, 381, 383, 385, 387, 389, 391, 393, 395, 397, 399, 401, 403, 405, 407, 409, 411, 413, 415, 417, 419, 421, 423, 425, 427, 429, 431, 433, 435,437, 439, 441, or 443, or selected from SEQ ID NO 2, 4, 6, 8, 10, 12, 14, 16, 18, 20, 22, 24, 26, 28, 30, 68, 70, 72, 75, 84, 86, 89, 100, 101, 102, 103, 104, 105, 106, 112, 114, 116, 118, 120, 122, 124, 126, 128, 130, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 226, 228, 230, 232, 234, 236, 238, 240, 242, 246, 248, 250, 252, 254, 256, 258, 260, 262, 264, 266, 268, 270, 272, 274, 276, 278, 280, 282, 284, 286, 288, 290, 292, 294, 296, 298, 300, 302, 310, 312, 314, or 316, such as selected from SEQ ID NO 2, 4, 6, 8, 10, 12, 14, 16, 18, 20, 22, 24, 26, 28, 30, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, or 216.

The nucleic acid may be conjugated to a ligand as herein described.

The nucleotides of the first and/or second strand may be modified, as herein described.

Preferably, the nucleic acid comprises SEQ ID NO:17 and SEQ ID NO:18 conjugated to a ligand of formula I (as set out above), particularly of the formula shown in FIG. 8a, and wherein the first strand is modified with a 2'OMe modification on the odd numbered nucleotides, and modified with a 2'F on the even numbered nucleotides, and the second strand is modified with a 2'OMe on the even numbered nucleotides and modified with a 2'F on the odd numbered nucleotides.

More preferably, the nucleic acid comprises SEQ ID NO:17 and SEQ ID NO:18, wherein the nucleic acid is conjugated to a ligand of formula I (as set out above), and furthermore wherein the nucleic acid has a modification pattern as shown below which is an extract of Table 1 as herein provided.

| SEQ ID NO: 17 | 5'aaccagaagaagca gguga 3' | 6273646282647284546 |
|---|---|---|
| SEQ ID NO: 18 | 5'ucaccugcuucuuc ugguu 3' | 1727354715351718451 | wherein the specific modifications are depicted by numbers
1=2'F-dU,
2=2'F-dA,
3=2'F-dC,
4=2'F-dG,
5=2'-OMe-rU;
6=2'-OMe-rA;
7=2'-OMe-rC;
8=2'-OMe-rG.

The ligand may comprise GalNAc and FIG. 8a or FIG. 8b or FIG. 8c further illustrate the present invention.

Other preferred nucleic acids are listed above and below.

A cleavable linking group is a linker which is stable outside the cell but is cleaved upon entry into a target cell. Cleavage releases the two parts the linker is holding together.

In a preferred embodiment, the nucleic acid disclosed herein comprises a cleavable linking group that is cleaved at least 10 times or more, preferably at least 100-fold faster in a target cell or under a first reference condition (which can, for example, be selected to mimic or represent intracellular conditions) than in the blood of a subject, or under a second reference condition (which can, for example, be selected to mimic or represent conditions found in the blood or serum).

Cleavable linking groups are susceptible to cleavage agents, e.g. pH, redox potential, or the presence of degradative molecules. Degradative molecules include oxidative or reductive enzymes, reductive agents (such as mercaptans), esterases, endosomes or agents than can create an acidic environment, enzymes that can hydrolyze or degrade an acid cleavable linking group by acting as a general acid, peptidases, and phosphatases.

A cleavable linking group may be a disulphide bond, which is susceptible to pH.

A linker may include a cleavable linking group that is cleavable by a particular enzyme. The type of cleavable linking group incorporated into a linker can depend on the target cell. For example, a linker that includes an ester group is preferred when a liver cell is the target. Linkers that contain peptide bonds can be used when targeting cells rich in peptidases, such as liver cells and synoviocytes.

In general, the suitability of a candidate cleavable linking group can be evaluated by testing the ability of a degradative agent (or condition) to cleave the candidate linking group. It will also be desirable to also test the candidate cleavable linking group for the ability to resist cleavage in the blood or when in contact with other non-target tissue. In preferred embodiments, useful candidate compounds are cleaved at least 2, 4, 10 or 100 times faster in the cell (or under in vitro conditions selected to mimic intracellular conditions) as compared to blood or serum (or under in vitro conditions selected to mimic extracellular conditions).

In one aspect, the cleavable linking group may be a redox cleavable linking group. The redox cleavable linking group may be a disulphide linking group.

In one aspect, the linking group may be a phosphate-based cleavable linking group. Preferred embodiments are —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O—, —S—P(S)(H)—O—, —S—P(O)(H)—S—, —O—P(S)(H)—S—. A preferred embodiment is —O—P(O)(OH)—O—.

In one aspect, the cleavable linking group may be an acid cleavable linking group. Preferably the acid cleavable linking group are cleaved in environments where the pH is 6.5 or lower, or are cleaved by agents such as enzymes that can act as a general acid. Examples of acid cleavable linking groups include but are not limited to hydrazones, esters, and esters of amino acids. Acid cleavable groups can have the general formula —C=NN—; C(O)O, or —OC(O). A preferred embodiment is a linking group where the carbon attached to the oxygen of the ester (the alkoxy group) is an aryl group, substituted alkyl group, or tertiary alkyl group such as dimethyl pentyl or t-butyl.

In one embodiment, the cleavable linking group may be an ester-based cleavable linking group. Examples of ester-based cleavable linking groups include but are not limited to esters of alkylene, alkenylene and alkynylene groups.

In one embodiment, the cleavable linking group may be a peptide-based cleavable linking group. Peptide-based cleavable linking groups are peptide bonds formed between amino acids to yield oligopeptides (e.g., dipeptides, tripeptides etc.) and polypeptides. The peptide based cleavage group is generally limited to the peptide bond (i.e., the amide bond) formed between amino acids yielding peptides and proteins and does not include the entire amide functional group. Peptide-based cleavable linking groups have the general formula -NHCHR$^A$C(O)NHCHR$^B$C(O)—, where RA and RB are the R groups of the two adjacent amino acids.

The nucleic acid as described herein may be formulated with a lipid in the form of a liposome. Such a formulation may be described in the art as a lipoplex. The formulation with a lipid/liposome may be used to assist with delivery of the nucleic acid disclosed herein to the target cells. The lipid delivery system herein described may be used as an alternative to a conjugated ligand. The modifications herein described may be present when using the nucleic acid disclosed herein with a lipid delivery system or with a ligand conjugate delivery system.

Such a lipoplex may comprise a lipid formulation comprising:
i) a cationic lipid, or a pharmaceutically acceptable salt thereof;
ii) a steroid;
iii) a phosphatidylethanolamine phospholipid;
iv) a PEGylated lipid.

The cationic lipid may be an amino cationic lipid.
The cationic lipid may have the formula (IV):

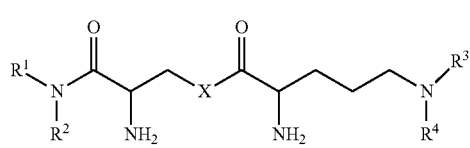

or a pharmaceutically acceptable salt thereof, wherein:

X represents O, S or NH;

$R^1$ and $R^2$ each independently represents a $C_4$-$C_{22}$ linear or branched alkyl chain or a $C_4$-$C_{22}$ linear or branched alkenyl chain with one or more double bonds, wherein the alkyl or alkenyl chain optionally contains an intervening ester, amide or disulfide;

when X represents S or NH, $R^3$ and $R^4$ each independently represent hydrogen, methyl, ethyl, a mono- or polyamine moiety, or $R^3$ and $R^4$ together form a heterocyclyl ring;

when X represents O, $R^3$ and $R^4$ each independently represent hydrogen, methyl, ethyl, a mono- or polyamine moiety, or $R^3$ and $R^4$ together form a heterocyclyl ring, or $R^3$ represents hydrogen and $R^4$ represents C(NH)(NH$_2$).

The cationic lipid may have the formula (V):

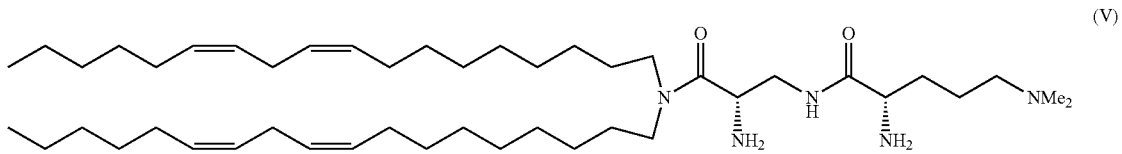 [SMILES: CCCCC/C=C\C/C=C\CCCCCCCCN(CCCCCCCC/C=C\C/C=C\CCCCC)C(=O)[C@@H](N)CNC(=O)[C@@H](N)CCCN(C)C]

or a pharmaceutically acceptable salt thereof.
The cationic lipid may have the formula (VI):

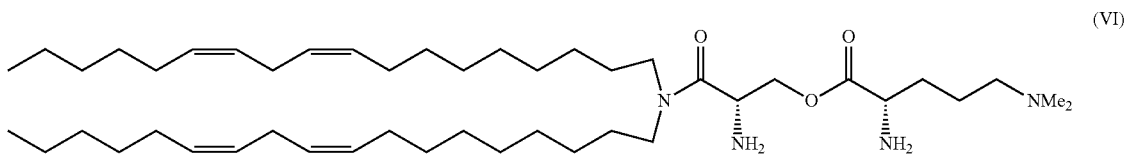 [SMILES: CCCCC/C=C\C/C=C\CCCCCCCCN(CCCCCCCC/C=C\C/C=C\CCCCC)C(=O)[C@@H](N)COC(=O)[C@@H](N)CCCN(C)C]

or a pharmaceutically acceptable salt thereof.

The content of the cationic lipid component may be from about 55 mol % to about 65 mol % of the overall lipid content of the formulation. In particular, the cationic lipid component is about 59 mol % of the overall lipid content of the formulation.

The formulations further comprise a steroid. The steroid may be cholesterol. The content of the steroid may be from about 26 mol % to about 35 mol % of the overall lipid content of the lipid formulation. More particularly, the content of steroid may be about 30 mol % of the overall lipid content of the lipid formulation.

The phosphatidylethanolamine phospholipid may be selected from group consisting of 1,2-diphytanoyl-sn-glycero-3-phosphoethanolamine (DPhyPE), 1,2-dioleoyl-sn-glycero-3-phosphoethanolamine (DOPE), 1,2-distearoyl-sn-glycero-3-phosphoethanolamine (DSPE), 1,2-Dilauroyl-sn-glycero-3-phosphoethanolamine (DLPE), 1,2-Dimyristoyl-sn-glycero-3-phosphoethanolamine (DMPE), 1,2-Dipalmitoyl-sn-glycero-3-phosphoethanolamine (DPPE), 1,2-Dilinoleoyl-sn-glycero-3-phosphoethanolamine (DLoPE), 1-Palmitoyl-2-oleoyl-sn-glycero-3-phosphoethanolamine (POPE), 1,2-Dierucoyl-sn-glycero-3-phosphoethanolamine (DEPE), 1,2-Disqualeoyl-sn-glycero-3-phosphoethanolamine (DSQPE) and 1-Stearoyl-2-linoleoyl-snglycero-3-phosphoethanolamine (SLPE). The content of the phospholipid may be about 10 mol % of the overall lipid content of the formulation.

The PEGylated lipid may be selected from the group consisting of 1,2-dimyristoyl-sn-glycerol, methoxypolyethylene glycol (DMG-PEG) and C16-Ceramide-PEG. The content of the PEGylated lipid may be about 1 to 5 mol % of the overall lipid content of the formulation.

The content of the cationic lipid component in the formulation may be from about 55 mol % to about 65 mol % of the overall lipid content of the lipid formulation, preferably about 59 mol % of the overall lipid content of the lipid formulation.

The formulation may have a molar ratio of the components of i):ii):iii):iv) selected from 55:34:10:1; 56:33:10:1; 57:32:10:1; 58:31:10:1; 59:30:10:1; 60:29:10:1; 61:28:10:1; 62:27:10:1; 63:26:10:1; 64:25:10:1; and 65:24:10:1.

The formulation may comprise a cationic lipid having the structure

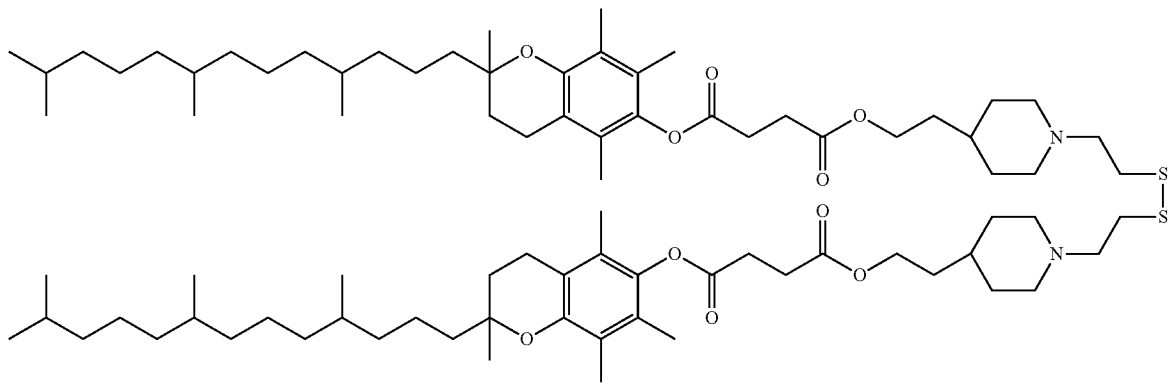 [SMILES: Cc1c(C)c2c(c(C)c1OC(=O)CCC(=O)OCCC1CCN(CCSSCCN3CCC(CCOC(=O)CCC(=O)Oc4c(C)c(C)c5c(c4C)CCC(C)(CCCC(C)CCCC(C)CCCC(C)C)O5)CC3)CC1)CCC(C)(CCCC(C)CCCC(C)CCCC(C)C)O2]

a steroid having the structure

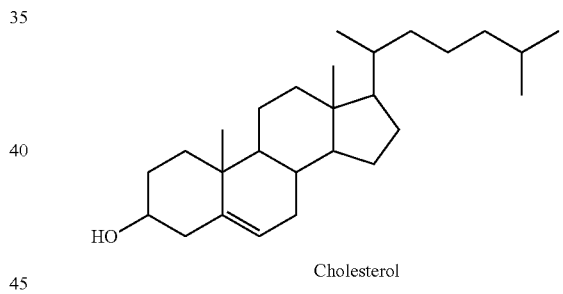

Cholesterol a phosphatidylethanolamine phospholipid having the structure

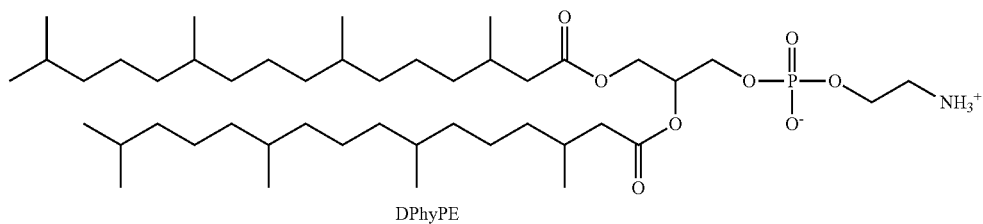 [SMILES: CC(C)CCCC(C)CCCC(C)CCCC(C)CC(=O)OCC(COP(=O)([O-])OCC[NH3+])OC(=O)CC(C)CCCC(C)CCCC(C)CCCC(C)C]

DPhyPE

And a PEGylated lipid having the structure

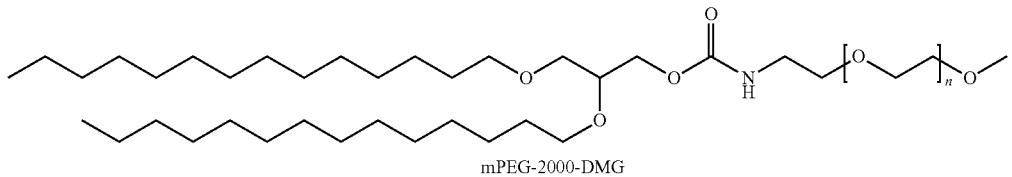

mPEG-2000-DMG

Neutral liposome compositions may be formed from, for example, dimyristoyl phosphatidylcholine (DMPC) or dipalmitoyl phosphatidylcholine (DPPC). Anionic liposome compositions may be formed from dimyristoyl phosphatidylglycerol, while anionic fusogenic liposomes may be formed primarily from dioleoyl phosphatidylethanolamine (DOPE). Another type of liposomal composition may be formed from phosphatidylcholine (PC) such as, for example, soybean PC, and egg PC. Another type is formed from mixtures of phospholipid and/or phosphatidylcholine and/or cholesterol.

A positively charged synthetic cationic lipid, N—[I-(2,3-dioleyloxy)propyl]-N,N,N-trimethylammonium chloride (DOTMA) can be used to form small liposomes that interact spontaneously with nucleic acid to form lipid-nucleic acid complexes which are capable of fusing with the negatively charged lipids of the cell membranes of tissue culture cells. DOTMA analogues can also be used to form liposomes.

Derivatives and analogues of lipids described herein may also be used to form liposomes.

A liposome containing a nucleic acid can be prepared by a variety of methods. In one example, the lipid component of a liposome is dissolved in a detergent so that micelles are formed with the lipid component. For example, the lipid component can be an amphipathic cationic lipid or lipid conjugate. The detergent can have a high critical micelle concentration and may be nonionic. Exemplary detergents include cholate, CHAPS, octylglucoside, deoxycholate, and lauroyl sarcosine. The nucleic acid preparation is then added to the micelles that include the lipid component. The cationic groups on the lipid interact with the nucleic acid and condense around the nucleic acid to form a liposome. After condensation, the detergent is removed, e.g., by dialysis, to yield a liposomal preparation of nucleic acid.

If necessary a carrier compound that assists in condensation can be added during the condensation reaction, e.g., by controlled addition. For example, the carrier compound can be a polymer other than a nucleic acid (e.g., spermine or spermidine). pH can also be adjusted to favour condensation.

Nucleic acid formulations may include a surfactant. In one embodiment, the nucleic acid is formulated as an emulsion that includes a surfactant.

A surfactant that is not ionized is a non-ionic surfactant. Examples include non-ionic esters, such as ethylene glycol esters, propylene glycol esters, glyceryl esters etc., nonionic alkanolamides, and ethers such as fatty alcohol ethoxylates, propoxylated alcohols, and ethoxylated/propoxylated block polymers.

A surfactant that carries a negative charge when dissolved or dispersed in water is an anionic surfactant. Examples include carboxylates, such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates.

A surfactant that carries a positive charge when dissolved or dispersed in water is a cationic surfactant. Examples include quaternary ammonium salts and ethoxylated amines.

A surfactant that has the ability to carry either a positive or negative charge is an amphoteric surfactant. Examples include acrylic acid derivatives, substituted alkylamides, N-alkylbetaines and phosphatides.

"Micelles" are defined herein as a particular type of molecular assembly in which amphipathic molecules are arranged in a spherical structure such that all the hydrophobic portions of the molecules are directed inward, leaving the hydrophilic portions in contact with the surrounding aqueous phase. The converse arrangement exists if the environment is hydrophobic. A micelle may be formed by mixing an aqueous solution of the nucleic acid, an alkali metal alkyl sulphate, and at least one micelle forming compound.

Exemplary micelle forming compounds include lecithin, hyaluronic acid, pharmaceutically acceptable salts of hyaluronic acid, glycolic acid, lactic acid, chamomile extract, cucumber extract, oleic acid, linoleic acid, linolenic acid, monoolein, monooleates, monolaurates, borage oil, evening of primrose oil, menthol, trihydroxy oxo cholanyl glycine and pharmaceutically acceptable salts thereof, glycerin, polyglycerin, lysine, polylysine, triolein, polyoxyethylene ethers and analogues thereof, polidocanol alkyl ethers and analogues thereof, chenodeoxycholate, deoxycholate, and mixtures thereof.

Phenol and/or m-cresol may be added to the mixed micellar composition to act as a stabiliser and preservative. An isotonic agent such as glycerine may as be added.

A nucleic acid preparation may be incorporated into a particle such as a microparticle. Microparticles can be produced by spray-drying, lyophilisation, evaporation, fluid bed drying, vacuum drying, or a combination of these methods.

Iron Chelators

Iron chelation therapy is used to reduce iron overload. Iron is removed from different tissues at different rates. The aim of chelation therapy is to prevent the accumulation of iron excess and its complication such as hepatic endocrinological and cardiac dysfunction. Several iron chelators have been designed to excrete tissue iron through the urine or faeces by forming complexes.

1. Deferoxamine: This is a clinically approved chelator, which is effective for long term iron chelation therapy in β-thalassaemia and other diseases with iron overload. Because of its short plasma half-life, it is given by continuous intravenous or subcutaneous infusion in order to be effective.
2. Deferiprone: This is an oral chelator usually taken 3 times a day 3. Deferasirox (Exjade): This is another oral iron chelator with an extended half-life. It is prescribed for daily use.
4. Deferasirox (Jadenu): This is a film coated tablet, with a formulation different from Deferasirox (Exjade). The advantage is, that it can be taken together with a light meal.

The preferred iron chelator in the context of this disclosure is deferiprone.

The different chelators have a different spectrum of side effects, i.e. injection site reactions by Deferoxamine, renal insufficiencies by Deferoxamine, and Deferasirox, athralgia and neutropenia with Deferiprone. Gastrointestinal disturbances are side effects reported by all classes of chelators. Patient compliance to chelation therapy continues to be an issue, but has improved with the availability or iron chelators that can be taken orally (Chalmers A W, Shammo J M. 2016. 'Evaluation of a new tablet formulation of deferasirox to reduce chronic iron overload after long-term blood transfusions', Ther Clin Risk Manag, 12: 201-8; and Mobarra N, Shanaki M, Ehteram H, Nasiri H, Sahmani M, Saeidi M, Goudarzi M, Pourkarim H, Azad M. 2016. 'A Review on Iron Chelators in Treatment of Iron Overload Syndromes', Int J Hematol Oncol Stem Cell Res, 10: 239-47).

One advantage of using the present combination of a chelator and an siRNA that inhibits TMPRSS6, especially for hemochromatosis treatment is that the combined treatment allows to reduce iron liver levels quickly and efficiently (see example 47). After the initial combination treatment, the amount of chelator doses can be drastically reduced and treatment can continue essentially only with the siRNA, supplemented with the chelator as and when is necessary. This is highly beneficial for patients due to the side effects they experience from iron chelators. Accordingly, one aspect of the present invention is a combination, a combination for use, a nucleic acid for use, a kit, a composition, a composition for use or a method of treatment wherein a nucleic acid and an iron chelator as described herein are administered in combination in a first phase of the treatment and wherein the dosage of iron chelator is strongly reduced in a second phase of the treatment compared to the first phase. Strongly reduced in this context means reduced by at least 50%, preferably at least 60%, more preferably at least 70% and most preferably at least 80% between comparable amounts of time of the first and second phase. The duration of the first phase is preferably three weeks or less, more preferably two weeks or less.

The present invention also provides pharmaceutical compositions comprising a nucleic acid or conjugated nucleic acid of the disclosure, in combination with one or more iron chelators. The pharmaceutical compositions may be used as medicaments or as diagnostic agents, alone or in combination with other agents. For example, a nucleic acid or conjugated nucleic acid and/or iron chelator can be combined with a delivery vehicle (e.g., liposomes) and excipients, such as carriers, diluents. Other agents such as preservatives and stabilizers can also be added. Methods for the delivery of nucleic acids are known in the art and within the knowledge of the person skilled in the art.

The nucleic acid or conjugated nucleic acid and the one or more iron chelators can be administered separately, sequentially or simultaneously, e.g., as a combined unit dose.

It should be noted that a combination in the context of this disclosure does not necessarily mean that two elements (such as the nucleic acid and the chelator) are combined in a single composition. Rather it preferably means that the two elements, such as the nucleic acid and the chelator are for combined administration, which can occur at the same time for both elements or within a short period of time of each other. A short period of time is preferably one week, but more preferably 6 days, more preferably 5 days, more preferably 4 days, more preferably 3 days, more preferably 2 days, more preferably 1 day and most preferably less than one day, such as 12 hours, 6 hours, 4 hours, 2 hours or 1 hour.

A nucleic acid or conjugated nucleic acid of the disclosure, in combination with one or more iron chelators can also be administered in combination with other therapeutic compounds, either administrated separately or simultaneously, e.g., as a combined unit dose. The invention also includes a pharmaceutical composition comprising a nucleic acid or conjugated nucleic acid of the disclosure, in combination with one or more iron chelators, in a physiologically/pharmaceutically acceptable excipient, such as a stabilizer, preservative, diluent, buffer, and the like. The invention also includes a pharmaceutical composition comprising a nucleic acid or conjugated nucleic acid in a physiologically/pharmaceutically acceptable excipient, such as a stabilizer, preservative, diluent, buffer, and the like, and a pharmaceutical composition comprising one or more iron chelators in a physiologically/pharmaceutically acceptable excipient, such as a stabilizer, preservative, diluent, buffer, and the like.

The pharmaceutical composition may be specially formulated for administration in solid or liquid form. The composition may be formulated for oral administration, parenteral administration (including, for example, subcutaneous, intramuscular, intravenous, or epidural injection), topical application, intravaginal or intrarectal administration, sublingual administration, ocular administration, transdermal administration, or nasal administration. Delivery using subcutaneous or intravenous methods are preferred.

In one embodiment, a unit dose may contain between about 0.01 mg/kg and about 100 mg/kg body weight of nucleic acid or conjugated nucleic acid. Alternatively, the dose can be from 10 mg/kg to 25 mg/kg body weight, or 1 mg/kg to 10 mg/kg body weight, or 0.05 mg/kg to 5 mg/kg body weight, or 0.1 mg/kg to 5 mg/kg body weight, or 0.1 mg/kg to 1 mg/kg body weight, or 0.1 mg/kg to 0.5 mg/kg body weight, or 0.5 mg/kg to 1 mg/kg body weight. Dosage levels may also be calculated via other parameters such as, e.g., body surface area.

The pharmaceutical composition may be a sterile injectable aqueous suspension or solution, or in a lyophilized form. In one embodiment, the pharmaceutical composition may comprise lyophilized lipoplexes or an aqueous suspension of lipoplexes. The lipoplexes preferably comprises a nucleic acid disclosed herein. Such lipoplexes may be used to deliver the nucleic acid disclosed hereinto a target cell either in vitro or in vivo.

The pharmaceutical compositions and medicaments of the present invention may be administered to a mammalian subject in a pharmaceutically effective dose. The mammal may be selected from a human, a non-human primate, a simian or prosimian, a dog, a cat, a horse, cattle, a pig, a goat, a sheep, a mouse, a rat, a hamster, a hedgehog and a guinea pig, or other species of relevance. On this basis, the wording "TMPRSS6" as used herein denotes nucleic acid or protein in any of the above mentioned species, but preferably this wording denotes human nucleic acids or proteins.

A further aspect of the invention relates to a nucleic acid disclosed herein or the pharmaceutical composition comprising the nucleic acid disclosed herein, in combination with one or more iron chelators, for use in the treatment or prevention of a disease or disorder. The disease or disorder may be selected from the group comprising hemochromatosis, porphyria cutanea tarda and blood disorders, such as β-thalassemias or sickle cell disease, congenital dyserythropoietic anemia, marrow failure syndrome, myelodysplasia and transfusional iron overload. The disorder may be associated with iron overload and the disorder associated with iron overload may be Parkinson's Disease, Alzheimer's Disease or Friedreich's Ataxia. Preferably, the disorder is hemochromatosis.

In particular, preferred aspects of the invention include:
Any nucleic acid as disclosed herein in combination with one or more iron chelators for use in one or more or all of:
  (i) treatment of anemia, optionally suitably determined by an increase in haemoglobin or haematocrit or by decrease in reticulocytes as disclosed by the methods herein; and/or
  (ii) reduction of splenomegaly, optionally determined by a reduction in spleen size by weight as disclosed by the methods herein; and/or
  (iii) amelioration of ineffective erythropoiesis in spleen, optionally determined by reduction in relative proportion of immature erythroid cells in spleen determined by FACS analysis, as described herein; and/or
  (iv) Improvement of red blood cell maturation/erythropoiesis in the bone marrow, optionally determined by a decrease in relative proportion of erythroid progenitor cells and increase in enucleated erythroid cells determined by FACS analysis, as described herein;
  (v) treatment of hemochromatosis;
  (vi) treatment of iron overload.

The invention includes a pharmaceutical composition comprising one or more RNAi molecule disclosed herein in combination with one or more iron chelators in a physiologically/pharmaceutically acceptable excipient, such as a stabiliser, preservative, diluent, buffer and the like.

The invention includes a pharmaceutical composition comprising one or more RNAi molecule disclosed herein in a physiologically/pharmaceutically acceptable excipient, such as a stabiliser, preservative, diluent, buffer and the like, and a pharmaceutical composition comprising one or more iron chelators in a physiologically/pharmaceutically acceptable excipient, such as a stabiliser, preservative, diluent, buffer and the like.

The pharmaceutical composition may be a sterile injectable aqueous suspension or solution, or in a lyophilised form.

Pharmaceutically acceptable compositions may comprise a therapeutically-effective amount of one or more nucleic acid(s) in any embodiment according to the invention, taken alone or formulated with one or more pharmaceutically acceptable carriers, excipient and/or diluents.

Examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) lubricating agents, such as magnesium state, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; and (22) other non-toxic compatible substances employed in pharmaceutical formulations.

Stabilisers may be agents that stabilise the nucleic acid agent, for example a protein that can complex with the nucleic acid, chelators (e.g. EDTA), salts, RNAse inhibitors, and DNAse inhibitors.

In some cases it is desirable to slow the absorption of the drug from subcutaneous or intramuscular injection in order to prolong the effect of a drug. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

The nucleic acid described herein may be capable of inhibiting the expression of TMPRSS6. The nucleic acid described herein may be capable of partially inhibiting the expression of TMPRSS6 in a cell. Inhibition may be complete, i.e. 0% of the expression level of TMPRSS6 expression in the absence of the nucleic acid disclosed herein. Inhibition of TMPRSS6 expression may be partial, i.e. it may be 15%, 20%, 30%, 40%, 50%, 60%, 70%, 75%, 80%, 85%, 90%, 95% of TMRPSS6 expression in the absence of a nucleic acid disclosed herein. Inhibition may last 2 weeks, 3 weeks, 4 weeks, 5 weeks, 6 weeks, 7 weeks, 8 weeks, 10 weeks, 11 weeks, 12 weeks, 13 weeks, 14 weeks, or up to 6 months, when used in a subject, such as a human subject. A nucleic acid or conjugated nucleic acid disclosed herein, or compositions including the same, may be for use in a regimen comprising treatments once or twice weekly, every week, every two weeks, every three weeks, every four weeks, every five weeks, every six weeks, every seven weeks, or every eight weeks, or in regimens with varying dosing frequency such as combinations of the before-mentioned intervals. The nucleic acid may be for use subcutaneously, intravenously or using any other application routes such as oral, rectal or intraperitoneal.

In cells and/or subjects treated with or receiving the nucleic acid disclosed herein, the TMPRSS6 expression may be inhibited compared to untreated cells and/or subjects by a range from 15% up to 100% but at least about 30%, 35%, 40%, 45%, 50%, 55%, 60%, 65%, 70%, 75%, 80%, 85%, 90%, 95%, 98%, or 100%. The level of inhibition may allow treatment of a disease associated with TMPRSS6 expression or overexpression, or may allow further investigation into the functions of the TMPRSS6 gene product.

Hepcidin gene expression in cells and/or subjects treated with a nucleic acid or conjugated nucleic acid disclosed herein may be increased compared to untreated cells and/or subjects by at least about 1.2 fold, about 1.5-fold, about 2-fold, about 3-fold, about 4-fold, or about 5-fold, due to the complete or partial inhibition of TMPRSS6 gene expression. This may lead to serum hepcidin concentration in subjects treated a nucleic acid or conjugated nucleic acid disclosed herein may be increased compared to untreated subjects by at least about 10%, about 25%, about 50%, about 100%, about 150%, about 200%, about 250%, about 300%, or about 500%.

Serum or plasma iron concentration in subjects treated with a nucleic acid or conjugated nucleic acid disclosed herein may be decreased compared to untreated subjects by at least about 10%, about 20%, about 30%, about 40%, about 50%, about 60%, about 70%, about 80%. Transferrin saturation is a medical laboratory test that measures the amount of transferrin that is bound to iron. Transferrin saturation, measured as a percentage, is a medical laboratory value that measures the value of serum iron divided by the total transferrin iron-binding capacity. Transferrin saturation in subjects treated with a nucleic acid or conjugated nucleic acid disclosed herein may be decreased compared to untreated subjects by at least about 10%, about 20%, about 30%, about 40%, about 50%, about 60%, about 70%, about 80%.

A further aspect of the invention relates to a nucleic acid disclosed herein in combination with one or more iron chelators in the manufacture of a medicament for treating or preventing a disease or disorder, such as disease or disorder as listed above.

Also included in the invention is a method of treating or preventing a disease or disorder, such as those listed above, comprising administration of a pharmaceutical composition comprising a nucleic acid or conjugated nucleic acid disclosed herein in combination with one or more iron chelators, to an individual in need of treatment. The composition may be administered twice every week, once every week, every two weeks, every three weeks, every four weeks, every five weeks, every six weeks, every seven weeks, or every eight weeks. The nucleic acid or conjugated nucleic acid in combination with one or more iron chelators may be for use subcutaneously or intravenously or other application routes such as oral, rectal or intraperitoneal. The nucleic acid and chelator can be administered as a single composition that comprises both or in different compositions that are administered separately, either by the same route or by a different route, at the same or different dosage, and at the same or different dosage frequencies.

In one embodiment, a subject is administered an initial dose and one or more maintenance doses of a nucleic acid agent. The maintenance dose or doses can be the same or lower than the initial dose, e.g., one-half less of the initial dose. The maintenance doses are, for example, administered no more than once every 2, 5, 10, or 30 days. The treatment regimen may last for a period of time which will vary depending upon the nature of the particular disease, its severity and the overall condition of the patient. The subject may be administered a chelator in combination with the siRNA either throughout the treatment with the siRNA or only for part of the treatment with the siRNA. The dosage of the chelator that is administered in combination with the siRNA may be adapted to the particular need of the subject. The need of the subject may be determined for example based on the measurement of liver iron levels or other markers that indicate the need for a combined treatment.

In one embodiment, the composition includes a plurality of nucleic acid agent species. In another embodiment, the nucleic acid agent species has sequences that are non-overlapping and non-adjacent to another species with respect to a naturally occurring target sequence. In another embodiment, the plurality of nucleic acid agent species is specific for different naturally occurring target genes. In another embodiment, the nucleic acid agent is allele specific.

A nucleic acid or conjugated nucleic acid of the disclosure, in combination with one or more iron chelators, can also be administered or for use in combination with other therapeutic compounds, either administered separately or simultaneously, e.g. as a combined unit dose.

The nucleic acid or conjugated nucleic acid of the present disclosure, in combination with one or more iron chelators, can be produced using routine methods in the art including chemical synthesis or expressing the nucleic acid either in vitro (e.g., run off transcription) or in vivo. For example, using solid phase chemical synthesis or using a nucleic acid-based expression vector including viral derivates or partially or completely synthetic expression systems. In one embodiment, the expression vector can be used to produce the nucleic acid disclosed herein in vitro, within an intermediate host organism or cell type, within an intermediate or the final organism or within the desired target cell. Methods for the production (synthesis or enzymatic transcription) of the nucleic acid described herein are known to persons skilled in the art.

In further embodiments of the invention, the invention relates to any nucleic acid, conjugated nucleic acid, nucleic acid for use, method, combination, combination for use, kit, composition or use according to any disclosure herein, wherein the nucleic acid comprises a vinyl-(E)-phosphonate modification, such as a 5' vinyl-(E)-phosphonate modification, preferably a 5' vinyl-(E)-phosphonate modification in combination with a 2'-F modification at the second position of the first strand.

In further embodiments of the invention, the invention relates to any nucleic acid, conjugated nucleic acid, nucleic acid for use, method, combination, combination for use, kit, composition or use according to any disclosure herein, wherein the terminal nucleotide at the 3' end of at least one of the first strand and the second strand is an inverted nucleotide and is attached to the adjacent nucleotide via the 3' carbon of the terminal nucleotide and the 3' carbon of the adjacent nucleotide and/or the terminal nucleotide at the 5' end of at least one of the first strand and the second strand is an inverted nucleotide and is attached to the adjacent nucleotide via the 5' carbon of the terminal nucleotide and the 5' carbon of the adjacent nucleotide, optionally wherein a. the 3' and/or 5' inverted nucleotide of the first and/or second strand is attached to the adjacent nucleotide via a phosphate group by way of a phosphodiester linkage; or b. the 3' and/or 5' inverted nucleotide of the first and/or second strand is attached to the adjacent nucleotide via a phosphorothioate group or c. the 3' and/or 5' inverted nucleotide of the first and/or second strand is attached to the adjacent nucleotide via a phosphorodithioate group.

In further embodiments of the invention, the invention relates to any nucleic acid, conjugated nucleic acid, nucleic acid for use, method, combination, combination for use, kit, composition or use according to any disclosure herein, wherein the nucleic acid comprises a phosphorodithioate linkage, optionally wherein the linkage is between the 2 most 5' nucleotides and/or the 2 most 3' nucleotides of the second strand, and/or optionally wherein the nucleic acid additionally does not comprise any internal phosphorothioate linkages.

In further embodiments of the invention, the invention relates to a nucleic acid sequence disclosed herein, in combination with one or more iron chelators, wherein the first strand and/or the second strand of the nucleic acid comprises at least a first and a second type of modified ribonucleotide, and wherein there is more of the first type of modified ribonucleotide than the second type of modified nucleotide (for example more of a 2' O methyl modification than a 2' fluoro modification), either as counted on each strand individually, or across both the first and second strand.

For the avoidance of doubt the nucleic acid may have more than two types of modification.

Another embodiment of the invention relates to any nucleic acid sequence disclosed herein, in combination with one or more iron chelators, wherein greater than 50% of the nucleotides of the first and/or second strand comprise a 2' O-methyl modification, such as greater than 55%, 60%, 65%, 70%, 75%, 80%, or 85%, or more, of the first and/or second strand comprise a 2' O-methyl modification, preferably measured as a percentage of the total nucleotides of both the first and second strands.

Another embodiment of the invention relates to any nucleic acid sequence disclosed herein, in combination with one or more iron chelators, wherein greater than 50% of the nucleotides of the first and/or second strand comprise a naturally occurring RNA modification, such as wherein greater than 55%, 60%, 65%, 70%, 75%, 80%, or 85% or more of the first and/or second strands comprise such a modification, preferably measured as a percentage of the total nucleotides of both the first and second strands. Suitable naturally occurring modifications include, as well as 2-O' methyl, other 2' sugar modifications, in particular a 2'-H modification resulting in a DNA nucleotide.

Another embodiment of the invention relates to any nucleic acid sequence disclosed herein, in combination with one or more iron chelators, comprising no more than 20%, such as no more than 15%, such as no more than 10%, of nucleotides which have 2' modifications that are not 2' O methyl modifications on the first and/or second strand, preferably as a percentage of the total nucleotides of both the first and second strands.

Another embodiment of the invention relates to any nucleic acid sequence disclosed herein, in combination with one or more iron chelators, comprising no more than 20%, (such as no more than 15% or no more than 10%) of 2' fluoro modifications on the first and/or second strand, preferably as a percentage of the total nucleotides of both strands.

Another embodiment of the invention relates to a nucleic acid for inhibiting expression of TMPRSS6 in combination with one or more iron chelators, comprising at least one duplex region that comprises at least a portion of a first strand and at least a portion of a second strand that is at least partially complementary to the first strand, wherein said first strand is at least partially complementary to at least a portion of RNA transcribed from the TMPRSS6 gene, wherein said first strand comprises a nucleotide sequence of HC18A as below; and optionally wherein said second strand comprises the nucleotide sequence of HC18b as below:

| TMPRSS6-hc-18A | UUUUCUCUUGGAGUCCUCA (SEQ ID NO: 422) |
| TMPRSS6-hc-18B | UGAGGACUCCAAGAGAAAA (SEQ ID NO: 423) |

Optionally the nucleic acid sequences are either TMPRSS6-hc-18A, or both of TMPRSS6-hc-18A and 18B as below:

| TMPRSS6-hc-18A | mU(ps)fU(ps)mUfUmCfUmCfUmUfGmGfAmGfUmCf CmU(ps)fC(ps)mA (SEQ ID NO: 199) |
| TMPRSS6-hc-18B | fUmGfAmGfGmAfCmUfCmCfAmAfGmAfGmAfA(ps)mA (ps)fA (SEQ ID NO: 200) |

Optionally the nucleic acid sequences are either or both of the sequences listed below.

| TMPRSS6-hc-18A | mU(ps)fU(ps)mUfUmCfUmCfUmUfGmGfAmGfUm CfCmU(ps)fC(ps)mA (SEQ ID NO: 199) |
| TMPRSS6-hc-18B | GN3-fUmGfAmGfGmAfCmUfCmCfAmAfGmAfGmAfA (ps)mA(ps)fA (SEQ ID NO: 200) |

All sequences are listed 5'-3'. A nucleic acid for inhibiting expression of TMPRSS6, comprising at least one duplex region that comprises at least a portion of a first strand and at least a portion of a second strand that is at least partially complementary to the first strand, wherein said first strand is at least partially complementary to at least a portion of RNA transcribed from the TMPRSS6 gene, wherein said first strand comprises a nucleotide sequence of HC23A as below; and optionally wherein said second strand comprises the nucleotide sequence of HC23B as below:

| TMPRSS6-hc-23A | CUGUUCUGGAUCGUCCACU (SEQ ID NO: 430) |
| TMPRSS6-hc-23B | AGUGGACGAUCCAGAACAG (SEQ ID NO: 431) |

Optionally the nucleic acid sequences are either TMPRSS6-hc-23A, or both of TMPRSS6-hc-23A and 23B as below:

| TMPRSS6-hc-23A | mC(ps)fU(ps)mGfUmUfCmUfGmGfAmUfCmGfUmCf CmA(ps)fC(ps)mU (SEQ ID NO: 207) |
| TMPRSS6-hc-23B | fAmGfUmGfGmAfCmGfAmUfCmCfAmGfAmAfC(ps) mA(ps)fG (SEQ ID NO: 208) |

Optionally the nucleic acid sequences are either or both of the sequences listed below.

| TMPRSS6-hc-23A | mC(ps)fU(ps)mGfUmUfCmUfGmGfAmUfCmGfUmCf CmA(ps)fC(ps)mU (SEQ ID NO: 207) |
| TMPRSS6-hc-23B | GN3-fAmGfUmGfGmAfCmGfAmUfCmCfAmGfAmAfC (ps)mA(ps)fG (SEQ ID NO: 208) |

Another embodiment of the invention is a nucleic acid for inhibiting expression of TMPRSS in combination with one or more iron chelators in a cell, comprising at least one duplex region that comprises at least a portion of a first strand and at least a portion of a second strand that is at least partially complementary to the first strand, wherein said first strand is at least partially complementary to at least a portion of RNA transcribed from the TMPRSS gene, wherein the expression of TMPRSS in a cell is reduced to levels which are at least 15% lower than expression levels observed in same test conditions but in the absence of the nucleic acid or conjugated nucleic acid or in the presence of a non-silencing control.

The nucleic acid may be any disclosed herein.

Certain Preferred Embodiments

1. A combination comprising a nucleic acid for inhibiting expression of TMPRSS6 and one or more iron chelators, wherein the nucleic acid comprises at least one duplex region that comprises at least a portion of a first strand and at least a portion of a second strand that is at least partially complementary to the first strand, wherein said first strand is at least partially complementary to at least a portion of RNA transcribed from the TMPRSS6 gene, wherein said first strand comprises a nucleotide sequence selected from the following sequences: SEQ ID NOs: 333, 317, 319, 321, 323, 325, 327, 329, 331, 335, 337, 339, 341, 343, 345, 353, 356, 358, 360, 362, 364, 366, 368, 370, 372, 374, 376, 378, 380, 382, 384, 386, 388, 390, 392, 394, 396, 398, 400, 402, 404, 406, 407, 410, 412, 414, 416, 418, 420, 422, 424, 426, 428, 430, 432, 434, 436, 438, 440, or 442, preferably SEQ ID NO: 333.

2. A combination for use in the treatment of hemochromatosis, porphyria cutanea tarda, blood disorders, such as β-thalassemia or sickle cell disease, congenital dyserythropoietic anemia, marrow failure syndromes, myelodysplasia, transfusional iron overload, a disorder associated with iron overload, Parkinson's Disease, Alzheimer's Disease or Friedreich's Ataxia associated with iron overload, and infections and non-relapse related mortality associated with bone marrow transplantation, preferably for the treatment of hemochromatosis, the combination (or composition) comprising a nucleic acid for inhibiting expression of TMPRSS6 and one or more iron chelators, wherein the nucleic acid comprises at least one duplex region that comprises at least a portion of a first strand and at least a portion of a second strand that is at least partially complementary to the first strand, wherein said first strand is at least partially complementary to at least a portion of RNA transcribed from the TMPRSS6 gene, wherein said first strand comprises a nucleotide sequence selected from the following sequences: SEQ ID NOs: 333, 317, 319, 321, 323, 325, 327, 329, 331, 335, 337, 339, 341, 343, 345, 353, 356, 358, 360, 362, 364, 366, 368, 370, 372, 374, 376, 378, 380, 382, 384, 386, 388, 390, 392, 394, 396, 398, 400, 402, 404, 406, 407, 410, 412, 414, 416, 418, 420, 422, 424, 426, 428, 430, 432, 434, 436, 438, 440, or 442, preferably SEQ ID NO: 333.

3. A nucleic acid for use as a medicament, preferably a nucleic acid for use in the treatment of hemochromatosis, porphyria cutanea tarda, blood disorders, such as β-thalassemia or sickle cell disease, congenital dyserythropoietic anemia, marrow failure syndromes, myelodysplasia, transfusional iron overload, a disorder associated with iron overload, Parkinson's Disease, Alzheimer's Disease or Friedreich's Ataxia associated with iron overload, and infections and non-relapse related mortality associated with bone marrow transplantation, preferably for the treatment of hemochromatosis, wherein the nucleic acid inhibits expression of TMPRSS6, wherein the nucleic acid comprises at least one duplex region that comprises at least a portion of a first strand and at least a portion of a second strand that is at least partially complementary to the first strand, wherein said first strand is at least partially complementary to at least a portion of RNA transcribed from the TMPRSS6 gene, wherein said first strand comprises a nucleotide sequence selected from the following sequences: SEQ ID NOs: 333, 317, 319, 321, 323, 325, 327, 329, 331, 335, 337, 339, 341, 343, 345, 353, 356, 358, 360, 362, 364, 366, 368, 370, 372, 374, 376, 378, 380, 382, 384, 386, 388, 390, 392, 394, 396, 398, 400, 402, 404, 406, 407, 410, 412, 414, 416, 418, 420, 422, 424, 426, 428, 430, 432, 434, 436, 438, 440, or 442, preferably SEQ ID NO: 333, wherein the nucleic acid is administered with one or more iron chelators.

4. A kit comprising a nucleic acid for inhibiting expression of TMPRSS6 and one or more iron chelators, wherein the nucleic acid comprises at least one duplex region that comprises at least a portion of a first strand and at least a portion of a second strand that is at least partially complementary to the first strand, wherein said first strand is at least partially complementary to at least a portion of RNA transcribed from the TMPRSS6 gene, wherein said first strand comprises a nucleotide sequence selected from the following sequences: SEQ ID NOs: 333, 317, 319, 321, 323, 325, 327, 329, 331, 335, 337, 339, 341, 343, 345, 353, 356, 358, 360, 362, 364, 366, 368, 370, 372, 374, 376, 378, 380, 382, 384, 386, 388, 390, 392, 394, 396, 398, 400, 402, 404, 406, 407, 410, 412, 414, 416, 418, 420, 422, 424, 426, 428, 430, 432, 434, 436, 438, 440, or 442, preferably SEQ ID NO: 333.

5. A pharmaceutical composition comprising a nucleic acid for inhibiting expression of TMPRSS6 and one or more iron chelators, wherein the nucleic acid comprises at least one duplex region that comprises at least a portion of a first strand and at least a portion of a second strand that is at least partially complementary to the first strand, wherein said first strand is at least partially complementary to at least a portion of RNA transcribed from the TMPRSS6 gene, wherein said first strand comprises a nucleotide sequence selected from the following sequences: SEQ ID NOs: 333, 317, 319, 321, 323, 325, 327, 329, 331, 335, 337, 339, 341, 343, 345, 353, 356, 358, 360, 362, 364, 366, 368, 370, 372, 374, 376, 378, 380, 382, 384, 386, 388, 390, 392, 394, 396, 398, 400, 402, 404, 406, 407, 410, 412, 414, 416, 418, 420, 422, 424, 426, 428, 430, 432, 434, 436, 438, 440, or 442, preferably SEQ ID NO: 333, wherein the nucleic acid, iron chelator or both are combined with a physiologically acceptable excipient.

6. A pharmaceutical composition for use in the treatment of hemochromatosis, porphyria cutanea tarda, blood disorders, such as β-thalassemia or sickle cell disease, congenital dyserythropoietic anemia, marrow failure syndromes, myelodysplasia, transfusional iron overload, a disorder associated with iron overload, Parkinson's Disease, Alzheimer's Disease or Friedreich's Ataxia associated with iron overload, and infections and non-relapse related mortality associated with bone marrow transplantation, preferably for the treatment of hemochromatosis, wherein the pharmaceutical composition comprises a nucleic acid for inhibiting expression of TMPRSS6 and one or more iron chelators, wherein the nucleic acid comprises at least one duplex region that comprises at least a portion of a first strand and at least a portion of a second strand that is at least partially complementary to the first strand, wherein said first strand is at least partially complementary to at least a portion of RNA transcribed from the TMPRSS6 gene, wherein said first strand comprises a nucleotide sequence selected from the following sequences: SEQ ID NOs: 333, 317, 319, 321, 323, 325, 327, 329, 331, 335, 337, 339, 341, 343, 345, 353, 356, 358, 360, 362, 364, 366, 368, 370, 372, 374, 376, 378, 380, 382, 384, 386, 388, 390, 392, 394, 396, 398, 400, 402, 404, 406, 407, 410, 412, 414, 416, 418, 420, 422, 424, 426, 428, 430, 432, 434, 436, 438, 440, or 442, preferably SEQ ID NO: 333 wherein the nucleic acid, iron chelator or both are combined with a physiologically acceptable excipient.

7. The combination of preferred embodiment 1, combination for use of preferred embodiment 2, nucleic acid for use of preferred embodiment 3, kit of preferred embodiment 4, composition of preferred embodiment 5 or composition for use of preferred embodiment 6, wherein the second strand comprises a nucleotide sequence of SEQ ID NO: 334, 318, 320, 322, 324, 326, 328, 330, 332, 336, 338, 340, 342, 344, 346, 357, 359, 361, 363, 365, 367, 369, 371, 373, 375, 377, 379, 381, 383, 385, 387, 389, 391, 393, 395, 397, 399, 401, 403, 405, 407, 409, 411, 413, 415, 417, 419, 421, 423, 425, 427, 429, 431, 433, 435,437, 439, 441, or 443, preferably SEQ ID NO: 334.

8. The combination, combination for use, nucleic acid for use, kit, composition or composition for use according to any of the preferred embodiments 1-7, wherein the one or more iron chelators are selected from deferoxamine, deferiprone, deferasirox (Exjade) and deferairox (Jadenu), optionally wherein the iron chelator is deferiprone.

9. The combination, combination for use, nucleic acid for use, kit, composition or composition for use according to any of the preferred embodiments 1-8, wherein one or more nucleotides on the first and/or second strand are modified, to form modified nucleotides. The nucleic acid may comprise a modification that is 2'-O-methyl (2'OMe) that may be a first modification, and a second modification that is 2'-F. Modified nucleotides are evidently nucleotides that conserve there base identity (A, C, G, T, U) but have one or several modifications for example on the sugar, such as a modification of the 2'-OH to a 2'OMe or 2'F.

10. The combination, combination for use, or nucleic acid for use according to preferred embodiment 9, wherein said first strand comprises a nucleotide sequence of SEQ ID NO:17, and wherein said second strand comprises the nucleotide sequence of SEQ ID NO:18

| SEQ ID NO: 17 | 5'aaccagaagaagca gguga 3' | 6273646282647284546 |
|---|---|---|
| SEQ ID NO: 18 | 5'ucaccugcuucuuc ugguu 3' | 1727354715351718451 | wherein the specific modifications are depicted by the following numbers
1=2'F-dU,
2=2'F-dA,
3=2'F-dC,
4=2'F-dG,
5=2'-OMe-rU;
6=2'-OMe-rA;
7=2'-OMe-rC;
8=2'-OMe-rG.

11. A combination comprising a nucleic acid for inhibiting expression of TMPRSS6 and deferiprone,
wherein the nucleic acid comprises at least one duplex region that comprises at least a portion of a first strand and at least a portion of a second strand that is at least partially complementary to the first strand, wherein said first strand is at least partially complementary to at least a portion of RNA transcribed from the TMPRSS6 gene, wherein the first strand comprises the nucleotide sequence of SEQ ID NO:17 and the second strand comprises the nucleotide sequence of SEQ ID NO:18.

12. A combination for use in the treatment of hemochromatosis, porphyria cutanea tarda, blood disorders, such as β-thalassemia or sickle cell disease, congenital dyserythropoietic anemia, marrow failure syndromes, myelodysplasia, transfusional iron overload, a disorder associated with iron overload, Parkinson's Disease, Alzheimer's Disease or Friedreich's Ataxia associated with iron overload, and infections and non-relapse related mortality associated with bone marrow transplantation, preferably for the treatment of hemochromatosis,
comprising a nucleic acid for inhibiting expression of TMPRSS6 and deferiprone, wherein the nucleic acid comprises at least one duplex region that comprises at least a portion of a first strand and at least a portion of a second strand that is at least partially complementary to the first strand, wherein said first strand is at least partially complementary to at least a portion of RNA transcribed from the TMPRSS6 gene, wherein the first strand comprises the nucleotide sequence of SEQ ID NO:17 and the second strand comprises the nucleotide sequence of SEQ ID NO:18.

13. A nucleic acid for use as a medicament, preferably a nucleic acid for use in the treatment of hemochromatosis, porphyria cutanea tarda, blood disorders, such as β-thalassemia or sickle cell disease, congenital dyserythropoietic anemia, marrow failure syndromes, myelodysplasia, transfusional iron overload, a disorder associated with iron overload, Parkinson's Disease, Alzheimer's Disease or Friedreich's Ataxia associated with iron overload, and infections and non-relapse related mortality associated with bone marrow transplantation, preferably for the treatment of hemochromatosis,
wherein the nucleic acid inhibits expression of TMPRSS6, wherein the nucleic acid comprises at least one duplex region that comprises at least a portion of a first strand and at least a portion of a second strand that is at least partially complementary to the first strand, wherein said first strand is at least partially complementary to at least a portion of RNA transcribed from the TMPRSS6 gene, wherein the first strand comprises the nucleotide sequence of SEQ ID NO:17 and the second strand comprises the nucleotide sequence of SEQ ID NO:18, and
wherein the nucleic acid is administered with deferiprone.

14. The combination, combination for use, nucleic acid for use, kit, composition or composition for use according to any of the preferred embodiments 1-13, wherein the nucleic acid and one or more iron chelators are administered simultaneously, separately or sequentially. Preferably the nucleic acid and the chelator are administered not in a single dose but separately. This allows to adapt the dosage of the nucleic acid and especially of the chelator to the need of the subject.

15. The combination, combination for use, nucleic acid for use, kit, composition or composition for use according to any of the preferred embodiments 1-14, wherein the nucleic acid is conjugated to a ligand, optionally at the 5' end of the second strand, optionally wherein the ligand comprises (i) one or more N-acetyl galactosamine (GalNAc) moieties and derivatives thereof, and (ii) a linker, wherein the linker conjugates the GalNAc moieties to the nucleic acid.

16. The combination, combination for use, nucleic acid for use, kit, composition or composition for use according to preferred embodiment 15, wherein the conjugated nucleic acid has the structure:

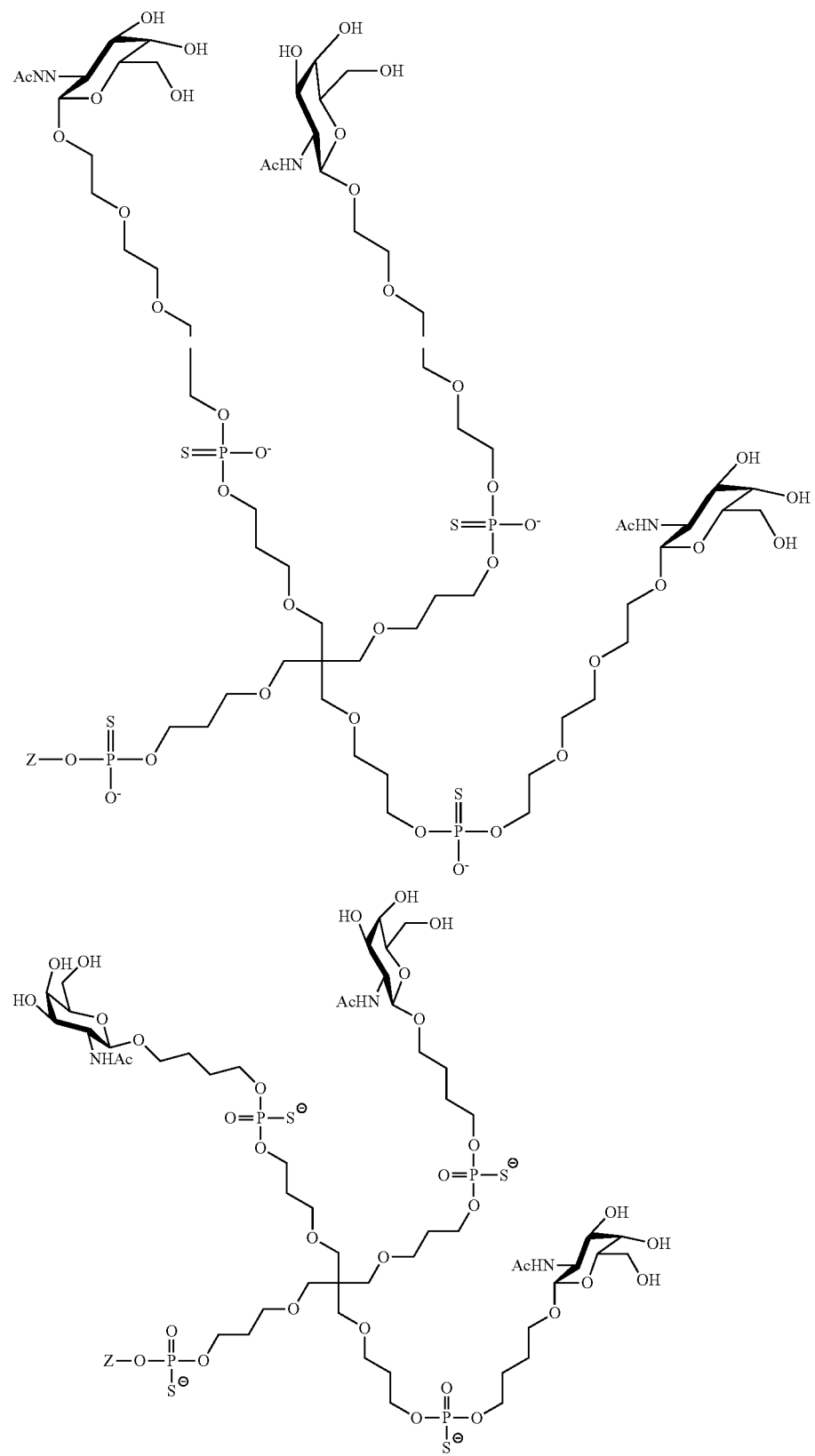

-continued
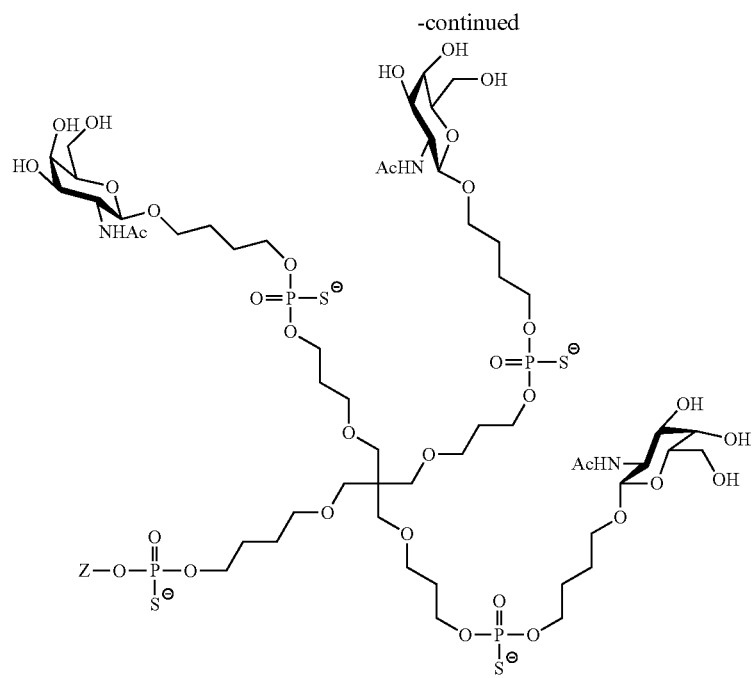
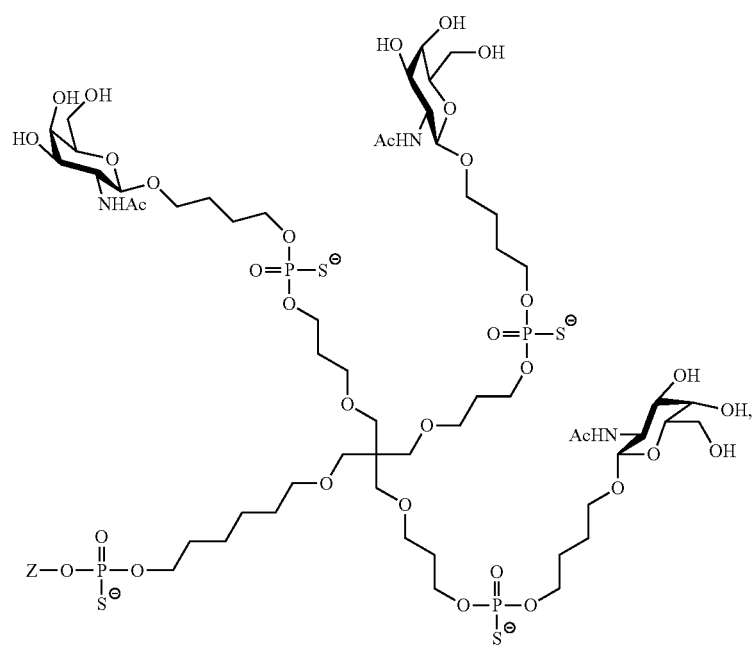

-continued
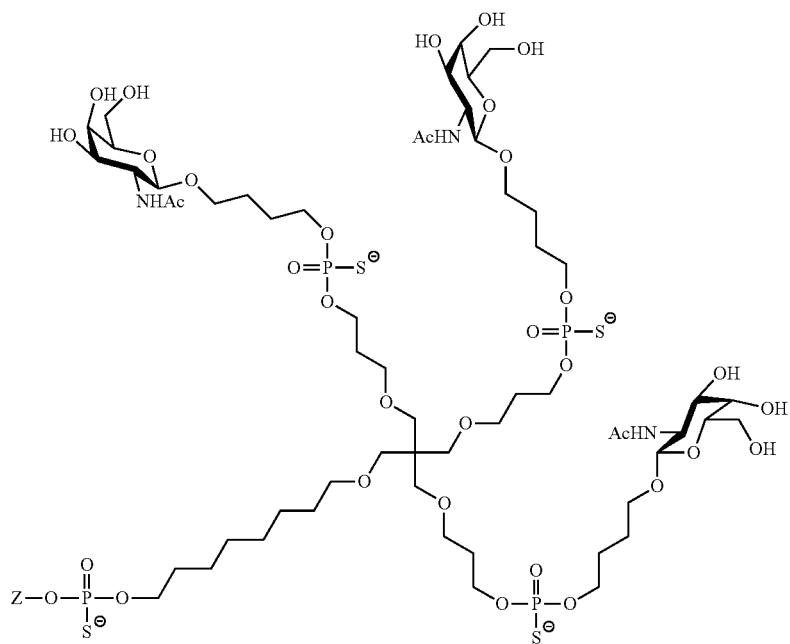
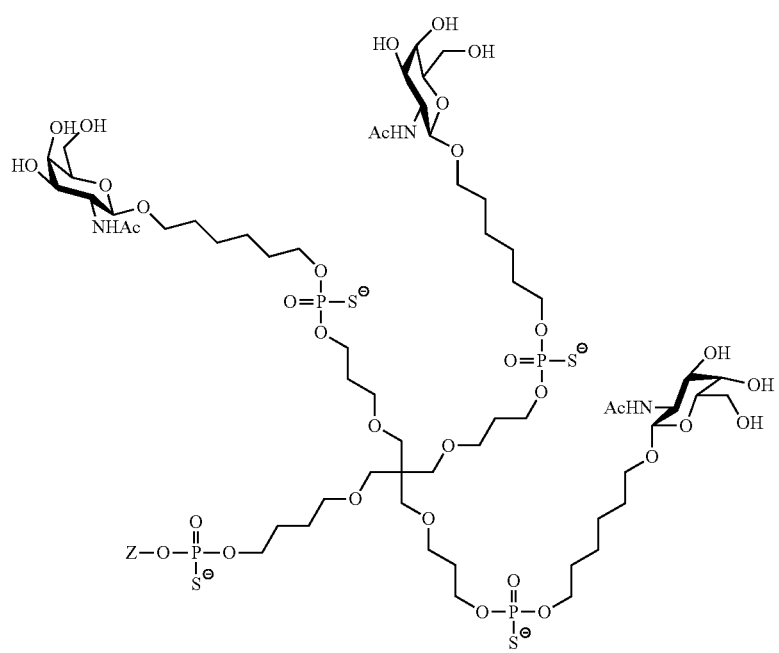

-continued

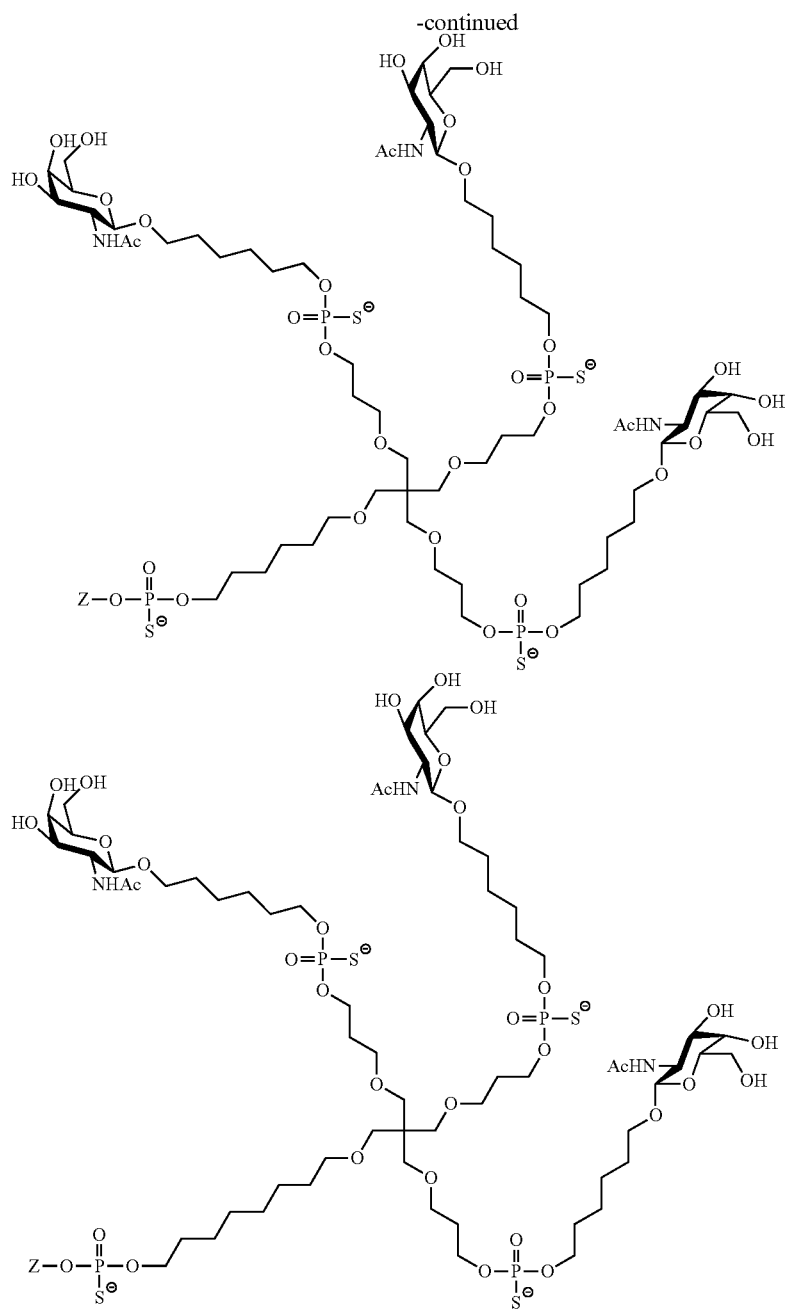

wherein Z is a nucleic acid according to any of preferred embodiments 1 to 14.

17. A combination, combination for use, or nucleic acid for use according to any one of preferred embodiments 1 to 14, or a conjugated nucleic acid according to preferred embodiments 15-16, wherein the nucleic acid is stabilised at the 5' and/or 3' end of either or both strands, optionally wherein the nucleic acid comprises two phosphorothioate linkages between each of the three terminal 3' and between each of the three terminal 5' nucleotides on the first strand, and two phosphorothioate linkages between the three terminal nucleotides of the 3' end of the second strand, having the structure

| 5'-3' | TMPRSS6-hcm-9A | 6 (ps) 2 (ps) 736462826472845 (ps) 4 (ps) 6 |
| 5'-3' | TMPRSS6-hcm-9B | 17273547153517184 (ps) 5 (ps) 1 | wherein the specific modifications are depicted by the following numbers
1=2'F-dU,
2=2'F-dA,
3=2'F-dC,
4=2'F-dG,
5=2'-OMe-rU;
6=2'-OMe-rA;
7=2'-OMe-rC;
8=2'-OMe-rG
(ps)=phosphorothioate linkage.

18. A method of treating a disease or disorder, preferably hemochromatosis, comprising administration of a combination comprising a nucleic acid or conjugated nucleic acid and one or more iron chelators according to any of the preferred embodiments 1-17 to an individual in need of treatment thereof.

The first strand of the nucleic acid preferably comprises, or consists of the nucleotide sequence SEQ ID NO: 333, preferably as modified in SEQ ID NO: 17 and optionally as stabilised with phosphorothioate linkages as shown in SEQ ID NO: 217.

The second strand of the nucleic acid preferably comprises, or consists of the nucleotide sequence SEQ ID NO: 334, preferably as modified in SEQ ID NO: 18 and optionally as stabilised with phosphorothioate linkages as shown in SEQ ID NO: 218. The ligand can be the ligand as shown in SEQ ID NO: 218 or a different ligand, but the ligand is preferably as shown in SEQ ID NO: 218.

The nucleic acid is preferably conjugated to a ligand, optionally at the 5' end of the second strand, optionally wherein the ligand is GN (FIG. 8a), GN2 (FIG. 8b) or GN3 (FIG. 8c), more preferably GN2.

The first stand of the nucleic acid preferably comprises, or consists of SEQ ID NO: 217 and/or the second strand of the nucleic acid preferably comprises, or consists of SEQ ID NO: 218, in both cases with all modifications, including internucleotide modifications, and with the ligand as shown.

Preferably, the disease or disorder to be treated is hemochromatosis, and most preferably hereditary hemochromatosis. Alternatively, or in addition, the disease or disorder is preferably iron overload, such as transfusional iron overload, a disorder associated with iron overload or Friedreich's Ataxia associated with iron overload Preferably, multiple doses of the siRNA are administered. The nucleic acid disclosed herein, or compositions including the same, may be for use in a regimen comprising treatments once or twice weekly, every week, every two weeks, every three weeks, every four weeks, every five weeks, every six weeks, every seven weeks, or every eight weeks, or in regimens with varying dosing frequency such as combinations of the before-mentioned intervals. In one embodiment, a subject is administered an initial dose and one or more maintenance doses of a nucleic acid agent. The maintenance dose or doses can be the same or lower than the initial dose, e.g., one-half less of the initial dose. The maintenance doses are, for example, administered no more than once every 2, 5, 10, or 30 days.

The preferred embodiments can be combined with any other aspects, embodiments, statements and features disclosed herein.

Certain preferred features are listed below:

Statements

1. A nucleic acid for inhibiting expression of TMPRSS6, comprising at least one duplex region that comprises at least a portion of a first strand and at least a portion of a second strand that is at least partially complementary to the first strand, wherein said first strand is at least partially complementary to at least a portion of RNA transcribed from the TMPRSS6 gene, wherein said first strand comprises a nucleotide sequence selected from the following sequences: SEQ ID NOs:1, 3, 5, 7, 9, 11, 13, 15, 17, 19, 21, 23, 25, 27, 29, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, or 215.

2. A nucleic acid of statement 1, wherein the second strand comprises a nucleotide sequence of SEQ ID NO:2, 4, 6, 8, 10, 12, 14, 16, 18, 20, 22, 24, 26, 28, 30, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, or 216.

3. A nucleic acid of statement 1 or statement 2, wherein said first strand comprises a nucleotide sequence of SEQ ID NO:17.

4. A nucleic acid of any one of statements 1 to 3, wherein said second strand comprises the nucleotide sequence of SEQ ID NO:18.

5. A nucleic acid according to any one of statements 1 to 4, wherein said first strand and/or said second strand are each from 17-35 nucleotides in length.

6. A nucleic acid of any one of statements 1 to 5, wherein the at least one duplex region consists of 19-25 consecutive nucleotide base pairs.

7. A nucleic acid of any preceding statement, which
a) is blunt ended at both ends; or
b) has an overhang at one end and a blunt end at the other; or
c) has an overhang at both ends.

8. A nucleic acid according to any preceding statement, wherein one or more nucleotides on the first and/or second strand are modified, to form modified nucleotides.

9. A nucleic acid of statement 8, wherein one or more of the odd numbered nucleotides of the first strand are modified.

10. A nucleic acid according to statement 9, wherein one or more of the even numbered nucleotides of the first strand are modified by at least a second modification, wherein the at least second modification is different from the modification of statement 9.

11. A nucleic acid of statement 10, wherein at least one of the one or more modified even numbered nucleotides is adjacent to at least one of the one or more modified odd numbered nucleotides.

12. A nucleic acid of any one of statements 9 to 11, wherein a plurality of odd numbered nucleotides are modified.

13. A nucleic acid of statement 10 to 12, wherein a plurality of even numbered nucleotides are modified by a second modification.

14. A nucleic acid of any of statements 8 to 13, wherein the first strand comprises adjacent nucleotides that are modified by a common modification.

15. A nucleic acid of any of statements 9 to 14, wherein the first strand comprises adjacent nucleotides that are modified by a second modification that is different to the modification of statement 9.

16. A nucleic acid of any of statements 9 to 15, wherein one or more of the odd numbered nucleotides of the second strand are modified by a modification that is different to the modification of statement 9.

17. A nucleic acid according to any of statements 9 to 15, wherein one or more of the even numbered nucleotides of the second strand are modified by the modification of statement 9.

18. A nucleic acid of statement 16 or 17, wherein at least one of the one or more modified even numbered nucleotides of the second strand is adjacent to the one or more modified odd numbered nucleotides of the second strand.

19. A nucleic acid of any of statements 16 to 18, wherein a plurality of odd numbered nucleotides of the second strand are modified by a common modification.

20. A nucleic acid of any of statements 16 to 19, wherein a plurality of even numbered nucleotides are modified by a modification according to statement 9.

21. A nucleic acid of any of statements 16 to 20, wherein a plurality of odd numbered nucleotides on the second strand are modified by a second modification, wherein the second modification is different from the modification of statement 9.

22. A nucleic acid of any of statements 16 to 21, wherein the second strand comprises adjacent nucleotides that are modified by a common modification.

23. A nucleic acid of any of statements 16 to 22, wherein the second strand comprises adjacent nucleotides that are modified by a second modification that is different from the modification of statement 9.

24. A nucleic acid according to any one of statements 8 to 23, wherein each of the odd numbered nucleotides in the first strand and each of the even numbered nucleotides in the second strand are modified with a common modification.

25. A nucleic acid of statement 24, wherein each of the even numbered nucleotides are modified in the first strand with a second modification and each of the odd numbered nucleotides are modified in the second strand with a second modification.

26. A nucleic acid according to any one of statements 8 to 25, wherein the modified nucleotides of the first strand are shifted by at least one nucleotide relative to the unmodified or differently modified nucleotides of the second strand.

27. A nucleic acid according to any one of statements 8 to 26, wherein the modification and/or modifications are each and individually selected from the group consisting of 3'-terminal deoxy-thymine, 2'-O-methyl, a 2'-deoxy-modification, a 2'-amino-modification, a 2'-alkyl-modification, a morpholino modification, a phosphoramidate modification, 5'-phosphorothioate group modification, a 5' phosphate or 5' phosphate mimic modification and a cholesteryl derivative or a dodecanoic acid bisdecylamide group modification.

28. A nucleic acid according to any one of statements 8 to 27, wherein the modification is any one of a locked nucleotide, an abasic nucleotide or a non-natural base comprising nucleotide.

29. A nucleic acid according to any one of statements 8 to 28, wherein at least one modification is 2'-O-methyl.

30. A nucleic acid according to any one of statements 8 to 29, wherein at least one modification is 2'-F.

31. A nucleic acid for inhibiting expression of TMPRSS6 in a cell, comprising at least one duplex region that comprises at least a portion of a first strand and at least a portion of a second strand that is at least partially complementary to the first strand, wherein said first strand is at least partially complementary to at least a portion of a RNA transcribed from the TMPRSS6 gene, wherein said first strand comprises a nucleotide sequence selected from the following sequences: SEQ ID Nos:1, 3, 5, 7, 9, 11, 13, 15, 17, 19, 21, 23, 25, 27, 29, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, or 215, wherein the nucleotides of first strand are modified by first modification on the odd numbered nucleotides, and modified by a second modification on the even numbered nucleotides, and nucleotides of the second strand are modified by a third modification on the even numbered nucleotides and modified by a fourth modification on the odd numbered nucleotides, wherein at least the first modification is different to the second modification and the third modification is different to the fourth modification.

32. A nucleic acid of statement 31, wherein second sequence comprises a nucleotide sequence of SEQ ID NO:2, 4, 6, 8, 10, 12, 14, 16, 18, 20, 22, 24, 26, 28, 30, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, or 216.

33. A nucleic acid of statement 31 or 32, wherein the fourth modification and the second modification are the same.

34. A nucleic acid of any one of statements 31 to 33, wherein the first modification and the third modification are the same.

35. A nucleic acid of any one of statements 31 to 34, wherein the first modification is 2'O-Me and the second modification is 2'F.

36. A nucleic acid of any one of statements 31 to 35, wherein the first strand comprises the nucleotide sequence of SEQ ID NO:17 and the second strand comprises the nucleotide sequence of SEQ ID NO:18.

37. A nucleic acid of any one of statements 31 to 36, comprising a sequence and modifications as shown in the table below:

| SEQ ID NO: 17 | 5'aaccagaagaagca gguga 3' | 6273646282647284546 |
|---|---|---|
| SEQ ID NO: 18 | 5'ucaccugcuucuuc ugguu 3' | 1727354715351718451 | wherein, the specific modifications are depicted by numbers 1=2'F-dU, 2=2'F-dA, 3=2'F-dC, 4=2'F-dG, 5=2'-OMe-rU;

6=2'-OMe-rA;

7=2'-OMe-rC;

8=2'-OMe-rG.

38. A nucleic acid according to any one of statements 1 to 37, conjugated to a ligand.

39. A nucleic acid according to any one of statements 1 to 38, comprising a phosphorothioate linkage between the terminal one, two or three 3' nucleotides and/or 5' nucleotides of the first and/or the second strand.

40. A nucleic acid according to any one of statements 1 to 39 comprising two phosphorothioate linkage between each of the three terminal 3' and between each of the three terminal 5' nucleotides on the first strand, and two phosphorothioate linkages between the three terminal nucleotides of the 3' end of the second strand.

41. A nucleic acid for inhibiting expression of TMPRSS6 in a cell, comprising at least one duplex region that comprises at least a portion of a first strand and at least a portion of a second strand that is at least partially complementary to the first strand, wherein said first strand is at least partially complementary to at least a portion of a RNA transcribed from the TMPRSS6 gene, wherein said first strand comprises a nucleotide sequence selected from the following sequences: SEQ ID NOs:1, 3, 5, 7, 9, 11, 13, 15, 17, 19, 21, 23, 25, 27, 29, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, or 215, wherein said nucleic acid conjugated to a ligand.

42. A nucleic acid according to statement 41, wherein the ligand comprises (i) one or more N-acetyl galactosamine (GalNAc) moieties and derivatives thereof, and (ii) a linker, wherein the linker conjugates the GalNAc moieties to a nucleic acid as defined in statement 41

43. A nucleic acid according to statement 41 or 42, wherein linker may be a bivalent or trivalent or tetravalent branched structure.

44. A nucleic acid according to any of statements 41 to 43, wherein the nucleotides are modified as defined in any preceding statements.

45. A nucleic acid of any preceding statement, wherein the ligand comprises the formula I:

[S-X$^1$-P-X$^2$]$_3$-A-X$^3$-  (I)

wherein:
 S represents a saccharide, wherein the saccharide is N-acetyl galactosamine;
 X$^1$ represents C$_3$-C$_6$ alkylene or (—CH$_2$—CH$_2$—O)$_m$ (—CH$_2$)$_2$— wherein m is 1, 2, or 3;
 P is a phosphate or modified phosphate (preferably a thiophosphate);
 X$^2$ is alkylone or an alkylene other of the formula (—CH$_2$)—O—CH$_2$— where n=1-8;
 A is a branching unit;
 X$^3$ represents a bridging unit;
 wherein a nucleic acid as defined in any of statements 1 to 40 is conjugated to X$^3$ via a phosphate or modified phosphate (preferably a thiophosphate).

46. A conjugated nucleic acid having one of the following structures

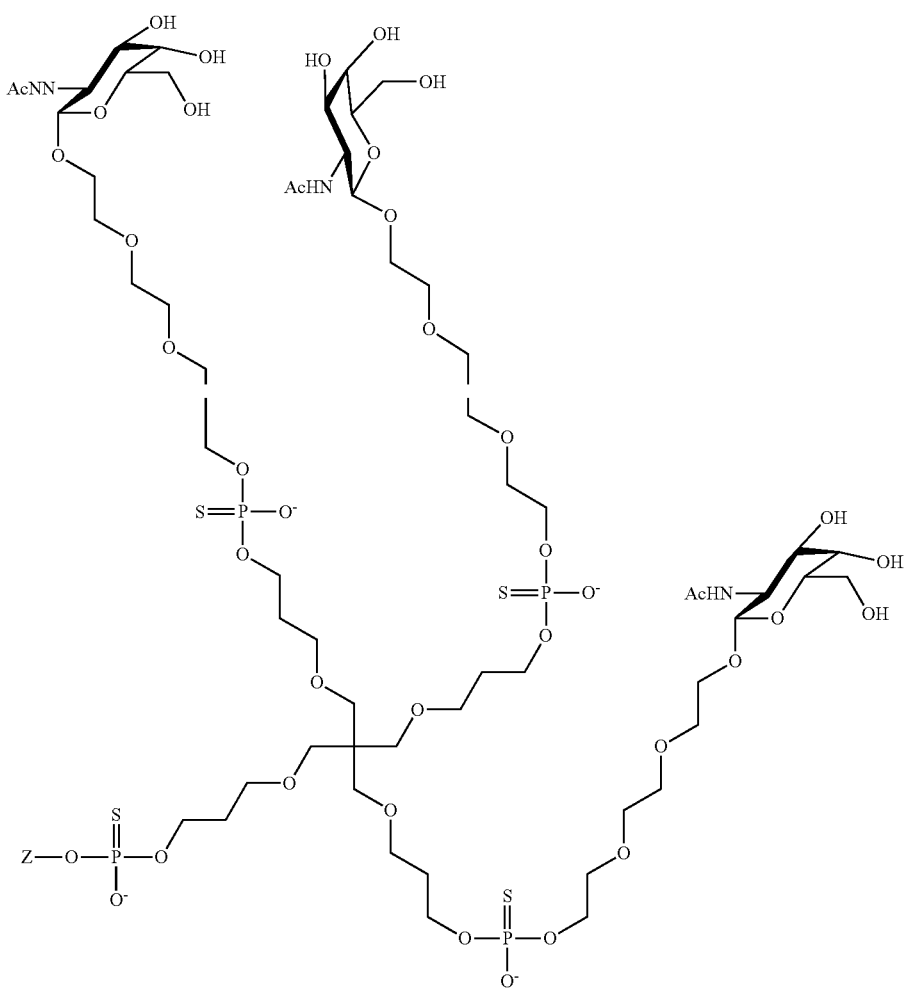

-continued
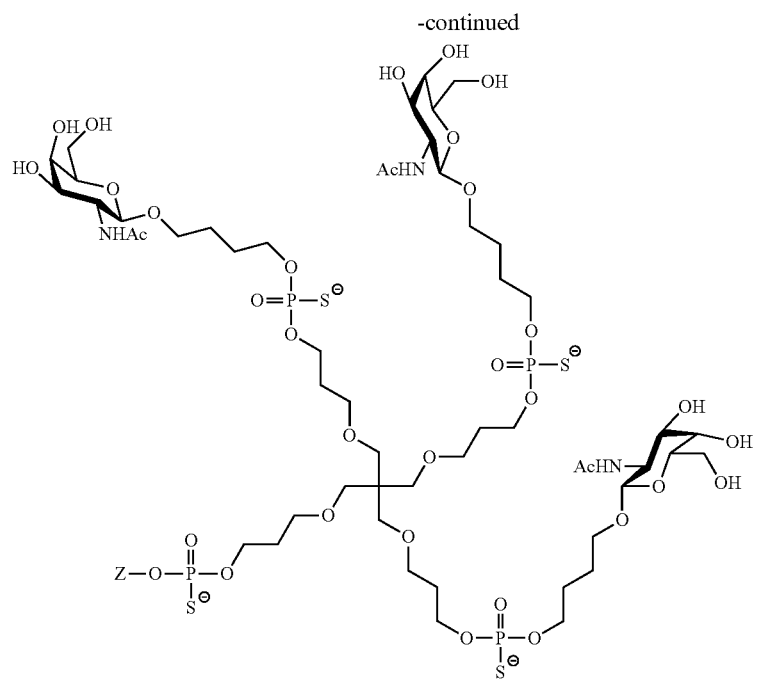
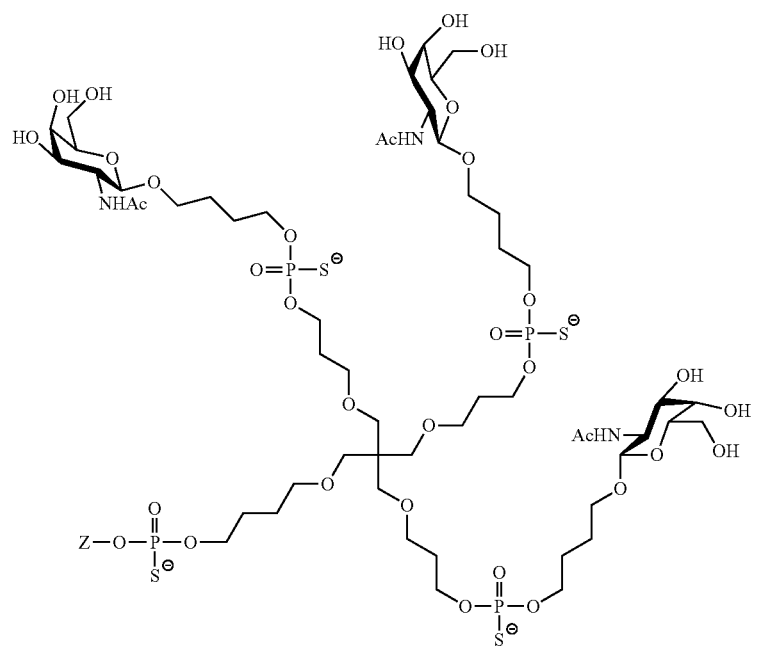

-continued
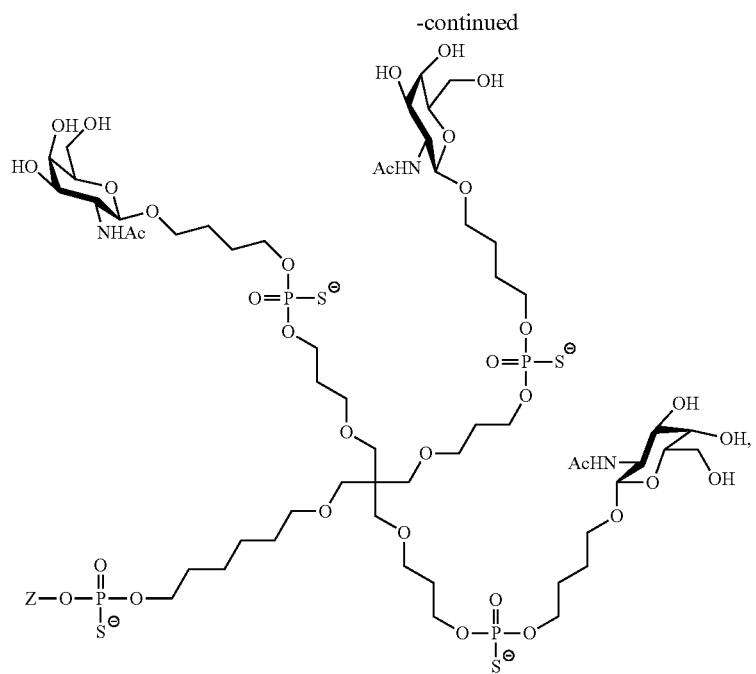
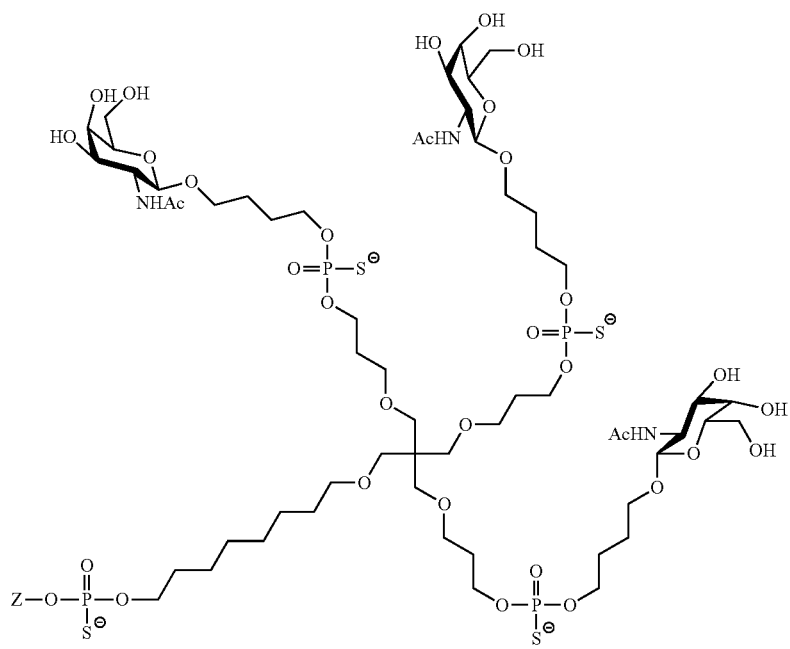

-continued
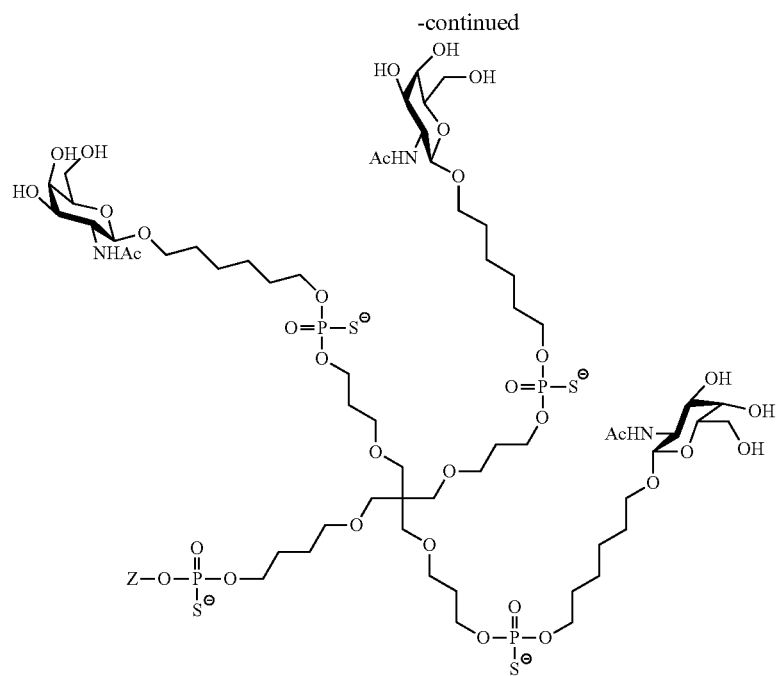
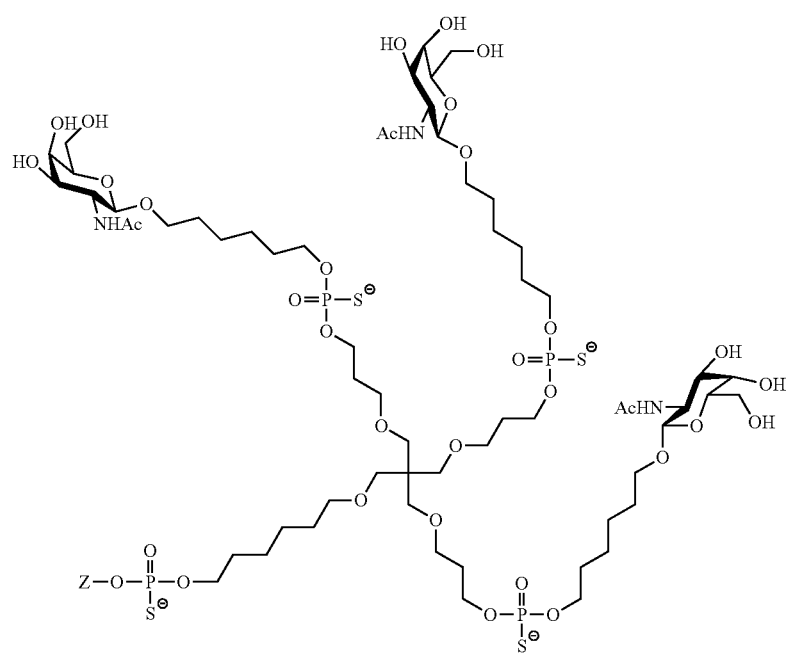

-continued

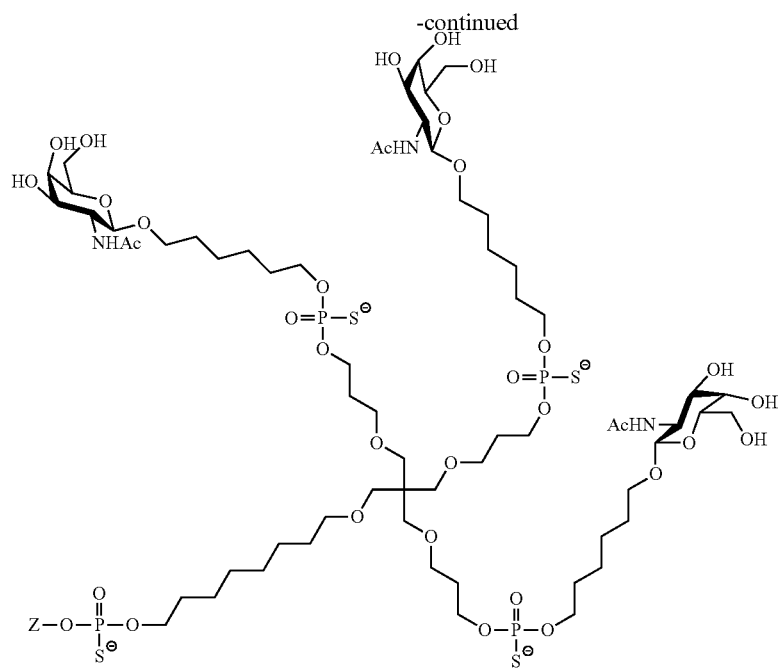

wherein Z is a nucleic acid according to any of statements 1 to 40.

47. A nucleic acid according to any of statements 1 to 40, which is conjugated to a ligand of the following structure

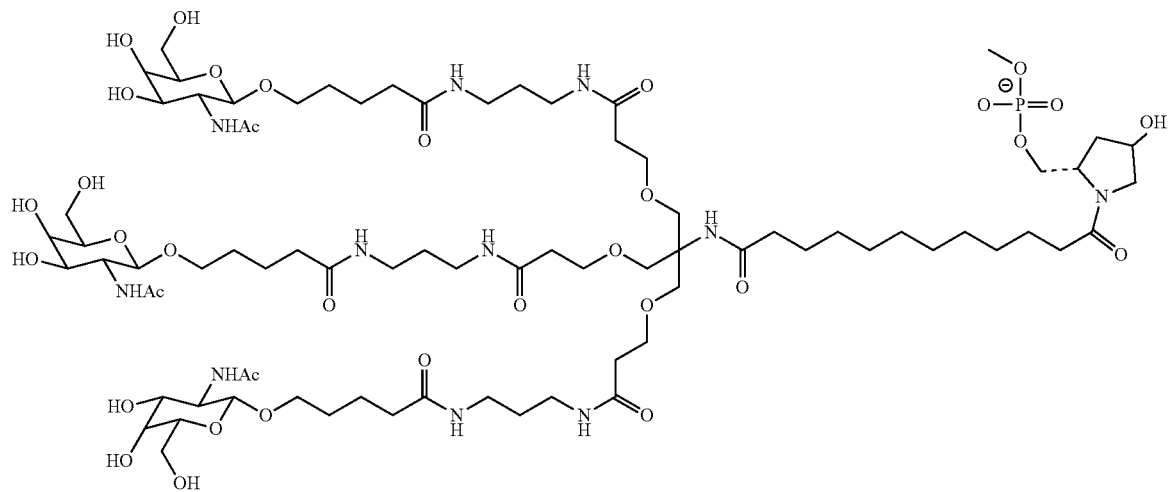

48. A nucleic acid or conjugated nucleic acid of any preceding statement, wherein the duplex comprises separate strands.

49. A nucleic acid or conjugated nucleic acid of any preceding statement, wherein the duplex comprises a single strand comprising a first strand and a second strand.

50. A composition comprising a nucleic acid or conjugated nucleic acid as defined in any preceding statement and a formulation comprising:
 i) a cationic lipid, or a pharmaceutically acceptable salt thereof;
 ii) a steroid;
 iii) a phosphatidylethanolamine phospholipid;
 iv) a PEGylated lipid.

51. A composition according to statement 50, wherein in the formulation the content of the cationic lipid component is from about 55 mol % to about 65 mol % of the overall lipid content of the lipid formulation, preferably about 59 mol % of the overall lipid content of the lipid formulation.

52. A composition as statemented in statement 50, wherein the formulation comprises;

A cationic lipid having the structure;

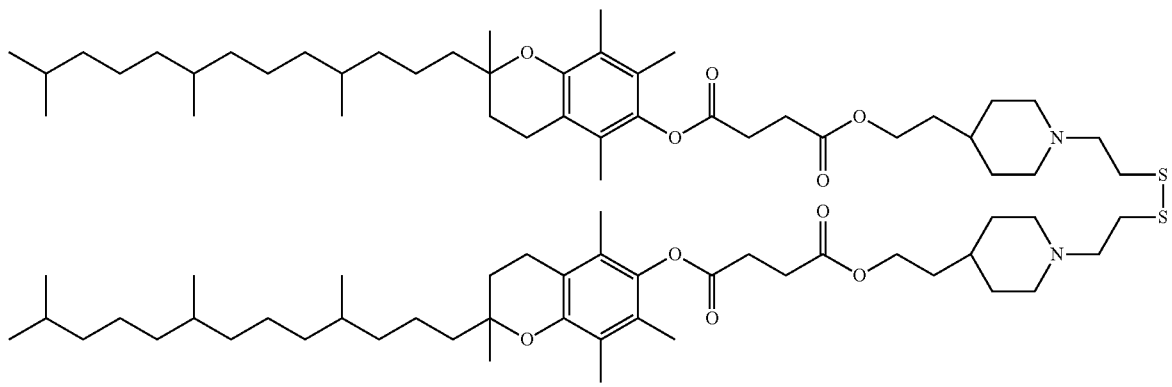 [SMILES: Cc1c(C)c2c(c(C)c1OC(=O)CCC(=O)OCCC1CCN(CCSSCCN3CCC(CCOC(=O)CCC(=O)Oc4c(C)c(C)c5c(c4C)CCC(C)(CCCC(C)CCCC(C)CCCC(C)C)O5)CC3)CC1)CCC(C)(CCCC(C)CCCC(C)CCCC(C)C)O2]

the steroid has the structure;

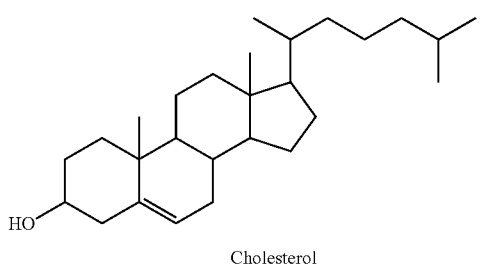 [SMILES: CC(C)CCCC(C)C1CCC2C3CC=C4CC(O)CCC4(C)C3CCC12C]

Cholesterol the a phosphatidylethanolamine phospholipid has the structure;

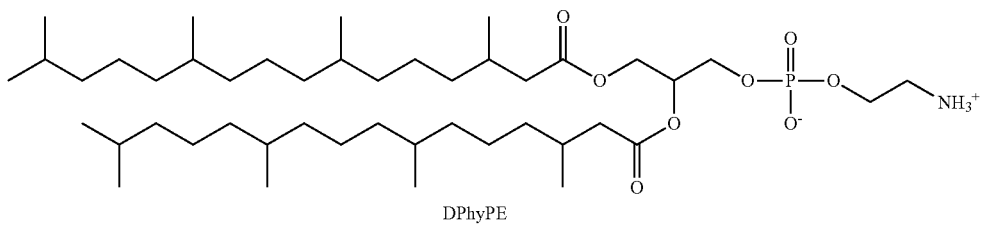 [SMILES: CC(C)CCCC(C)CCCC(C)CCCC(C)CC(=O)OCC(COP(=O)([O-])OCC[NH3+])OC(=O)CC(C)CCCC(C)CCCC(C)CCCC(C)C]

DPhyPE

And the PEGylated lipid has the structure;

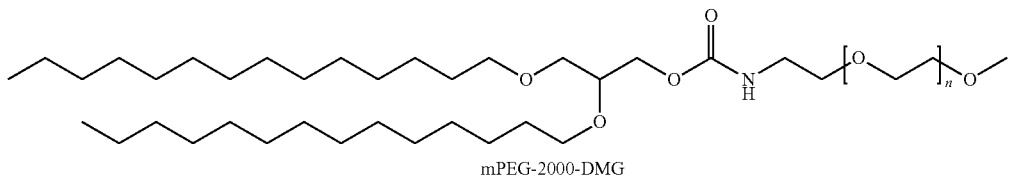

mPEG-2000-DMG

53. A composition comprising a nucleic acid or conjugated nucleic acid of any preceding statement and a physiologically acceptable excipient.

54. A nucleic acid or conjugated nucleic acid according to any preceding statement for use in the treatment of a disease or disorder.

55. Use of a nucleic acid or conjugated nucleic acid according to any preceding statement in the manufacture of a medicament for treating a disease or disorder.

56. A method of treating a disease or disorder comprising administration of a composition comprising a nucleic acid or conjugated nucleic acid according to any one preceding statement to an individual in need of treatment.

57. The method of statement 55, wherein the nucleic acid or conjugated nucleic acid is administered to the subject subcutaneously or intravenously.

58. Use or method according to any of statements 54 to 56, wherein said disease or disorder is selected from the group comprising hemochromatosis, erythropoietic porphyria, transfusional iron overload and blood disorders.

59. Use or method according to statement 58, wherein the blood disorder is β-thalassemias, sickle cell anaemia, congenital sideroblastic anemia, aplastic anemia or myelodysplastic syndrome.

60. Use or method according to any of statements 54 to 59, wherein the disorder is associated with iron overload.

61. Use or method according to statement 60, wherein the disorder associated with iron overload is Parkinson's Disease, Alzheimer's Disease or Friedreich's Ataxia.

62. A process for making a nucleic acid or conjugated nucleic acid according to any of statements 1 to 49.

BRIEF DESCRIPTION OF THE DRAWINGS

The invention will now be described with reference to the following non-limiting figures and examples in which:

FIG. 7 shows the GalNAc conjugated RNAi molecules used in examples 1, 3, 4, 26 to 31 and 34 to 38;

FIG. 12 shows the sequences and modifications of the GalNAc-siRNA molecules of Examples 8, 9 and 10;

FIG. 47 shows sequences and modification pattern of GalNAc siRNA conjugates that were tested for inhibition of TMPRSS6 expression in primary human hepatocytes.

FIG. 48 shows specific sequences of nucleic acids used in Example 44.

EXAMPLES

Example 1

Figure 1:
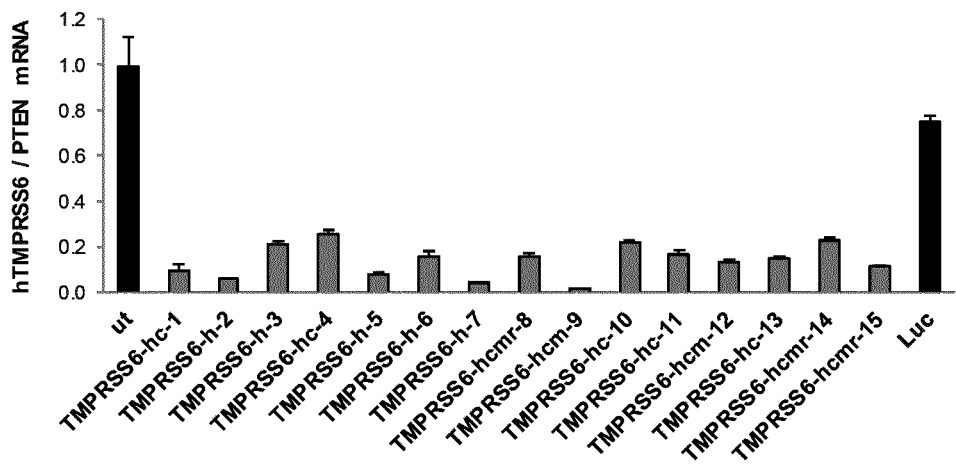
FIG. 1 shows the results of an RNAi molecule screen for inhibition of TMPRSS6 expression in human Hep3B cells.

Nucleic acids in accordance with the disclosure were synthesised, using the oligos as set out in the tables below.

The method of synthesis was as follows, using one of the sequences of the disclosure as an example:

STS012 (GN-TMPRSS6-hcm-9)
First Strand
5'mA (ps) fA (ps) mC fC mA fG mA fA mG fA mA fG mC fA mG fG mU (ps) fG (ps) mA 3' (SEQ ID NO: 111)
Second Strand
5'[ST23 (ps)]3 long trebler (ps) fU mC fA mC fC mU fG mC fU mU fC mU fU mC fU mG fG (ps) mU (ps) fU 3' (SEQ ID NO: 112)

fN (N=A, C, G, U) denotes 2'Fluoro, 2' DeoxyNucleosides mN (N=A, C, G, U) denotes 2'O Methyl Nucleosides (ps) indicates a phosphorothioate linkage ST23 is a GalNAc C4 phosphoramidite (structure components as below)

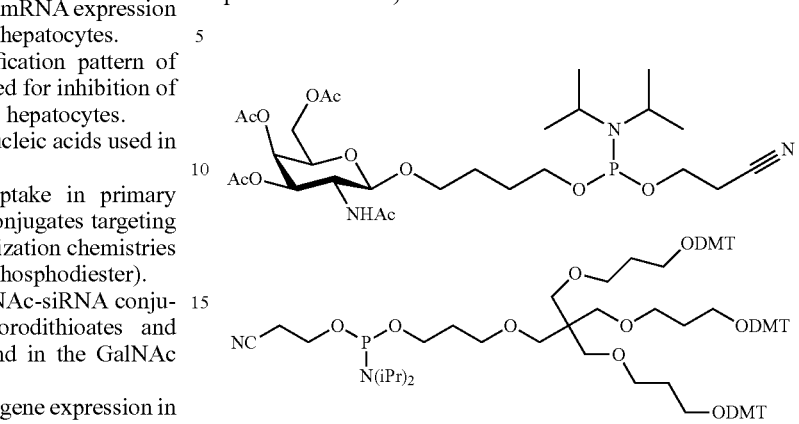

Long Trebler (STKS)

A further example is GN2-TMPRSS6-hcm-9 (STS12009L4):
First Strand
5'mA (ps) fA (ps) mC fC mA fG mA fA mG fA mA fG mC fA mG fG mU (ps) fG (ps) mA 3' (SEQ ID NO: 217)
Second Strand
5'[ST23 (ps)]3 ST41 (ps) fU mC fA mC fC mU fG mC fU mU fC mU fU mC fU mG fG (ps) mU (ps) fU 3' (SEQ ID NO: 218)

fN (N=A, C, G, U) denotes 2'Fluoro, 2' DeoxyNucleosides mN (N=A, C, G, U) denotes 2'O Methyl Nucleosides (ps) indicates a phosphorothioate linkage ST23 is as above.

ST41 is as follows (and as described in WO2017/174657):

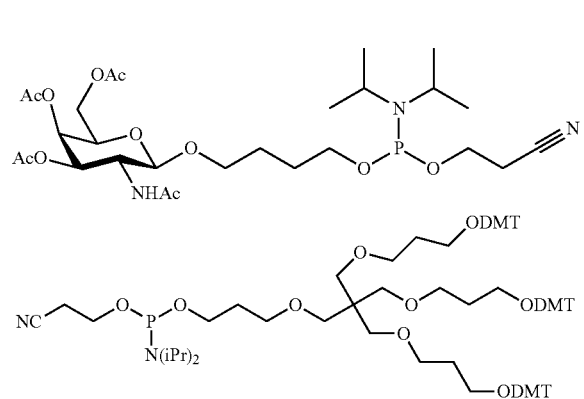

All Oligonucleotides were either obtained from a commercial oligonucleotide manufacturer (Eurogentech, Belgium; Biospring, Germany) or synthesized on an AKTA oligopilot synthesizer using standard phosphoramidite chemistry. Commercially available solid support and 2'-O-Methyl RNA phosphoramidtes, 2'Fluoro DNA phosphoramidites (all standard protection) and commercially available long trebler phosphoramidite (Glen research) were used. Synthesis was performed using 0.1 M solutions of the phosphoramidite in dry acetonitrile and benzylthiotetrazole (BTT) was used as activator (0.3M in acetonitrile). All other reagents were commercially available standard reagents.

Synthesis of PS2 containing oligonucleotides was performed according to the instructions of the manufacturer (Glen Research, AM Biotech). Vinyl-(E)-phosphonate 2'OMe-Uracil phosphoramidite was synthesized and used in oligonucleotide synthesis according to literature published methods (Haraszti et al., Nuc. Acids Res., 45(13), 2017, 7581-7592).

Conjugation of the GalNAc synthon (ST23) was achieved by coupling of the respective phosphoramidite to the 5'end of the oligochain under standard phosphoramidite coupling conditions. Phosphorothioates were introduced using standard commercially available thiolation reagents (EDITH, Link technologies).

The single strands were cleaved off the CPG by using Methylamine. Where TBDMS protected RNA nucleosides were used, additional treatment with TEA*3HF was performed to remove the silyl protection. The resulting crude oligonucleotide was purified by ion exchange chromatography (Resource Q, 6 mL, GE Healthcare) on a AKTA Pure HPLC System using a Sodium chloride gradient. Product containing fractions were pooled, desalted on a size exclusion column (Zetadex, EMP Biotech) and lyophilised.

For annealing, equimolar amounts of the respective single strands were dissolved in water and heated to 80° C. for 5 min. After cooling the resulting Duplex was lyophilised.

The sequences of the resulting nucleic acids (siRNAs) are set out in Table 1.

TABLE 1 nucleic acid sequences tested for inhibition of TMPRSS6 expression.
Nucleic acids were synthesized by Biospring, Frankfurt.
Nucleotides modifications are depicted by the following numbers
(column 4), 1 = 2'F-dU, 2 = F'-dA, 3 = 2F'-dC, 4 = 2'F-dG,
5 = 2'-OMe-dU; 6 = 2'-OMe-rA; 7 = 2'-OMe-dC; 8 = 2'-OMe-dG.

| SEQ ID NO: | Name - TMPRSS6- . . . | Sequence | Modifications |
|---|---|---|---|
| 1 | hc-1A | 5' augucuuucacacuggcuu 3' | 6181715172727184715 |
| 2 | hc-1B | 5' aagccagugugaaagacau 3' | 2647364545462646361 |
| 3 | h-2A | 5' auugaguacacgcagacug 3' | 6154645272747282718 |
| 4 | h-2B | 5' cagucugcguguacucaau 3' | 3645354745452717261 |
| 5 | h-3A | 5' aaguugauggugaucccgg 3' | 6281546184546173748 |
| 6 | h-3B | 5' ccgggaucaccaucaacuu 3' | 3748461727361726351 |
| 7 | hc-4A | 5' uucuggaucguccacuggc 3' | 5171846174537271847 |
| 8 | hc-4B | 5' gccaguggacgauccagaa 3' | 4736454827461736462 |
| 9 | h-5A | 5' auucacagaacagaggaac 3' | 6153636462728284627 |
| 10 | h-5B | 5' guuccucuguucugugaau 3' | 4517353545171818261 |
| 11 | h-6A | 5' guagucauggcuguccucu 3' | 8164536184718173535 |
| 12 | h-6B | 5' agaggacagccaugacuac 3' | 2828463647361827163 |
| 13 | h-7A | 5' aguuguaguaaguucccag 3' | 6451816452645173728 |
| 14 | h-7B | 5' cugggaacuuacuacaacu 3' | 3548462715271636271 |
| 15 | hcmr-8A | 5' uuguacccuaggaaauacc 3' | 5181637352846261637 |
| 16 | hcmr-8B | 5' gguauuuccugagguacaa 3' | 4816151735284816362 |
| 17 | hcm-9A | 5' aaccagaagaagcagguga 3' | 6273646282647284546 |
| 18 | hcm-9B | 5' ucaccugcuucuucugguu 3' | 1727354715351718451 |
| 19 | hc-10A | 5' uaacaacccagcguggaau 3' | 5263627372838184625 |
| 20 | hc-10B | 5' auuccacgcugggguuguua 3' | 2517363835484518152 |
| 21 | hc-11A | 5' guuucucucauccaggccg 3' | 8151717172537284738 |
| 22 | hc-11B | 5' cggccuggaugagagaaac 3' | 3847354825464646263 |
| 23 | hcm-12A | 5' gcaucuucgggcuuuggc 3' | 8361715354847151847 |
| 24 | hcm-12B | 5' gccaaagcccagaagaugc 3' | 4736264737282646183 |
| 25 | hc-13A | 5' ucacacuggaaggugaaug 3' | 5363635482648182618 |
| 26 | hc-13B | 5' cauucaccuuccaguguga 3' | 3615363715372818182 |
| 27 | hcmr-14A | 5' cacagaugugucgaccccg 3' | 7272825454538273738 |

TABLE 1-continued nucleic acid sequences tested for inhibition of TMPRSS6 expression.
Nucleic acids were synthesized by Biospring, Frankfurt.
Nucleotides modifications are depicted by the following numbers
(column 4), 1 = 2'F-dU, 2 = F'-dA, 3 = 2F'-dC, 4 = 2'F-dG,
5 = 2'-OMe-dU; 6 = 2'-OMe-rA; 7 = 2'-OMe-dC; 8 = 2'-OMe-dG.

| SEQ ID NO: | Name - TMPRSS6-... | Sequence | Modifications |
|---|---|---|---|
| 28 | hcmr-14B | 5'cggggucgacacaucugug 3' | 3848453827272535454 |
| 29 | hcmr-15A | 5'uguacccuaggaaauacca 3' | 5452737164826252736 |
| 30 | hcmr-15B | 5'ugguauuuccuagggguaca 3' | 1845251537164845272 |
| 31 | Luc-siRNA-1A | 5'ucgaaguauuccgcguacg 3' | 5382645251738381638 |
| 32 | Luc-siRNA-1B | 5'cguacgcggaauacuucga 3' | 3816383856252715382 |
| 33 | PTEN-A | 5'uaaguucuagcuguggugg 3' | 5a6g5u7u6g7u8u8g5g8 |
| 34 | PTEN-B | 5'ccaccacagcuagaacuua 3' | c7a7c6c6g7u6g6a7u5a |

TABLE 2 the start position of each nucleic acid sequence
within the TMPRSS6 mRNA sequence
Ref NM_001289000.1.

| Start | Oligo | Corresponding nucleic acid | SEQ ID NO: |
|---|---|---|---|
| 253 | GGUAUUUCCUAGGGUACAA | TMPRSS6-hcmr-8 | 16 |
| 305 | CAGUCUGCGUGUACUCAAU | TMPRSS6-h-2 | 4 |
| 381 | GCCAAAGCCCAGAAGAUGC | TMPRSS6-hcm-12 | 24 |
| 426 | CUGGGAACUUACUACAACU | TMPRSS6-h-7 | 14 |
| 478 | UCACCUGCUUCUUCUGGUU | TMPRSS6-hcm-9 | 18 |
| 652 | AAGCCAGUGUGAAAGACAU | TMPRSS6-hc-1 | 2 |
| 682 | AUUCCACGCUGGGUUGUUA | TMPRSS6-hc-10 | 20 |
| 1234 | GCCAGUGGACGAUCCAGAA | TMPRSS6-hc-4 | 8 |
| 1318 | CCGGGAUCACCAUCAACUU | TMPRSS6-h-3 | 6 |
| 1418 | GUUCCUCUGUUCUGUGAAU | TMPRSS6-h-5 | 10 |
| 1481 | CGGCCUGGAUGAGAGAAAC | TMPRSS6-hc-11 | 22 |
| 1633 | CAUUCACCUUCCAGUGUGA | TMPRSS6-hc-13 | 26 |
| 1824 | CGGGGUCGACACAUCUGUG | TMPRSS6-hcmr-14 | 28 |
| 2018 | AGAGGACAGCCAUGACUAC | TMPRSS6-h-6 | 12 |
| 252 | UGGUAUUUCCUAGGGUACA | TMPRRS6-hcmr-15 | 30 |

Screen for Inhibition TMPRSS6 Expression in Human Hep3B Cells.

Cells were plated at a cell density of 80,000 cells per 6 well dish. The following day cells were transfected with 20 nM nucleic acid (listed in Table 1) and 1 μg/ml AtuFECT (50:50 formulation of cationic lipid Atufect01 and fusogenic lipid DPhyPE). Two days after transfection cells were lysed and TMPRSS6 mRNA levels were determined by q-RT-PCR using the amplicons in Table 3. TMPRSS6 mRNA levels were normalized to expression levels of the house keeping gene PTEN. Nucleic acids for Luciferase and PTEN were used as non targeting control nucleic acids. Results are shown in FIG. 1.

TABLE 3

Sequences of TMPRSS6, Actin, PTEN and HAMP amplicon sets
that were used to measure mRNA levels of respective genes.

| | | SEQ ID NO: |
|---|---|---|
| hTMPRSS6 (upper) | 5'CCGCCAAAGCCCAGAAG 3' | 35 |
| hTMPRSS6 (lower) | 5'GGTCCCTCCCCAAAGGAATAG 3' | 36 |
| hTMPRSS6 (probe) | 5'CAGCACCCGCCTGGGAACTTACTACAAC 3' | 37 |
| mTMPRSS6 (upper) | 5'CGGCACCTACCTTCCACTCTT 3' | 38 |
| mTMPRSS6 (lower) | 5'TCGGTGGTGGGCATCCT 3' | 39 |
| mTMPRSS6 (probe) | 5'CCGAGATGTTTCCAGCTCCCCTGTTCTA 3' | 40 |

TABLE 3-continued

Sequences of TMPRSS6, Actin, PTEN and HAMP amplicon sets that were used to measure mRNA levels of respective genes.

| | | SEQ ID NO: |
|---|---|---|
| h-Aktin (upper) | 5'GCATGGGTCAGAAGGATTCCTAT 3' | 41 |
| h-Aktin (lower) | 5'TGTAGAAGGTGTGGTGCCAGATT 3' | 42 |
| h-Aktin (probe) | 5'TCGAGCACGGCATCGTCACCAA 3' | 43 |
| mAktin (upper) | 5'GTTTGAGACCTTCAACACCCCA 3' | 44 |
| mAktin (lower) | 5'GACCAGAGGCATACAGGGACA 3' | 45 |
| mAktin (probe) | 5'CCATGTACGTAGCCATCCAGGCTGTG 3' | 46 |
| PTEN (upper) | 5'CACCGCCAAATTTAACTGCAGA 3' | 47 |
| PTEN (lower) | 5'AAGGGTTTGATAAGTTCTAGCTGT 3' | 48 |
| PTEN (probe) | 5'TGCACAGTATCCTTTTGAAGACCATAACCCA 3' | 49 |
| mHAMP: (upper) | 5'CCTGTCTCCTGCTTCTCCTCCT 3' | 50 |
| mHAMP: (lower) | 5'AATGTCTGCCCTGCTTTCTTCC 3' | 51 |
| mHAMP: (probe) | 5'TGAGCAGCACCACCTATCTCCATCAACA3' | 52 |

Example 2

Dose Response of TMPRSS6 Nucleic Acids for Inhibition of TMPRSS6 Expression in Human Hep3B Cells.

Figure 2:
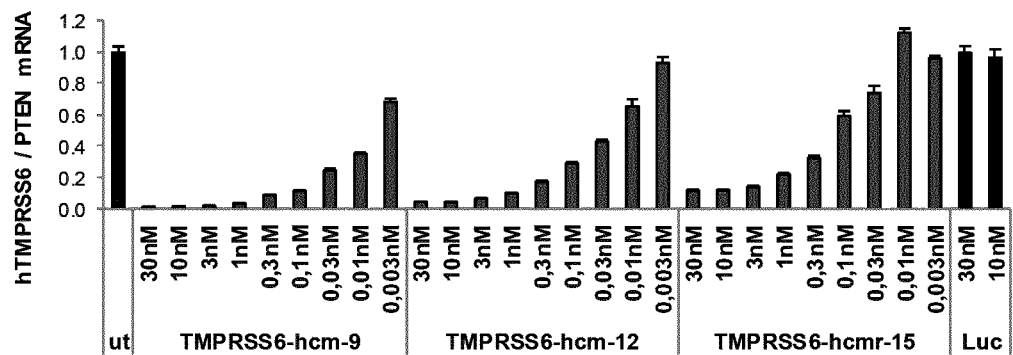
FIG. 2 shows the dose response of TMPRSS6 RNAi molecules in human Hep3B cells.

Cells were plated at a cell density of 150,000 cells per 6 well dish. The following day cells were transfected with 1 µg/ml AtuFECT (50:50 formulation of cationic lipid Atufect01 and fusogenic lipid DPhyPE) and different amounts of TMPRSS6 nucleic acids (30; 10; 3; 1; 0.3; 0.1, 0.003 nM, respectively) as depicted by the X-axis of the graph in FIG. 2. For non targeting control samples, cells were transfected with 30 and 10 nM nucleic acid for Luciferase. Two days after the transfection cells were lysed and mRNA levels were determined by q-RT-PCR. TMPRSS6 mRNA levels were normalized to the expression levels of the house keeping gene PTEN. The highest reduction of TMPRSS6 mRNA expression was observed by TMPRSS6-hcm9 nucleic acid. Transfection with Luciferase nucleic acid did not affect TMPRSS6 mRNA levels. Results are shown in FIG. 2. Sequences of RNAi molecules are depicted in Table 1.

Example 3

Inhibition of TMPRSS6 Expression in Liver Tissue by Different Doses of GalNAc Nucleic Acids.

Figure 3:
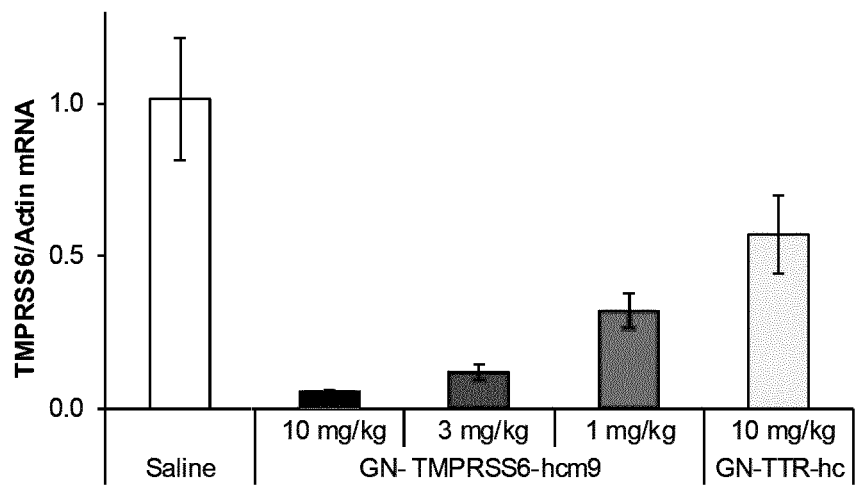
FIG. 3 shows the reduction of TMPRSS6 expression in mouse liver tissue by different doses of GalNAc siRNA molecules.

C57/BL6 mice were treated with a single dose of 10, 3 or 1 mg/kg of GalNAc nucleic acid conjugates by subcutaneous administration. Sequence and modifications of respective siRNA conjugates are shown in FIG. 7. The siRNAs are conjugated to GalNAc linker (GN) depicted in FIG. 8a and described therein. Control groups were treated with isotonic saline or with non targeting control conjugate, GN-TTR-hc, respectively. Target gene expression in liver tissue was assessed by qRT PCR three days after subcutaneous injection of the conjugates. Total RNA was isolated from snap frozen tissue samples and qRT-PCR was performed as described previously (Kuhla et al. 2015, Apoptosis Vol 4, 500-11). TaqMan probes that were used are shown in Table 3. Results are shown in FIG. 3.

Example 4

Duration of Target Gene Inhibition by TMPRSS6 RNAi Molecules.

Figure 4:
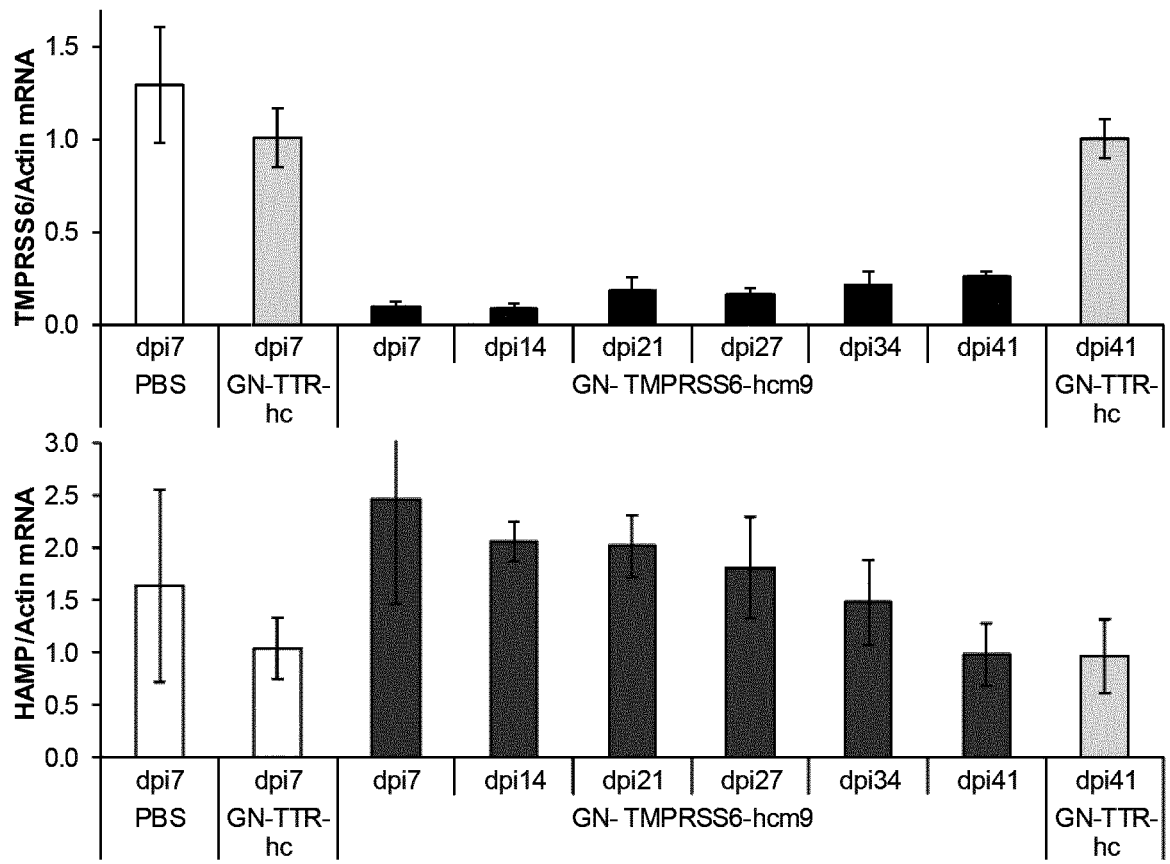
FIG. 4 shows the duration of TMPRSS6 target gene inhibition by TMPRSS6 siRNA molecules and the induction of HAMP mRNA expression in mice.

Mice were treated with 3 mg/kg GalNAc-TMPRSS6 RNAi molecules by subcutaneous injection. Sequence and modifications of respective siRNA conjugates are shown in FIG. 7. Target mRNA expression was assessed in liver tissue at day 7, 14, 21, 27, 34 or day 41 after treatment (days post injection, dpi). Reduction of TMPRSS6 expression in the liver is observed until day 41 after injection. HAMP (hepcidin) mRNA expression is upregulated in the liver of mice treated with GN-TMPRSS6 RNAi molecule. Results are shown in FIG. 4.

Example 5

Inhibition of TMPRSS6 Expression by Treatment with TMPRSS6 siRNA Reduces Iron Levels in Blood.

Figure 5:
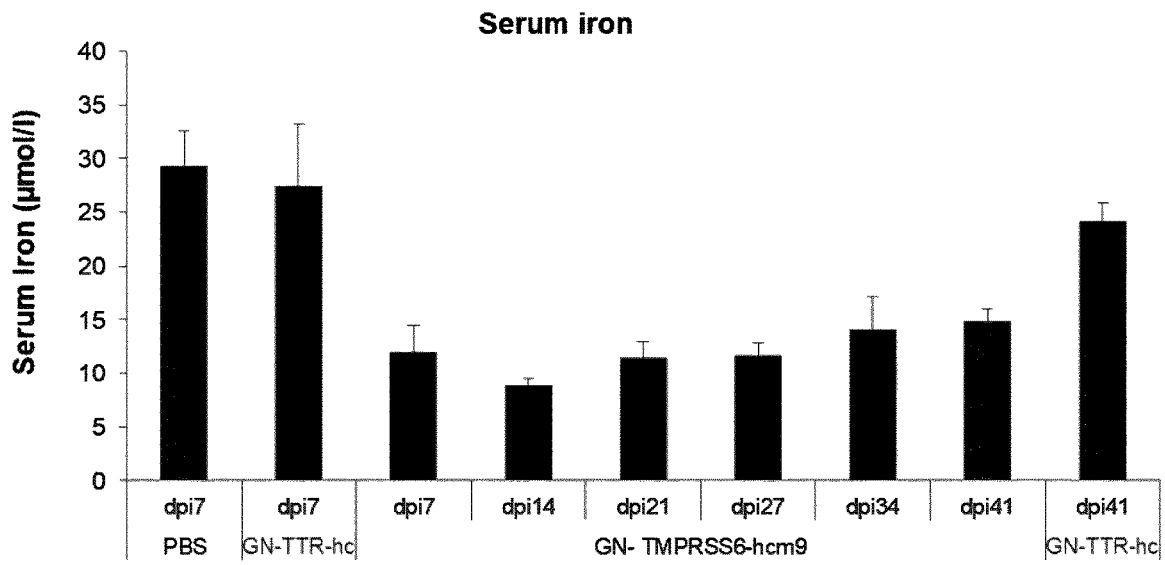
FIG. 5 shows that the inhibition of TMPRSS6 expression by treatment with TMPRSS6 siRNA molecules reduces iron levels in serum for an extended time.

Iron levels were analyzed in serum 7, 14, 21, 27, 34 and 41 days after mice were treated subcutaneously with 3 mg/kg GalNAc nucleic acid conjugates. Serum iron levels were reduced up to 41 days post injection (dpi 41). Sequence and modifications of respective siRNA conjugates are shown in FIG. 7. Results are shown in FIG. 5.

Example 6

Inhibition of TMPRSS6 Expression by Receptor Mediated Uptake.

Figure 6:
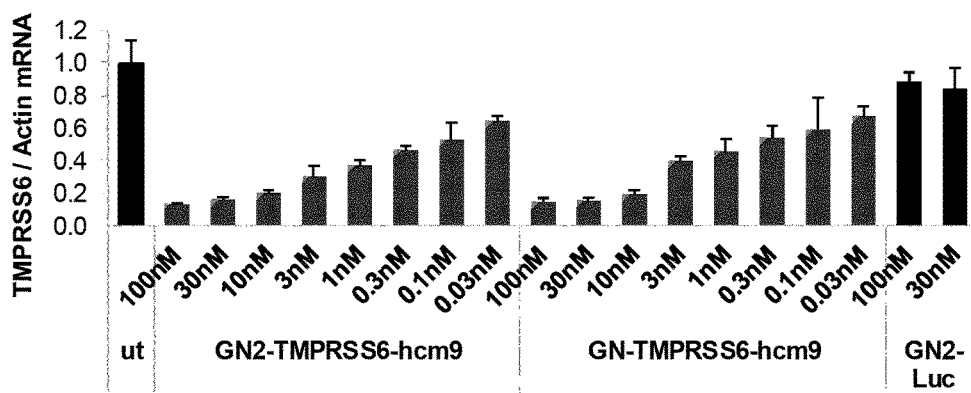
FIG. 6 shows the reduction of TMRPSS6 expression in 1° mouse hepatocytes by receptor mediated uptake of GalNAc conjugated RNAi molecules.

Primary mouse hepatocytes were plated on collagen coated dishes and incubated with siRNA conjugates diluted in cell culture medium at a concentration of 100 nM to 0.03 nM as indicated. 24 hours after exposing the cells to siRNA conjugates, total RNA was extracted and TMPRSS6 expression was quantified by Taqman qRT-PCR. TMPRSS6 mRNA levels were normalized to Actin mRNA levels. Dose dependent inhibition of TMPRSS6 expression was observed by both GalNAc-TMPRSS6 siRNA conjugates. GN2-Luc-siRNA1 GalNAc conjugate (GN2-Luc) was used as non targeting control and did not affect TMPRSS6 mRNA expression. Sequence and modifications of respective siRNA conjugates are depicted in FIG. 7. Results are shown in FIG. 6.

Example 7

Further TMPRSS6 siRNAs were synthesised, in accordance with the method described above. The sequences and modifications are shown in Table 4 below:

Modification variants of an siRNA targeting TMPRSS6 (Sequence ID 17 and ID18). For each duplex, the first sequence (A strand) is listed on top and the second sequence (B strand) below. All sequences correspond to SEQ ID NO:17 (top) and SEQ ID NO:18 (bottom). Modification codes are listed at the end of the Table 4.

TABLE 4

Modifications are depicted by numbers shown in the rows at the bottom of the table, and for each duplex the first strand is on top and the second strand is below.

| Duplex ID | A strand B strand | sequence (5'-3') | sequence and chemistry (5'-3') |
|---|---|---|---|
| TMP01 | TMPJH01A | aaccagaagaagcagguga | 6273646282647284546 |
|  | TMPJH01B | ucaccugcuucuucggguu | 1727354715351718451 |
| TMP02 | TMPJH02A | aaccagaagaagcagguga | 2237242282243284142 |
|  | TMPJH02B | ucaccugcuucuucggguu | 1723314715355754815 |
| TMP03 | TMPJH03A | aaccagaagaagcagguga | 2273282646283248182 |
|  | TMPJH03B | ucaccugcuucuucggguu | 5363718351715354815 |
| TMP04 | TMPJH04A | aaccagaagaagcagguga | 2273282646683248182 |
|  | TMPJH03B | ucaccugcuucuucggguu | 5363718351715354815 |
| TMP05 | TMPJH01A | aaccagaagaagcagguga | 6273646282647284546 |
|  | TMPJH03B | ucaccugcuucuucggguu | 5363718351715354815 |
| TMP06 | TMPJH05A | aaccagaagaagcagguga | 2273242242643244542 |
|  | TMPJH05B | ucaccugcuucuucggguu | 5727354315355754455 |
| TMP07 | TMPJH06A | aaccagaagaagcagguga | 2277646242643244542 |
|  | TMPJH05B | ucaccugcuucuucggguu | 5727354315355754455 |
| TMP08 | TMPJH07A | aaccagaagaagcagguga | 2277686242643244542 |
|  | TMPJH05B | ucaccugcuucuucggguu | 5727354315355754455 |
| TMP09 | TMPJH08A | aaccagaagaagcagguga | 2273242246687244542 |
|  | TMPJH05B | ucaccugcuucuucggguu | 5727354315355754455 |
| TMP10 | TMPJH09A | aaccagaagaagcagguga | 2273242682687244542 |
|  | TMPJH05B | ucaccugcuucuucggguu | 5727354315355754455 |
| TMP11 | TMPJH10A | aaccagaagaagcagguga | 2273242242643284586 |
|  | TMPJH05B | ucaccugcuucuucggguu | 5727354315355754455 |
| TMP12 | TMPJH11A | aaccagaagaagcagguga | 2273242242643288586 |
|  | TMPJH05B | ucaccugcuucuucggguu | 5727354315355754455 |
| TMP13 | TMPJH12A | aaccagaagaagcagguga | 2273242246687284586 |
|  | TMPJH05B | ucaccugcuucuucggguu | 5727354315355754455 |
| TMP14 | TMPJH13A | aaccagaagaagcagguga | 6277646246687284586 |
|  | TMPJH13B | ucaccugcuucuucggguu | 5767354315755758855 |
| TMP15 | TMPJH14A | aaccagaagaagcagguga | 2273282282283284182 |
|  | TMPJH14B | ucaccugcuucuucggguu | 5327318315315318415 |
| TMP16 | TMPJH15A | aaccagaagaagcagguga | 2273282282643284182 |
|  | TMPJH14B | ucaccugcuucuucggguu | 5327318315315318415 |
| TMP17 | TMPJH16A | aaccagaagaagcagguga | 2237242242247244582 |
|  | TMPJH16B | ucaccugcuucuucggguu | 1723314355311358411 |
| TMP18 | TMPJH10A | aaccagaagaagcagguga | 2273242242643284586 |
|  | TMPJH01B | ucaccugcuucuucggguu | 1727354715351718451 |

TABLE 4-continued

Modifications are depicted by numbers shown in the rows at the bottome of the table, and for each duplex the first strand is on top and the second strand is below.

| Duplex ID | A strand B strand | sequence (5'-3') | sequence and chemistry (5'-3') |
|---|---|---|---|
| TMP19 | TMPJH10A<br>TMPJH02B | aaccagaagaagcagguga<br>ucaccugcuucuucugguu | 2273242242643284586<br>1723314715355754815 |
| TMP20 | TMPJH10A<br>TMPJH03B | aaccagaagaagcagguga<br>ucaccugcuucuucugguu | 2273242242643284586<br>5363718351715354815 |
| TMP21 | TMPJH10A<br>TMPJH13B | aaccagaagaagcagguga<br>ucaccugcuucuucugguu | 2273242242643284586<br>5767354315755758855 |
| TMP22 | TMPJH10A<br>TMPJH14B | aaccagaagaagcagguga<br>ucaccugcuucuucugguu | 2273242242643284586<br>5327318315315318415 |
| TMP23 | TMPJH10A<br>TMPJH16B | aaccagaagaagcagguga<br>ucaccugcuucuucugguu | 2273242242643284586<br>1723314355311358411 |
| TMP24 | TMPJH02A<br>TMPJH01B | aaccagaagaagcagguga<br>ucaccugcuucuucugguu | 2237242282243284142<br>1727354715351718451 |
| TMP25 | TMPJH02A<br>TMPJH03B | aaccagaagaagcagguga<br>ucaccugcuucuucugguu | 2237242282243284142<br>5363718351715354815 |
| TMP26 | TMPJH02A<br>TMPJH05B | aaccagaagaagcagguga<br>ucaccugcuucuucugguu | 2237242282243284142<br>5727354315355754455 |
| TMP27 | TMPJH02A<br>TMPJH13B | aaccagaagaagcagguga<br>ucaccugcuucuucugguu | 2237242282243284142<br>5767354315755758855 |
| TMP28 | TMPJH02A<br>TMPJH14B | aaccagaagaagcagguga<br>ucaccugcuucuucugguu | 2237242282243284142<br>5327318315315318415 |
| TMP29 | TMPJH02A<br>TMPJH16B | aaccagaagaagcagguga<br>ucaccugcuucuucugguu | 2237242282243284142<br>1723314355311358411 |
| TMP30 | TMPJH13A<br>TMPJH01B | aaccagaagaagcagguga<br>ucaccugcuucuucugguu | 6277646246687284586<br>1727354715351718451 |
| TMP31 | TMPJH13A<br>TMPJH02B | aaccagaagaagcagguga<br>ucaccugcuucuucugguu | 6277646246687284586<br>1723314715355754815 |
| TMP32 | TMPJH13A<br>TMPJH03B | aaccagaagaagcagguga<br>ucaccugcuucuucugguu | 6277646246687284586<br>5363718351715354815 |
| TMP33 | TMPJH13A<br>TMPJH05B | aaccagaagaagcagguga<br>ucaccugcuucuucugguu | 6277646246687284586<br>5727354315355754455 |
| TMP34 | TMPJH13A<br>TMPJH14B | aaccagaagaagcagguga<br>ucaccugcuucuucugguu | 6277646246687284586<br>5327318315315318415 |
| TMP35 | TMPJH13A<br>TMPJH16B | aaccagaagaagcagguga<br>ucaccugcuucuucugguu | 6277646246687284586<br>1723314355311358411 |
| TMP36 | TMPJH10A<br>TMPJH01B | aaccagaagaagcagguga<br>ucaccugcuucuucugguu | 2273242242643284586<br>1727354715351718451 |
| TMP37 | TMPJH17A<br>TMPJH01B | aaccagaagaagcagguga<br>ucaccugcuucuucugguu | 2273282242643284586<br>1727354715351718451 |
| TMP38 | TMPJH18A<br>TMPJH01B | aaccagaagaagcagguga<br>ucaccugcuucuucugguu | 6277682242643288142<br>1727354715351718451 |
| TMP39 | TMPJH19A<br>TMPJH01B | aaccagaagaagcagguga<br>ucaccugcuucuucugguu | 6277682242643288586<br>1727354715351718451 |
| TMP40 | TMPJH20A<br>TMPJH01B | aaccagaagaagcagguga<br>ucaccugcuucuucugguu | 2233282242643284142<br>1727354715351718451 |
| TMP41 | TMPJH21A<br>TMPJH01B | aaccagaagaagcagguga<br>ucaccugcuucuucugguu | 2277282242643284586<br>1727354715351718451 |
| TMP42 | TMPJH22A<br>TMPJH01B | aaccagaagaagcagguga<br>ucaccugcuucuucugguu | 2273282642643284586<br>1727354715351718451 |

TABLE 4-continued

Modifications are depicted by numbers shown in the rows at the bottome of the table, and for each duplex the first strand is on top and the second strand is below.

| Duplex ID | A strand B strand | sequence (5'-3') | sequence and chemistry (5'-3') |
|---|---|---|---|
| TMP43 | TMPJH23A<br>TMPJH01B | aaccagaagaagcagguga<br>ucaccugcuucuucugguu | 2273282282643284586<br>17273547153517184451 |
| TMP44 | TMPJH24A<br>TMPJH01B | aaccagaagaagcagguga<br>ucaccugcuucuucugguu | 2273282246643284586<br>17273547153517184451 |
| TMP45 | TMPJH25A<br>TMPJH01B | aaccagaagaagcagguga<br>ucaccugcuucuucugguu | 2273282242683284586<br>17273547153517184451 |
| TMP46 | TMPJH26A<br>TMPJH01B | aaccagaagaagcagguga<br>ucaccugcuucuucugguu | 2273282242647284586<br>17273547153517184451 |
| TMP47 | TMPJH01A<br>TMPJH05B | aaccagaagaagcagguga<br>ucaccugcuucuucugguu | 6273646282647284546<br>5727354315355754455 |
| TMP48 | TMPJH01A<br>TMPJH27B | aaccagaagaagcagguga<br>ucaccugcuucuucugguu | 6273646282647284546<br>5727754715355754855 |
| TMP49 | TMPJH01A<br>TMPJH28B | aaccagaagaagcagguga<br>ucaccugcuucuucugguu | 6273646282647284546<br>1723314311351714411 |
| TMP50 | TMPJH01A<br>TMPJH29B | aaccagaagaagcagguga<br>ucaccugcuucuucugguu | 6273646282647284546<br>5767354315355754455 |
| TMP51 | TMPJH01A<br>TMPJH30B | aaccagaagaagcagguga<br>ucaccugcuucuucugguu | 6273646282647284546<br>5727754315355754455 |
| TMP52 | TMPJH01A<br>TMPJH31B | aaccagaagaagcagguga<br>ucaccugcuucuucugguu | 6273646282647284546<br>5727358315355754455 |
| TMP53 | TMPJH01A<br>TMPJH32B | aaccagaagaagcagguga<br>ucaccugcuucuucugguu | 6273646282647284546<br>5727354315755754455 |
| TMP54 | TMPJH01A<br>TMPJH33B | aaccagaagaagcagguga<br>ucaccugcuucuucugguu | 6273646282647284546<br>5727354315355758455 |

1 = 2'F-dU
2 = 2'F-dA
3 = 2'F-dC
4 = 2'F-dG
5 = 2'OMe-rU
6 = 2'OMe-rA
7 = 2'OMe-rC
8 = 2'OMe-rG

Figure 9:
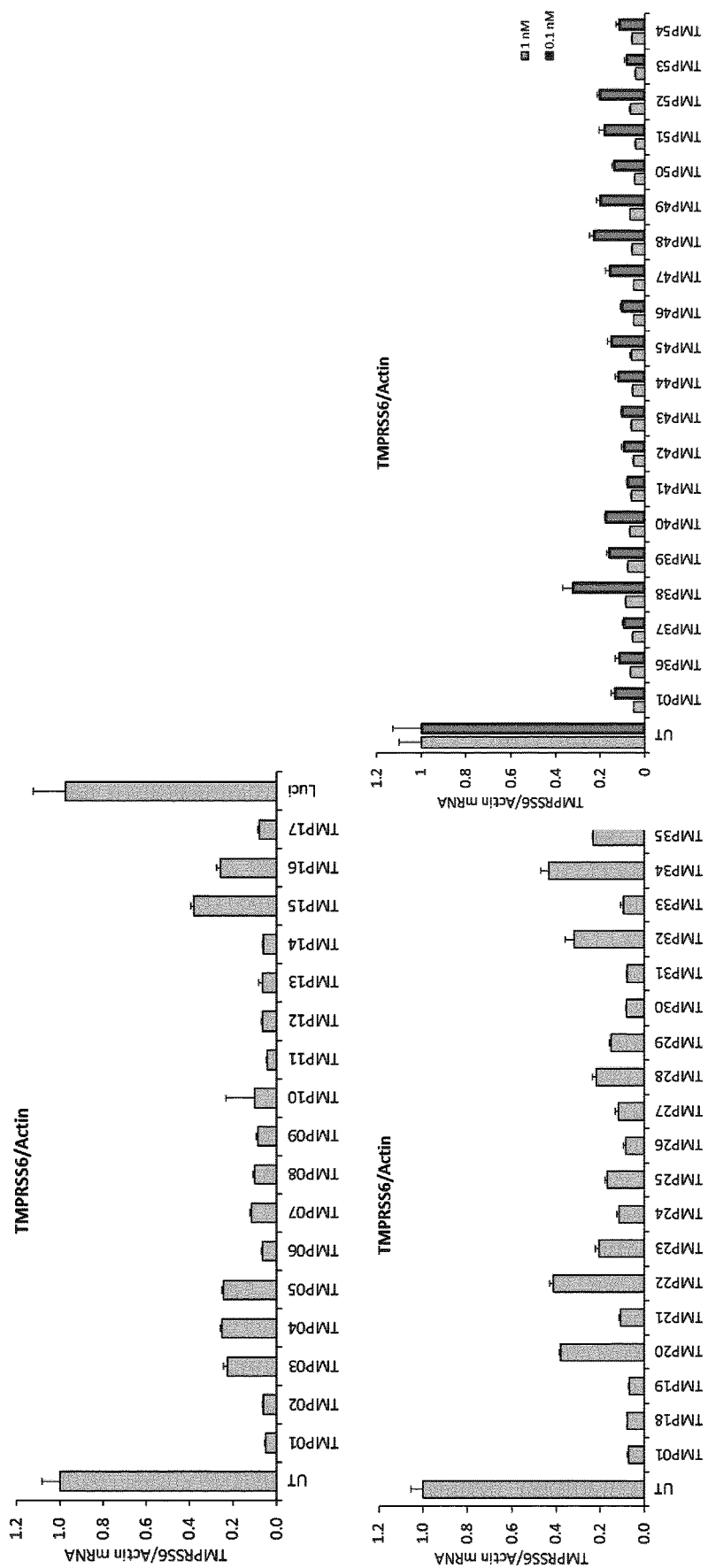
FIG. 9 shows the reduction of TMPRSS6 expression by different siRNA modification variants in human Hep3B cells.

Different modification variants of one siRNA targeting TMPRSS6 were tested in human Hep3B cells. siRNAs targeting PTEN and Luciferase were used as non-related and non-targeting controls, respectively. All siRNAs were transfected with 1 μg/ml Atufect at 1 nM (0.1 nM when indicated). Total RNA was extracted 48 h after transfection and TMPRSS6 mRNA levels were quantified by Taqman qRT-PCR. TMPRSS6 mRNA levels were normalized to Actin mRNA levels. Each bar represents mean+/−SD of three technical replicates. The results are shown in FIG. 9.

Example 8

Modification variants of a GalNAc-conjugated siRNA targeting TMPRSS6 were synthesised and are shown in FIG. 12. For each duplex, the first strand sequence is listed on top and the second strand sequence below. Modifications are depicted as numbers and are as follows: GN indicates conjugation to a GalNAc linker in accordance with FIG. 8*a*. The sequence and modification of STS12 (GN-TMPRSS6-hcm9) is also depicted in FIG. 7.

Example 9

Figure 10:
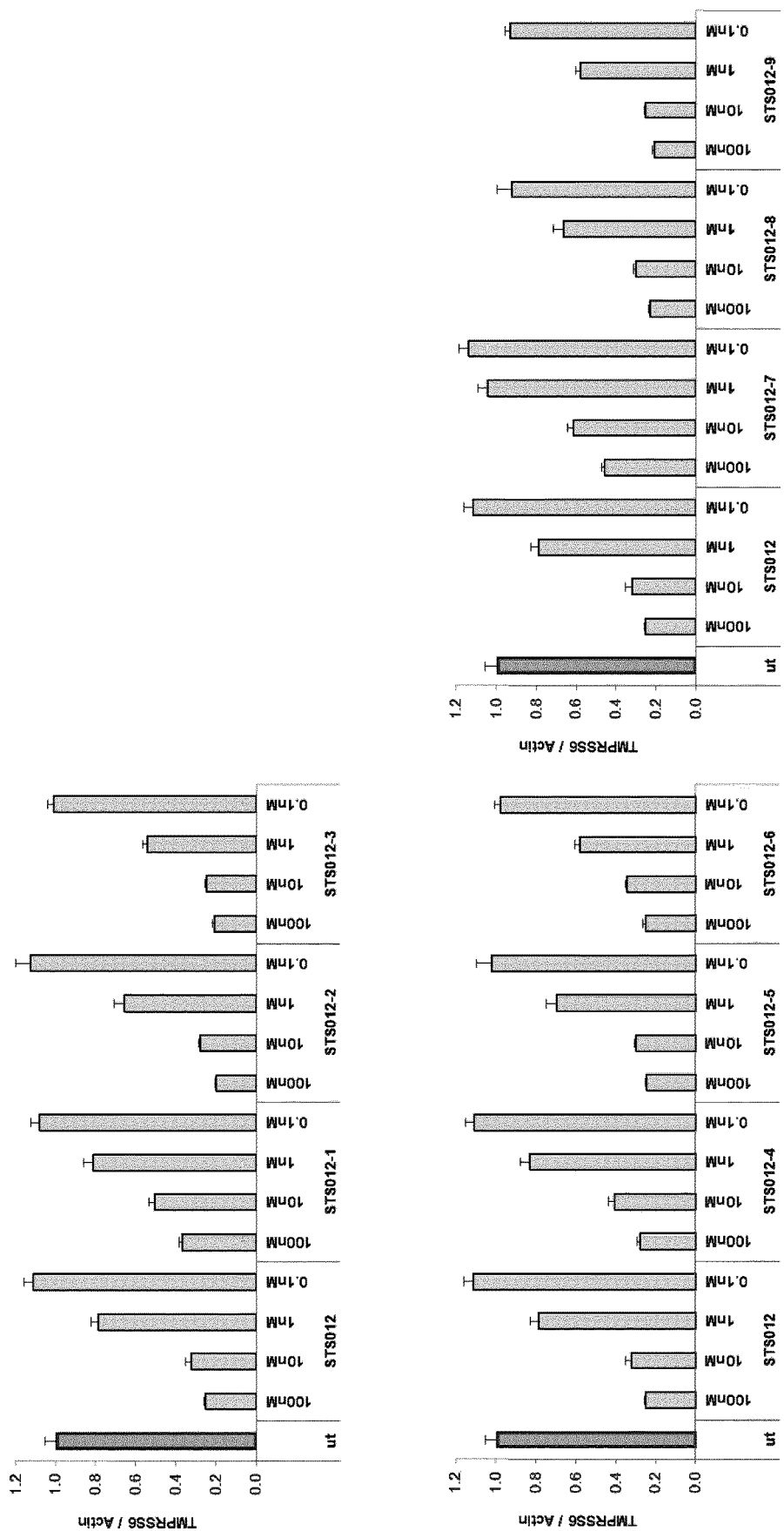
FIG. 10 shows the reduction of TMPRSS6 expression by different GalNAc-siRNA conjugates by receptor mediated uptake.

Different modification variants of one GalNAc conjugated sequence targeting TMPRSS6 (STS012) reduce TMPRSS6 expression in mouse primary hepatocytes. For receptor-mediated uptake, cells were incubated with 100, 10, 1 and 0.1 nM siRNA conjugate for 24 hours. Total RNA was extracted and TMPRSS6 mRNA levels were quantified by Taqman qRT-PCR. TMPRSS6 mRNA levels were normalized to Actin mRNA levels. Mean+/−SD of each three technical replicates are shown in FIG. 10.

Example 10

Figure 11:
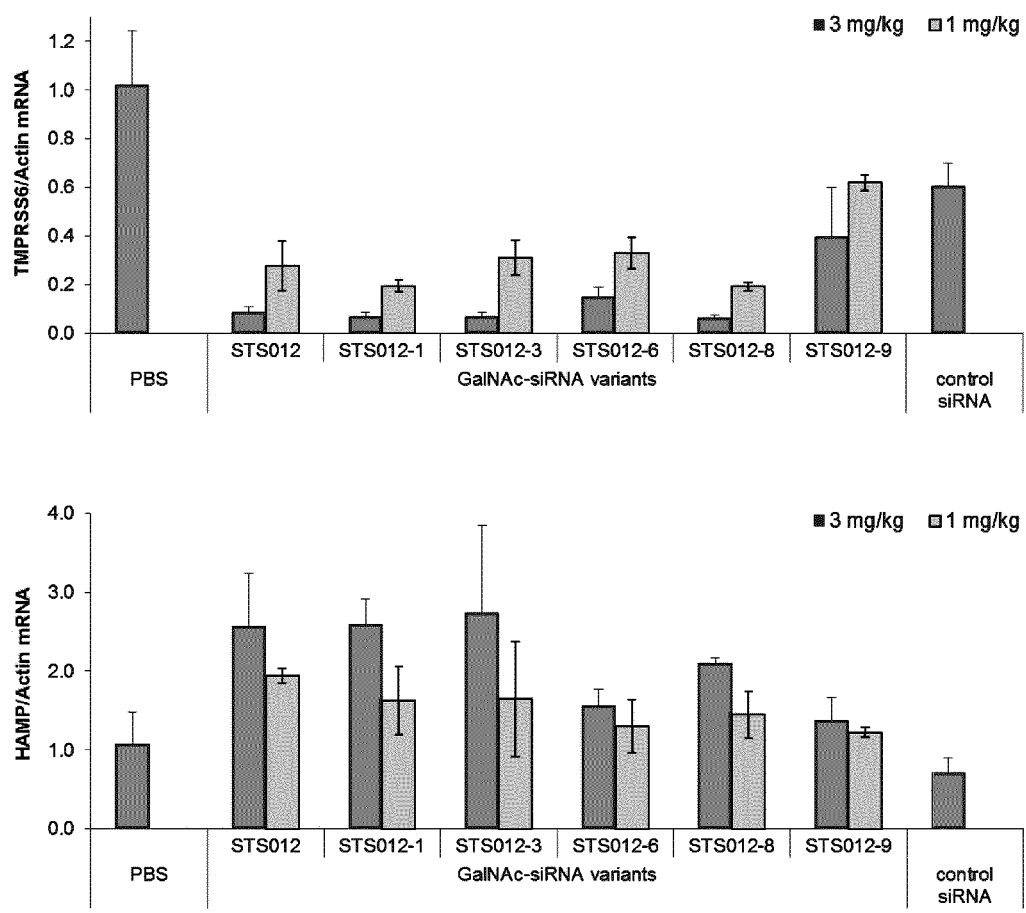
FIG. 11 shows the reduction of TMPRSS6 and the induction of HAMP expression by different GalNAc-siRNA conjugates in mice.

Different modification variants of one GalNAc-conjugated sequence targeting TMPRSS6 (STS012, GN-TMPRSS6-hcm9) were tested in vivo. 1 mg/kg and 3 mg/kg GalNAc-siRNA conjugate were subcutaneously injected into male C57BL/6JOIaHsd mice. 14 days after treatment, TMPRSS6 (A) and HAMP (B) mRNA levels in the liver were analyzed by Taqman qRT-PCR. Bars represent mean of at least 4 animals+/−SD. Results are shown in FIG. 11.

Example 11

Figure 13:
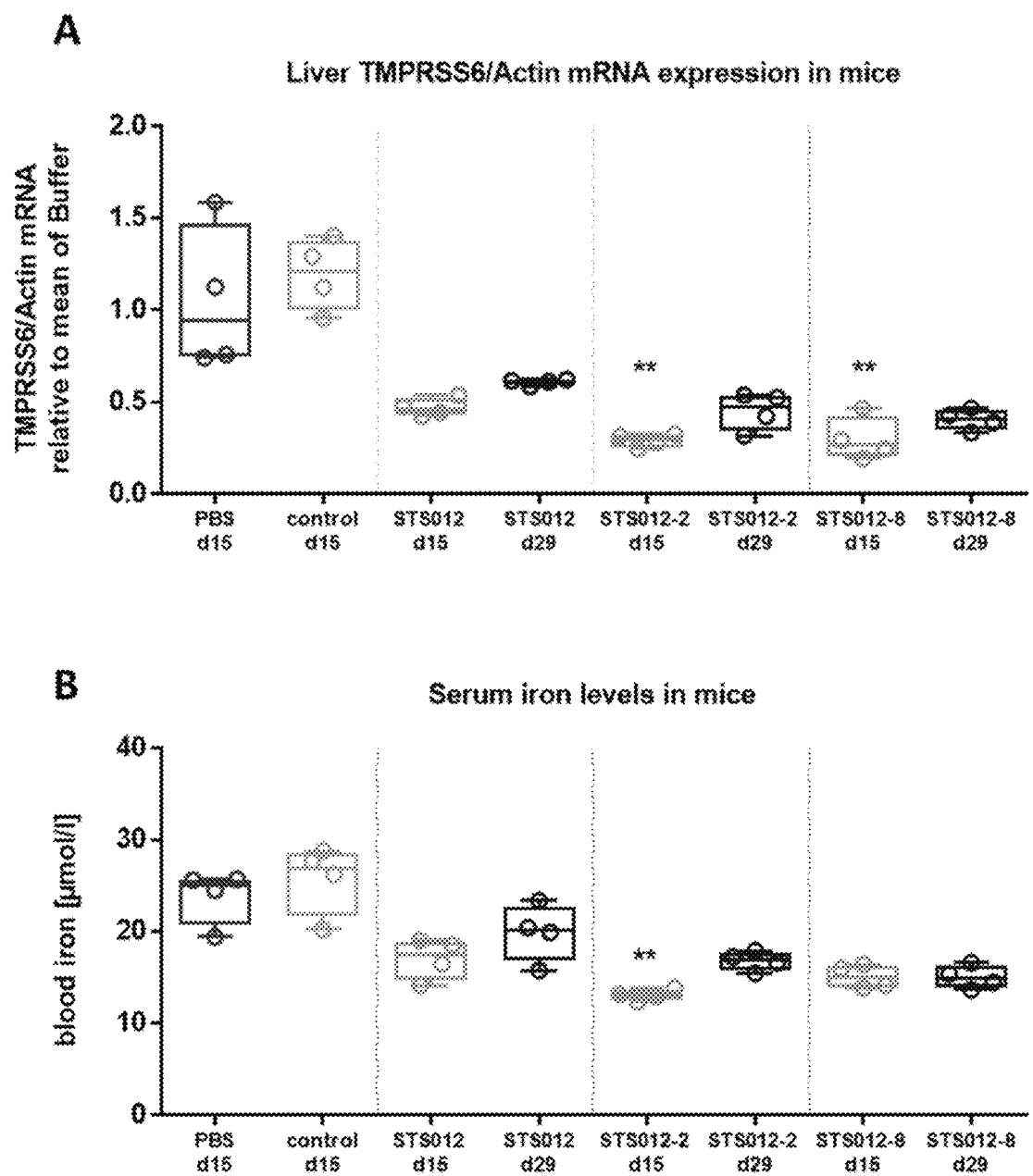
FIG. 13 shows the reduction of TMPRSS6 expression in the liver tissue and the reduction of serum iron levels in mice at different time points after single injection with siRNA conjugates.

Two different modification variants of one GalNAc-conjugated sequence targeting TMPRSS6 (STS012) were tested in vivo. 1 mg/kg GalNAc-siRNA conjugates were subcutaneously injected into male C57BL/6JOIaHsd mice. 14 and 28 days after treatment, TMPRSS6 mRNA levels in the liver were analyzed by Taqman qRT-PCR (A). In addition, serum iron levels were analyzed (B). Results are shown in FIG. 13. Box plots represent median of 4 animals. Statistical analysis is based on Kruskal-Wallis test with Dunn's multiple comparison test against PBS group.

The sequences are as in Example 10.

Example 12

Figure 14:
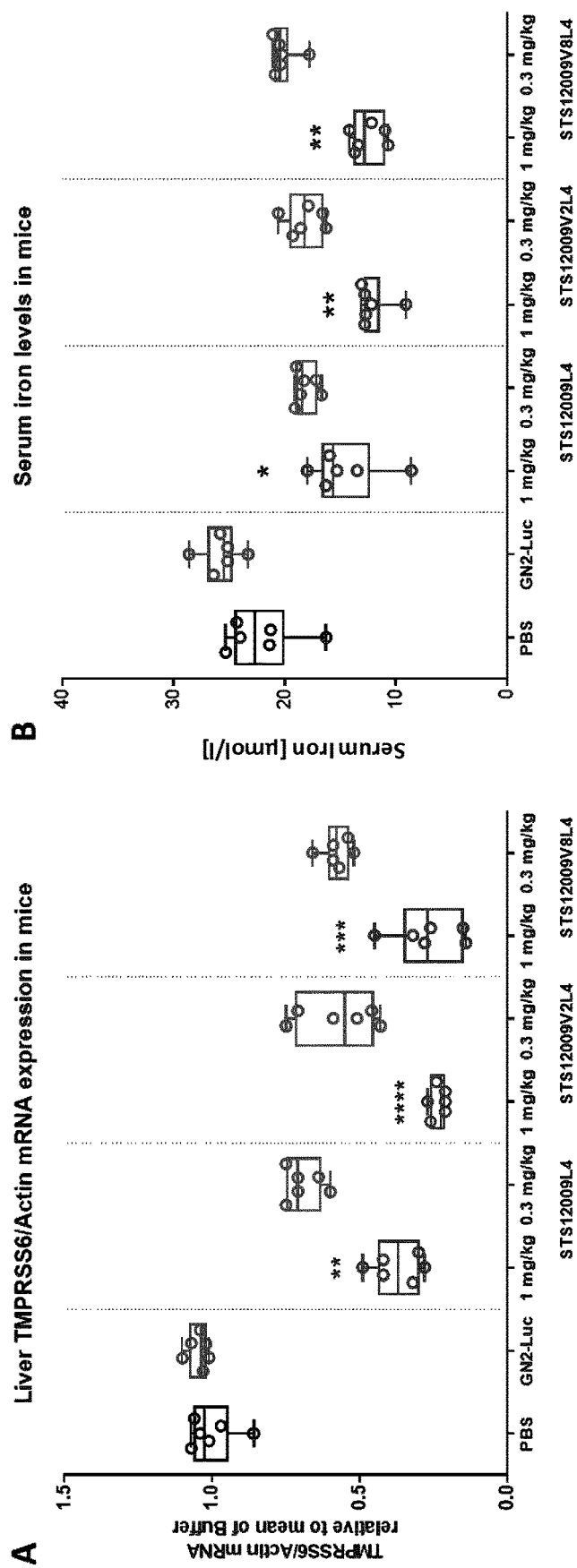
FIG. 14 shows the reduction of TMPRSS6 mRNA levels in liver and the reduction of serum iron levels in mice by different doses of GalNAc conjugated siRNA molecules.

Two different modification variants of one GalNAc-conjugated sequence targeting TMPRSS6 (STS12009L4, GN2-TMPRSS6-hcm9) were tested in vivo. 1 mg/kg and 0.3 mg/kg GalNAc-siRNA conjugates were subcutaneously injected into male C57BL/6JOIaHsd mice. 14 days after treatment, TMPRSS6 mRNA levels in the liver were analyzed by Taqman qRT-PCR (A). In addition, serum iron levels were analyzed (B). Results are shown in FIG. 14. Box plots represent median of 4 animals. Statistical analysis is based on Kruskal-Wallis test with Dunn's multiple comparison test against PBS group.

The duplexes used are shown below in Table 5. All sequences correspond to SEQ ID NO:17 and SEQ ID NO:18

TABLE 5

Modification variants of GalNAc-conjugated sequences targeting TMPRSS6.

Figure 8A:
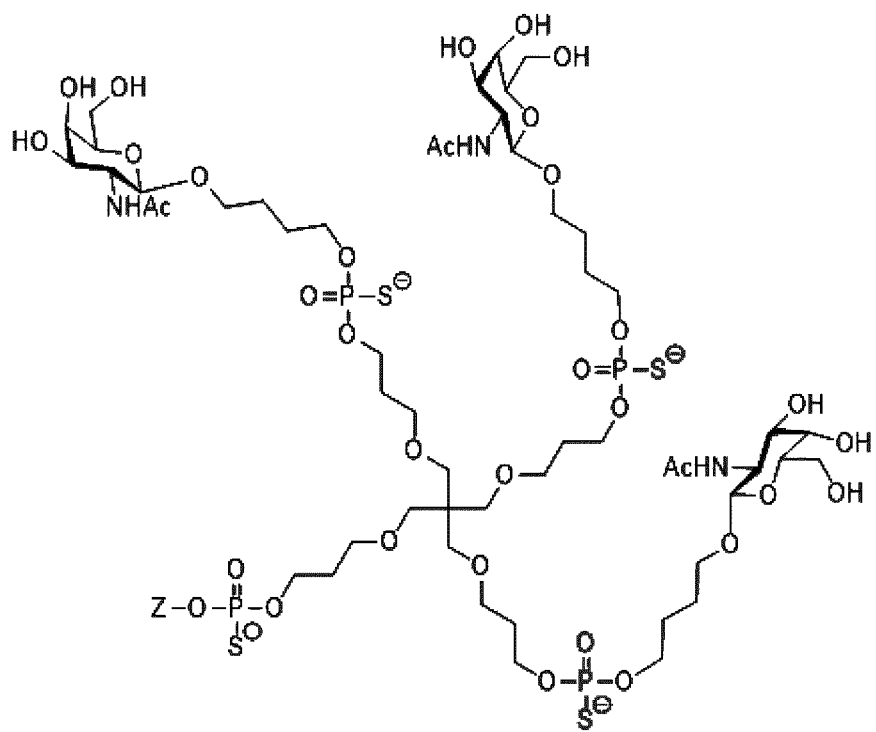
FIGS. 8a, 8b and 8c show the structure of the GalNAc ligands referred to herein respectively as GN, GN2, and GN3 to which the oligonucleotides were conjugated (see also below this nomenclature in the Examples where TMPRSS6 hcm-9 is conjugated to each of GN, GN2 and GN3)
Figure 8B:
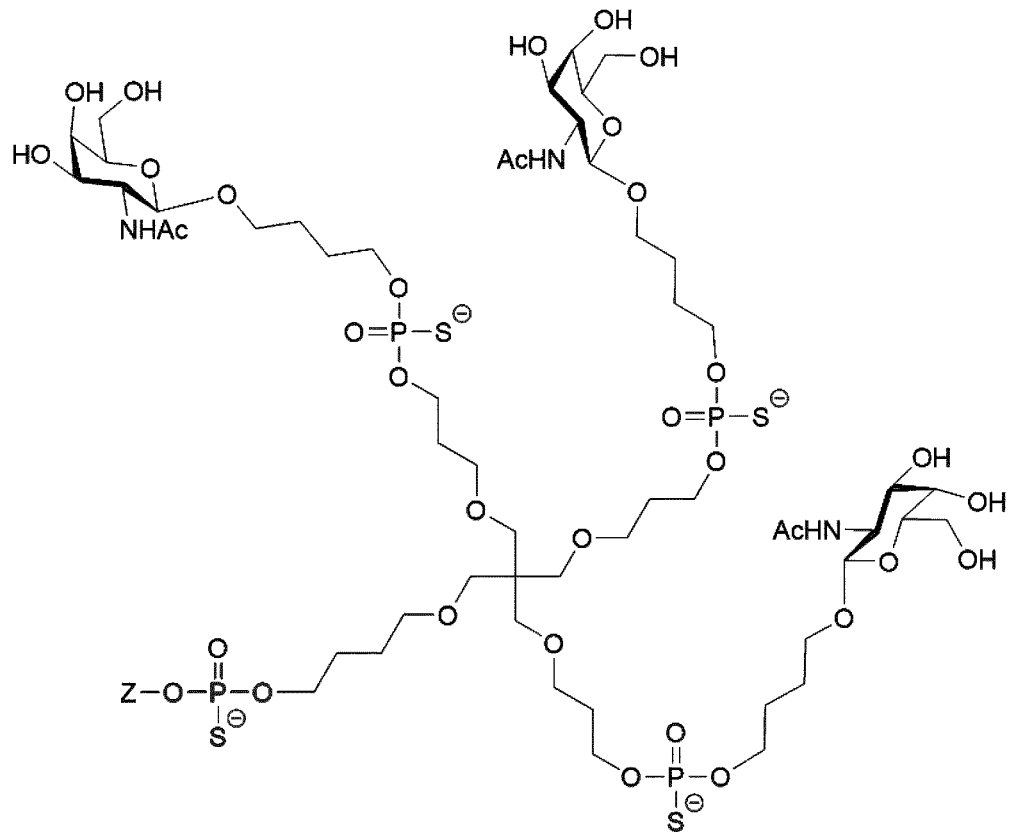

| duplex ID | sequence and chemistry (top: first strand, bottom: second strand, both 5'-3') |
|---|---|
| STS12009L4 | mA(ps)fA(ps)mCfCmAfGmAfAmGfAmAfGmCfAmGfGmU(ps)fG(ps)mA<br>GN2-fUmCfAmCfCmUfGmCfUmUfCmUfUmCfUmGfG(ps)mU(ps)fU |
| STS12009V2L4 | mA(ps)fA(ps)mCfCmAfGmAfAmGfAmAfGmCfAmGfGmU(ps)fG(ps)mA<br>GN2-mUmCmAmCfCmUfGfCfUmUmCmUmUmCmUmGmG(ps)mU(ps)mU |
| STS12009V8L4 | mA(ps)fA(ps)mCmCmAmGmAmAmGmAmAfGmCfAmGmGmU(ps)mG(ps)mA<br>GN2-mUmCmAmCfCmUfGfCfUmUmCmUmUmCmUmGmG(ps)mU(ps)mU |
| GN2-Luc | mU(ps)fU(ps)mAfGmUfAmAfAmCfCmUfUmUfUmGfAmG(ps)fA(ps)mC<br>GN2-fGmUfCmUfCmAfAmAfAmGfGmUfUmUfAmCfU(ps)mA(ps)fA | mA, mU, mC, mG - 2'-OMe RNA
fA, fU, fC, fG - 2'-F DNA
(ps) - phosphorothioate
GN2 = GalNAc structure according to FIG. 8B

TABLE 6

Different modification variants of one siRNA targeting TMPRSS6.

| duplex ID | sequence and chemistry (top: first strand, bottom: second strand, both 5'-3') |
|---|---|
| TMP01 | mAfAmCfCmAfGmAfAmGfAmAfGmCfAmGfGmUfGmA<br>fUmCfAmCfCmUfGmCfUmUfCmUfUmCfUmGfGmUfU |
| TMP66 | mAfAmCfCmAmGfAmAmGmAmAmGmCfAmGmGmUmGmA<br>mUmCmAmCmCmUfGmCfUmUmCmUmUmCmUmGmGmUmU |
| TMP69 | fAfAfCfCfAmGfAfAfGfAmAfGfCfAmGfGfUfGfA<br>fUmCfAfCfCfUfGfGfCfUfUfCmUfUmCfUfGfGfUfU |
| TMP79 | fAfAmCfCfAmGfAfAfGfAmAfGfCfAmGfGmUmGmA<br>mUmCfAmCfCmUfGfCfUmUmCmUmUmCmUfGfGmUmU |
| TMP80 | fAfAmCmCfAmGfAfAfGfAmAfGfCfAmGfGmUmGmA<br>mUmCfAmCfCmUfGfCfUmUmCmUmUmCmUfGfGmUmU |
| TMP81 | fAfAmCfCfAmGfAfAfGfAmAfGmCfAmGfGmUmGmA<br>mUmCfAmCfCmUfGfCfUmUmCmUmUmCmUfGfGmUmU | mA, mU, mC, mG - 2'-OMe RNA
fA, fU, fC, fG - 2'-F DNA
(ps) - phosphorothioate

Example 13

Figure 15:
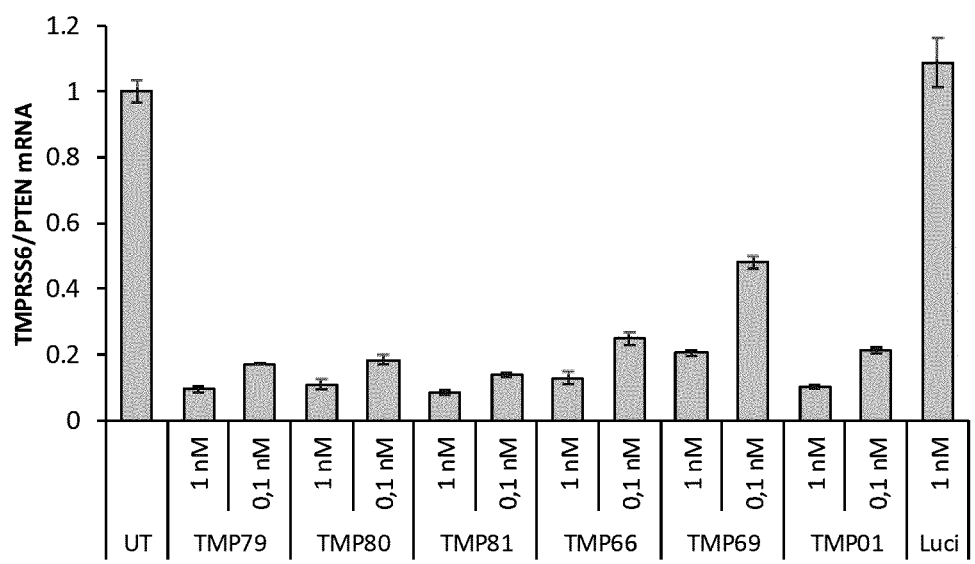
FIG. 15 shows the effect of different modification patterns on the activity of an siRNA molecule in human Hep3B cells.

Different modification variants of one siRNA targeting TMPRSS6 were tested in human Hep3B cells. An siRNA targeting Luciferase was used as non-targeting control. All siRNAs were transfected with 1 µg/ml Atufect at 1 nM and 0.1 nM. Total RNA was extracted 48 h after transfection and TMPRSS6 mRNA levels were quantified by Taqman qRT-PCR. TMPRSS6 mRNA levels were normalized to PTEN mRNA levels. Results are shown in FIG. 15. Each bar represents mean+/−SD of three technical replicates.

The sequences are shown in Table 6 below. All sequences correspond to SEQ ID NO:17 (top) and SEQ ID NO:18 (bottom).

Example 14

Figure 16:
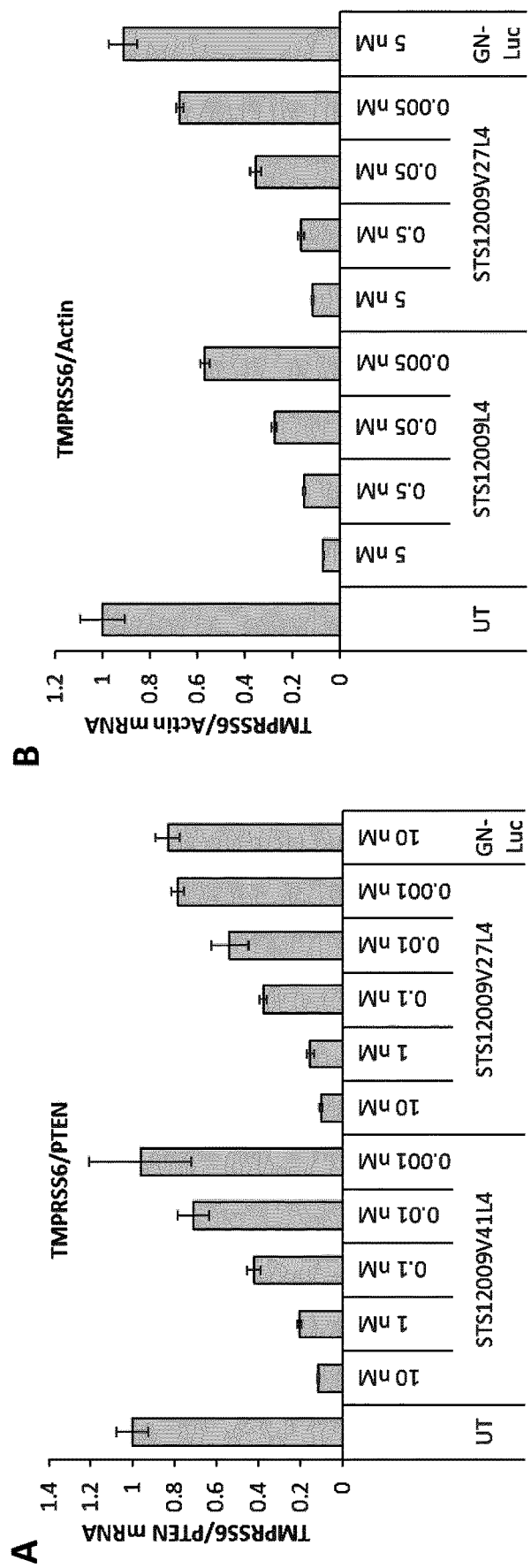
FIG. 16 shows the effect of different modification variants of GalNAc conjugated siRNA molecules on inhibition of TMPRSS6 expression in human Hep3B cells.

Modification variants of a GalNAc-conjugated siRNA targeting TMPRSS6 were tested in human Hep3B cells. 150,000 cells were seeded per 6-well. After 24 h, siRNA conjugates were transfected with 1 µg/ml Atufect at 10, 1, 0.1, 0.01, and 0.001 nM (A) or 5, 0.5, 0.05, 0.005 nM (B). A GalNAc-siRNA against Luciferase was used as non-targeting control. Total RNA was extracted 72 h after transfection and TMPRSS6 mRNA levels were quantified by Taqman qRT-PCR. TMPRSS6 mRNA levels were normalized to PTEN mRNA levels (A) or Actin mRNA levels (B). Results are shown in FIG. 16. Each bar represents mean+/−SD of three technical replicates.

Sequences are shown in Table 7, below

TABLE 7

Modification variants of a GalNAc-conjugated siRNA targeting TMPRSS6

| duplex ID | sequence and chemistry (top: first strand, bottom: second strand, both 5'-3') |
|---|---|
| STS12009L4 | mA(ps)fA(ps)mCfCmAfGmAfAmGfAmAfGmCfAmGfGmU(ps)fG(ps)mA<br>GN2-fUmCfAmCfCmUfGmCfUmUfCmUfUmCfUmGfG(ps)mU(ps)fU |
| STS12009V27L4 | mA(ps)fA(ps)mCmCmAmGmAmAmGmAmAfGmCfAmGmGmU(ps)mG(ps)mA<br>GN2-mUmCmAmCmCmUfGfCfUmUmCmUmUmCmUmGmG(ps)mU(ps)mU |
| STS12009V41L4 | mA(ps)fA(ps)mCmCmAmGmAmAmGmAmAfGmCfAmGmGmU(ps)mG(ps)mA<br>GN2-fUmCfAmCfCmUfGmCfUmUfCmUfUmCfUmGfG(ps)mU(ps)fU | mA, mU, mC, mG - 2'-OMe RNA
fA, fU, fC, fG - 2'-F DNA
(ps) - phosphorothioate
GN2 = GalNAc structure according to FIG. 8B Example 15

Figure 17:
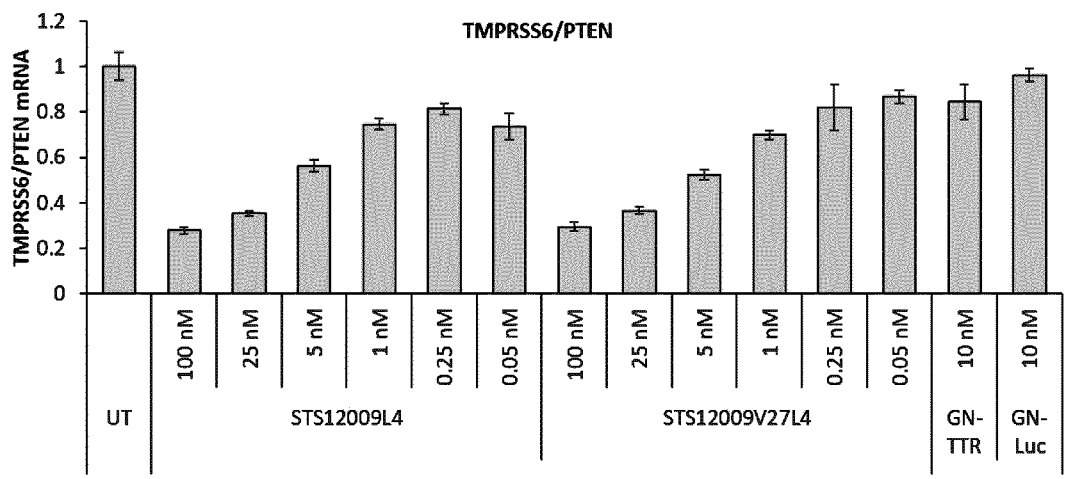
FIG. 17 shows the effect of a modification variant of a GalNAc conjugated siRNAs on inhibition of TMPRSS6 expression in primary mouse hepatocytes by receptor mediated uptake.

A modification variant of a GalNAc-conjugated sequence targeting TMPRSS6 (STS12009L4) was tested in mouse primary hepatocytes. For receptor-mediated uptake, cells were incubated with 100, 25, 5, 1, 0.25 and 0.05 nM siRNA conjugate for 24 h. A GalNAc-siRNA targeting an unrelated sequence (GN-TTR) and a non-targeting GalNAc-siRNA (GN-Luc) were used as controls. Total RNA was extracted and TMPRSS6 mRNA levels were quantified by Taqman qRT-PCR. TMPRSS6 mRNA levels were normalized to PTEN mRNA levels. Results are shown in FIG. 17. Mean+/−SD of each three technical replicates are shown.

Sequences are shown in Table 7, above.

Example 16

Figure 18:
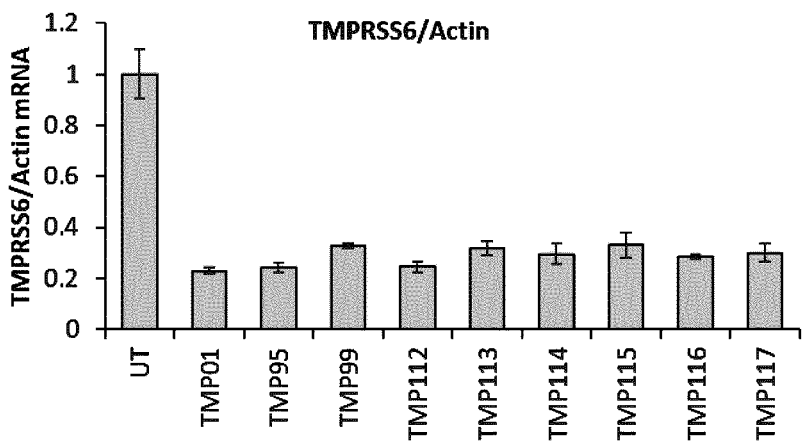
FIG. 18 shows the reduction of TMPRSS6 expression by different siRNA modification variants in human Hep3B cells.

Different DNA- and LNA-containing variants of one siRNA targeting TMPRSS6 were tested in human Hep3B cells. Therefore, 150,000 cells were seeded per 6-well. After 24 h, siRNAs were transfected with 1 µg/ml Atufect at 0.1 nM siRNA. Total RNA was extracted 48 h after transfection and TMPRSS6 mRNA levels were quantified by Taqman qRT-PCR. TMPRSS6 mRNA levels were normalized to Actin mRNA levels. Results are shown in FIG. 18. Each bar represents mean+/−SD of three technical replicates.

Sequences are shown in Table 8, below. All sequences correspond to SEQ ID NO:17 (top) and SEQ ID NO:18 (bottom).

TABLE 8

Different DNA- and LNA-containing variants of one siRNA targeting TMPRSS6.

| duplex ID | sequence and chemistry (top: first strand, bottom: second strand, both 5'-3') |
|---|---|
| TMP01 | mAfAmCfCmAfGmAfAmGfAmAfGmCfAmGfGmUfGmA<br>fUmCfAmCfCmUfGmCfUmUfCmUfUmCfUmGfGmUfU |
| TMP95 | mAfAmCmCmAmGmAmAmGmAmAmGmCfAmGmGmUmGmA<br>fUmCfAmCfCmUfGmCfUmUfCmUfUmCfUmGfGmUfU |
| TMP99 | mAfAmCfCmAfGmAfAmGfAmAfGmCfAmGfGmUfGmA<br>mUmCmAmCmCmUfGmCfUmUmCmUmUmCmUmGmGmUmU |
| TMP112 | mA[A]mCmCmAmGmAmAmGmAmAmGmCfAmGmGmUmGmA<br>fUmCfAmCfCmUfGmCfUmUfCmUfUmCfUmGfGmUfU |

TABLE 8-continued

Different DNA- and LNA-containing variants of one siRNA targeting TMPRSS6.

| duplex ID | sequence and chemistry (top: first strand, bottom: second strand, both 5'-3') |
|---|---|
| TMP114 | mAfAmCfCmAfGmAfAmGfAmAfGmCfAmGfGmUfGmA<br>mUmCmAmCmCmU{G}mCfUmUmCmUmUmCmUmGmGmUmU |
| TMP115 | mAfAmCfCmAfGmAfAmGfAmAfGmCfAmGfGmUfGmA<br>mUmCmAmCmCmUfGmC{U}mUmCmUmUmCmUmGmGmUmU |
| TMP116 | mAfAmCfCmAfGmAfAmGfAmAfGmCfAmGfGmUfGmA<br>mUmCmAmCmCmU[G]mCfUmUmCmUmUmCmUmGmGmUmU |
| TMP117 | mAfAmCfCmAfGmAfAmGfAmAfGmCfAmGfGmUfGmA<br>mUmCmAmCmCmUfGmC[U]mUmCmUmUmCmUmGmGmUmU | mA, mU, mC, mG - 2'-OMe RNA
fA, fU, fC, fG - 2'-F DNA
[A], [T], [C], [G] - DNA
{A}, {U}, {C}, {G} - LNA
(ps) - phosphorothioate Example 17

The influence of inverted A and G RNA nucleotides at terminal 3' positions was analyzed using an siRNA against TMPRSS6. TMP70 contains phosphorothioates at all termini, whereas TMP82 and TMP83 contain ivA (TMP82) and ivG (TMP83) at the 3'-end of the antisense and at the 3'-end of the sense. Both inverted nucleotides are present in addition to the terminal nucleotide of the respective strands and are linked via a phosphorothioate bond. A non-related siRNA (PTEN) and a non-targeting siRNA (Luci) were included as controls. All tested variants show comparable activity under the tested conditions.

Figure 19:
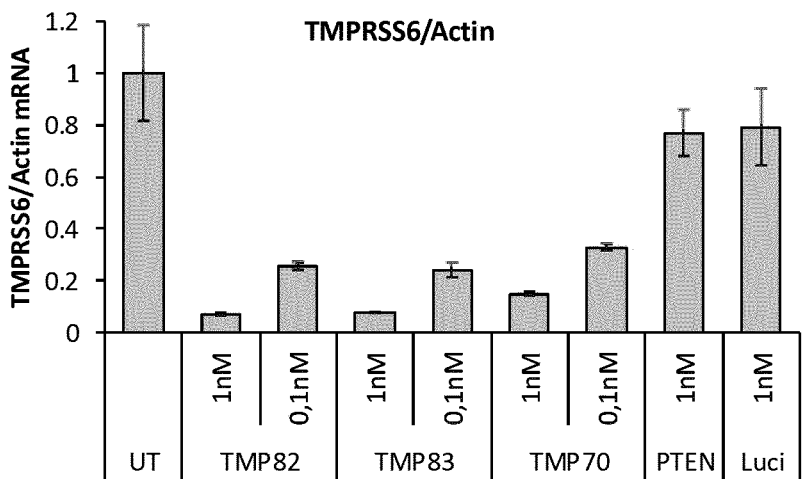
FIG. 19 shows the influence of inverted A and G nucleotides on RNAi activity in human Hep3B cells.

The experiment was conducted in Hep3B cells. Cells were seeded at a density of 150,000 cells per 6-well, transfected with 1 nM and 0.1 nM siRNA and 1 µg/ml Atufect after 24 h and lysed after 48 h. Total RNA was extracted and TMPRSS6 and Actin mRNA levels were determined by Taqman qRT-PCR. Results are shown in FIG. 19. Each bar represents mean+SD from three technical replicates.

The sequences are shown below in Table 9. Sequences correspond to SEQ ID NO:17 (top) or SEQ ID NO:18 (bottom).

TABLE 9

An siRNA against TMPRSS6 including inverted
RNA nucleotides at different positions.

| duplex ID | sequence and chemistry (top: first strand, bottom: second strand, both 5'-3') |
|---|---|
| TMP70 | mA(ps)fA(ps)mCfCmAfGmAfAmGfAmAfGmCfAmGfGmU(ps)fG(ps)mA<br>fU(ps)mC(ps)fAmCfCmUfGmCfUmUfCmUfUmCfUmGfG(ps)mU(ps)fU |
| TMP82 | mA(ps)fA(ps)mCfCmAfGmAfAmGfAmAfGmCfAmGfGmUfGmA(ps)ivA<br>fU(ps)mC(ps)fAmCfCmUfGmCfUmUfCmUfUmCfUmGfGmUfU(ps)ivA |
| TMP83 | mA(ps)fA(ps)mCfCmAfGmAfAmGfAmAfGmCfAmGfGmUfGmA(ps)ivG<br>fU(ps)mC(ps)fAmCfCmUfGmCfUmUfCmUfUmCfUmGfGmUfU(ps)ivG | mA, mU, mC, mG - 2'-OMe RNA
fA, fU, fC, fG - 2'-F DNA
ivA, ivG - inverted RNA (3'-3')
(ps) - phosphorothioate

Example 18

Different siRNA duplexes containing inverted RNA nucleotides at both 3'-ends were tested for serum stability. TMP84-TMP87 contain inverted RNA in addition to the last nucleotide in the sense strand and instead of the last nucleotide in the antisense strand. TMP88-TMP91 contain inverted RNA in addition to the last nucleotide in the antisense strand and instead of the last nucleotide in the sense strand. All inverted RNA nucleotides substitute for terminally used phosphorothioates. In the design of TMP84-TMP87, ivA and ivG confer higher stability to the tested sequence than ivU and ivC (part A). In the design of TMP88-TMP91, there is no influence of base identity on duplex stability (part B).

Figure 20:
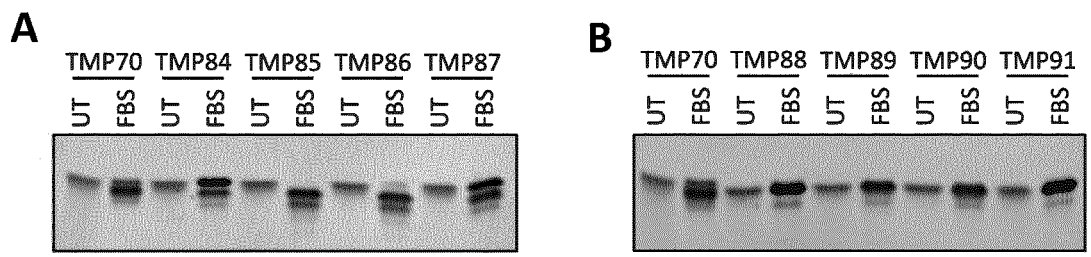
FIG. 20 shows the influence of inverted RNA nucleotides on siRNA stability.

Results are shown in FIG. 20. "UT" indicates untreated samples. "FBS" indicates siRNA duplexes which were incubated at 5 µM final concentration with 50% FBS for 3 d, phenol/chloroform-extracted and precipitated with Ethanol. Samples were analyzed on 20% TBE polyacrylamide gels in native gel electrophoresis.

Sequences are show in the Table 10, below, and correspond to SEQ ID NO:17 (top) and SEQ ID NO:18 (bottom).

TABLE 10

Different siRNA duplexes containing inverted RNA
nucleotides at both 3'-ends.

| duplex ID | sequence and chemistry (top: first strand, bottom: second strand, both 5'-3') |
|---|---|
| TMP70 | mA(ps)fA(ps)mCfCmAfGmAfAmGfAmAfGmCfAmGfGmU(ps)fG(ps)mA<br>fU(ps)mC(ps)fAmCfCmUfGmCfUmUfCmUfUmCfUmGfG(ps)mU(ps)fU |
| TMP84 | mA(ps)fA(ps)mCfCmAfGmAfAmGfAmAfGmCfAmGfGmUfG ivA<br>fU(ps)mC(ps)fAmCfCmUfGmCfUmUfCmUfUmCfUmGfGmUfU ivG |
| TMP85 | mA(ps)fA(ps)mCfCmAfGmAfAmGfAmAfGmCfAmGfGmUfG ivU<br>fU(ps)mC(ps)fAmCfCmUfGmCfUmUfCmUfUmCfUmGfGmUfU ivG |
| TMP86 | mA(ps)fA(ps)mCfCmAfGmAfAmGfAmAfGmCfAmGfGmUfG ivC<br>fU(ps)mC(ps)fAmCfCmUfGmCfUmUfCmUfUmCfUmGfGmUfU ivG |
| TMP87 | mA(ps)fA(ps)mCfCmAfGmAfAmGfAmAfGmCfAmGfGmUfG ivG<br>fU(ps)mC(ps)fAmCfCmUfGmCfUmUfCmUfUmCfUmGfGmUfU ivG |
| TMP88 | mA(ps)fA(ps)mCfCmAfGmAfAmGfAmAfGmCfAmGfGmUfGmA ivG<br>fU(ps)mC(ps)fAmCfCmUfGmCfUmUfCmUfUmCfUmGfGmU ivA |
| TMP89 | mA(ps)fA(ps)mCfCmAfGmAfAmGfArnAfGmCfAmGfGmUfGmA ivG<br>fU(ps)mC(ps)fAmCfCmUfGmCfUmUfCmUfUmCfUmGfGmU ivU |
| TMP90 | mA(ps)fA(ps)mCfCmAfGmAfAmGfAmAfGmCfAmGfGmUfGmA ivG<br>fU(ps)mC(ps)fAmCfCmUfGmCfUmUfCmUfUmCfUmGfGmU ivC |
| TMP91 | mA(ps)fA(ps)mCfCmAfGmAfAnnGfAmAfGmCfAmGfGmUfGmA ivG<br>fU(ps)mC(ps)fAmCfCmUfGmCfUmUfCmUfUmCfUmGfGmU ivG | mA, mU, mC, mG - 2'-OMe RNA
fA, fU, fC, fG - 2'-F DNA
ivA, ivU, ivC, ivG - inverted RNA (3'-3')
(ps) - phosphorothioate

Example 19

The influence of inverted RNA nucleotides at terminal 3' positions was analyzed using an siRNA against TMPRSS6. TMP70 contains phosphorothioates at all termini, whereas TMP84-TMP87 contain ivG at the 3'-end of the sense strand.

The inverted RNA nucleotide is present in addition to the last nucleotide and substitutes for two phosphorothioates. At the antisense 3'-end, ivA (TMP84), ivU (TMP85), ivC (TMP86) and ivG (TMP87) were tested. These inverted RNA nucleotides were added instead of the terminal nucleotide and substitute for phosphorothioates. A non-related siRNA (PTEN) and a non-targeting siRNA (Luci) were included as controls. All tested variants show comparable activity under the tested conditions.

Figure 21:
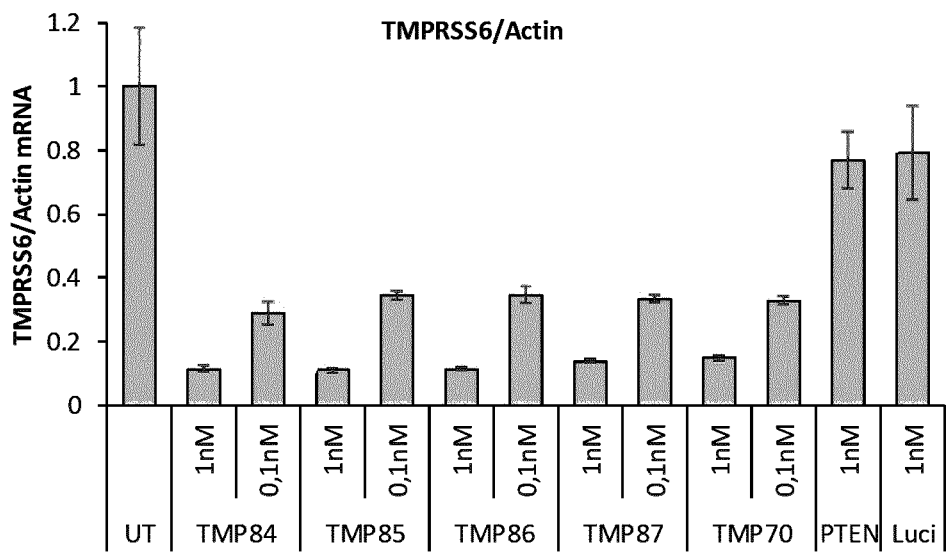
FIG. 21 shows the influence of inverted RNA nucleotides on siRNA activity in human Hep3B cells.

The experiment was conducted in Hep3B. Cells were seeded at a density of 150,000 cells per 6-well, transfected with 1 nM and 0.1 nM siRNA and 1 µg/ml Atufect after 24 h and lysed after 48 h. Total RNA was extracted and TMPRSS6 and Actin mRNA levels were determined by Taqman qRT-PCR. Results are shown in FIG. 21. Each bar represents mean+SD from three technical replicates.

The sequences are as in Table 10, above.

Example 20

The influence of inverted RNA nucleotides at terminal 3' positions was analyzed using an siRNA against TMPRSS6. TMP70 contains phosphorothioates at all termini, whereas TMP88-TMP91 contain ivG at the 3'-end of the antisense strand. The inverted RNA nucleotide is present in addition to the last nucleotide and substitutes for two phosphorothioates. At the sense 3'-end, ivA (TMP88), ivU (TMP89), ivC (TMP90) and ivG (TMP91) were tested. These inverted RNA nucleotides were added instead of the terminal nucleotide and substitute for phosphorothioates. A non-related siRNA (PTEN) and a non-targeting siRNA (Luci) were included as controls. All tested variants show comparable activity under the tested conditions.

Figure 22:
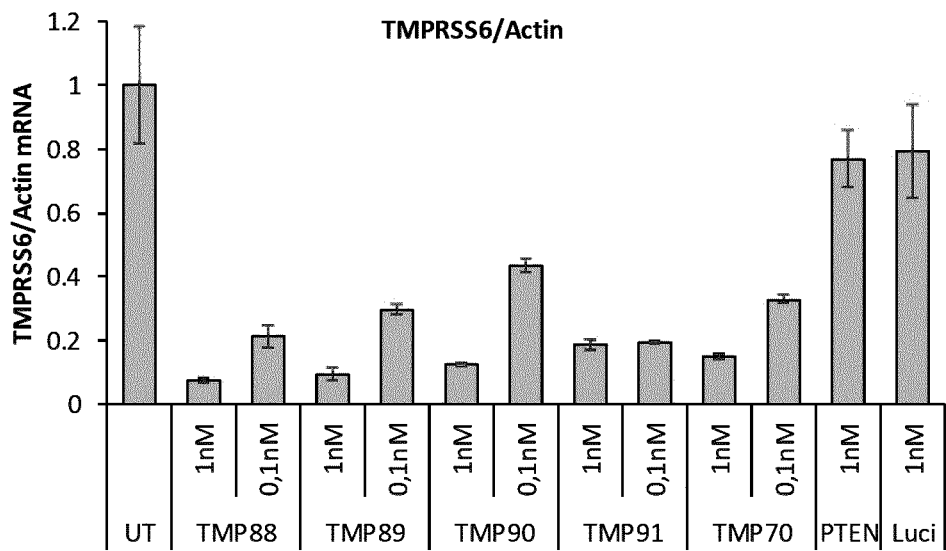
FIG. 22 shows the influence of inverted RNA nucleotides on RNAi activity in human Hep3B cells.

The experiment was conducted in Hep3B. Cells were seeded at a density of 150,000 cells per 6-well, transfected with 1 nM and 0.1 nM siRNA and 1 µg/ml Atufect after 24 h and lysed after 48 h. Total RNA was extracted and TMPRSS6 and Actin mRNA levels were determined by Taqman qRT-PCR. Results are shown in FIG. 22. Each bar represents mean+SD from three technical replicates.

Sequences are as shown in Table 10, above.

Example 21

The influence of inverted RNA nucleotides at terminal 3' positions was analyzed using a GalNAc-siRNA conjugate targeting TMPRSS6 in liposomal transfections. STS12009-L4 contains phosphorothioates at all non-conjugated termini, whereas the tested variants contain an inverted RNA nucleotide at the 3'-end of both sense and antisense strand. The inverted RNA is present in addition to the last nucleotide and substitutes for two terminal phosphorothioates (STS12009V10-L4 and -V11-L4) or is used in addition to the terminal phosphorothioates (STS12009V29-L4 and STS12009V30-L4). Inverted A (STS12009V10-L4 and -V29-L4) and inverted G (STS12009V11-L4 and -V30-L4) were used. All tested variants show comparable activity under the tested conditions.

Figure 23:
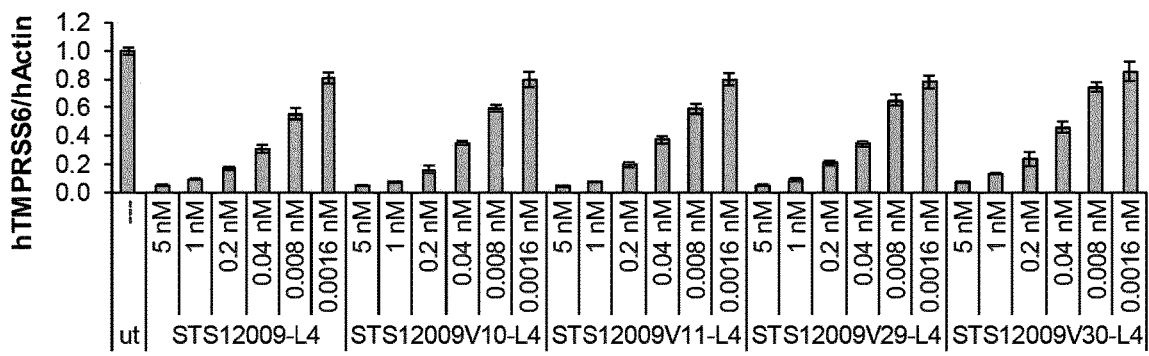
FIG. 23 shows the influence of inverted RNA nucleotides on the activity of GalNAc conjugated siRNAs in primary mouse hepatocytes by receptor mediated uptake.

The experiment was conducted in Hep3B. Cells were seeded at a density of 150,000 cells per 6-well, transfected with 5 nM to 0.0016 nM siRNA and 1 µg/ml Atufect after 24 h and lysed after 48 h. Total RNA was extracted and TMPRSS6 and Actin mRNA levels were determined by Taqman qRT-PCR. Results are shown in FIG. 23. Each bar represents mean±SD of three technical replicates.

Sequences are set out in Table 11, below and correspond to SEQ ID NO:17 (top) and SEQ ID NO:18 (bottom).

TABLE 11

An siRNA sequence including inverted RNA nucleotides at the 3' ends

| Duplex ID | sequence and chemistry (top: first strand, bottom: second strand, both 5'-3') |
|---|---|
| STS12009L4 | mA(ps)fA(ps)mCfCmAfGmAfAmGfAmAfGmCfAmGfGmU(ps)fG(ps)mA<br>GN2-fUmCfAmCfCmUfGmCfUmUfCmUfUmCfUmGfG(ps)mU(ps)fU |
| STS12009V10L4 | mA(ps)fA(ps)mCfCmAfGmAfAmGfAmAfGmCfAmGfGmUfGmAivA<br>GN2-fUmCfAmCfCmUfGmCfUmUfCmUfUmCfUmGfGmUfUivA |
| STS12009V11L4 | mA(ps)fA(ps)mCfCmAfGmAfAmGfAmAfGmCfAmGfGmUfGmAivG<br>GN2-fUmCfAmCfCmUfGmCfUmUfCmUfUmCfUmGfGmUfUivG |
| STS12009V29L4 | mA(ps)fA(ps)mCfCmAfGmAfAmGfAmAfGmCfAmGfGmU(ps)fG(ps)mAivA<br>GN2-fUmCfAmCfCmUfGmCfUmUfCmUfUmCfUmGfG(ps)mU(ps)fUivA |
| STS12009V30L4 | mA(ps)fA(ps)mCfCmAfGmAfAmGfAmAfGmCfAmGfGmU(ps)fG(ps)mAivG<br>GN2-fUmCfAmCfCmUfGmCfUmUfCmUfUmCfUmGfG(ps)mU(ps)fUivG | mA, mU, mC, mG - 2'-OMe RNA
fA, fU, fC, fG - 2'-F DNA
ivA, ivG - inverted RNA (3'-3')
(ps) - phosphorothioate
GN2 = GalNAc structure according to FIG. 8B Example 22

Figure 24:
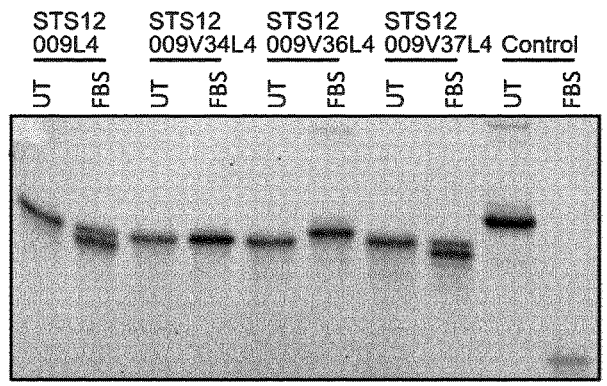
FIG. 24 shows the effect of phosphorodithioate linkage on stability of GalNAc conjugated siRNA molecules.

Serum stability assay of GalNAc-siRNA conjugates containing one PS2 at individual ends. GalNAc was conjugated to the 5'-end of the sense strand and is internally stabilized by four PS. Phosphorodithioate modifications were placed at the 5'-antisense (STS12009V37L4), 3'-antisense (STS12009V36L4) and 3'-sense (STS12009V34L4) ends. STS12009L4 contains each two terminal PS at 5'-antisense, 3'-antisense and 3'-sense ends, GalNAc is attached to the sense 5'-end and stabilized by four internal PS. 5 UM GalNAc-siRNA conjugates were incubated with 50% FBS for 3 d at 37° C. RNA was extracted and analyzed on 20% TBE polyacrylamide gels. Results are shown in FIG. 24. "UT" indicates untreated samples, "FBS" indicates FBS treatment. "Control" indicates a less stabilized GalNAc-siRNA conjugate of different sequence.

Sequences are shown in Table 12, below, and correspond to SEQ ID NO:17 (top) and SEQ ID NO:18 (bottom).

TABLE 12

GalNAc-siRNA conjugates containing one PS2
(phosphorodithioate) at individual ends.

| duplex ID | sequence and chemistry<br>(top: first strand, bottom: second strand, both 5'-3') |
|---|---|
| STS12009L4 | mA(ps)fA(ps)mCfCmAfGmAfAmGfAmAfGmCfAmGfGmU(ps)fG(ps)mA<br>GN2-fUmCfAmCfCmUfGmCfUmUfCmUfUmCfUmGfG(ps)mU(ps)fU |
| STS12009V34L4 | mA(ps)fA(ps)mCfCmAfGmAfAmGfAmAfGmCfAmGfGmU(ps)fG(ps)mA<br>GN2-fUmCfAmCfCmUfGmCfUmUfCmUfUmCfUmGfGmU(ps2)fU |
| STS12009V36L4 | mA(ps)fA(ps)mCfCmAfGmAfAmGfAmAfGmCfAmGfGmUfG(ps2)mA<br>GN2-fUmCfAmCfCmUfGmCfUmUfCmUfUmCfUmGfG(ps)mU(ps)fU |
| STS12009V37L4 | mA(ps2)fAmCfCmAfGmAfAmGfAmAfGmCfAmGfGmU(ps)fG(ps)mA<br>GN2-fUmCfAmCfCmUfGmCfUmUfCmUfUmCfUmGfG(ps)mU(ps)fU | mA, mU, mC, mG - 2'-OMe RNA
fA, fU, fC, fG - 2'-F DNA
(ps) - phosphorothioate
(ps2) - phosphorodithioate
GN2 = GalNAc structure according to FIG. 8B

Example 23

Figure 25:
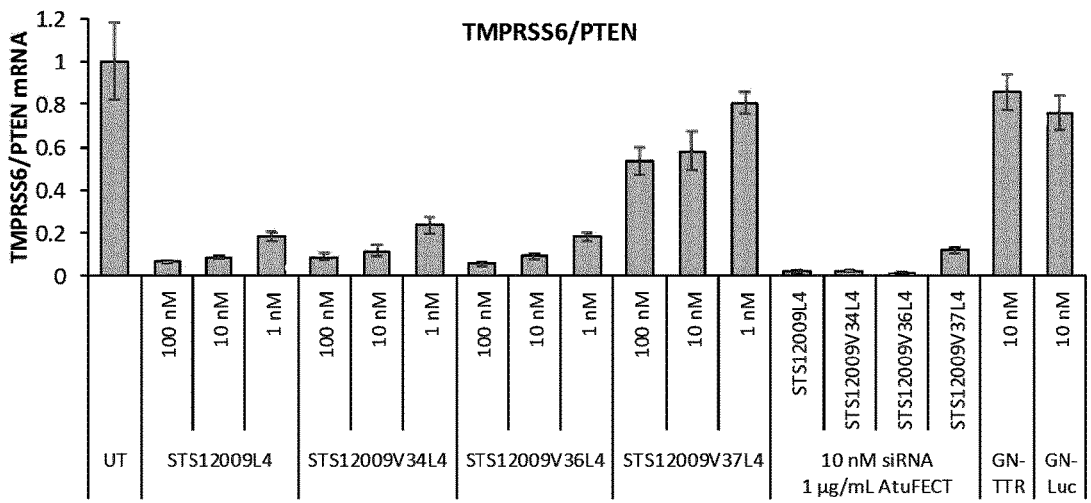
FIG. 25 shows the effect of phosphorodithioate linkage on activity of a GalNAc conjugated siRNA molecule on TMPRSS6 expression in mouse primary hepatocytes.

Activity of GalNAc-siRNA conjugates containing one PS2 at individual ends. GalNAc was conjugated to the 5'-end of the sense strand and is internally stabilized by four PS. Phosphorodithioate modifications were placed at the 5'-antisense (STS12009V37L4), 3'-antisense (STS12009V36L4) and 3'-sense (STS12009V34L4) ends. The experiment was conducted in mouse primary hepatocytes. Cells were seeded at a density of 250,000 cells per 6-well and treated with 100 nM, 10 nM and 1 nM GalNAc-siRNA. Transfections with 10 nM GalNAc-siRNA and 1 µg/ml Atufect served as control. Cells were lysed after 24 h, total RNA was extracted and TMPRSS6 and PTEN mRNA levels were determined by Taqman qRT-PCR. Results are shown in FIG. 25. Each bar represents mean+SD from three technical replicates.

Sequences are as set out in Table 12, above.

Example 24

Figure 26:
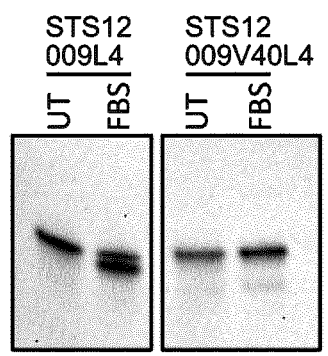
FIG. 26 shows the effect of phosphorodithioate linkage on stability of a GalNAc conjugated siRNA molecule.

Serum stability assay of a GalNAc-siRNA conjugate (STS12009V40L4) containing each one PS2 at the second strand 5'-end and at the second strand 3'-end. GalNAc was conjugated to the 5'-end of the second strand and is not stabilized by any internal PS. STS12009L4 contains each two terminal PS at 5'-antisense, 3'-antisense and 3'-sense ends, GalNAc is attached to the sense 5'-end and stabilized by four internal PS. 5 µM GalNAc-siRNA conjugates were incubated with 50% FBS for 3 d at 37° C. RNA was extracted and analyzed on 20% TBE polyacrylamide gels. Results are shown in FIG. 26. "UT" indicates untreated samples, "FBS" indicates FBS treatment. "Control" indicates a less stabilized GalNAc-siRNA conjugate of different sequence.

Sequences are set out in Table 13, below, and are SEQ ID NO:17 (top) and SEQ ID NO:18 (bottom).

TABLE 13

GalNAc-siRNA conjugate containing each one PS2 at the
second strand 5'-end and at the second strand 3'-end.

| duplex ID | sequence and chemistry<br>(top: first strand, bottom: second strand, both 5'-3') |
|---|---|
| STS12009L4 | mA(ps)fA(ps)mCfCmAfGmAfAmGfAmAfGmCfAmGfGmU(ps)fG(ps)mA<br>GN2-fUmCfAmCfCmUfGmCfUmUfCmUfUmCfUmGfG(ps)mU(ps)fU |
| STS12009V40L4 | mA(ps)fA(ps)mCfCmAfGmAfAmGfAmAfGmCfAmGfGmU(ps)fG(ps)mA<br>GNo-fU(ps2)mCfAmCfCmUfGmCfUmUfCmUfUmCfUmGfGmU(ps2)fU | mA, mU, mC, mG - 2'-OMe RNA
fA, fU, fC, fG - 2'-F DNA
(ps) - phosphorothioate
(ps2) - phosphorodithioate
GN2 - GalNAc, structure according to FIG. 8B
GNo - GN2 with phosphodiesters instead of (ps)

Table 13: GalNAc-siRNA conjugate containing each one PS2 at the second strand 5'-end and at the second strand 3'-end.

Example 25

Figure 27:
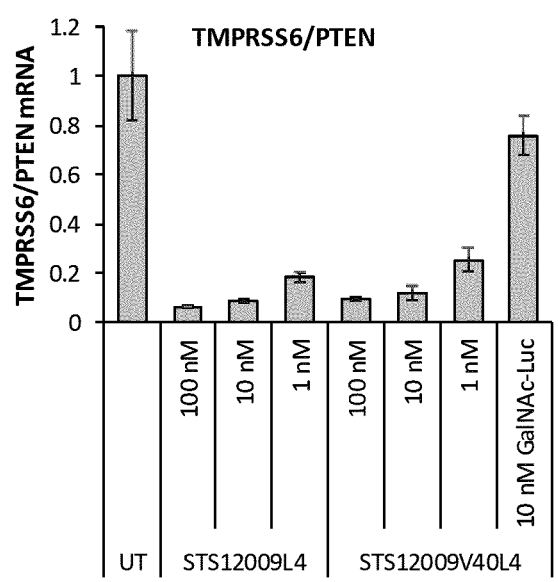
FIG. 27 shows the inhibition of TMPRSS6 expression in mouse primary hepatocytes by a GalNAc siRNA conjugate containing phosphorodithioate linkages.

Activity of a GalNAc-siRNA conjugate (STS12009V40L4) containing each one PS2 at the sense strand 5'-end and at the sense strand 3'-end. GalNAc was conjugated to the 5'-end of the sense strand and is not stabilized by any internal PS. STS12009L4 contains each two terminal PS at 5'-antisense, 3'-antisense and 3'-sense ends, GalNAc is attached to the sense 5'-end and stabilized by four internal PS. The experiment was conducted in mouse primary hepatocytes. Cells were seeded at a density of 250,000 cells per 6-well and treated with 100 nM, 10 nM and 1 nM GalNAc-siRNA. A GalNAc conjugate of an siRNA against Luciferase ("GalNAc-Luc") served as control. Cells were lysed after 24 h, total RNA was extracted and TMPRSS6 and PTEN mRNA levels were determined by Taqman qRT-PCR. Results are shown in FIG. 27. Each bar represents mean+SD from three technical replicates.

Sequences are as set out in Table 13, above.

Example 26

Figure 28:
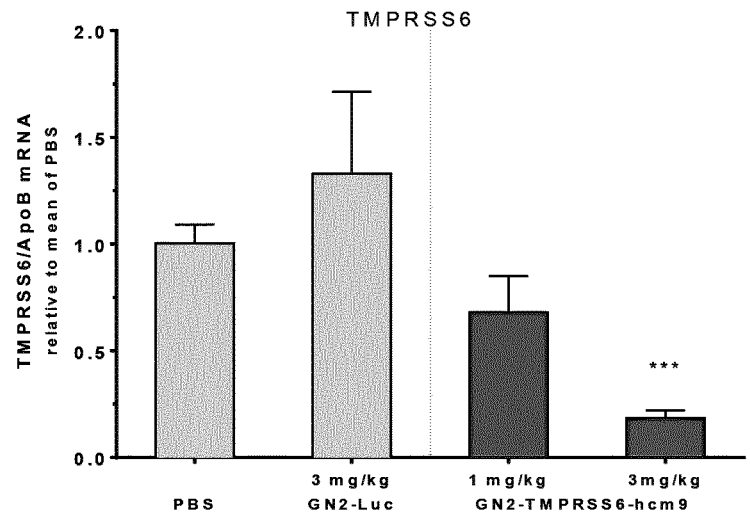
FIG. 28 shows the reduction of TMPRSS6 expression by different doses of GalNAc siRNAs in an animal model for hereditary hemochromatosis.

Inhibition of TMPRSS6 expression by different doses of GalNAc siRNAs in animal model for hereditary hemochromatosis. HFE$^{-/-}$ female mice (Herrmann et al., J. Mol. Med (Berl), 2004 82, 39-48) were treated subcutaneously with a single dose of 1 or 3 mg/kg of GalNAc siRNA conjugate, respectively. Control groups were treated with PBS or with the non targeting control GN2-Luc siRNA1 (GN2-Luc) by subcutaneous injection. Target gene expression in liver tissue was assessed by qRT PCR three weeks after the injection of the conjugates. Group mean and +/−SD. Statistics: Kruskal-Wallis test with uncorrected Dunn. Sequence and modification of siRNA conjugates are depicted in FIG. 7. Results are shown in FIG. 28. P values: ** P<0.001; * P<0.005; ** 0.01; * P<0.05.

Example 27

Figure 29:
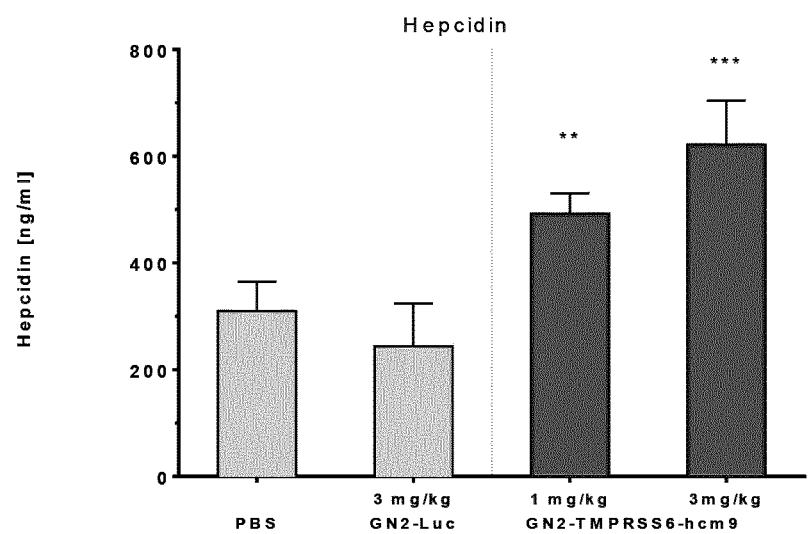
FIG. 29 shows the increase of serum Hepcidin levels by different doses of GalNAc siRNAs in an animal model for hereditary hemochromatosis.

Increase of serum Hepcidin levels by different doses of GalNAc siRNAs in an animal model for hereditary hemochromatosis. HFE$^{-/-}$ mice were treated with single dose of 1 or 3 mg/kg of GalNAc siRNA conjugate by subcutaneous injection. Control groups were treated with PBS or with non targeting control conjugate GN2-Luc siRNA 1 (GN2-Luc). Hepcidin levels were determined in serum samples collected three weeks after injection of the conjugates using ELISA kit (Intrinsic Life Science). Group means with SD. Kruskal-Wallis test with uncorrected Dunn's test against control group (GN2-Luc siRNA). Results are shown in FIG. 29. P values: ** P<0.001; * P<0.005; ** 0.01; * P<0.05.

Example 28

Figure 30:
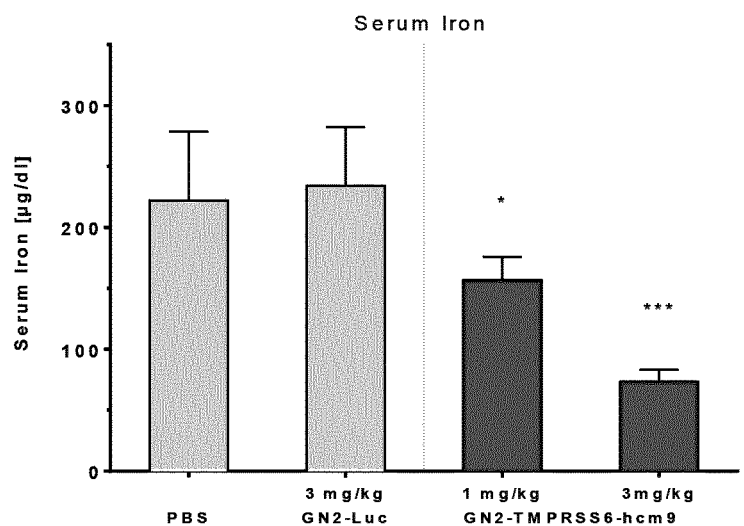
FIG. 30 shows the reduction of serum iron levels by different doses of GalNAc siRNAs in an animal model for hereditary hemochromatosis.

Reduction of serum iron levels by different doses of GalNAc siRNAs in animal model for hereditary hemochromatosis. HFE$^{-/-}$ mice were treated with single dose of 1 or 3 mg/kg of GalNAc siRNA conjugate by subcutaneous administration. Control groups were treated with PBS or with non targeting control conjugate (GN2-Luc siRNA). Serum iron levels were determined three weeks after the treatment. Group means+/−SD. Kruskal-Wallis test with uncorrected Dunn's test against control group (GN2-Luc). Sequences and modifications of siRNA conjugates are depicted in FIG. 7. Results are shown in FIG. 30. P values: ** P<0.001; * P<0.005; **0.01; * P<0.05.

Example 29

Figure 31:
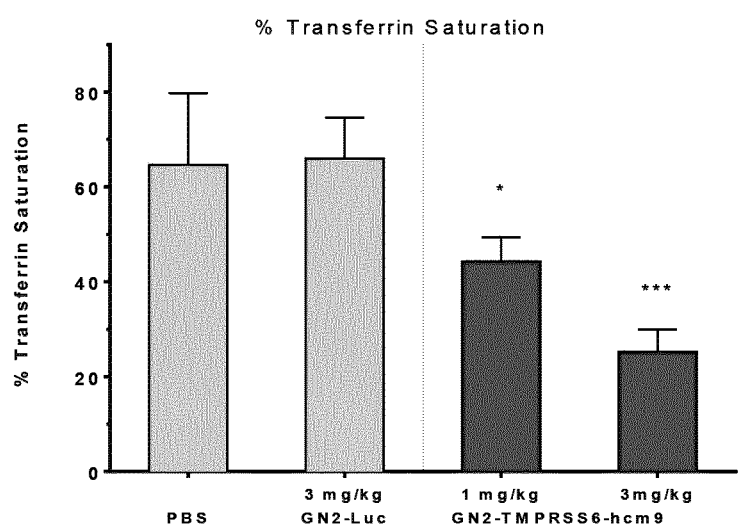
FIG. 31 shows the reduction of transferrin saturation by different doses of GalNAc siRNAs in an animal model for hereditary hemochromatosis.

Reduction of transferrin saturation by different doses of GalNAc siRNAs in animal model for hereditary hemochromatosis. HFE$^{-/-}$ mice were treated with single dose of 1 or 3 mg/kg of GalNAc siRNA conjugate by subcutaneous administration. Control groups were treated with PBS or with non targeting control conjugate GN2-Luc siRNA1 (GN2-Luc). The % transferrin saturation in blood samples was determined three weeks after the treatment. Group means with SD. Kruskal-Wallis test with uncorrected Dunn's test against control group (GN2-Luc). Sequence and modification of siRNA conjugates are depicted in FIG. 7. Results are shown in FIG. 31. P values: ** P<0.001; * P<0.005; ** 0.01; * P<0.05.

Example 30

Figure 32:
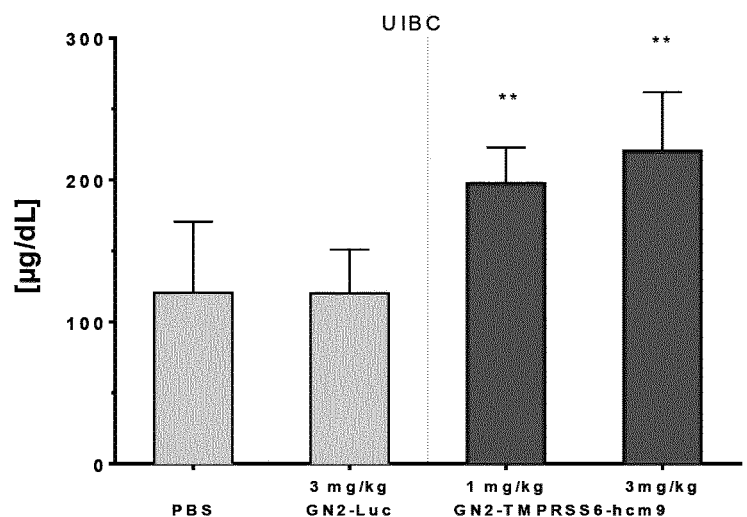
FIG. 32 shows the increase in Unsaturated Iron Binding Capacity by different doses of GalNAc siRNAs in an animal model for hereditary hemochromatosis.

Increase in Unsaturated Iron Binding Capacity (UIBC) in animal model for hereditary hemochromatosis. HFE$^{-/-}$-mice were treated with single dose of 1 or 3 mg/kg of GalNAc siRNA conjugate by subcutaneous administration. Control groups were treated with PBS or with non targeting control conjugate GN2-Luc siRNA1 (GN2-LUC). Serum samples were collected three weeks after treatment for determination of UIBC. Group means with SD. Kruskal-Wallis test with uncorrected Dunn's test against control group (GN2-Luc). Results are shown in FIG. 32. P values: ** P<0.001; * P<0.005; ** 0.01; * P<0.05.

Example 31

Figure 33:
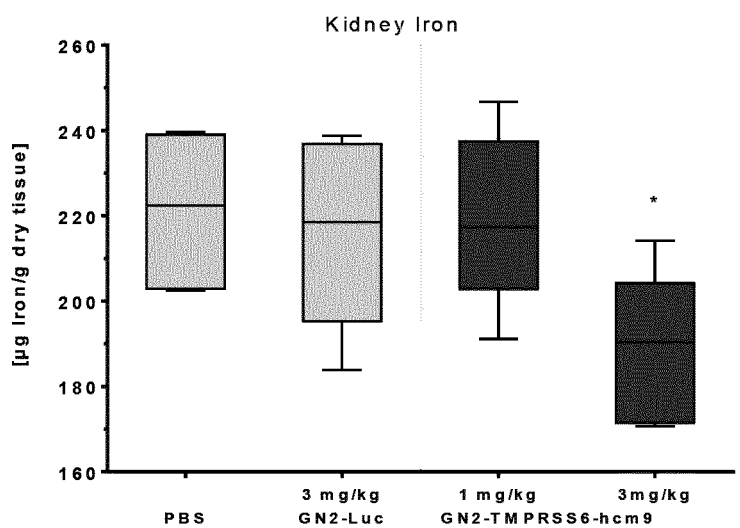
FIG. 33 shows the reduction of tissue iron levels by GalNAc siRNAs in an animal model for hereditary hemochromatosis.

Reduction of tissue iron levels by GalNAc siRNAs in animal model for hereditary hemochromatosis. HFE$^{-/-}$ mice were treated with single dose of 1 or 3 mg/kg of GalNAc siRNA conjugate by subcutaneous administration. Control groups were treated with PBS or with non targeting control conjugate GN2-Luc siRNA1 (GN2-Luc). Iron levels in kidney tissue was assessed three weeks after the treatment. Box and Wiskers (Tukey, median values) Kruskal-Wallis test with uncorrected Dunn's test against control group (GN2-Luc). Results are shown in FIG. 33.

Example 32

Reduction of TMPRSS6 mRNA Expression by Different siRNAs in Hep3B Cells.

Figure 34:
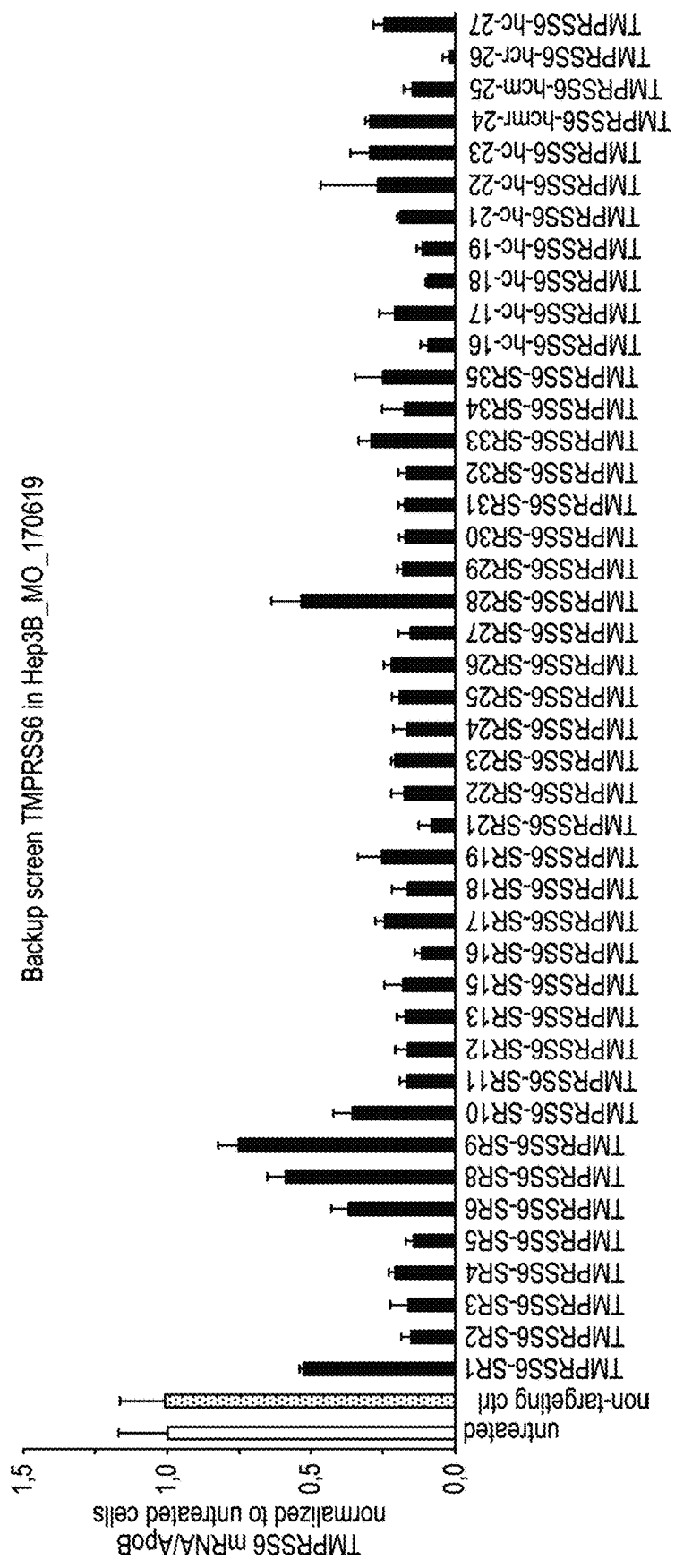
FIG. 34 shows the reduction of human TMPRSS6 mRNA levels in Hep3B cells by liposomal delivery of 43 additional siRNAs.

8000 cells per well were plated in 96-well plates. The following day cells were transfected with 20 nM siRNA and 1 µg/ml AtuFECT. Two days after transfection cells were lysed and TMPRSS6 mRNA levels were determined by q-RT-PCR. TMPRSS6 mRNA levels were normalized to expression levels of the house keeping gene ApoB. An siRNAs against Luciferase was used as non targeting control. Average inhibition and standard deviation of triplicate values relative to untreated cells are shown in FIG. 34. The sequences of the siRNAs are shown in Table 14, below.

TABLE 14

Sequences of siRNAs against TMPRSS6 tested in example 32.
fU, fA, fC, fG - 2'F modified deoxynucleotides. mU, mA, mC, mG - 2'O-methyl modified nucleotides.

| Duplex ID | strand ID | SEQ ID NO: | siRNA sequence |
|---|---|---|---|
| TMPRSS6-SR1 | hcTMP-SR1-A | 133 | mCfUmGfAmGfGmAfCmGfCmCfCmUfGmGfGmAfGmU |
| | hcTMP-SR1-B | 134 | fAmCfUmCfCmCfAmGfGmGfCmGfUmCfCmUfCmAfG |
| TMPRSS6-SR2 | hcTMP-SR2-A | 135 | mGfCmUfGmAfGmGfAmCfGmCfCmCfUmGfGmGfAmG |
| | hcTMP-SR2-B | 136 | fCmUfCmCfCmAfGmGfGmCfGmUfCmCfUmCfAmGfC |
| TMPRSS6-SR3 | hcTMP-SR3-A | 137 | mUfGmCfUmGfAmGfGmAfCmGfCmCfCmUfGmGfGmA |
| | hcTMP-SR3-B | 138 | fUmCfCmCfAmGfGmGfCmGfUmCfCmUfCmAfGmCfA |
| TMPRSS6-SR4 | hcTMP-SR4-A | 139 | mGfUmGfCmUfGmAfGmGfAmCmGfCmCfCmUfGmGfG |
| | hcTMP-SR4-B | 140 | fCmCfCmAfGmGmGfCmGfUmCfCmUfCmAfGmCfAmC |
| TMPRSS6-SR5 | hcTMP-SR5-A | 141 | mGfGmUfGmCfUmGfAmGfGmAfCmGfCmCfCmUfGmG |
| | hcTMP-SR5-B | 142 | fCmCfAmGfGmGfCmGfUmCfCmUfCmAfGmCfAmCfC |
| TMPRSS6-SR6 | hcTMP-SR6-A | 143 | mGfGmGfUmGfCmUfGmAfGmGfAmCfGmCfCmCfUmG |
| | hcTMP-SR6-B | 144 | fCmAfGmGfGmCfGmUfCmCfUmCfAmGfCmAfCmCfC |
| TMPRSS6-SR8 | hcTMP-SR8-A | 145 | mCfGmGfGmUfGmCfUmGfAmGfGmAfCfGmCfCmC |
| | hcTMP-SR8-B | 146 | fGmGfGmCfGmUfCmCfUmCfAmGfCmAfCmCfCmCfG |
| TMPRSS6-SR9 | hcTMP-SR9-A | 147 | mAfCmGfGmGfUmGfCmUfGmAfGmGfAmCfGmCfCmC |
| | hcTMP-SR9-B | 148 | fGmGfCmGfUmCfCmUfCmAfGmCfAmCfCmCfCmGfU |
| TMPRSS6-SR10 | hcTMP-SR10-A | 149 | mUfAmCfGmGfGmUfGmCfUmGfAmGfGmAfCmGfCmC |
| | hcTMP-SR10-B | 150 | fGmCfGmUfCmCfUmCfAmGfCmAfCmCfCmCfGmUfA |
| TMPRSS6-SR11 | hcTMP-SR11-A | 151 | mGfUmAfCmGfGmGfUmGfCmUfGmAfGmGfAmCfGmC |
| | hcTMP-SR11-B | 152 | fCmGfUmCfCmUfCmAfGmCfAmCfCmCfCmGfUmAfC |
| TMPRSS6-SR12 | hcTMP-SR12-A | 153 | mAfGmUfAmCfGmGfGmGfUmGfCmUfGmAfGmGfAmC |
| | hcTMP-SR12-B | 154 | fGmUfCmCfUmCfAmGfCmAfCmCfCmCfGmUfAmCfU |
| TMPRSS6-SR13 | hcTMP-SR13-A | 155 | mAfAmGfUmAfCmGfGmGfGmUfGmCfUmGfAmGfGmA |
| | hcTMP-SR13-B | 156 | fUmCfCmUfCmAfGmCfAmCfCmCfCmGfUmAfCmUfU |
| TMPRSS6-SR15 | hcTMP-SR15-A | 157 | mGfGmAfAmGfUmAfCmGfGmGfGmUfGmCfUmGfAmG |
| | hcTMP-SR15-B | 158 | fCmUfCmAfGmCfAmCfCmCfCmGfUmAfCmUfUmCfC |
| TMPRSS6-SR16 | hcTMP-SR16-A | 158 | mGfGmGfAmAmGfUmAfCmGfGmGfGmUfGmCfUmGmA |
| | hcTMP-SR16-B | 160 | fUmCfAmGfCmAfCmCfCmCfGmUfAmCfUmUfCmCfC |
| TMPRSS6-SR17 | hcTMP-SR17-A | 161 | mGfGmGfGmAfAmGfUmAfCmGfGmGfGmUfGmCfUmG |
| | hcTMP-SR17-B | 162 | fCmAfGmCfAmCfCmCfCmGfUmAfCmUfUmCfCmCfC |
| TMPRSS6-SR18 | hcTMP-SR18-A | 163 | mUfGmGfGmGfAmAmGfUmAfCmGfGmGfGmUfGmCmU |
| | hcTMP-SR18-B | 164 | fAmGfCmAfCmCfCmCfGmUfAmCfUmUfCmCfCmCfA |
| TMPRSS6-SR19 | hcTMP-SR19-A | 165 | mCfUmGfGmGfGmAfAmGfUmAfCmGfGmGfGmUfGmC |
| | hcTMP-SR19-B | 166 | fGmCfAmCfCmCfCmGfUmAfCmUfUmCfCmCfCmAfG |
| TMPRSS6-SR21 | hcTMP-SR21-A | 167 | mAfGmCfUmGfGmGfGmAfAmGfUmAfCmGfGmGfGmU |
| | hcTMP-SR21-B | 168 | fAmCfCmCfCmGfUmAfCmUfUmCfCmCfCmAfGmCfU |
| TMPRSS6-SR22 | hcTMP-SR22-A | 169 | mUfAmGfCmUfGmGfGmGfAmAmGfUmAfCmGfGmGfGmG |
| | hcTMP-SR22-B | 170 | fCmCfCmCfGmUfAmCfUmUfCmCfCmCfAmGfCmUfA |
| TMPRSS6-SR23 | hcTMP-SR23-A | 171 | mGfUmAfGmCfUmGfGmGfGmAfAmGfUmAfCmGfGmG |
| | hcTMP-SR23-B | 172 | fCmCfCmGfUmAfCmUfUmCfCmCfCmAfGmCfUmAfC |
| TMPRSS6-SR24 | hcTMP-SR24-A | 173 | mAfGmUfAmGfCmUfGmGfGmGfAmAfGmUfAmCfGmG |
| | hcTMP-SR24-B | 174 | fCmCfGmUfAmCfUmUfCmCfCmCfAmGfCmUfAmCfU |
| TMPRSS6-SR26 | hcTMP-SR26-A | 175 | mGfUmAfGmUfAmGfCmUfGmGfGmGfAmAfGmUfAmC |
| | hcTMP-SR26-B | 176 | fGmUfAmCfUmUfCmCfCmCfAmGfCmUfAmCfUmAfC |
| TMPRSS6-SR27 | hcTMP-SR27-A | 177 | mAfGmUfAmGfUmAfGmCfUmGfGmGfGmAfAmGfUmA |
| | hcTMP-SR27-B | 178 | fUmAfCmUfUmCfCmCfCmAfGmCfUmAfCmUfAmCfU |
| TMPRSS6-SR28 | hcTMP-SR28-A | 179 | mGfAmGfUmAfGmUfAmGfCmUfGmGfGmGfAmAfGmU |
| | hcTMP-SR28-B | 180 | fAmCfUmUfCmCfCmCfAmGfCmUfAmCfUmAfCmUfC |

TABLE 14-continued

Sequences of siRNAs against TMPRSS6 tested in example 32.
fU, fA, fC, fG - 2'F modified deoxynucleotides. mU, mA, mC, mG -
2'O-methyl modified nucleotides.

| Duplex ID | strand ID | SEQ ID NO: | siRNA sequence |
|---|---|---|---|
| TMPRSS6-SR29 | hcTMP-SR29-A | 181 | mCfGmAfGmUfAmGfUmAfGmCfUmGfGmGfGmAfAmG |
| | hcTMP-SR29-B | 182 | fCmUfUmCfCmCfCmAfGmCfUmAfCmUfAmCfUmCfG |
| TMPRSS6-SR30 | hcTMP-SR30-A | 183 | mGfCmGfAmGfUmAfGmUfAmGfCmUfGmGfGmAfAmA |
| | hcTMP-SR30-B | 184 | fUmUfCmCfCmCfAmGfCmUfAmCfUmAfCmUfCmGfC |
| TMPRSS6-SR31 | hcTMP-SR31-A | 185 | mGfGmCfGmAfGmUfAmGfUmAfGmCfUmGfGmGfGmA |
| | hcTMP-SR31-B | 186 | fUmCfCmCfCmAfGmCfUmAfCmUfAmCfUmCfGmCfC |
| TMPRSS6-SR32 | hcTMP-SR32-A | 187 | mGfGmGfCmGfAmGfUmAfGmUfAmGfCmUfGmGfGmG |
| | hcTMP-SR32-B | 188 | fCmCfCmCfAmGfCmUfAmCfUmAfCmUfCmGfCmCfC |
| TMPRSS6-SR33 | hcTMP-SR33-A | 189 | mGfGmGfGmCfGmAfGmUfAmGfUmAfGmCfUmGfGmG |
| | hcTMP-SR33-B | 190 | fCmCfCmAfGmCfUmAfCmUfAmCfUmCfGmCfCmCfC |
| TMPRSS6-SR34 | hcTMP-SR34-A | 191 | mUfGmGfGmGfCmGfAmGfUmAfGmUfAmGfCmUfGmG |
| | hcTMP-SR34-B | 192 | fCmCfAmGfCmUfAmCfUmAfCmUfCmGfCmCfCmCfA |
| TMPRSS6-SR35 | hcTMP-SR35-A | 193 | mUfUmGfGmGfGmCfGmAfGmUfAmGfUmAfGmCfUmG |
| | hcTMP-SR35-B | 194 | fCmAfGmCfUmAfCmUfAmCfUmCfGmCfCmCfCmAfA |
| TMPRSS6-hc-16 | TMPRSS6-hc-16A | 195 | mUfAmUfUmCfCmAfAmAfGmGfGmCfAmGfCmUfGmA |
| | TMPRSS6-hc-16B | 196 | fUmCfAmGfCmUfGmCfCmCfUmUfUmGfGmAfAmUfA |
| TMPRSS6-hc-17 | TMPRSS6-hc-17A | 197 | mAfUmCfUmUfCmUfGmGfGmCfUmUfUmGfCmCfGmG |
| | TMPRSS6-hc-17B | 198 | fCmCfGmCfCmAfAmAfGmCfCmCfAmGfAmAfGmAfU |
| TMPRSS6-hc-18 | TPRSS6-hc-18A | 199 | mUfUmUfUmCfUmCfUmGfGmAfGmUfCmCfCmUfCmA |
| | TMPRSS6-hc-18B | 200 | fUmGfAmGfGmAfCmUfCmCfAmAfGmAfGmAfAmAfA |
| TMPRSS6-hc-19 | TMPRSS6-hc-19A | 201 | mGfAmAfUmAfGmAfCmGfCmAfGmCfUmGfGmAfGmU |
| | TMPRSS6-hc-19B | 202 | fAmCfUmCfCmAfGmCfUmCfCmGfUmCfUmAfUmUfC |
| TMPRSS6-hc-21 | TMPRSS6-hc-21A | 203 | mUfAmGfUmAfGmCfUmGfGmGfGmAfAmGfUmAfCmG |
| | TMPRSS6-hc-21B | 204 | fCmGfUmAfCmUfUmCfCmCfCmAfGmCfUmAfCmUfA |
| TMPRSS6-hc-22 | TMPRSS6-hc-22A | 205 | mAfGmAfUmCfCmUfGmGfGmAfGmAfAmGfUmGfGmC |
| | TMPRSS6-hc-22B | 206 | fGmCfCmAfCmUfUmCfUmCfCmCfAmGfGmAfUmCfU |
| TMPRSS6-hc-23 | TMPRSS6-hc-23A | 207 | mCfUmGfUmUfCmUfGmGfAmUfCmGfUmCfCmAfCmU |
| | TMPRSS6-hc-23B | 208 | fAmGfUmGfGmAfCmGfAmUfCmCfAmGfAmAfCmAfG |
| TMPRSS6-hcmr-24 | TMPRSS6-hcmr-24A | 209 | mCfUmCfAmCfCmUfUmGfAmAfGmGfAmCfAmCfCmU |
| | TMPRSS6-hcmr-24B | 210 | fAmGfGmUfGmUfCmCfUmUfCmAfAmGfGmUfGmAfG |
| TMPRSS6-hcm-25 | TMPRSS6-hcm-25 | 211 | mAfGmUfUmUfCmUfCmUfCmAfUmCfCmAfGmCfCmC |
| | TMPRSS6-hcm-25 | 212 | fGmGfCmCfUmGfGmAfUmGfAmGfAmAfAmAfAmCfU |
| TMPRSS6-hcr-26 | TMPRSS6-hcr-26A | 213 | mGfUmAfCmCfCmUfAmGfGmAfAmAfUmAfCmCfAmG |
| | TMPRSS6-hcr-26B | 214 | fCmUfGmGfUmAfUmUfUmCfCmUfAmGfGmGfUmAfC |
| TMPRSS6-hc-27 | TMPRSS6-hc-27A | 215 | mCfUmGfUmUfGmAfCmUfGmUfGmGfAmCfAmGfCmA |
| | TMPRSS6-hc-27B | 216 | fUmGfCmUfGmUfCmCfAmCfAmGfUmCfAmAfCmAfG |

Example 33

Dose-Response of siRNAs Against TMPRSS6 in Hep3B Cells.

Figure 35:
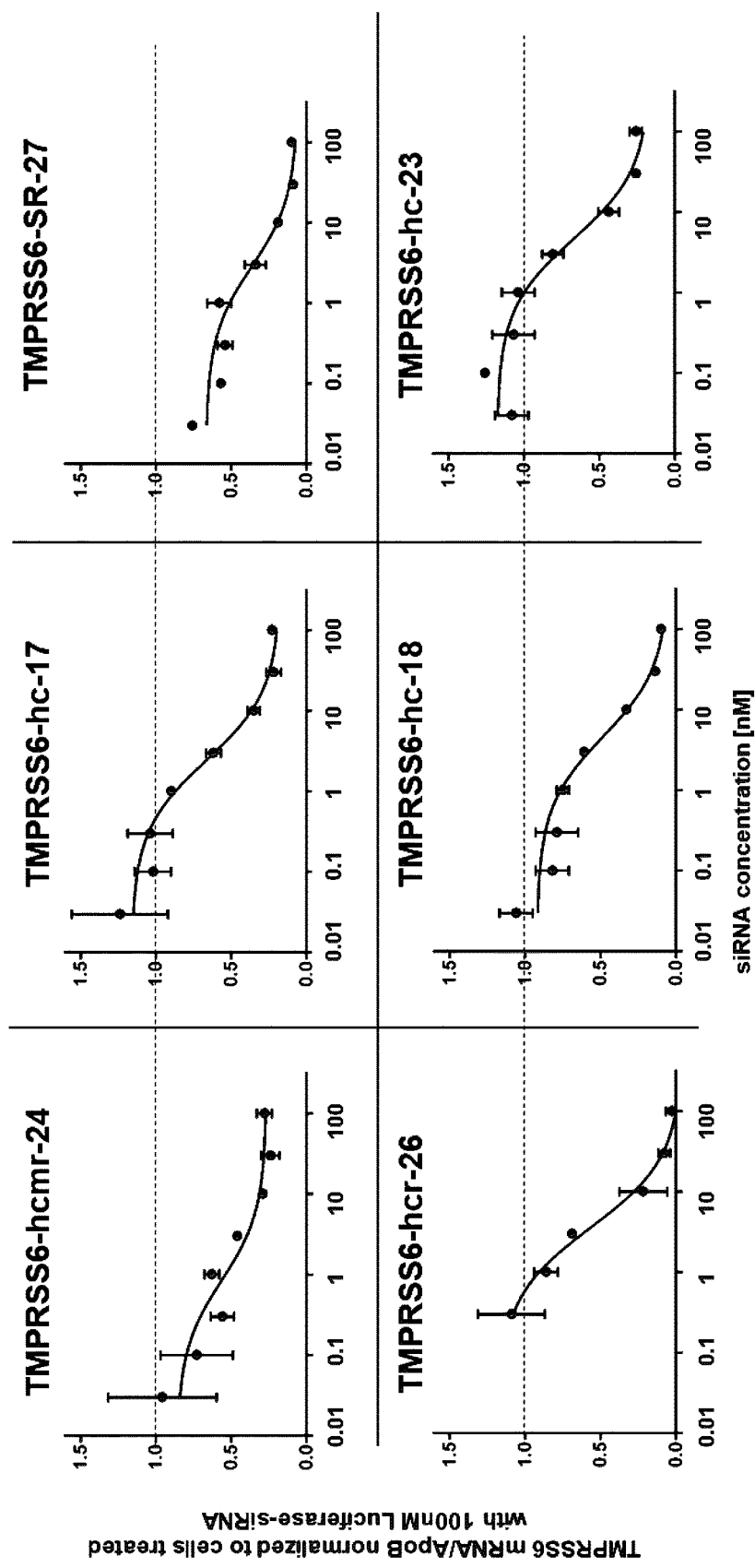
FIG. 35 shows the dose response curves of different siRNAs for inhibition of TMPRSS6 expression in Hep3B cells.
Figure 35:
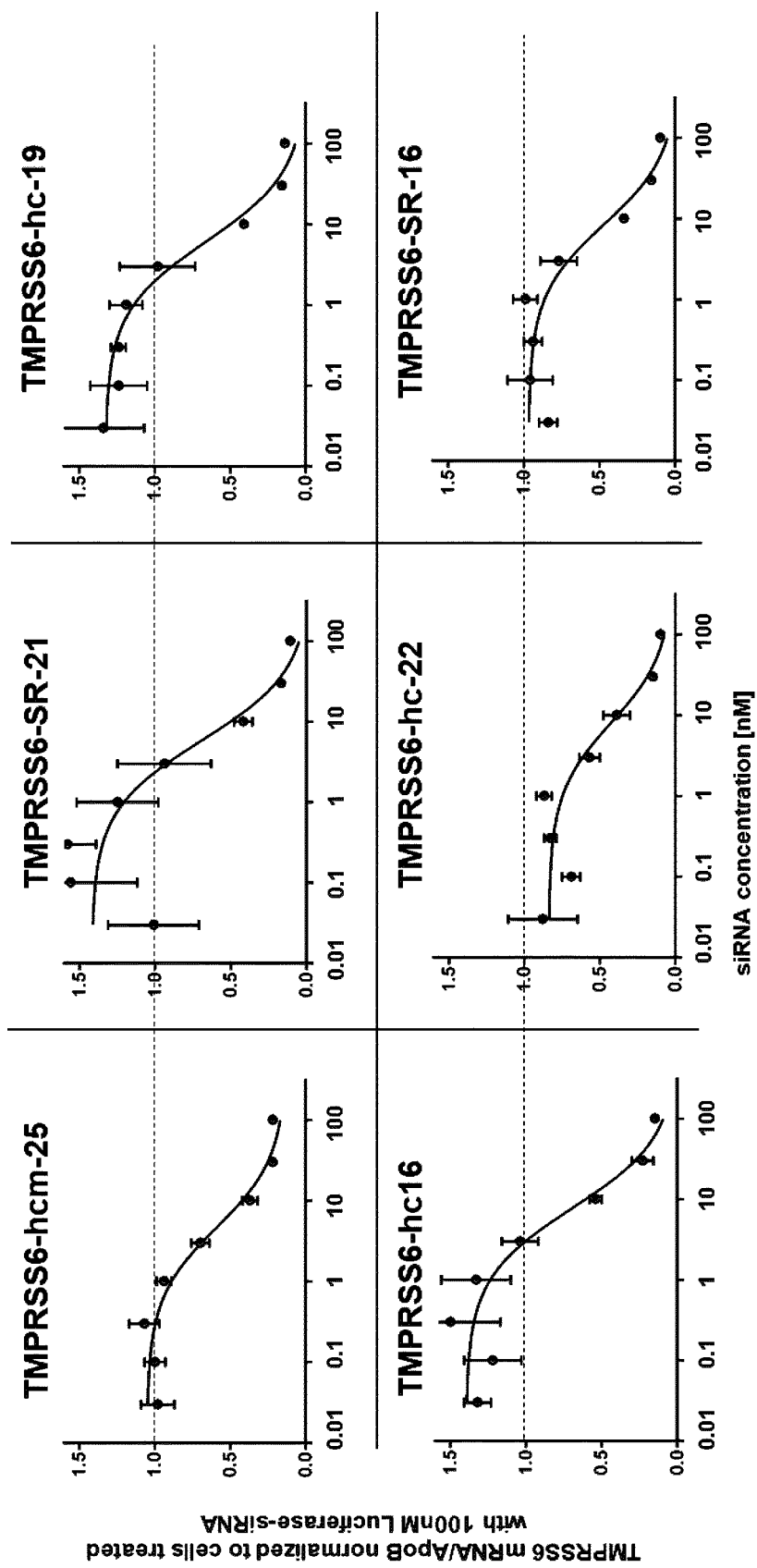
Figure 35:
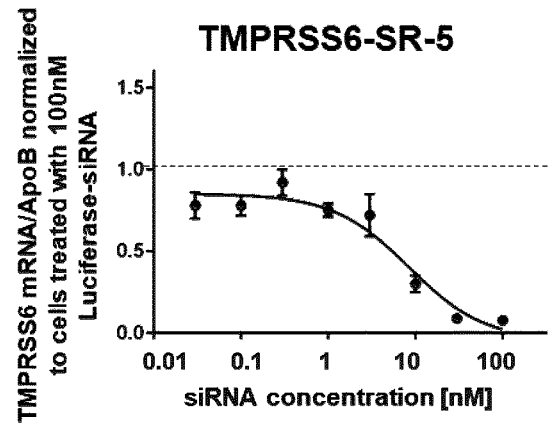

8000 cells per well were plated in 96-well plates. The following day cells were transfected with siRNA in indicated concentrations (100 nM-0.03 nM) and 1 µg/ml Atu-FECT. Two days after transfection cells were lysed and TMPRSS6 mRNA levels were determined by q-RT-PCR. TMPRSS6 mRNA levels were normalized to expression levels of the house keeping gene ApoB. Average inhibition and standard deviation of triplicate values relative to cells treated with 100 nM of a non-targeting Luciferase-control siRNA are shown in FIG. 35. Table 15, below, shows maximum inhibition, IC50 and 95% confidence interval according to dose-response curves shown in FIG. 35.

TABLE 15

| Duplex ID | Max inhibition | IC50 [nM] | 95% confidence interval [nM] | kd at 20 nM as shown in FIG. 34 | sd |
|---|---|---|---|---|---|
| TMPRSS6-hcmr-24 | 73% | 0.8 | 0.1-6.2 | 70% | 2% |
| TMPRSS-hc-17 | 82% | 2.4 | 1.1-5.0 | 79% | 5% |
| TMPRSS-SR-27 | 94% | 2.8 | 0.7-10.8 | 84% | 4% |
| TMPRSS-hcr-26 | 100% | 3.5 | 1.4-9.0 | 98% | 2% |
| TMPRSS-hc-18 | 95% | 4.6 | 1.5-14.1 | 90% | 1% |

TABLE 15-continued

| Duplex ID | Max inhibition | IC50 [nM] | 95% confidence interval [nM] | kd at 20 nM as shown in FIG. 34 | sd |
|---|---|---|---|---|---|
| TMPRSS-hc-23 | 83% | 4.6 | 1.9-11.1 | 70% | 7% |
| TMPRSS-hcm-25 | 87% | 4.6 | 2.1-10.2 | 85% | 3% |
| TMPRSS-SR-21 | 100% | 5.8 | 0.9-36.9 | 92% | 4% |
| TMPRSS-hc-19 | 100% | 6.1 | 3.0-12.5 | 89% | 2% |
| TMPRSS-hc-16 | 100% | 7.7 | 2.6-22.6 | 91% | 3% |
| TMPRSS-hc-22 | 99% | 8.1 | 2.1-31.1 | 73% | 20% |
| TMPRSS-SR-16 | 100% | 8.4 | 2.5-28.2 | 88% | 2% |
| TMPRSS-SR-5 | 100% | 8.4 | 2.4-29.0 | 85% | 2% |

Example 34

Inhibition of TMPRSS6 mRNA Expression by Receptor Mediated Uptake in 1° Human Hepatocytes.

Figure 36:
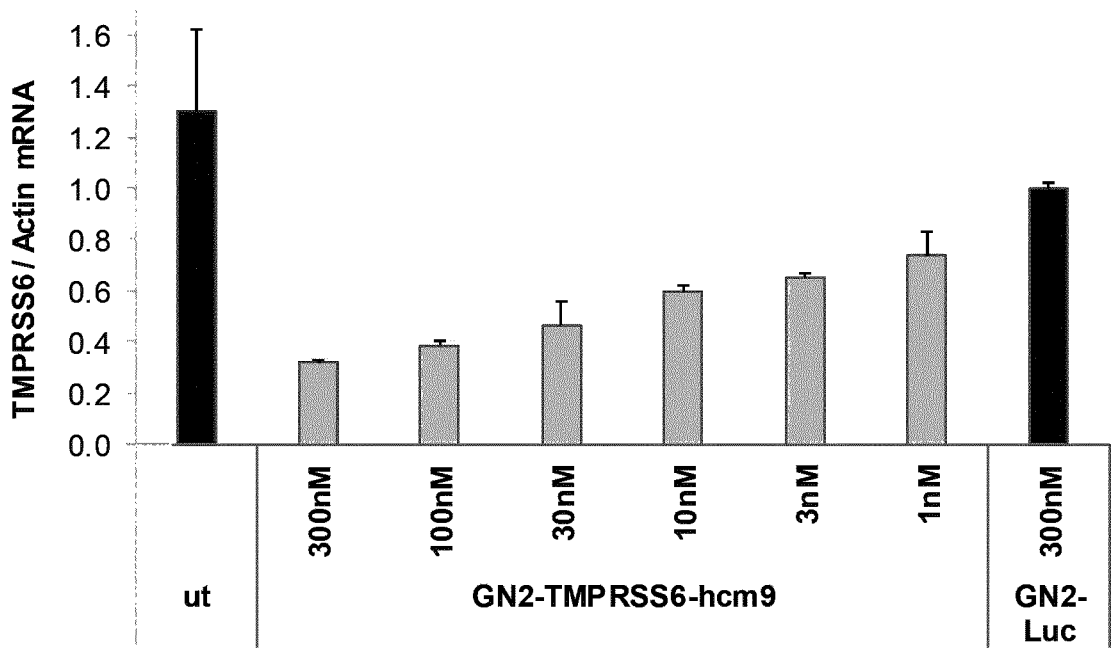
FIG. 36 shows the reduction of TMPRSS6 expression in primary human hepatocytes by receptor mediated uptake of GalNAc siRNA conjugates at different concentrations.

Primary human hepatocytes were plated on collagen coated dishes and incubated with siRNA conjugates diluted in cell culture medium at concentrations of 300 nM to 1 nM as indicated. 24 hours after exposing the cells to siRNA conjugates total RNA was extracted and TMPRSS6 expression was quantified by Taqman qRT-PCR. TMPRSS6 mRNA levels were normalized to Actin mRNA levels and to target mRNA levels of cells treated with non targeting control siRNA conjugate GN2-Luc siRNA 1 (GN2-Luc). Dose dependent inhibition of TMPRSS6 expression was observed by the GalNAc-TMPRSS6 siRNA conjugate. Sequences and modifications of the conjugates are depicted in FIG. 7. Results are shown in FIG. 36.

Example 35

GalNAc TMPRSS6 siRNA Raises Hematocrit Values in Rodent Model for β-Thalassemia Intermedia.

Figure 37:
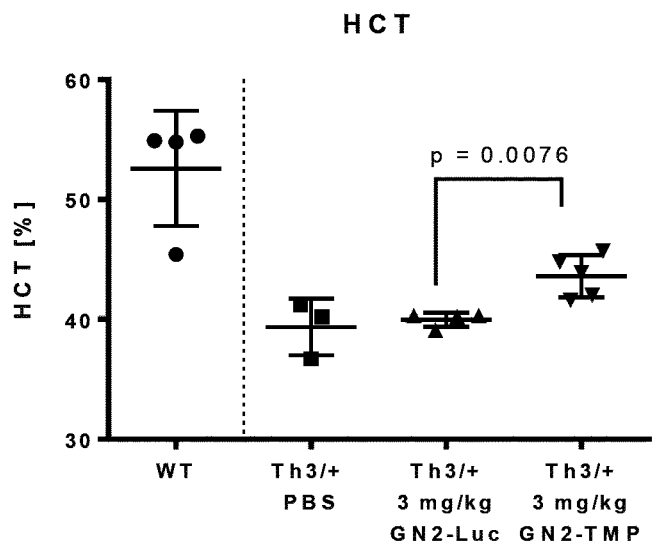
FIG. 37 shows the increase of haematocrit values in rodent model for β-thalassemia intermedia by treatment with GalNAc siRNA conjugates.

Hbb$^{th3/+}$ mice (Yang et al. 1995, PNAS Vol. 92, 11608-11612) were treated on d1 and on d15 Hbb subcutaneously with 3 mg/kg GN2-TMPRSS6-hcm9 (GN2-TMP), GN2-Luc siRNA 1 (GN2-Luc) or PBS as non targeting control or as vehicle control, respectively. On d36 whole blood was collected into heparin coated tubes for full blood examination. Hbb$^{th3/+}$ mice were obtained from Jackson Laboratory (Bar Harbor, ME) and maintained on a C57BL/6 background. Blood samples from untreated wild type (WT) mice (C57BL/6) were collected and analysed for comparisons. Scatter dot blot, mean+/−SD; n=3-6. Statistics: unpaired t test with Welch's correction. Results are shown in FIG. 37.

Example 36

GalNAc TMPRSS6 siRNA Reduces Red Blood Cell Distribution Width in Rodent Model for b-Thalassemia Intermedia.

Figure 38:
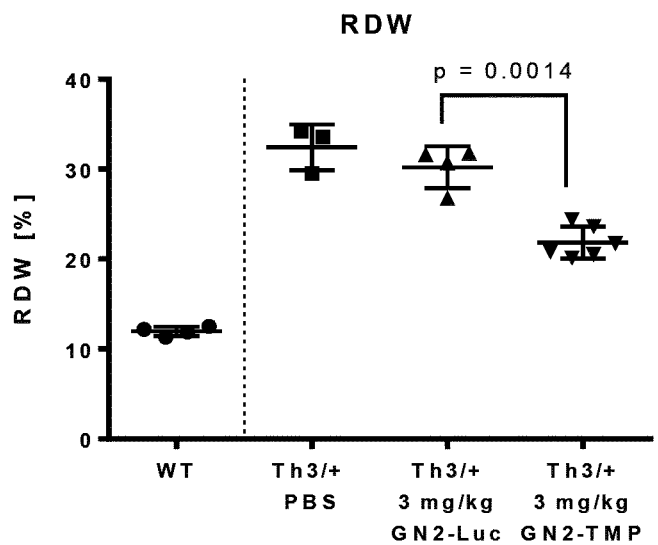
FIG. 38 shows the reduction in red blood cell distribution widths in rodent model for β-thalassemia intermedia by treatment with GalNAc siRNA conjugates.

Hbb$^{th3/+}$ mice (Yang et al. 1995, PNAS Vol. 92, 11608-11612) were treated on d1 and on d15 subcutaneously with 3 mg/kg GN2-TMPRSS6-hcm9 (GN2-TMP), GN2-Luc siRNA1 (GN2-Luc) or PBS as non targeting control or as vehicle control, respectively. On d36 whole blood was collected into heparin coated tubes for full blood examination. The Hbb$^{th3/+}$ mice were obtained from Jackson Laboratory (Bar Harbor, ME) and maintained on a C57BL/6 background. Blood samples from untreated wild type (WT) mice (C57BL/6) were collected and analysed for comparisons. Scatter dot blot, mean+/−SD; n=3-6. Statistics: unpaired t test with Welch's correction. Results are shown in FIG. 38.

Examples 37

GalNAc TMPRSS6 siRNA Reduces the Proportion of Reticulocytes in Rodent Model for β-Thalassemia Intermedia.

Figure 39:
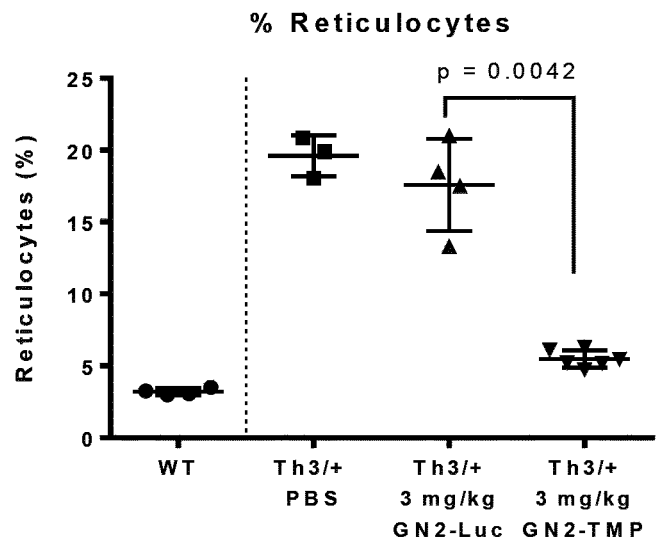
FIG. 39 shows the reduction in proportion of reticulocytes in blood of rodent model for β-thalassemia intermedia by treatment with GalNAc siRNA conjugates.

Hbb$^{th3/+}$ mice (Yang et al. 1995, PNAS Vol. 92, 11608-11612) were treated on d1 and on d15 subcutaneously with 3 mg/kg GN2-TMPRSS6 hcm9 (GN2-TMP), GN2-Luc siRNA 1 (GN2-Luc) or PBS as non targeting control or as vehicle control, respectively. On d 36 whole blood was collected into heparin coated tubes for full blood examination. The Hbb$^{th3/+}$ mice were obtained from Jackson Laboratory (Bar Harbor, ME) and maintained on a C57BL/6 background. Blood samples from untreated wild type (WT) mice (C57BL/6) were collected and analysed for comparisons. Scatter dot blot, mean+/−SD; n=3-6. Statistics: unpaired t test with Welch's correction. Results are shown in FIG. 39.

Examples 38

Figure 40:
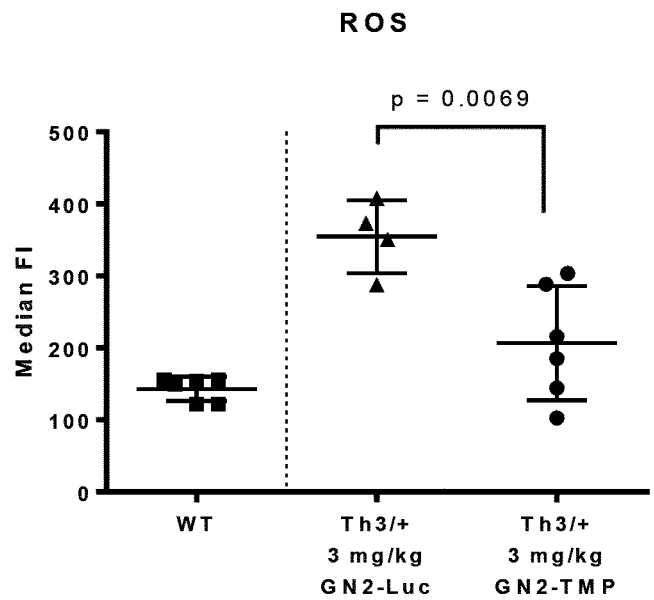
FIG. 40 shows the reduction of reactive oxygen species in red blood cells of rodent model for β-thalassemia intermedia by treatment with GalNAc siRNA conjugates.

GalNAc TMPRSS6 siRNA reduces the amount of reactive oxygen species (ROS) in rodent model for β-thalassemia intermedia. Hbb$^{th3/+}$ mice (Th3/+; Yang et al. 1995, PNAS Vol. 92, 11608-11612) were treated on d1 and on d15 subcutaneously with 3 mg/kg GN2-TMPRSS6 hcm9 (GN2-TMP) or GN2-Luc 1 siRNA (GN2-Luc) as non targeting control. On d 36 whole blood was collected into heparin coated tubes for full blood examination. ROS measurements were performed 5 min. after addition of 2'7' dichlorofluorescein as indicator (Siwaponanan et al, 2017 Blood, 129, 3087-3099). Blood samples from GN2-TMPRSS6 hcm9 treated mice were measured twice. The Hbb$^{th3/+}$ mice (Th3/+) were obtained from Jackson Laboratory (Bar Harbor, ME) and maintained on a C57BL/6 background. Blood samples from untreated wild type (WT) mice (C57BL/6) were collected and analysed for comparisons. Scatter dot blot, mean+/−SD; n=4-6. Statistic: unpaired t test with Welch's correction. Results are shown in FIG. 40.

Example 39

Figure 41:
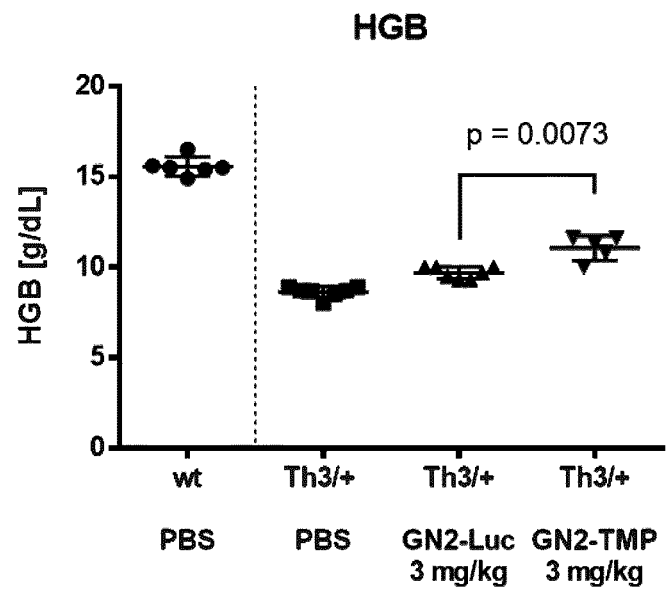
FIG. 41 shows GalNAc TMPRSS6 siRNA raises hemoglobin levels in rodent model for β-thalassemia intermedia.

GalNAc TMPRSS6 siRNA raises hemoglobin levels in rodent model for β-thalassemia intermedia. Hbb$^{th3/+}$ mice (Yang et al. 1995, PNAS Vol. 92, 11608-11612) were treated on d1 and on d15 subcutaneously with 3 mg/kg GN2-TMPRSS6-hcm9 (GN2-TMP), GN2-Luc-siRNA 1 (GN2-Luc) or PBS as non targeting control or as vehicle control, respectively. On d 36 whole blood was collected into heparin coated tubes for full blood examination. Hbb$^{th3/+}$ mice were obtained from Jackson Laboratory (Bar Harbor, ME) and maintained on a C57BL/6 background. Blood samples from untreated wild type (wt) mice (C57BL/6) were collected and analysed for comparisons. Scatter dot blot, mean+/−SD; n=5-7. Statistics: Welch's t-tests uncorrected for multiple comparison. Results are shown in FIG. 41. siRNA conjugates are depicted in FIG. 7.

Example 40

Figure 42:
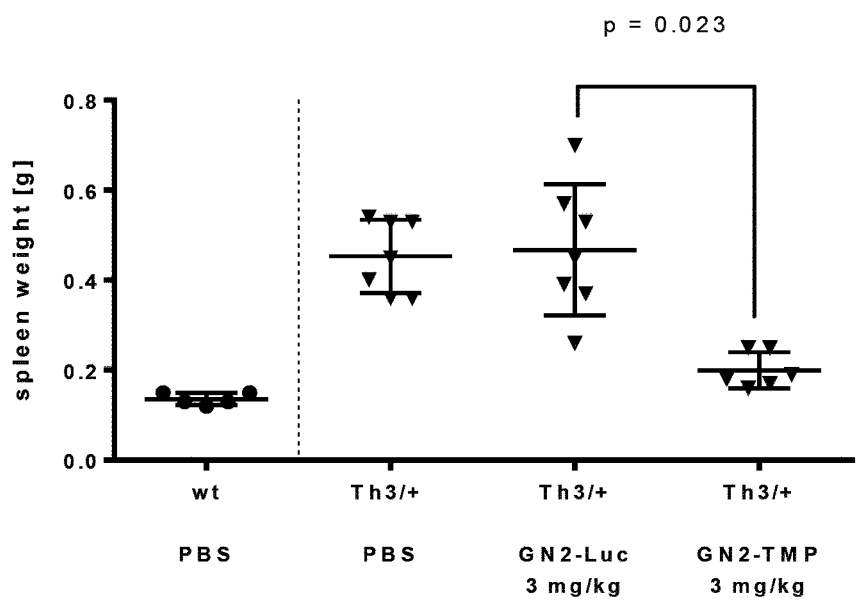
FIG. 42 shows GalNAc TMPRSS6 reduces splenomegaly in rodent model for β-thalassemia intermedia.

GalNAc TMPRSS6 reduces splenomegaly in rodent model for β-thalassemia intermedia. Hbb$^{th3/+}$ mice (Yang et al. 1995, PNAS Vol. 92, 11608-11612) were treated on d1 and on d15 subcutaneously with 3 mg/kg GN2-TMPRSS6-hcm9 (GN2-TMP), GN2-Luc-siRNA 1 (GN2-Luc) or PBS as non targeting control or as vehicle control, respectively. On d 39 spleen weights were assessed. Hbb$^{th3/+}$ mice were obtained from Jackson Laboratory (Bar Harbor, ME) and maintained on a C57BL/6 background. Spleen weights from wild type (wt) mice (C57BL/6) treated with PBS were assessed for comparisons. Scatter dot blot, mean+/−SD; n=5-7. Statistics: Welch's t-tests uncorrected for multiple comparison. Results are shown in FIG. 42. siRNA conjugates are depicted in FIG. 7.

Example 41

Figure 43:
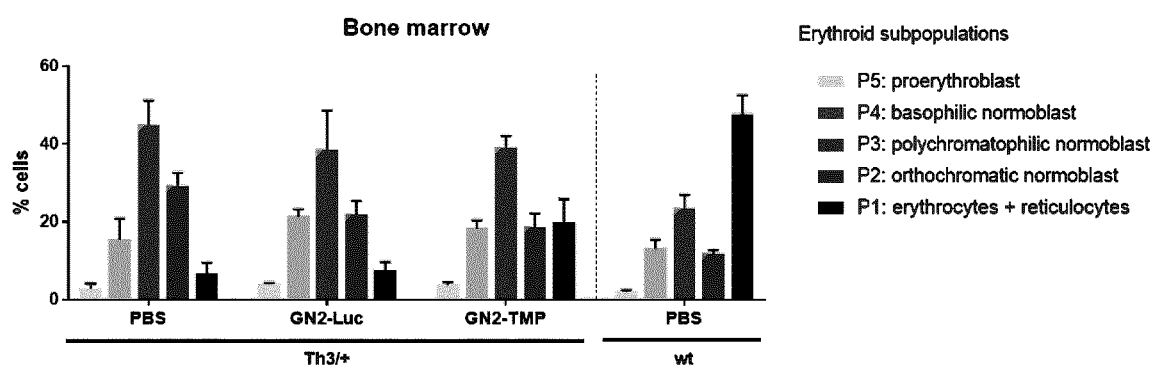
FIG. 43 shows GalNAc TMPRSS6 improves red blood cell maturation in the bone marrow.

GalNAc TMPRSS6 improves red blood cell maturation in the bone marrow. Hbb$^{th3/+}$ mice (Yang et al. 1995, PNAS Vol. 92, 11608-11612) were treated on d1 and on d15 subcutaneously with 3 mg/kg GN2-TMPRSS6-hcm9 (GN2-TMP), GN2-Luc-siRNA 1 (GN2-Luc) or PBS as non targeting control or as vehicle control, on d39 cells were collected from the bone marrow and analyzed by FACS analysis. Viable erythroid cells were separated into distinct populations based on CD71, Ter119 and CD44 staining. Hbb$^{th3/+}$ mice were obtained from Jackson Laboratory (Bar Harbor, ME) and maintained on a C57BL/6 background. Erythroid cells from the bone marrow of wild type (wt) mice (C57BL/6) treated with PBS were assessed for comparisons. Bar graph, mean+/−SD; n=5-7. Statistics: Welch's t-tests uncorrected for multiple comparison. Results are shown in FIG. 43. siRNA conjugates are depicted in FIG. 7.

Example 42

Figure 44:
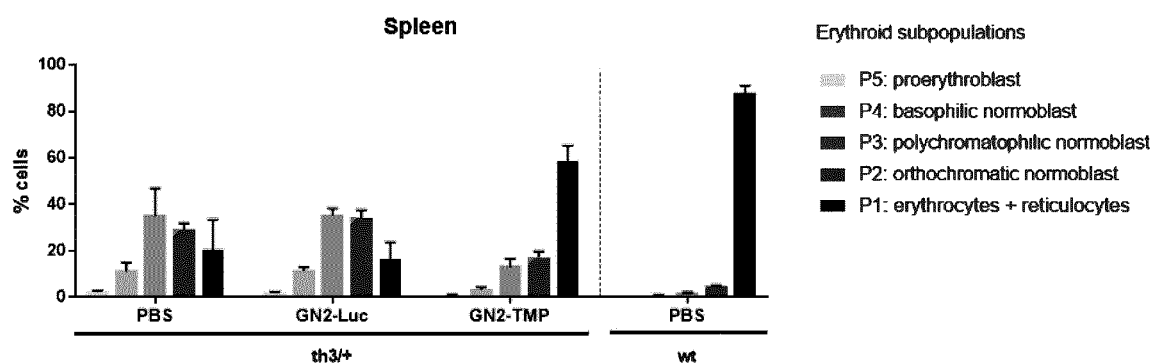
FIG. 44 shows GalNAc TMPRSS6 reduces ineffective erythropoiesis in the spleen.

GalNAc TMPRSS6 reduces ineffective erythropoiesis in the spleen. Hbb$^{th3/+}$ mice (Yang et al. 1995, PNAS Vol. 92, 11608-11612) were treated on d1 and on d15 subcutaneously with 3 mg/kg GN2-TMPRSS6 hcm9 (GN2-TMP), GN2-Luc siRNA 1 (GN2-Luc) or PBS as non targeting control or as vehicle control, respectively. On d 39 cells were collected from the spleen and analyzed by FACS analysis. Viable erythroid cells were separated into distinct populations based on CD71, Ter119 and CD44 staining. Hbb$^{th3/+}$ mice were obtained from Jackson Laboratory (Bar Harbor, ME) and maintained on a C57BL/6 background. Erythroid cells from the from wild type (wt) mice (C57BL/6) treated with PBS were assessed for comparisons. Bar graph, mean+/−SD; n=5-7. Statistics: Welch's t-tests uncorrected for multiple comparison. Results are shown in FIG. 44. siRNA conjugates are depicted in FIG. 7.

Example 43

Reduction of TMPRSS6 Expression in Human Hepatocytes by GalNAc siRNA Conjugates.

30,000 cpw human primary hepatocytes were seeded in collagen-coated 96-well plates. Cell were treated with indicated amounts of siRNA conjugates immediately after plating. Cells were lysed 24 hours post treatment and TMPRSS6 mRNA expression analyzed by TaqMan qRT-PCR. Triplicate values of TMPRSS6 normalized to ApoB (housekeeper) and to mean of untreated cells are shown.

Figure 45A:
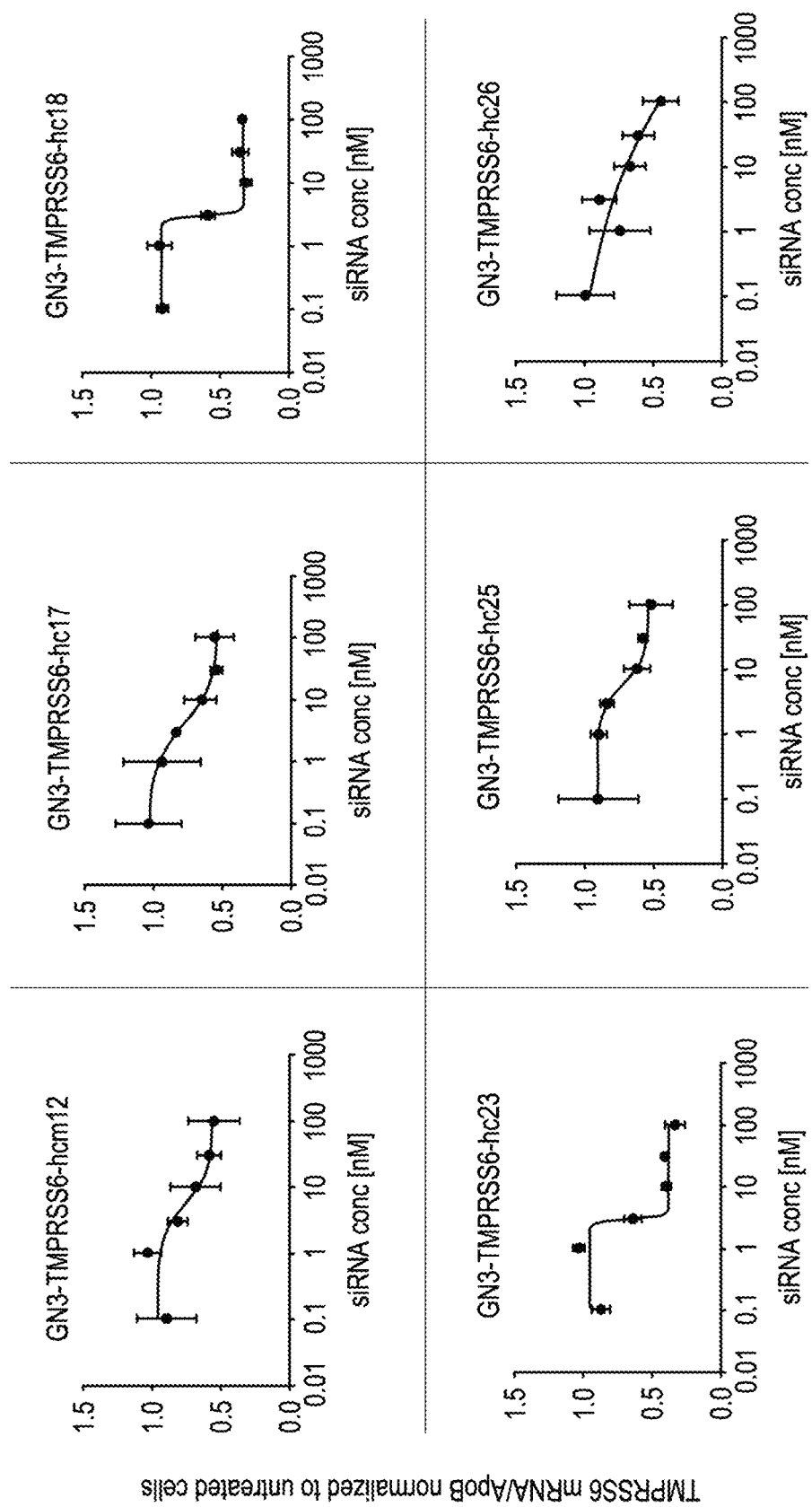
FIG. 45 a and b show dose-response curves of siRNA conjugates against TMPRSS6 in primary human hepatocytes.
Figures 45B, 46:
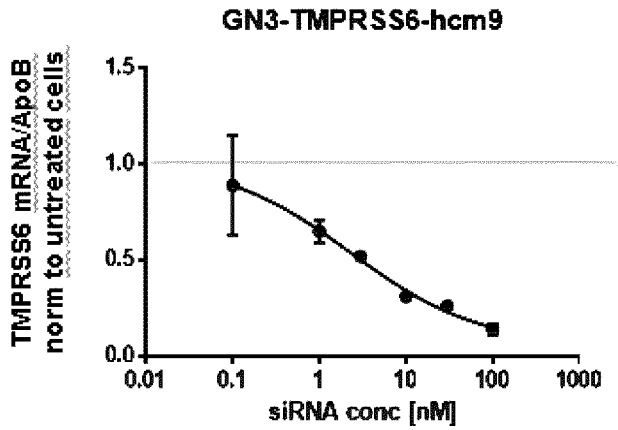
FIG. 46 shows inhibition of TMPRSS6 mRNA expression by siRNA conjugates in primary human hepatocytes.

Results are shown in FIG. 45a, 45b and FIG. 46, and sequences are shown in FIG. 47.

Figure 8C:
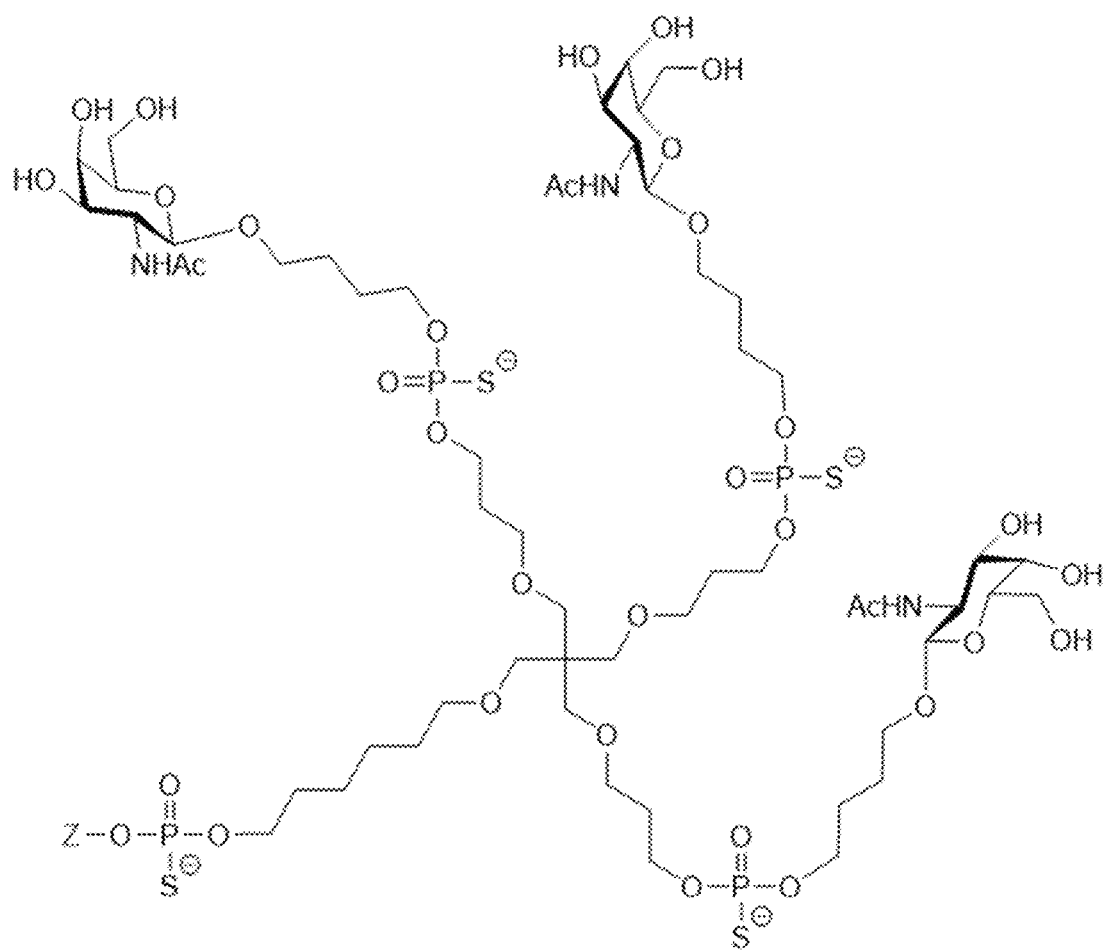

The GN3 linker described is shown in FIG. 8C.

Example 44

Serum stability assay of GalNAc-siRNA conjugates with phosphorothioates, phosphorodithioates and phosphodiesters in terminal positions and in the GalNAc moiety. GalNAc was conjugated to the 5'-end of the sense strand and is internally stabilized by four PS (STS12009L4) or not, then phosphodiester linkages are used instead (STS12009V54L50-V57L50). Phosphorodithioate modifications were placed at all terminal positions of the duplex except of the first strand 5'-end (-V54L50), at the 3'-ends only (-V55L50, -V57L50) or at the 3'-end of the second strand only (-V56L50). In certain designs, phosphodiesters were used in terminal positions of the siRNA duplex (-V56L50, -V57L50). 5 M GalNAc-siRNA conjugates were incubated with 50% FBS for 3 d at 37° C. RNA was extracted and analyzed on 20% TBE polyacrylamide gels. "UT" indicates untreated samples, "FBS" indicates FBS treatment. "Control" indicates a less stabilized GalNAc-siRNA conjugate of different sequence.

GalNAc conjugates of an siRNA targeting TMPRSS6 containing different end stabilization chemistries (phosphorothioate, phosphorodithioate, phosphodiester) were tested by receptor-mediated uptake in primary mouse hepatocytes. GalNAc was conjugated to the 5'-end of the second strand and is internally stabilized by four PS (STS12009L4) or not, then phosphodiester linkages used are instead (STS12009V54L50-V57L50). Phosphorodithioate modifications were placed at all terminal positions of the duplex except of the first strand 5'-end (-V54L50), at the 3'-ends only (-V55L50, -V57L50) or at the 3'-end of the second strand only (-V56L50). In certain designs, phosphodiesters were used in terminal positions of the siRNA duplex (-V56L50, -V57L50). The experiment was conducted in mouse primary hepatocytes. Cells were seeded at a density of 20,000 cells per 96-well and treated with 125 nM to 0.2 nM GalNAc-siRNA. Cells were lysed after 24 h, total RNA was extracted and TMPRSS6 and PTEN mRNA levels were determined by Taqman qRT-PCR. Each bar represents mean±SD of three technical replicates.

Figure 49:
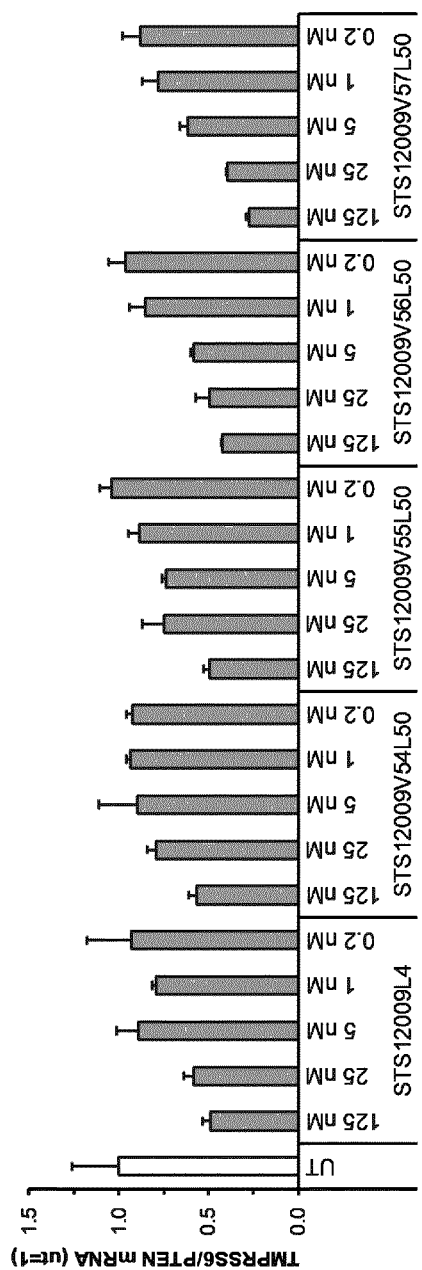
FIG. 49 shows receptor-mediated uptake in primary mouse hepatocytes by GalNAc siRNA conjugates targeting TMPRSS6 containing different end stabilization chemistries (phosphorothioate, phosphorodithioate, phosphodiester).
Figure 50:
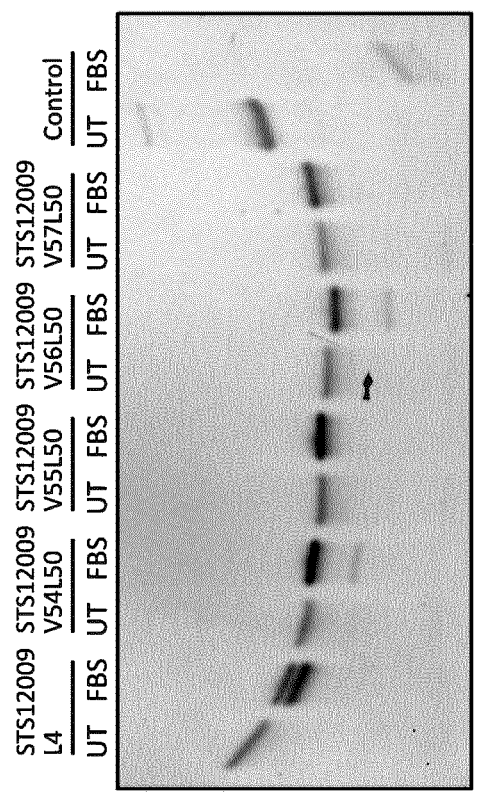
FIG. 50 shows serum stability of GalNAc-siRNA conjugates with phosphorothioates, phosphorodithioates and phosphodiesters in terminal positions and in the GalNAc moiety

Results and relevant sequences are shown in FIGS. 48-50.

Example 45

Reduction of TMPRSS6 expression in primary murine hepatocytes by GalNAc siRNA conjugates with 2'-O-methyl-uridine or 5'-(E)-vinylphosphonate-2'-O-methyl-uridine replacing the 2'-O-methyl-adenin at the 5' position of the first strand.

Murine primary hepatocytes were seeded into collagen pre-coated 96 well plates (Thermo Fisher Scientific, #A1142803) at a cell density of 30,000 cells per well and treated with siRNA-conjugates at concentrations ranging from 100 nM to 0.1 nM. 24 h post treatment cells were lysed and RNA extracted with InviTrap® RNA Cell HTS 96 Kit/C24×96 preps (Stratec #7061300400) according to the manufactures protocol. Transcripts levels of TMPRSS6 and housekeeping mRNA (PtenII) were quantified by TaqMan analysis.

siRNA Conjugates:                                                    Serum Stability

| siRNA duplex | first strand/ second strand | sequence & modification |
|---|---|---|
| STS12009L4 (X0027) | TMPRSS6-hcm9-A | mA (ps) fA (ps) mC fC mA fG mA fA mG fA mA fG mC fA mG fG mU (ps) fG (ps) mA |
| | TMPRSS6-hcm9-BL4 | GN2 fU mC fA mC fC mU fG mC fU mU fC mU fU mC fU mG fG (ps) mU (ps) fU |
| STS12209V4L4 (X0204) | TMPRSS6-hcm209AV4 | vinylphosphonate-mU (ps) fA (ps) mC fC mA fG mA fA mG fA mA fG mC fA mG fG mU (ps) fG (ps) mA |
| | TMPRSS6-hcm209-BL4 | GN2 fU mC fA mC fC mU fG mC fU mU fC mU fU mC fU mG fG (ps) mU (ps) fA |
| STS12209V5L4 (x0205) | TMPRSS6-hcm209-AV5 | vinylphosphonate-mU fA mC fC mA fG mA fA mG fA mA fG mC fA mG fG mU (ps) fG (ps) mA |
| | TMPRSS6-hcm209-BL4 | GN2 fU mC fA mC fC mU fG mC fU mU fC mU fU mC fU mG fG (ps) mU (ps) fA |
| STS12209L4 (x0207) | TMPRSS6-hcm209A | mU (ps) fA (ps) mC fC mA fG mA fA mG fA mA fG mC fA mG fG mU (ps) fG (ps) mA |
| | TMPRSS6-hcm209-BL4 | GN2 fU mC fA mC fC mU fG mC fU mU fC mU fU mC fU mG fG (ps) mU (ps) fA |
| STS12209V1L4 (x0208) | TMPRSS6-hcm9-AV1 | mU fA mC fC mA fG mA fA mG fA mA fG mC fA mG fG mU (ps) fG (ps) mA |
| | TMPRSS6-hcm209-BL4 | GN2 fU mC fA mC fC mU fG mC fU mU fC mU fU mC fU mG fG (ps) mU (ps) fA |
| STS18001 (X0028) | STS18001A | mU(ps)fC(ps)mGfAmAfGmUfAmUfUmCfCmGfCmGfUmA(ps)fC(ps)mG |
| | STS18001BL4 | GN2 fCmGfUmAfCmGfCmGfGmAfAmUfAmCfUmUfC (ps) mG (ps) fA |

Legend:
mN 2'-O-methyl ribonucleotide (e.g. mU - 2'-O-methyl Uracil)
fN 2'-fluoro ribonucleotide (e.g. fC - 2'-fluoro Cytidin)
(ps) phosphorothioate
vinylphosphonate vinyl-(E)-phosphonate
GN2 strcuture according to FIG. 8B TaqMan Primer and Probes

| PTEN-2 | CACCGCCAAATTTAACTGCAGA |
|---|---|
| PTEN-2 | AAGGGTTTGATAAGTTCTAGCTGT |
| PTEN-2 | FAM-TGCACAGTATCCTTTTGAAGACCATAAC CCA-TAMRA |
| hTMSS6:379U17 | CCGCCAAAGCCCAGAAG |
| hTMSS6:475L21 | GGTCCCTCCCCAAAGGAATAG |
| hTMSS6:416U28FL | FAM-CAGCACCCGCCTGGGAACTTACTACAAC-BHQ1 |

In Vitro Dose Response

Target gene expression in primary murine hepatocytes 24 h following treatment with TMPRSS6-siRNA carrying vinyl-(E)-phosphonate 2'OMe-Uracil at the 5'-position of the anti-sense strand and two phosphorothioate linkages between the first three nucleotides (STS12209V4L4), vinyl-(E)-phosphonate 2'OMe-Uracil at the 5'-position of the anti-sense strand and phosphodiester bonds between the first three nucleotides (STS12209V5L4), carrying 2'-O-methyl-Uracil and two phosphorothioate linkages between the first three nucleotides at the 5'-position (STS12209L4) or carrying 2'-O-methyl-Uracil and two phosphodiester linkages between the first three nucleotides at the 5'-position (STS12209V1L4) or) or (STS12009L4) as reference or a non-targeting GalNAc-siRNA (STS18001) at indicated concentrations or left untreated (UT).

Figure 51:
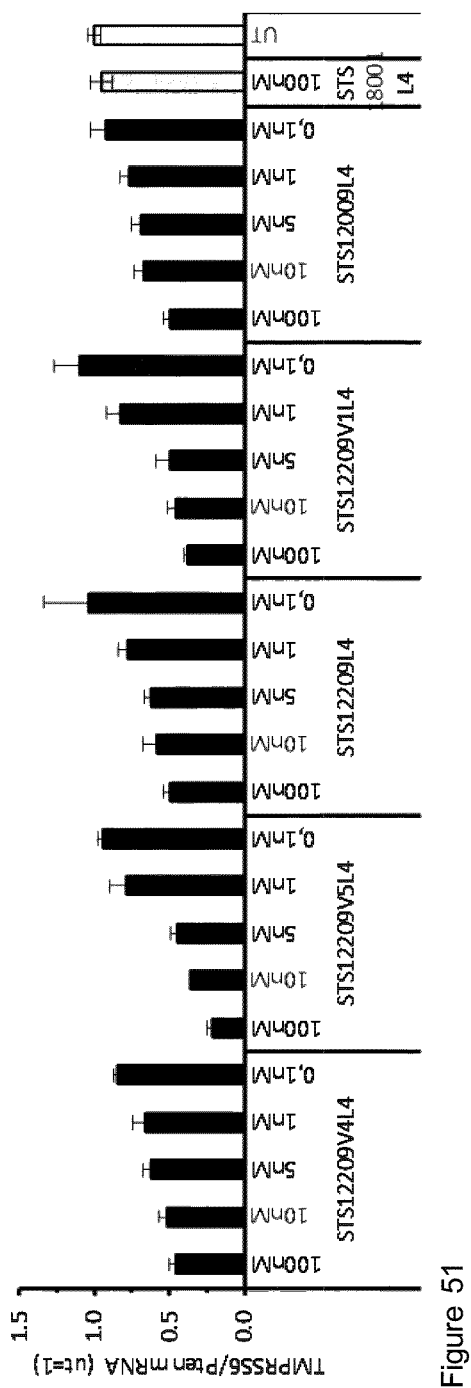
FIG. 51 shows inhibition of TMPRSS6 gene expression in primary murine hepatocytes 24 h following treatment with TMPRSS6-siRNA carrying vinyl-(E)-phosphonate 2'OMe-Uracil at the 5'-position of the anti-sense strand and two phosphorothioate linkages between the first three nucleotides (X0204), vinyl-(E)-phosphonate 2'OMe-Uracil at the 5'-position of the anti-sense strand and phosphodiester bonds between the first three nucleotides (X0205), (X0139) or tetrameric (X0140)) or a tree like trimeric GalNAc-cluster (X0004) or a non-targeting GalNAc-siRNA (X0028) at indicated concentrations or left untreated (UT).

Results are shown in FIG. 51.

Serum stability of siRNA conjugates incubated for 4 hours (4 h) or 3 days (3 d) or left untreated (0 h) in 50% FCS at 37° C. Following RNA was extracted by phenol/chlorophorm/isoamyl alcohol extraction. Degradation was visualized by TBE-Polyacrylamid-gel-electrophoresis and staining RNA with SybrGold.

Figure 52:
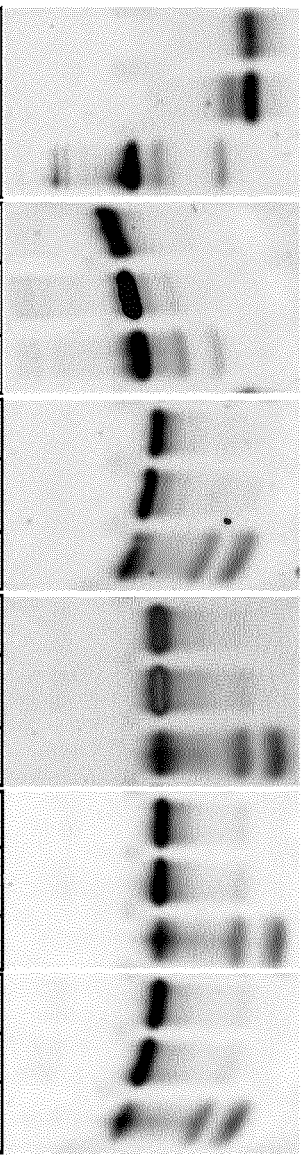
FIG. 52 shows serum stability of siRNA-conjugates vs. less stabilized positive control for nuclease degradation.

Results are shown in FIG. 52: Serum stability of siRNA-conjugates vs. less stabilized positive control for nuclease degradation.

Example 46

Reduction of transferrin saturation by TMPRSS6 siRNA treatment in animal model for hereditary hemochromatosis type 1. Three months old C57BL6/J congenic female HFE knock-out mice (−/−) and three months old female C57BL6/J wild type mice (+/+) were used in this study (Herrmann et al., Mol. Med, 2004. 82 (1): p1-3). HFE$^{−/−}$ mice (n=8) were treated on Day 1 (1×) or on Day 1 and on Day 22 (2×) subcutaneously with either PBS (PBS) or 3 mg/kg TMPRSS6 siRNA conjugate (TMP) or 3 mg/kg non-targeting siRNA conjugate (Luc). In addition, cohort 7 to 10 received Deferiprone supplied in drinking water at a concentration of 0.5 mg/ml. Cohorts 1 and 2 were terminated on Day 1 (Predose) all other cohorts on Day 43 (6 weeks after start of the treatment) to collect serum and tissue samples for analyses.

Serum iron levels (SFBC) and unsaturated iron binding capacity UIBC were assessed by calorimetric methods. Transferrin saturation (Tf Sat) was calculated using the following formula: TfSat=(SFBC/TIBC)λ100. Transferrin saturation is elevated in 3 months old HFE$^{-/-}$ mice at start of the treatment phase (cohort 2, Predose). Treatment with TMPRSS6 siRNA conjugates alone or in combination with Deferiprone reduced transferrin saturation in this rodent model for hereditary hemochromatosis and iron overload.

Figure 53:
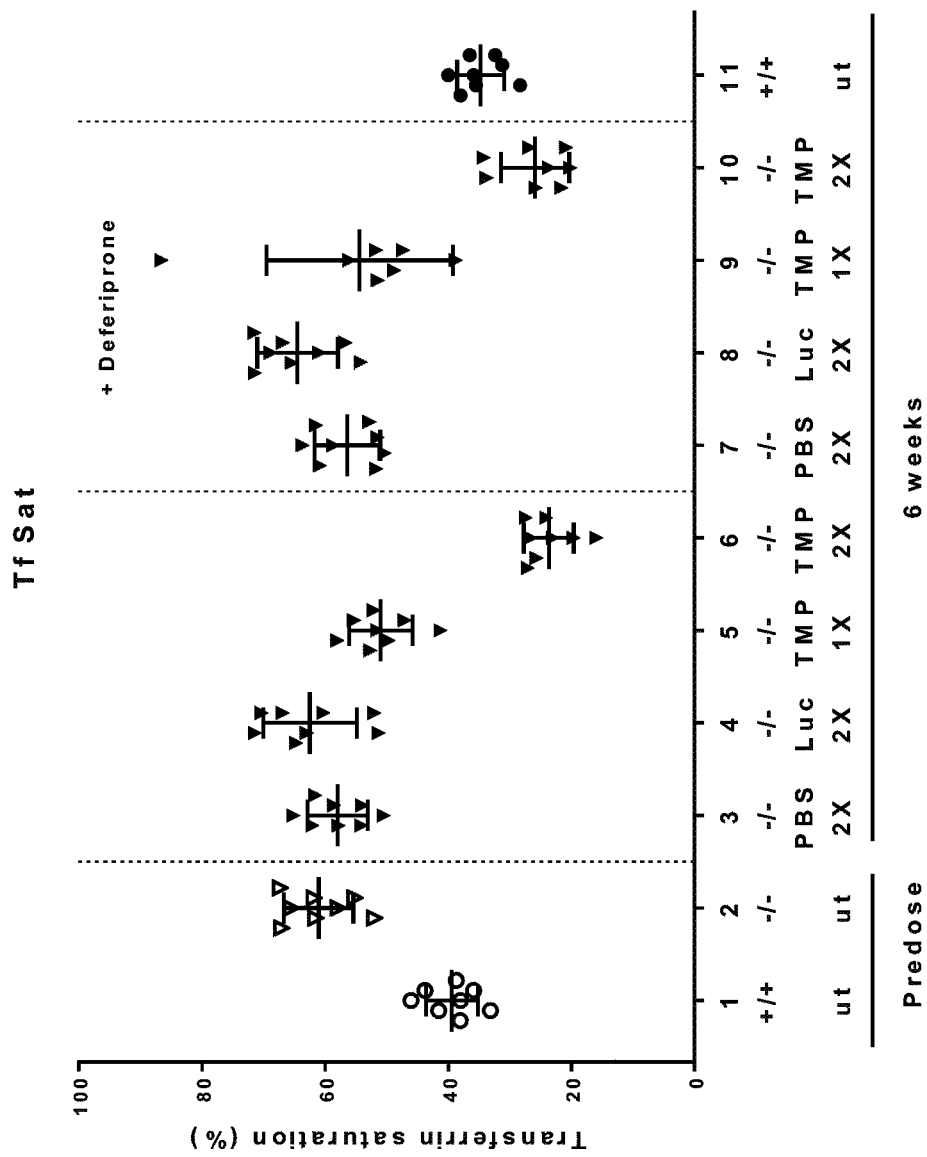
FIG. 53 shows reduction of transferrin saturation by TMPRSS6 siRNA treatment in animal model for hereditary hemochromatosis type 1.

Results are shown in FIG. 53.

siRNA Conjugates:

| siRNA conjugate | Single strands | Sequence and chemistry |
|---|---|---|
| TMP | TMP-A Strand SEQ ID NO: 217 | 5'mA (ps) fA (ps) mC fC mA fG mA fA mG fA mA fG mC fA mG fG mU (ps) fG (ps) mA 3' |
|  | TMP-B Strand SEQ ID NO: 218 | 5'GN2 fU mC fA mC fC mU fG mC fU mU fC mU fU mC fU mG fG (ps) mU (ps) fU 3' |
| Luc | Luc-A | 5'mU(ps)fC(ps)mGfAmAfGmUfAmUfUmCfCmGfCmGfUm A (ps) fC(ps) mG 3' |
|  | Luc-B | 5'GN2 fC mG fU mA fC mG fC mG fG mA fA mU fA mC fU mU fC (ps) mG (ps) fA 3' |

Legend:
fN (N = A, C, G, U) denotes 2'Fluoro, 2'DeoxyNucleosides
mN (N = A, C, G, U) denotes 2'O Methyl Nucleosides
(ps) indicates a phosphorothioate linkage
GN2 GalNAc structure as in FIG. 8B
TMP-A is identical to SEQ ID NO: 111
TMP-B is identical to SEQ ID NO: 112, except evidently that GN has been replaced by GN2
TMP-A base sequence is identical to SEQ ID NO: 333
TMP-B base sequence is identical to SEQ ID NO: 334
TMP-A modification pattern is identical to SEQ ID NO: 17
TMP-B modification pattern is identical to SEQ ID NO: 18
Luc-A is identical to SEQ ID NO: 109
Luc-B is identical to SEQ ID NO: 110
Luc-A base sequence is identical to SEQ ID NO: 347
Luc-B base sequence is identical to SEQ ID NO: 348
Luc-A modification pattern is identical to SEQ ID NO: 31
Luc-B modification pattern is identical to SEQ ID NO: 32

Example 47

Figure 54:
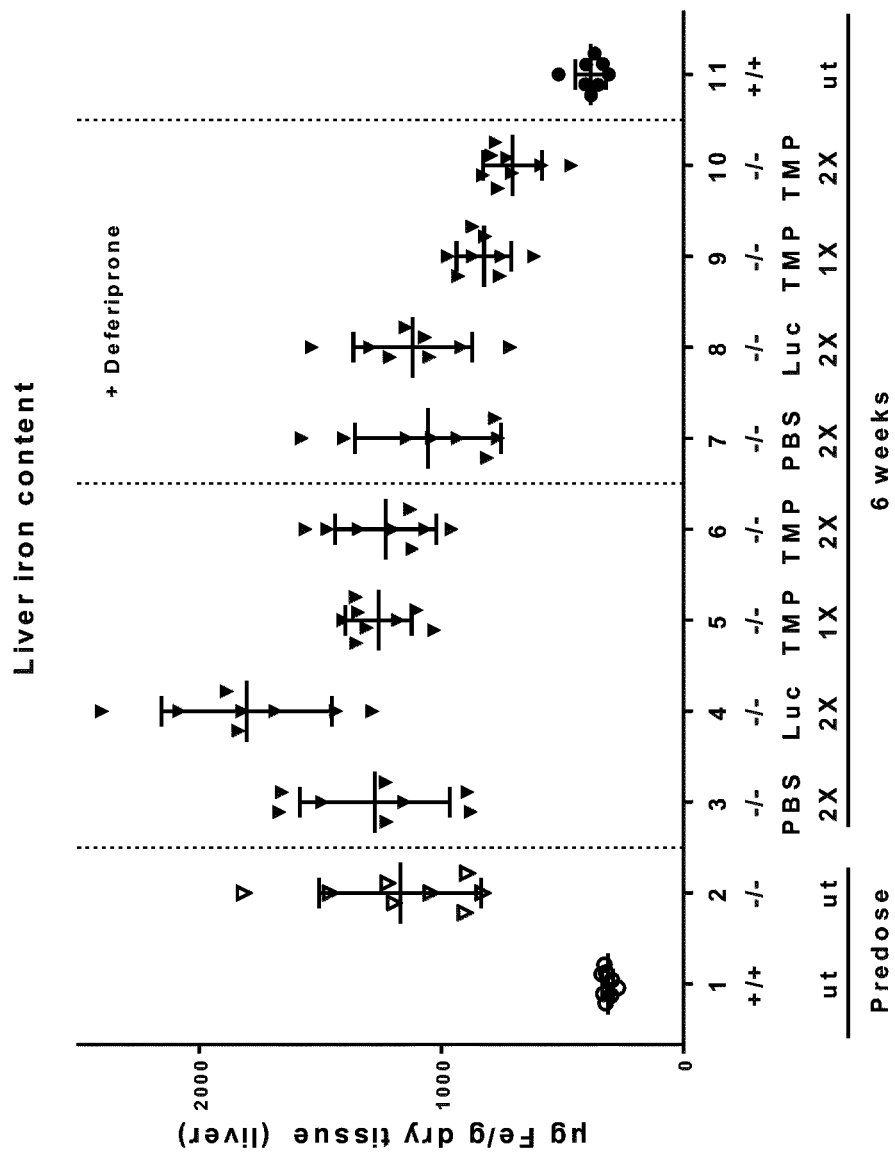
FIG. 54 shows treatment with TMPRSS6 siRNAs enhances the reduction of tissue iron levels by iron chelator.

Treatment with TMPRSS6 siRNAs enhances the reduction of tissue iron levels by iron chelator. 3 months old HFE$^{-/-}$ (rodent model for hereditary hemochromatosis and iron overload) or wild type mice were used for this study and treated as described in Example 46. Liver tissue samples were collected to assess liver iron concentrations before start of the treatment (predose) and at the end of the study at Day 43 (6 weeks after start of treatments). Liver tissue samples were dried and iron concentrations from dry weights were determined by acid extraction method. At the start of the study liver iron levels were already elevated in HFE$^{-/-}$ compared to wild type control mice (Predose). Treatment of HFE$^{-/-}$ mice with TMPRSS6 siRNA conjugates in combination with Deferiprone enhanced the reduction of tissue iron levels by the iron chelator. In other words, the combined siRNA/iron chelator treatment led to a much greater reduction of iron content in the liver than was achieved by the treatment with the siRNA or the chelator alone (compare columns 5 and 9 or 6 and 10). This is surprising because the treatment with the siRNA alone (compare column 3 with columns 5 and 6) or with the iron chelator alone (column 7) has little to no effect on the liver iron content. The liver iron content is further reduced by administration of multiple doses of the siRNA (compare columns 9 and 10).

siRNA conjugates are as described in Example 46 and results are shown in FIG. 54.

Summary SEQUENCE TABLE

| SEQ ID NO | Name | Sequence (5'-3') |
|---|---|---|
| 1 | TMPRSS6-hc-1A | 6181715172727184715 |
| 2 | TMPRSS6-hc-1B | 2647364545462646361 |
| 3 | TMPRSS6-h-2A | 6154645272747282718 |
| 4 | TMPRSS6-h-2B | 3645354745452717261 |
| 5 | TMPRSS6-h-3A | 6281546184546173748 |
| 6 | TMPRSS6-h-3B | 3748461727361726351 |
| 7 | TMPRSS6-hc-4A | 5171846174537271847 |
| 8 | TMPRSS6-hc-4B | 4736454827461736462 |
| 9 | TMPRSS6-h-5A | 6153636462728284627 |
| 10 | TMPRSS6-h-5B | 4517353545171818261 |
| 11 | TMPRSS6-h-6A | 8164536184718173535 |
| 12 | TMPRSS6-h-6B | 2828463647361827163 |
| 13 | TMPRSS6-h-7A | 6451816452645173728 |
| 14 | TMPRSS6-h-7B | 3548462715271636271 |
| 15 | TMPRSS6-hcmr-8A | 5181637352846261637 |
| 16 | TMPRSS6-hcmr-8B | 4816151735284816362 |
| 17 | TMPRSS6-hcm-9A | 6273646282647284546 |
| 18 | TMPRSS6-hcm-9B | 1727354715351718451 |
| 19 | TMPRSS6-hc-10A | 5263627372838184625 |
| 20 | TMPRSS6-hc-10B | 2517363835484518152 |
| 21 | TMPRSS6-hc-11A | 8151717172537284738 |
| 22 | TMPRSS6-hc-11B | 3847354825464646263 |
| 23 | TMPRSS6-hcm-12A | 8361715354847151847 |
| 24 | TMPRSS6-hcm-12B | 4736264737282646183 |
| 25 | TMPRSS6-hc-13A | 5363635482648182618 |
| 26 | TMPRSS6-hc-13B | 3615363715372818182 |
| 27 | TMPRSS6-hcmr-14A | 7272825454538273738 |
| 28 | TMPRSS6-hcmr-14B | 3848453827272535454 |
| 29 | TMPRSS6-hcmr-15A | 5452737164826252736 |
| 30 | TMPRSS6-hcmr-15B | 1845251537164845272 |
| 31 | TMPRSS6-Luc-siRNA-1A | 5382645251738381638 |
| 32 | TMPRSS6-Luc-siRNA-1B | 3816383856252715382 |
| 33 | TMPRSS6-PTEN-A | 5a6g5u7u6g7u8u8g5g8 |
| 34 | TMPRSS6-PTEN-B | c7a7c6c6g7u6g6a7u5a |
| 35 | hTMPRSS6 (upper) | ccgccaaagcccagaag |
| 36 | hTMPRSS6 (lower) | ggTcccTccccaaaggaaTag |
| 37 | hTMPRSS6 (probe) | cagcacccgccTgggaacTTacTacaac |
| 38 | mTMPRSS6 (upper) | cggcaccTaccTTccacTcTT |

-continued

Summary SEQUENCE TABLE

| SEQ ID NO | Name | Sequence (5'-3') |
|---|---|---|
| 39 | mTMPRSS6 (lower) | TcggTggTgggcaTccT |
| 40 | mTMPRSS6 (probe) | ccgagaTgTTTccagcTccccTgTTcTa |
| 41 | h-Aktin (upper) | gcaTgggTcagaaggaTTccTaT |
| 42 | h-Aktin (lower) | TgTagaaggTgTggTgccagaTT |
| 43 | h-Aktin (probe) | TcgagcacggcaTcgTcaccaa |
| 44 | mAktin (upper) | gTTTgagaccTTcaacacccca |
| 45 | mAktin (lower) | gaccagaggcaTacagggaca |
| 46 | mAktin (probe) | ccaTgTacgTagccaTccaggcTgTg |
| 47 | PTEN (upper) | caccgccaaaTTTaacTgcaga |
| 48 | PTEN (lower) | aagggTTTgaTaagTTcTagcTgT |
| 49 | PTEN (probe) | TgcacagTaTccTTTTgaagaccaTaaccca |
| 50 | mHAMP (upper) | ccTgTcTccTgcTTcTccTccT |
| 51 | mHAMP (lower) | aaTgTcTgcccTgcTTTcTTcc |
| 52 | mHAMP (probe) | TgagcagcaccaccTaTcTccaTcaaca |
| 53 | TMPRSS6-hcmr-8B | 4816151735284816362 |
| 54 | TMPRSS6-h-2B | 3645354745452717261 |
| 55 | TMPRSS6-hcm-12B | 4736264737282646183 |
| 56 | TMPRSS6-h-7B | 3548462715271636271 |
| 57 | TMPRSS6-hcm-9B | 1727354715351718451 |
| 58 | TMPRSS6-hc-1B | 2647364545462646361 |
| 59 | TMPRSS6-hc-10B | 2517363835484518152 |
| 60 | TMPRSS6-hc-4B | 4736454827461736462 |
| 61 | TMPRSS6-h-3B | 3748461727361726351 |
| 62 | TMPRSS6-h-5B | 4517353545171818261 |
| 63 | TMPRSS6-hc-11B | 3847354825464646263 |
| 64 | TMPRSS6-hc-13B | 3615363715372818182 |
| 65 | TMPRSS6-hcmr-14B | 3848453827272535454 |
| 66 | TMPRSS6-h-6B | 2828463647361827163 |
| 67 | TMPJH01A | 6273646282647284546 |
| 68 | TMPJH01B | 1727354715351718451 |
| 69 | TMPJH02A | 2237242282243284142 |
| 70 | TMPJH02B | 1723314715355754815 |
| 71 | TMPJH03A | 2273282646283248182 |
| 72 | TMPJH03B | 5363718351715354815 |
| 73 | TMPJH04A | 2273282646683248182 |
| 74 | TMPJH05A | 2273242242643244542 |
| 75 | TMPJH05B | 5727354315355754455 |

Summary SEQUENCE TABLE

| SEQ ID NO | Name | Sequence (5'-3') |
|---|---|---|
| 76 | TMPJH06A | 2277646242643244542 |
| 77 | TMPJH07A | 2277686242643244542 |
| 78 | TMPJH08A | 2273242246687244542 |
| 79 | TMPJH09A | 2273242682687244542 |
| 80 | TMPJH10A | 2273242242643284586 |
| 81 | TMPJH11A | 2273242242643288586 |
| 82 | TMPJH12A | 2273242246687284586 |
| 83 | TMPJH13A | 6277646246687284586 |
| 84 | TMPJH13B | 5767354315755758855 |
| 85 | TMPJH14A | 2273282282283284182 |
| 86 | TMPJH14B | 5327318315315318415 |
| 87 | TMPJH15A | 2273282282643284182 |
| 88 | TMPJH16A | 2237242242247244582 |
| 89 | TMPJH16B | 1723314355311358411 |
| 90 | TMPJH17A | 2273282242643284586 |
| 91 | TMPJH18A | 6277682242643288142 |
| 92 | TMPJH19A | 6277682242643288586 |
| 93 | TMPJH20A | 2233282242643284142 |
| 94 | TMPJH21A | 2277282242643284586 |
| 95 | TMPJH22A | 2273282642643284586 |
| 96 | TMPJH23A | 2273282282643284586 |
| 97 | TMPJH24A | 2273282246643284586 |
| 98 | TMPJH25A | 2273282242683284586 |
| 99 | TMPJH26A | 2273282242647284586 |
| 100 | TMPJH27B | 5727754715355754855 |
| 101 | TMPJH28B | 1723314311351714411 |
| 102 | TMPJH29B | 5767354315355754455 |
| 103 | TMPJH30B | 5727754315355754455 |
| 104 | TMPJH31B | 5727358315355754455 |
| 105 | TMPJH32B | 5727354315755754455 |
| 106 | TMPJH33B | 5727354315355758455 |
| 107 | GN-TTR-hc-A | ucuugguuacaugaaauccca |
| 108 | GN-TTR-hc-B | ugggauuucauguaaccaaga |
| 109 | GN2-Luc-siRNA 1-A | 5(ps)3(ps)826452517383816(ps)3(ps)8 |
| 110 | GN2-Luc-siRNA 1-B | GN2-38163838462527153(ps)8(ps)2 |
| 111 | STS012-A | 6(ps)2(ps)736462826472845(ps)4(ps)6 |
| 112 | STS012-B | GN-17273547153517184(ps)5(ps)1 |

Summary SEQUENCE TABLE

| SEQ ID NO | Name | Sequence (5'-3') |
|---|---|---|
| 113 | STS012-1-A | 6(ps)2(ps)736462826472845(ps)4(ps)6 |
| 114 | STS012-1-B | GN-57677547153517588(ps)5(ps)5 |
| 115 | STS012-2-A | 6(ps)2(ps)736462826472845(ps)4(ps)6 |
| 116 | STS012-2-B | GN-57673543157557588(ps)5(ps)5 |
| 117 | STS012-3-A | 6(ps)2(ps)736462826472845(ps)4(ps)6 |
| 118 | STS012-3-B | GN-57A7C547153517T8G(ps)5(ps)T |
| 119 | STS012-4-A | 6(ps)2(ps)776462466872845(ps)8(ps)6 |
| 120 | STS012-4-B | GN-57673543157557588(ps)5(ps)5 |
| 121 | STS012-5-A | 6(ps)2(ps)736462426472845(ps)4(ps)6 |
| 122 | STS012-5-B | GN-17273543153517184(ps)5(ps)1 |
| 123 | STS012-6-A | 6(ps)2(ps)73646242647284546(ps)7(ps)7 |
| 124 | STS012-6-B | GN-17273543153517184(ps)5(ps)1 |
| 125 | STS012-7-A | 6(ps)2(ps)776866866472885(ps)8(ps)6 |
| 126 | STS012-7-B | GN-57677547153517588(ps)5(ps)5 |
| 127 | STS012-8-A | 6(ps)2(ps)776866866472885(ps)8(ps)6 |
| 128 | STS012-8-B | GN-57673543157557588(ps)5(ps)5 |
| 129 | STS012-9-A | 2(ps)2(ps)772422422472445(ps)4(ps)2 |
| 130 | STS012-9-B | GN-57277547157557544(ps)5(ps)5 |
| 131 | control siRNA A | 5(ps)1(ps)645262735151828(ps)2(ps)7 |
| 132 | control siRNA B | GN-45353626284515271(ps)6(ps)2 |
| 133 | hcTMP-SR1-A | mCfUmGfAmGfGmAfCmGfCnnCfCmUfGmGfAmGfGmU |
| 134 | hcTMP-SR1-B | fAmCfUmCfCmCfAmGfGmGfCmGfUmCfCmUfCmAfG |
| 135 | hcTMP-SR2-A | mGfCmUfGmAfGmGfAmCfGmCfCmCfUmGfGmGfAmG |
| 136 | hcTMP-SR2-B | fCmUfCmCfCmAfGmGfGmCfGmUfCmCfUmCfAmGfC |
| 137 | hcTMP-SR3-A | mUfGmCfUmGfAmGfGmAfCmGfCmCfCmUfGmGfGmA |
| 138 | hcTMP-SR3-B | fUmCfCmCfAmGfGmGfCmGfUmCfCmUfCmAfGmCfA |
| 139 | hcTMP-SR4-A | mGfUmGfCmUfGmAfGmGfAmCfGmCfCmCfUmGfGmG |
| 140 | hcTMP-SR4-B | fCmCfCmAfGmGfGmCfGmUfCmCfUmCfAmGfCmAfC |
| 141 | hcTMP-SR5-A | mGfGmUfGmCfUmGfAmGfGmAfCmGfCmCfCmUfGmG |
| 142 | hcTMP-SR5-B | fCmCfAmGfGmGfCmGfUmCfCmUfCmAfGmCfAmCfC |
| 143 | hcTMP-SR6-A | mGfGmGfUmGfCmUfGmAfGmGfAmCfGmCfCmCfUmG |
| 144 | hcTMP-SR6-B | fCmAfGmGfGmCfGmUfCmCfUmCfAmGfCmAfCmCfC |
| 145 | hcTMP-SR8-A | mCfGmGfGmGfUmGfCmUfGmAfGmGfAmCfGmCfCmC |
| 146 | hcTMP-SR8-B | fGmGfGmCfGmUfCmCfUmCfAmGfCmAfCmCfCmCfG |
| 147 | hcTMP-SR9-A | mAfCmGfGmGfGmUfGmCfUmGfAmGfGmAfCmGfCmC |
| 148 | hcTMP-SR9-B | fGmGfCmGfUmCfCmUfCmAfGmCfAmCfCmCfCmGfU |
| 149 | hcTMP-SR10-A | mUfAmCfGmGfGmGfUmGfCmUfGmAfGmGfAmCfGmC |

-continued

Summary SEQUENCE TABLE

| SEQ ID NO | Name | Sequence (5'-3') |
|---|---|---|
| 150 | hcTMP-SR10-B | fGmCfGmUfCmCfUmCfAmGfCmAfCmCfCmCfGmUfA |
| 151 | hcTMP-SR11-A | mGfUmAfCmGfGmGfGmUfGmCfUmGfAmGfGmAfCmG |
| 152 | hcTMP-SR11-B | fCmGfUmCfCmUfCmAfGmCfAmCfCmCfCmGfUmAfC |
| 153 | hcTMP-SR12-A | mAfGmUfAmCfGmGfGmGfUmGfCmUfGmAfGmGfAmC |
| 154 | hcTMP-SR12-B | fGmUfCmCfUmCfAmGfCmAfCmCfCmCfGmUfAmCfU |
| 155 | hcTMP-SR13-A | mAfAmGfUmAfCmGfGmGfGmUfGmCfUmGfAmGfGmA |
| 156 | hcTMP-SR13-B | fUmCfCmUfCmAfGmCfAmCfCmCfCmGfUmAfCmUfU |
| 157 | hcTMP-SR15-A | mGfGmAfAmGfUmAfCmGfGmGfGmUfGmCfUmGfAmG |
| 158 | hcTMP-SR15-B | fCmUfCmAfGmCfAmCfCmCfCmGfUmAfCmUfUmCfC |
| 159 | hcTMP-SR16-A | mGfGmGfAmAfGmUfAmCfGmGfGmGfUmGfCmUfGmA |
| 160 | hcTMP-SR16-B | fUmCfAmGfCmAfCmCfCmCfGmUfAmCfUmUfCmCfC |
| 161 | hcTMP-SR17-A | mGfCmGfGmAfAmGfUmAfCmGfGmGfGmUfGmCfUmG |
| 162 | hcTMP-SR17-B | fCmAfGmCfAmCfCmCfCmGfUmAfCmUfUmCfCmCfC |
| 163 | hcTMP-SR18-A | mUfGmGfGmGfAmAfGmUfAmCfGmGfGmGfUmGfCmU |
| 164 | hcTMP-SR18-B | fAmGfCmAfCmCfCmCfGmUfAmCfUmUfCmCfCmCfA |
| 165 | hcTMP-SR19-A | mCfUmGfGmGfGmAfAmGfUmAfCmGfGmGfGmUfGmC |
| 166 | hcTMP-SR19-B | fGmCfAmCfCmCfCmGfUmAfCmUfUmCfCmCfCmAfG |
| 167 | hcTMP-SR21-A | mAfGmCfUmGfGmGfGmAfAmGfUmAfCmGfGmGfGmU |
| 168 | hcTMP-SR21-B | fAmCfCmCfCmGfUmAfCmUfUmCfCmCfCmAfGmCfU |
| 169 | hcTMP-SR22-A | mUfAmGfCmUfGmGfGmGfAmAfGmUfAmCfGmGfGmG |
| 170 | hcTMP-SR22-B | fCmCfCmCfGmUfAmCfUmUfCmCfCmCfAmGfCmUfA |
| 171 | hcTMP-SR23-A | mGfUmAfGmCfUmGfCmGfGmAfAmGfUmAfCmGfGmG |
| 172 | hcTMP-SR23-B | fCmCfCmGfUmAfCmUfUmCfCmCfCmAfGmCfUmAfC |
| 173 | hcTMP-SR24-A | mAfGmUfAmGfCmUfGmGfGmGfAmAfGmUfAmCfGmG |
| 174 | hcTMP-SR24-B | fCmCfGmUfAmCfUmUfCmCfCmCfAmGfCmUfAmCfU |
| 175 | hcTMP-SR26-A | mGfUmAfGmUfAmGfCmUfGmGfGmGfAmAfGmUfAmC |
| 176 | hcTMP-SR26-B | fGmUfAmCfUmUfCmCfCmCfAmGfCmUfAmCfUmAfC |
| 177 | hcTMP-SR27-A | mAfGmUfAmGfUmAfGmCfUmGfGmGfGmAfAmGfUmA |
| 178 | hcTMP-SR27-B | fUmAfCmUfUmCfCmCfCmAfGmCfUmAfCmUfAmCfU |
| 179 | hcTMP-SR28-A | mGfAmGfUmAfGmUfAmGfCmUfGmGfGmGfAmAfGmU |
| 180 | hcTMP-SR28-B | fAmCfUmUfCmCfCmCfAmGfCmUfAmCfUmAfCmUfC |
| 181 | hcTMP-SR29-A | mCfGmAfGmUfAmGfUmAfGmCfUmGfGmGfGmAfAmG |
| 182 | hcTMP-SR29-B | fCmUfUmCfCmCfCmAfGmCfUmAfCmUfAmCfUmCfG |
| 183 | hcTMP-SR30-A | mGfCmGfAmGfUmAfGmUfAmGfCmUfGmGfGmGfAmA |
| 184 | hcTMP-SR30-B | fUmUfCmCfCmCfAmGfCmUfAmCfUmAfCmUfCmGfC |
| 185 | hcTMP-SR31-A | mGfGmCfGmAfGmUfAmGfUmAfGmCfUmGfGmGfGmA |
| 186 | hcTMP-SR31-B | fUmCfCmCfCmAfGmCfUmAfCmUfAmCfUmCfGmCfC |

Summary SEQUENCE TABLE

| SEQ ID NO | Name | Sequence (5'-3') |
|---|---|---|
| 187 | hcTMP-SR32-A | mGfGmGfCmGfAmGfUmAfGmUfAmGfCmUfGmGfGmG |
| 188 | hcTMP-SR32-B | fCmCfCmCfAmGfCmUfAmCfUmAfCmUfCmGfCmCfC |
| 189 | hcTMP-SR33-A | mGfGmGfCmGfAmGfUmAfGmUfAmGfCmUfGmGfGmG |
| 190 | hcTMP-SR33-B | fCmCfCmAfGmCfUmAfCmUfAmCfUmCfGmCfCmCfC |
| 191 | hcTMP-SR34-A | mUfGmGfGmCfGmAfGmUfAmAfGmUfAmGfCmUfGmG |
| 192 | hcTMP-SR34-B | fCmCfAmGfCmUfAmCfUmAfCmUfCmGfCmCfCmCfA |
| 193 | hcTMP-SR35-A | mUfUmGfGmGfCmGfAmGfUfAmGfUmAfGfCmUfGmG |
| 194 | hcTMP-SR35-B | fCmAfGmCfUmAfCmUfAmCfUmCfGmCfCmCfCmAfA |
| 195 | TMPRSS6-hc-16A | mUfAmUfCmCfAmAfGmGfGmCfAmGfCmUfGmA |
| 196 | TMPRSS6-hc-16B | fUmCfAmGfCmUfGmCfCmCfUmUfGmGfAmUfA |
| 197 | TMPRSS6-hc-17A | mA (ps) fU (ps) mCfUmUfCmUfGmGfGmCfUmUfUmGfGmC (ps) fG (ps) mG |
| 198 | TMPRSS6-hc-17B | GN3-fCmCfGmCfCmAfAmAfGmCfCmCfAmGfAmAfG (ps) mA (ps) fU |
| 199 | TMPRSS6-hc-18A | mU (ps) fU (ps) mUfUmCfCmUfGmGfAmGfUmCfCmU (ps) fC (ps) mA |
| 200 | TMPRSS6-hc-18B | GN3-fUmGfAmGfGmAfCmUfCmCfAmGfGmAfGmAfA (ps) mA (ps) fA |
| 201 | TMPRSS6-hc-19A | mGfAmAfUmAfGmAfCmGfGmAfGmCfUmGfGmAfGmU |
| 202 | TMPRSS6-hc-19B | fAmCfUmCfCmAfGmCfUmCfCmGfUmCfUmAfUmUfC |
| 203 | TMPRSS6-hc-21A | mUfAmGfUmAfGmCfUmGfGmGfGmAfAmGfUmAfCmG |
| 204 | TMPRSS6-hc-21B | fCmGfUmAfCmUfUmCfCmCfCmAfGmCfUmAfCmUfA |
| 205 | TMPRSS6-hc-22A | mAfGmAfUmCfUmGfGmGfAmAfGmAfGmUfGmGfGmC |
| 206 | TMPRSS6-hc-22B | fGmCfCmAfCmUfCmUfUmCfCmCfAmGfAmUfCmCfU |
| 207 | TMPRSS6-hc-23A | mC (ps) fU (ps) mGfUmUfCmUfGmGfAmUfCmGfUmCfCmA (ps) fC (ps) mU |
| 208 | TMPRSS6-hc-23B | GN3-fAmGfUmGfGmAfCmGfAmUfCmCfAmGfAmAfC (ps) mA (ps) fG |
| 209 | TMPRSS6-hcmr-24A | mCfUmCfAmCfCmUfGmAfAmGfGmCfAmCfAmCfCmU |
| 210 | TMPRSS6-hcmr-24B | fAmGfGmUfGmUfCmCfUmUfCmAfAmGfGmUfGmAfG |
| 211 | TMPRSS6-hcm-25A | mA (ps) fG (ps) mUfUmUfCmUfCmUfCmAfUmCfCmAfGmG (ps) fC (ps) mC |
| 212 | TMPRSS6-hcm-25B | GN3-fGmGfCmCfUmGfGmAfUmGfAmGfAmGfAmAfA (ps) mC (ps) fU |
| 213 | TMPRSS6-hcr-26A | mG (ps) fU (ps) mAfCmCfCmUfAmGfGmAfAmAfUmAfCmC (ps) fA (ps) mG |
| 214 | TMPRSS6-hcr-26B | GN3-fCmUfGmGfUmAfUmUfUmCfCmUfAmGfGmGfU (ps) mA (ps) fC |
| 215 | TMPRSS6-hc-27A | mCfUmGfUmUfGmAfCmUfGmUfGmGfAmCfAmGfCmA |
| 216 | TMPRSS6-hc-27B | fUmGfCmUfGmUfCmCfAmCfAmGfUmCfAmAfCmAfG |
| 217 | STS12009L4-A | mA(ps)fA(ps)mCfCmAfGmAfAmGfAmAfGmCfAmGfGmU(ps)fG(ps)mA |
| 218 | STS12009L4-B | GN2-fUmCfAmCfCmUfGmCfUmUfCmUfUmCfUmGfG(ps)mU(ps)fU |
| 219 | STS12009V2L4-A | mA(ps)fA(ps)mCfCmAfGmAfAmGfAmAfGmCfAmGfGmU(ps)fG(ps)mA |
| 220 | STS12009V2L4-B | GN2-mUmCmAmCfCmUfGfCfUmUmCmUmUmCmUmGmG(ps)mU(ps)mU |
| 221 | STS12009V8L4-A | mA(ps)fA(ps)mCmCmAmGmAmAmGmAmAmGmCfAmGmGmU(ps)mG(ps)mA |
| 222 | STS12009V8L4-B | GN2-mUmCmAmCfCmUfGfCfUmUmCmUmUmCmUmGmG(ps)mU(ps)mU |
| 223 | GN2-Luc-A | mU(ps)fU(ps)mAfGmUfAmAfAmCfCmUfUmUfUmGfAmG(ps)fA(ps)mC |

Summary SEQUENCE TABLE

| SEQ ID NO | Name | Sequence (5'-3') |
|---|---|---|
| 224 | GN2-Luc-B | GN2-fGmUfCmUfCmAfAmAfAmGfGmUfUmUfAmCfU(ps)mA(ps)fA |
| 225 | TMP01-A | mAfAmCfCmAfGmAfAmGfAmAfGmCfAmGfGmUfGmA |
| 226 | TMP01-B | fUmCfAmCfCmUfGmCfUmUfCmUfUmCfUmGfGmUfU |
| 227 | TMP66-A | mAfAmCfCmAmGfAmAmGmAmAmGmCfAmGmGmUmGmA |
| 228 | TMP66-B | mUmCmAmCmCmUfGmCfUmUmCmUmUmCmUmGmGmUmU |
| 229 | TMP69-A | fAfAfCfCfAmGfAfAfGfAmAfGfCfAmGfGfUfGfA |
| 230 | TMP69-B | fUmCfAfCfCfUfGfCfUfUfCmUfUmCfUfGfGfUfU |
| 231 | TMP79-A | fAfAmCfCfAmGfAfAfGfAmAfGfCfAmGfGmUmGmA |
| 232 | TMP79-B | mUmCfAmCfCmUfGfCfUmUmCmUmUmCmUfGfGmUmU |
| 233 | TMP80-A | fAfAmCmCfAmGfAfAfGfAmAfGfCfAmGfGmUmGmA |
| 234 | TMP80-B | mUmCfAmCfCmUfGfCfUmUmCmUmUmCmUfGfGmUmU |
| 235 | TMP81-A | fAfAmCfCfAmGfAfAfGfAmAfGfCmAmGfGmUmGmA |
| 236 | TMP81-B | mUmCfAmCfCmUfGfCfUmUmCmUmUmCmUfGfGmUmU |
| 237 | STS12009V27L4-A | mA(ps)fA(ps)mCmCmAmGmAmAmAmGmAmAfGmCfAmGmGmU(ps)mG(ps)mA |
| 238 | STS12009V27L4-A | GN2-mUmCmAmCmCmUfGfCfUmUmCmUmUmCmUmGmG(ps)mU(ps)mU |
| 239 | STS12009V41L4-A | mA(ps)fA(ps)mCmCmAmGmAmAmAmGmAmAfGmCfAmGmGmU(ps)mG(ps)mA |
| 240 | STS12009V41L4-A | GN2-fUmCfAmCfCmUfGmCfUmUfCmUfUmCfUmGfG(ps)mU(ps)fU |
| 241 | TMP95-A | mAfAmCmCmAmGmAmAmGmAmAmGmCfAmGmGmUmGmA |
| 242 | TMP95-B | fUmCfAmCfCmUfGmCfUmUfCmUfUmCfUmGfGmUfU |
| 243 | TMP99-A | mAfAmCfCmAfGmAfAmGfAmAfGmCfAmGfGmUfGmA |
| 244 | TMP99-B | mUmCmAmCmCmUfGmCfUmUmCmUmUmCmUmGmGmUmU |
| 245 | TMP112-A | mA[A]mCmCmAmGmAmAmGmAmAmGmCfAmGmGmUmGmA |
| 246 | TMP112-B | fUmCfAmCfCmUfGmCfUmUfCmUfUmCfUmGfGmUfU |
| 247 | TMP114-A | mAfAmCfCmAfGmAfAmGfAmAfGmCfAmGfGmUfGmA |
| 248 | TMP114-B | mUmCmAmCmCmU{G}mCfUmUmCmUmUmCmUmGmGmUmU |
| 249 | TMP115-A | mAfAmCfCmAfGmAfAmGfAmAfGmCfAmGfGmUfGmA |
| 250 | TMP115-B | mUmCmAmCmCmUfGmC{U}mUmCmUmUmCmUmGmGmUmU |
| 251 | TMP116-A | mAfAmCfCmAfGmAfAmGfAmAfGmCfAmGfGmUfGmA |
| 252 | TMP116-B | mUmCmAmCmCmU[G]mCfUmUmCmUmUmCmUmGmGmUmU |
| 253 | TMP117-A | mAfAmCfCmAfGmAfAmGfAmAfGmCfAmGfGmUfGmA |
| 254 | TMP117-B | mUmCmAmCmCmUfGmC[U]mUmCmUmUmCmUmGmGmUmU |
| 255 | TMP70-A | mA(ps)fA(ps)mCfCmAfGmAfAmGfAmAfGmCfAmGfGmU(ps)fG(ps)mA |
| 256 | TMP70-B | fU(ps)mC(ps)fAmCfCmUfGmCfUmUfCmUfUmCfUmGfG(ps)mU(ps)fU |
| 257 | TMP82-A | mA(ps)fA(ps)mCfCmAfGmAfAmGfAmAfGmCfAmGfGmUfGmA(ps)ivA |
| 258 | TMP82-B | fU(ps)mC(ps)fAmCfCmUfGmCfUmUfCmUfUmCfUmGfGmUfU(ps)ivA |
| 259 | TMP83-A | mA(ps)fA(ps)mCfCmAfGmAfAmGfAmAfGmCfAmGfGmUfGmA(ps)ivG |
| 260 | TMP83-B | fU(ps)mC(ps)fAmCfCmUfGmCfUmUfCmUfUmCfUmGfGmUfU(ps)ivG |

Summary SEQUENCE TABLE

| SEQ ID NO | Name | Sequence (5'-3') |
|---|---|---|
| 261 | TMP84-A | mA(ps)fA(ps)mCfCmAfGmAfAmGfAmAfGmCfAmGfGmUfG ivA |
| 262 | TMP84-B | fU(ps)mC(ps)fAmCfCmUfGmCfUmUfCmUfUmCfUmGfGmUfU ivG |
| 263 | TMP85-A | mA(ps)fA(ps)mCfCmAfGmAfAmGfAmAfGmCfAmGfGmUfG ivU |
| 264 | TMP85-B | fU(ps)mC(ps)fAmCfCmUfGmCfUmUfCmUfUmCfUmGfGmUfU ivG |
| 265 | TMP86-A | mA(ps)fA(ps)mCfCmAfGmAfAmGfAmAfGmCfAmGfGmUfG ivC |
| 266 | TMP86-B | fU(ps)mC(ps)fAmCfCmUfGmCfUmUfCmUfUmCfUmGfGmUfU ivG |
| 267 | TMP87-A | mA(ps)fA(ps)mCfCmAfGmAfAmGfAmAfGmCfAmGfGmUfG ivG |
| 268 | TMP87-B | fU(ps)mC(ps)fAmCfCmUfGmCfUmUrnUfCmUfUmCfUmGfGmUfU ivG |
| 269 | TMP88-A | mA(ps)fA(ps)mCfCmAfGmAfAmGfAmAfGmCfAmGfGmUfGmA ivG |
| 270 | TMP88-B | fU(ps)mC(ps)fAmCfCmUfGmCfUmUfCmUfUmCfUmGfGmU ivA |
| 271 | TMP89-A | mA(ps)fA(ps)mCfCmAfGmAfAmGfAmAfGmCfAmGfGmUfGmA ivG |
| 272 | TMP89-B | fU(ps)mC(ps)fAmCfCmUfGmCfUmUfCmUfUmCfUmGfGmU ivU |
| 273 | TMP90-A | mA(ps)fA(ps)mCfCmAfGmAfAmGfAmAfGmCfAmGfGmUfGmA ivG |
| 274 | TMP90-B | fU(ps)mC(ps)fAmCfCmUfGmCfUmUfCmUfUmCfUmGfGmU ivC |
| 275 | TMP91-A | mA(ps)fA(ps)mCfCmAfGmAfAmGfAmAfGmCfAmGfGmUfGmA ivG |
| 276 | TMP91-B | fU(ps)mC(ps)fAmCfCmUfGmCfUmUfCmUfUmCfUmGfGmU ivG |
| 277 | STS12009V10L4-A | mA(ps)fA(ps)mCfCmAfGmAfAmGfAmAfGmCfAmGfGmUfGmAivA |
| 278 | STS12009V10L4-B | GN2-fUmCfAmCfCmUfGmCfUmUfCmUfUmCfUmGfGmUfUivA |
| 279 | STS12009V11L4-A | mA(ps)fA(ps)mCfCmAfGmAfAmGfAmAfGmCfAmGfGmUfGmAivG |
| 280 | STS12009V11L4-B | GN2-fUmCfAmCfCmUfGmCfUmUfCmUfUmCfUmGfGmUfUivG |
| 281 | STS12009V29L4-A | mA(ps)fA(ps)mCfCmAfGmAfAmGfAmAfGmCfAmGfGmU(ps)fG(ps)mAivA |
| 282 | STS12009V29L4-B | GN2-fUmCfAmCfCmUfGmCfUmUfCmUfUmCfUmGfG(ps)mU(ps)fUivA |
| 283 | STS12009V30L4-A | mA(ps)fA(ps)mCfCmAfGmAfAmGfAmAfGmCfAmGfGmU(ps)fG(ps)mAivG |
| 284 | STS12009V30L4-B | GN2-fUmCfAmCfCmUfGmCfUmUfCmUfUmCfUmGfG(ps)mU(ps)fUivG |
| 285 | STS12009V34L4-A | mA(ps)fA(ps)mCfCmAfGmAfAmGfAmAfGmCfAmGfGmU(ps)fG(ps)mA |
| 286 | STS12009V34L4-B | GN2-fUmCfAmCfCmUfGmCfUmUfCmUfUmCfUmGfGmU(ps2)fU |
| 287 | STS12009V36L4-A | mA(ps)fA(ps)mCfCmAfGmAfAmGfAmAfGmCfAmGfGmUfG(ps2)mA |
| 288 | STS12009V36L4-B | GN2-fUmCfAmCfCmUfGmCfUmUfCmUfUmCfUmGfG(ps)mU(ps)fU |
| 289 | STS12009V37L4-A | mA(ps2)fAmCfCmAfGmAfAmGfAmAfGmCfAmGfGmU(ps)fG(ps)mA |
| 290 | STS12009V37L4-B | GN2-fUmCfAmCfCmUfGmCfUmUfCmUfUmCfUmGfG(ps)mU(ps)fU |
| 291 | STS12009V40L4-A | mA(ps)fA(ps)mCfCmAfGmAfAmGfAmAfGmCfAmGfGmU(ps)fG(ps)mA |
| 292 | STS12009V40L4-B | GNo-fU(ps2)mCfAmCfCmUfGmCfUmUfCmUfUmCfUmGfGmU(ps2)fU |
| 293 | STS12209V4L4-A | vinylphosphonate-mU (ps) fA (ps) mC fC mA fG mA fA mG fA mA fG mC fA mG fG mU (ps) fG (ps) mA |
| 294 | STS12209V4L4-B | GN2 fU mC fA mC fC mU fG mC fU mU fC mU fU mC fU mG fG (ps) mU (ps) fA |

Summary SEQUENCE TABLE

| SEQ ID NO | Name | Sequence (5'-3') |
|---|---|---|
| 295 | STS12209V5L4-A | vinylphosphonate-mU fA mC fC mA fG mA fA mG fA mA fG mC fA mG fG mU (ps) fG (ps) mA |
| 296 | STS12209V5L4-B | GN2 fU mC fA mC fC mU fG mC fU mU fC mU fU mC fU mG fG (ps) mU (ps) fA |
| 297 | STS12209L4-A | mU (ps) fA (ps) mC fC mA fG mA fA mG fA mA fG mC fA mG fG mU (ps) fG (ps) mA |
| 298 | STS12209L4-6 | GN2 fU mC fA mC fC mU fG mC fU mU fC mU fU mC fU mG fG (ps) mU (ps) fA |
| 299 | STS12209V1L4-A | mU fA mC fC mA fG mA fA mG fA mA fG mC fA mG fG mU (ps) fG (ps) mA |
| 300 | STS12209V1L4-B | GN2 fU mC fA mC fC mU fG mC fU mU fC mU fU mC fU mG fG (ps) mU (ps) fA |
| 301 | STS18001-A | mU(ps)fC(ps)mGfAmAfGmUfAmUfUmCfCmGfCmGfUmA(ps)fC(ps)mG |
| 302 | STS18001-B | GN2 fCmGfUmAfCmGfCmGfGmAfAmUfAmCfUrnUfC (ps) mG (ps) fA |
| 303 | PTEN-2-A | caccgccaaaTTTaacTgcaga |
| 304 | PTEN-2-B | aagggTTTgaTaagTTcTagcTgT |
| 305 | PTEN-2-C | FAM-TgcacagTaTccTTTTgaagaccaTaaccca-TAMRA |
| 306 | hTMSS6: 379U17 | ccgccaaagcccagaag |
| 307 | hTMSS6: 475L21 | ggTcccTccccaaaggaaTag |
| 308 | hTMSS6: 416U28FL | FAM-cagcacccgccTgggaacTTacTacaac-BHQ1 |
| 309 | STS12009V54L50-A | mA (ps) fA (ps) mCfCmAfGmAfAmGfAmAfGmCfAmGfGmUfG (ps2) mA |
| 310 | STS12009V54L50-B | GNo - fU (ps2) mCfAmCfCmUfGmCfUmUfCmUfUmCfUmGfGmU (ps2) fU |
| 311 | STS12009V55L50-A | mA (ps) fA (ps) mCfCmAfGmAfAmGfAmAfGmCfAmGfGmUfG (ps2) mA |
| 312 | STS12009V55L50-B | GNo - fUmCfAmCfCmUfGmCfUmUfCmUfUmCfUmGfGmU (ps2) fU |
| 313 | STS12009V56L50-A | mAfAmCfCmAfGmAfAmGfAmAfGmCfAmGfGmUfGmA |
| 314 | STS12009V56L50-B | GNo - fUmCfAmCfCmUfGmCfUmUfCmUfUmCfUmGfGmU (ps2) fU |
| 315 | STS12009V57L50-A | mAfAmCfCmAfGmAfAmGfAmAfGmCfAmGfGmUfG (ps2) mA |
| 316 | STS12009V57L50-B | GNo - fUmCfAmCfCmUfGmCfUmUfCmUfUmCfUmGfGmU (ps2) fU |
| 317 | TMPRSS6-hc-1A | augucuuucacacuggcuu |
| 318 | TMPRSS6-hc-1B | aagccagugugaaagacau |
| 319 | TMPRSS6-h-2A | auugaguacacgcagacug |
| 320 | TMPRSS6-h-2B | cagucugcguguacucaau |
| 321 | TMPRSS6-h-3A | aaguugauggugaucccgg |
| 322 | TMPRSS6-h-3B | ccgggaucaccaucaacuu |
| 323 | TMPRSS6-hc-4A | uucuggaucguccacuggc |
| 324 | TMPRSS6-hc-4B | gccaguggacgauccagaa |
| 325 | TMPRSS6-h-5A | auucacagaacagaggaac |
| 326 | TMPRSS6-h-5B | guuccucguucugugaau |
| 327 | TMPRSS6-h-6A | guagucauggcuguccucu |
| 328 | TMPRSS6-h-6B | agaggacagccaugacuac |
| 329 | TMPRSS6-h-7A | aguuguaguaaguucccag |
| 330 | TMPRSS6-h-7B | cugggaacuuacuacaacu |

Summary SEQUENCE TABLE

| SEQ ID NO | Name | Sequence (5'-3') |
|---|---|---|
| 331 | TMPRSS6-hcmr-8A | uuguacccuaggaaauacc |
| 332 | TMPRSS6-hcmr-8B | gguauuuccuagggguacaa |
| 333 | TMPRSS6-hcm-9A | aaccagaagaagcagguga |
| 334 | TMPRSS6-hcm-9B | ucaccugcuucuucugguu |
| 335 | TMPRSS6-hc-10A | uaacaacccagcguggaau |
| 336 | TMPRSS6-hc-10B | auuccacgcuggguuguua |
| 337 | TMPRSS6-hc-11A | guuucucucauccaggccg |
| 338 | TMPRSS6-hc-11B | cggccuggaugagagaaac |
| 339 | TMPRSS6-hcm-12A | gcaucuucuggggcuuuggc |
| 340 | TMPRSS6-hcm-12B | gccaaagcccagaagaugc |
| 341 | TMPRSS6-hc-13A | ucacacuggaaggugaaug |
| 342 | TMPRSS6-hc-13B | cauucaccuuccaguguga |
| 343 | TMPRSS6-hcmr-14A | cacagaugugucgaccccg |
| 344 | TMPRSS6-hcmr-14B | cggggucgacacaucugug |
| 345 | TMPRSS6-hcmr-15A | uguacccuaggaaauacca |
| 346 | TMPRSS6-hcmr-15B | ugguauuuccuagggguaca |
| 347 | TMPRSS6-Luc-siRNA-1A | ucgaaguauuccgcguacg |
| 348 | TMPRSS6-Luc-siRNA-1B | cguacgcggaauacuucga |
| 349 | TMPRSS6-PTEN-A | uaaguucuagcugugguug |
| 350 | TMPRSS6-PTEN-B | ccaccacagcuagaacuua |
| 351 | GN-TTR-hc-A | ucuugguuacaugaaauccc a |
| 352 | GN-TTR-hc-B | ugggauuucauguaaccaag a |
| 353 | STS012-6-A | aaccagaagaagcaggugacc |
| 354 | control siRNA A | uuaguaaaccuuuugagac |
| 355 | control siRNA B | gucucaaaagguuuacuaa |
| 356 | hcTMP-SR1-A | cugaggacgcccugggagu |
| 357 | hcTMP-SR1-B | acucccagggcguccucag |
| 358 | hcTMP-SR2-A | gcugaggacgcccugggag |
| 359 | hcTMP-SR2-B | cucccagggcguccucagc |
| 360 | hcTMP-SR3-A | ugcugaggacgcccuggga |
| 361 | hcTMP-SR3-B | ucccagggcguccucagca |
| 362 | hcTMP-SR4-A | gugcugaggacgcccuggg |
| 363 | hcTMP-SR4-B | cccagggcguccucagcac |
| 364 | hcTMP-SR5-A | ggugcugaggacgcccugg |
| 365 | hcTMP-SR5-B | ccagggcguccucagcacc |
| 366 | hcTMP-SR6-A | gggugcugaggacgcccug |
| 367 | hcTMP-SR6-B | cagggcguccucagcaccc |

Summary SEQUENCE TABLE

| SEQ ID NO | Name | Sequence (5'-3') |
|---|---|---|
| 368 | hcTMP-SR8-A | cggggugcugaggacgccc |
| 369 | hcTMP-SR8-B | gggcguccucagcaccccg |
| 370 | hcTMP-SR9-A | acggggugcugaggacgcc |
| 371 | hcTMP-SR9-B | ggcguccucagcaccccgu |
| 372 | hcTMP-SR10-A | uacggggugcugaggacgc |
| 373 | hcTMP-SR10-B | gcguccucagcaccccgua |
| 374 | hcTMP-SR11-A | guacggggugcugaggacg |
| 375 | hcTMP-SR11-B | cguccucagcaccccguac |
| 376 | hcTMP-SR12-A | aguacggggugcugaggac |
| 377 | hcTMP-SR12-B | guccucagcaccccguacu |
| 378 | hcTMP-SR13-A | aaguacggggugcugagga |
| 379 | hcTMP-SR13-B | uccucagcaccccguacuu |
| 380 | hcTMP-SR15-A | ggaaguacggggugcugag |
| 381 | hcTMP-SR15-B | cucagcaccccguacuucc |
| 382 | hcTMP-SR16-A | gggaaguacggggugcuga |
| 383 | hcTMP-SR16-B | ucagcaccccguacuuccc |
| 384 | hcTMP-SR17-A | ggggaaguacggggugcug |
| 385 | hcTMP-SR17-B | cagcaccccguacuucccc |
| 386 | hcTMP-SR18-A | uggggaaguacggggugcu |
| 387 | hcTMP-SR18-B | agcaccccguacuucccca |
| 388 | hcTMP-SR19-A | cuggggaaguacggggugc |
| 389 | hcTMP-SR19-B | gcaccccguacuuccccag |
| 390 | hcTMP-SR21-A | agcuggggaaguacggggu |
| 391 | hcTMP-SR21-B | accccguacuuccccagcu |
| 392 | hcTMP-SR22-A | uagcuggggaaguacgggg |
| 393 | hcTMP-SR22-B | ccccguacuuccccagcua |
| 394 | hcTMP-SR23-A | guagcuggggaaguacggg |
| 395 | hcTMP-SR23-B | cccguacuuccccagcuac |
| 396 | hcTMP-SR24-A | aguagcuggggaaguacgg |
| 397 | hcTMP-SR24-B | ccguacuuccccagcuacu |
| 398 | hcTMP-SR26-A | guaguagcuggggaaguac |

Summary SEQUENCE TABLE

| SEQ ID NO | Name | Sequence (5'-3') |
|---|---|---|
| 399 | hcTMP-SR26-B | guacuucccagcuacuac |
| 400 | hcTMP-SR27-A | aguaguagcuggggaagua |
| 401 | hcTMP-SR27-B | uacuucccagcuacuacu |
| 402 | hcTMP-SR28-A | gaguaguagcuggggaagu |
| 403 | hcTMP-SR28-B | acuucccagcuacuacuc |
| 404 | hcTMP-SR29-A | cgaguaguagcuggggaag |
| 405 | hcTMP-SR29-B | cuucccagcuacuacucg |
| 406 | hcTMP-SR30-A | gcgaguaguagcuggggaa |
| 407 | hcTMP-SR30-B | uucccagcuacuacucgc |
| 408 | hcTMP-SR31-A | ggcgaguaguagcugggga |
| 409 | hcTMP-SR31-B | ucccagcuacuacucgcc |
| 410 | hcTMP-SR32-A | gggcgaguaguagcugggg |
| 411 | hcTMP-SR32-B | ccccagcuacuacucgccc |
| 412 | hcTMP-SR33-A | ggggcgaguaguagcuggg |
| 413 | hcTMP-SR33-B | cccagcuacuacucgcccc |
| 414 | hcTMP-SR34-A | uggggcgaguaguagcugg |
| 415 | hcTMP-SR34-B | ccagcuacuacucgcccca |
| 416 | hcTMP-SR35-A | uuggggcgaguaguagcug |
| 417 | hcTMP-SR35-B | cagcuacuacucgccccaa |
| 418 | TMPRSS6-hc-16A | uauuccaaagggcagcuga |
| 419 | TMPRSS6-hc-16B | ucagcugcccuuuggaaua |
| 420 | TMPRSS6-hc-17A | aucuucugggcuuuggcgg |
| 421 | TMPRSS6-hc-17B | ccgccaaagcccagaagau |
| 422 | TMPRSS6-hc-18A | uuuucucuuggaguccuca |
| 423 | TMPRSS6-hc-18B | ugaggacuccaagagaaaa |
| 424 | TMPRSS6-hc-19A | gaauagacggagcuggagu |
| 425 | TMPRSS6-hc-19B | acuccagcuccgucuauuc |
| 426 | TMPRSS6-hc-21A | uaguagcuggggaaguacg |
| 427 | TMPRSS6-hc-21B | cguacuucccagcuacua |
| 428 | TMPRSS6-hc-22A | agauccgggagaaguggc |
| 429 | TMPRSS6-hc-22B | gccacuucucccaggaucu |
| 430 | TMPRSS6-hc-23A | cuguucuggaucguccacu |
| 431 | TMPRSS6-hc-23B | aguggacgauccagaacag |
| 432 | TMPRSS6-hcmr-24A | cucaccuugaaggacaccu |
| 433 | TMPRSS6-hcmr-24B | aggugccuucaaggugag |
| 434 | TMPRSS6-hcm-25A | aguuucucuauccaggcc |
| 435 | TMPRSS6-hcm-25B | ggccuggaugagagaaacu |

Summary SEQUENCE TABLE

| SEQ ID NO | Name | Sequence (5'-3') |
|---|---|---|
| 436 | TMPRSS6-hcr-26A | guacccuaggaaauaccag |
| 437 | TMPRSS6-hcr-26B | cugguauuccuaggguac |
| 438 | TMPRSS6-hc-27A | cuguugacuguggacagca |
| 439 | TMPRSS6-hc-27B | ugcuguccacagucaacag |
| 440 | STS12209V4L4-A | uaccagaagaagcagguga |
| 441 | STS12209V4L4-B | ucaccugcuucuucuggua |
| 442 | STS18001-A | ucgaaguauuccgcguacg |
| 443 | STS18001-B | cguacgcggaauacuucga |
| 444 | PTEN-2-A | caccgccaaaTTTaacTgcaga |
| 445 | PTEN-2-B | aagggTTTgaTaagTTcTagcTgT |
| 446 | PTEN-2-C | TgcacagTaTccTTTTgaagaccaTaaccca |
| 447 | hTMSS6: 379U17 | ccgccaaagcccagaag |
| 448 | hTMSS6: 475L21 | ggTcccTccccaaaggaaTag |
| 449 | hTMSS6: 416U28FL | cagcacccgccTgggaacTTacTacaac |

```
Key
1 = 2'F-dU
2 = 2'dA
3 = 2'F-dC
4 = 2'F-dG
5 = 2'OMe-rU
6 = 2'OMe-rA
7 = 2'OMe-rC
8 = 2'OMe-rG
T = dT
mA, mU, mC, mG - 2'-OMe RNA
fA, fU, fC, fG - 2'-F DNA
(ps) - phosphorothioate
GN = GalNAc linker GN according to fig. 8A
GN2 = GalNAc structure according to fig. 8B
GN3 = GalNAc linker structure according to fig. 8O
GNo = GN2 with phosphodiesters instead of (ps)
[A], [T], [C], [G] - DNA
{A}, {U}, {C}, {G} - LNA
ivA, ivC, ivU, ivG - inverted RNA (3'-3')
(ps2) - phosphorodithioate
vinylphosphonate vinyl-(E)-phosphonate
FAM - 6-Carboxyfluorescein
TAMRA - 5-Carboxytetramethylrhodamine
BHQ - Black Hole Quencher 1
```

Where specific linkers and or modified linkages are taught within an RNA sequence, such as PS, PS2, GN, GN2, GN3 etc, these are optional parts of the sequence, but are a preferred embodiment of that sequence.
The following abbreviations may be used:
GN
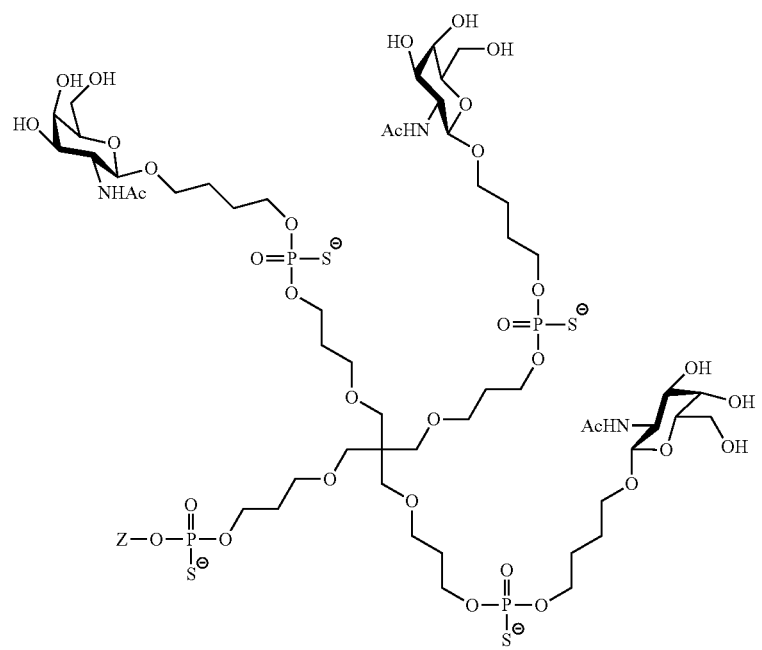
GN2
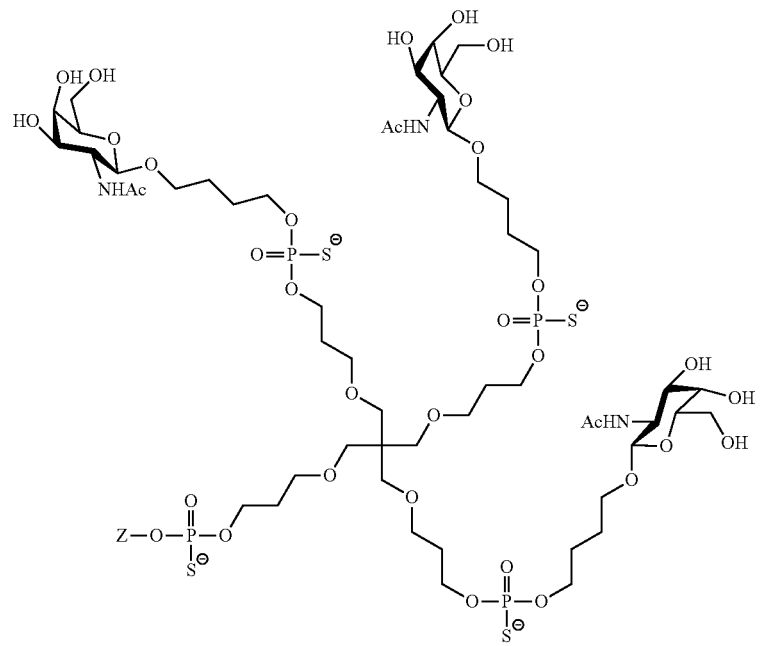

GN3 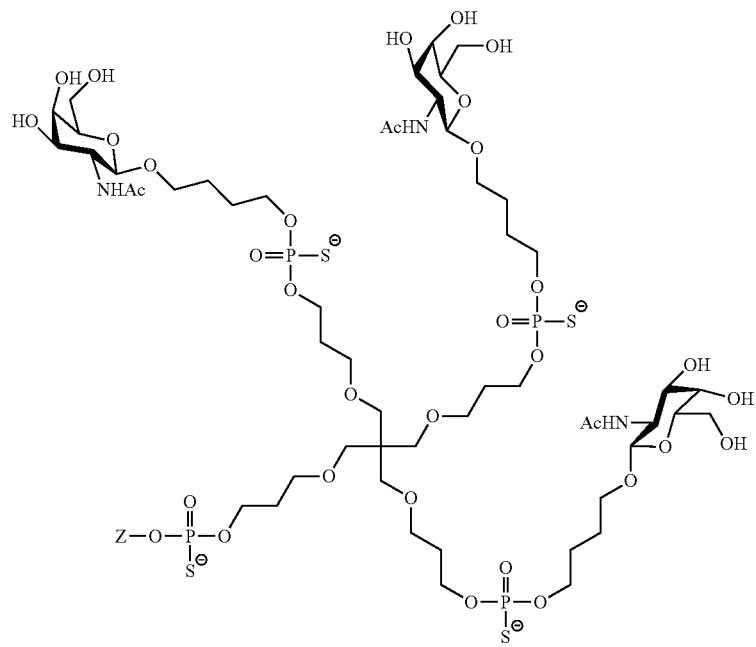
GNo  Same as GN2 but with phosphodiesters instead of phosphorothioates
ST23
(building
block for
synthesis)
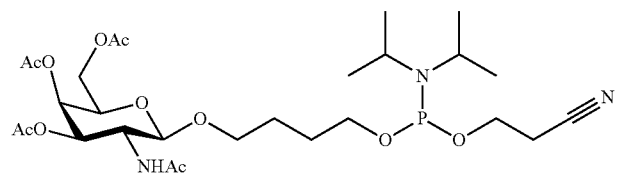
ST41/C4XLT
(building block for
synthesis)
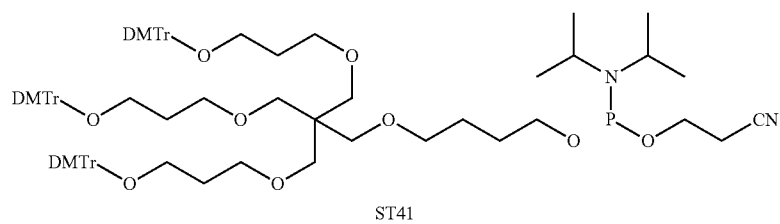
ST41
ST43/C6XLT
(building block for
synthesis)
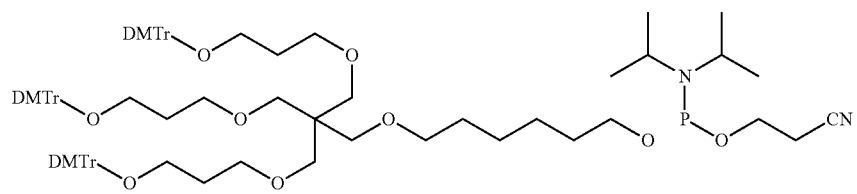
Long
trebler/ltrb/STKS
(building block for
synthesis)
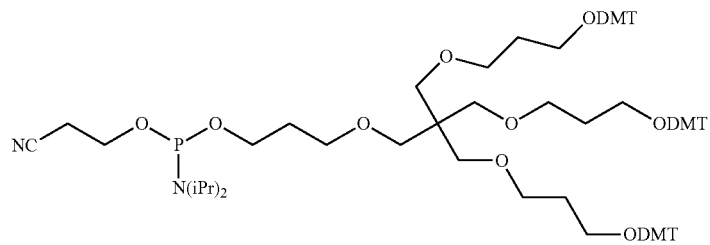

| | |
|---|---|
| [ST23 (ps)]3 ST41 (ps) | GN2 (see above) |
| [ST23 (ps)]3 ST43 (ps) | GN3 (see above) |
| ST23(ps) long trebler(ps) | GN (see above) |

What is claimed is:

1. A combination comprising a nucleic acid for inhibiting expression of TMPRSS6 and one or more iron chelators, wherein the nucleic acid comprises at least one duplex region that comprises at least a portion of a first strand and at least a portion of a second strand that is at least partially complementary to the first strand, wherein said first strand is at least partially complementary to at least a portion of RNA transcribed from the TMPRSS6 gene, and wherein said first strand comprises the nucleotide sequence 5'aaccagaagaagcagguga 3' (SEQ ID NO:17) comprising modifications 6273646282647284546, and wherein said second strand comprises the nucleotide sequence 5'ucaccugcuucuucugguu 3' (SEQ ID NO:18) comprising modifications 1727354715351718451, wherein the specific modifications are depicted by the following numbers 1=2'F-dU;
2=2'F-dA;
3=2'F-dC;
4=2'F-dG;
5=2'-OMe-rU;
6=2'-OMe-rA;
7=2'-OMe-rC; and
8=2'-OMe-rG.

2. The combination according to claim 1, wherein the nucleic acid is conjugated to a ligand, optionally at the 5' end of the second strand, optionally wherein the ligand comprises (i) one or more N-acetyl galactosamine (GalNAc) moieties and derivatives thereof, and (ii) a linker, wherein the linker conjugates the GalNAc moieties to the nucleic acid.

3. The combination according to claim 2, wherein the conjugated nucleic acid has the structure:

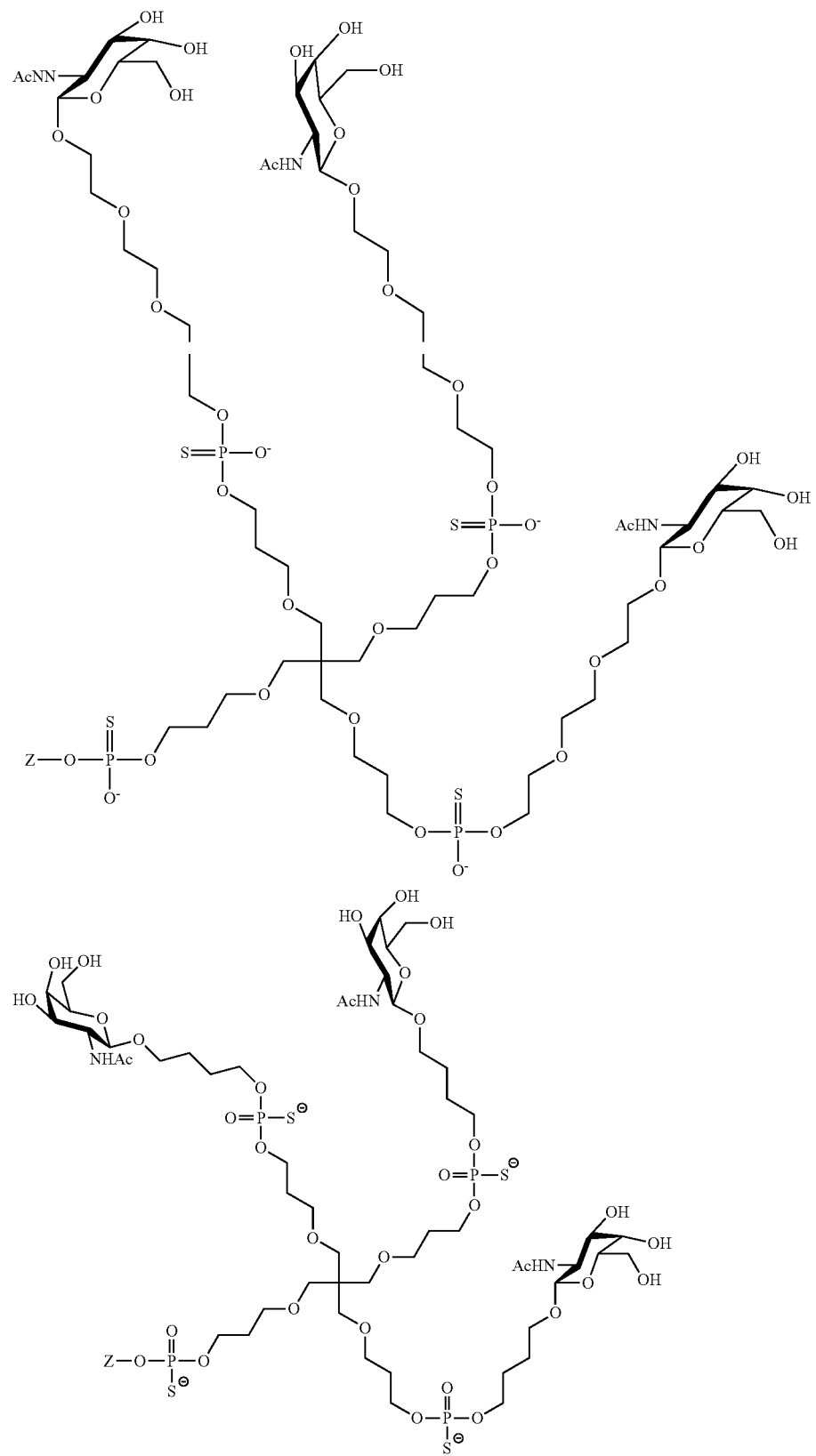

311
-continued
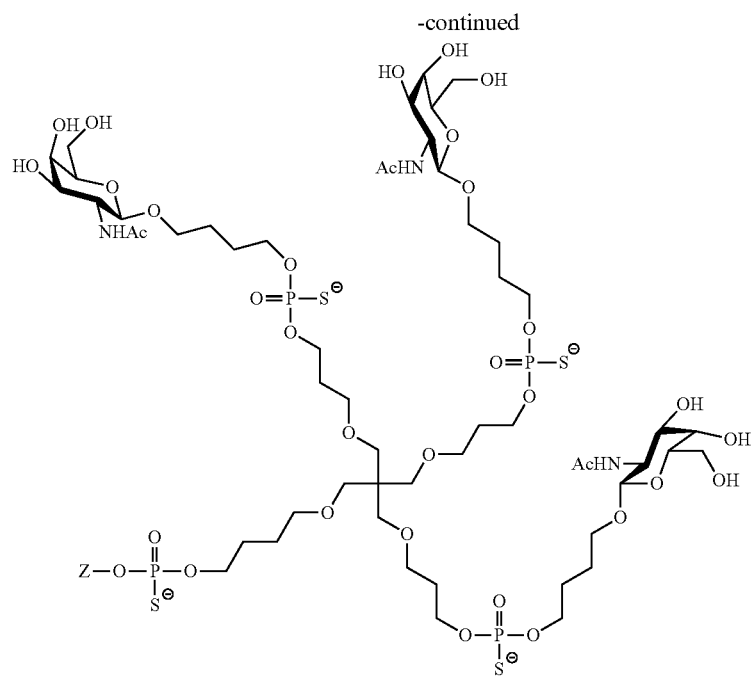
312
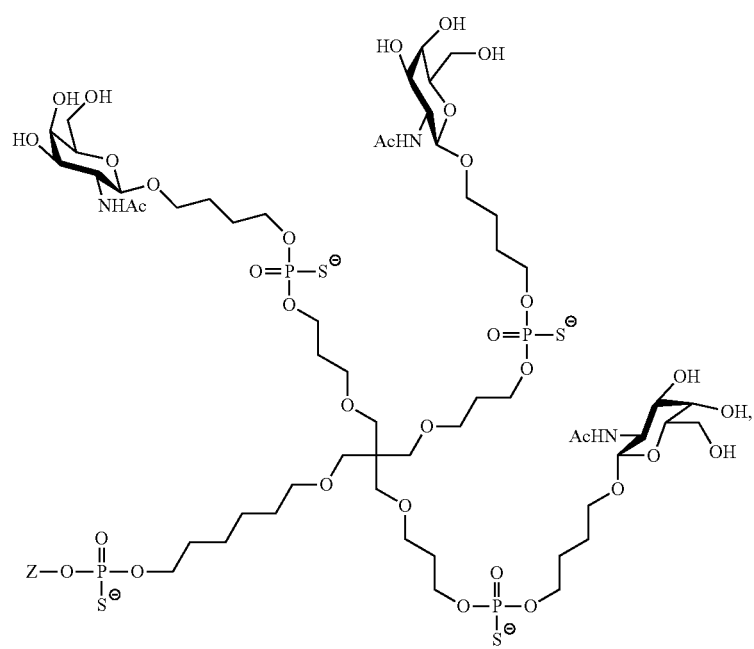

313
-continued
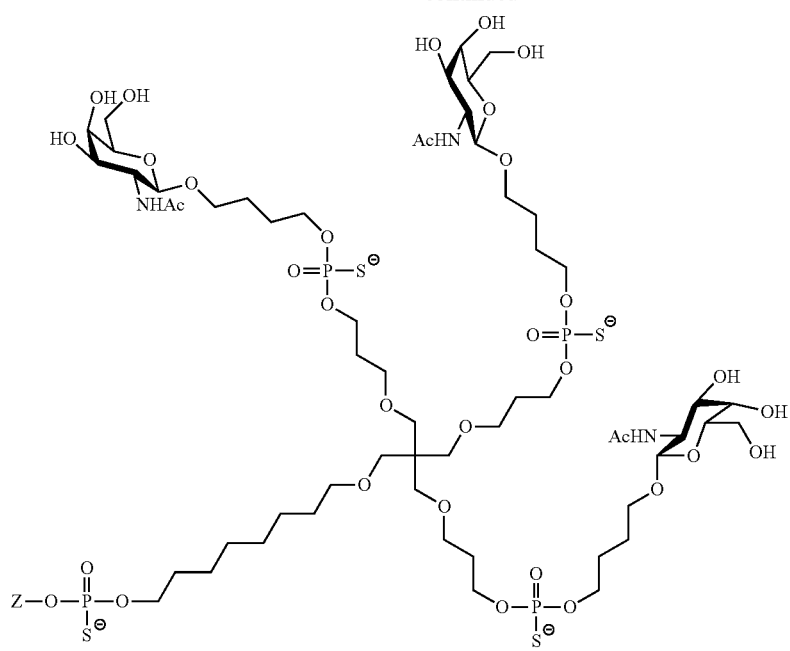
314
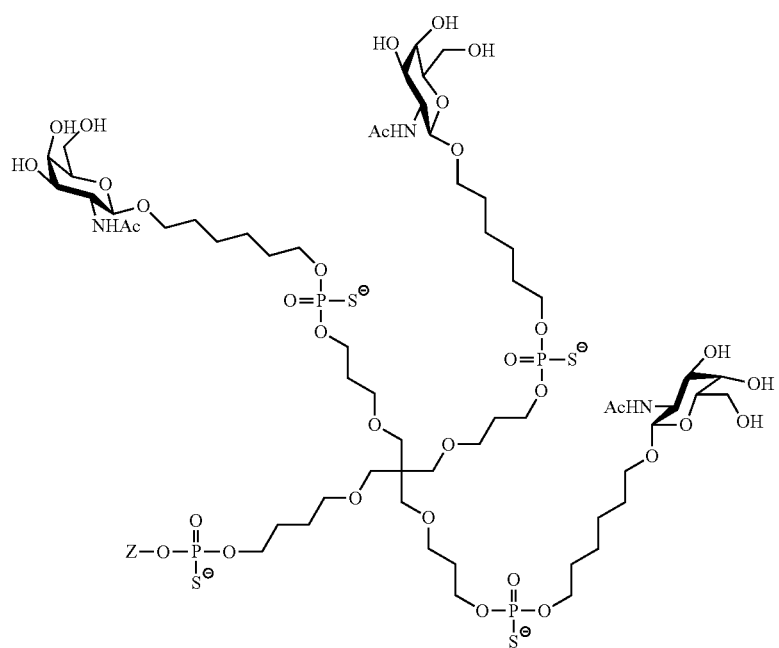

-continued

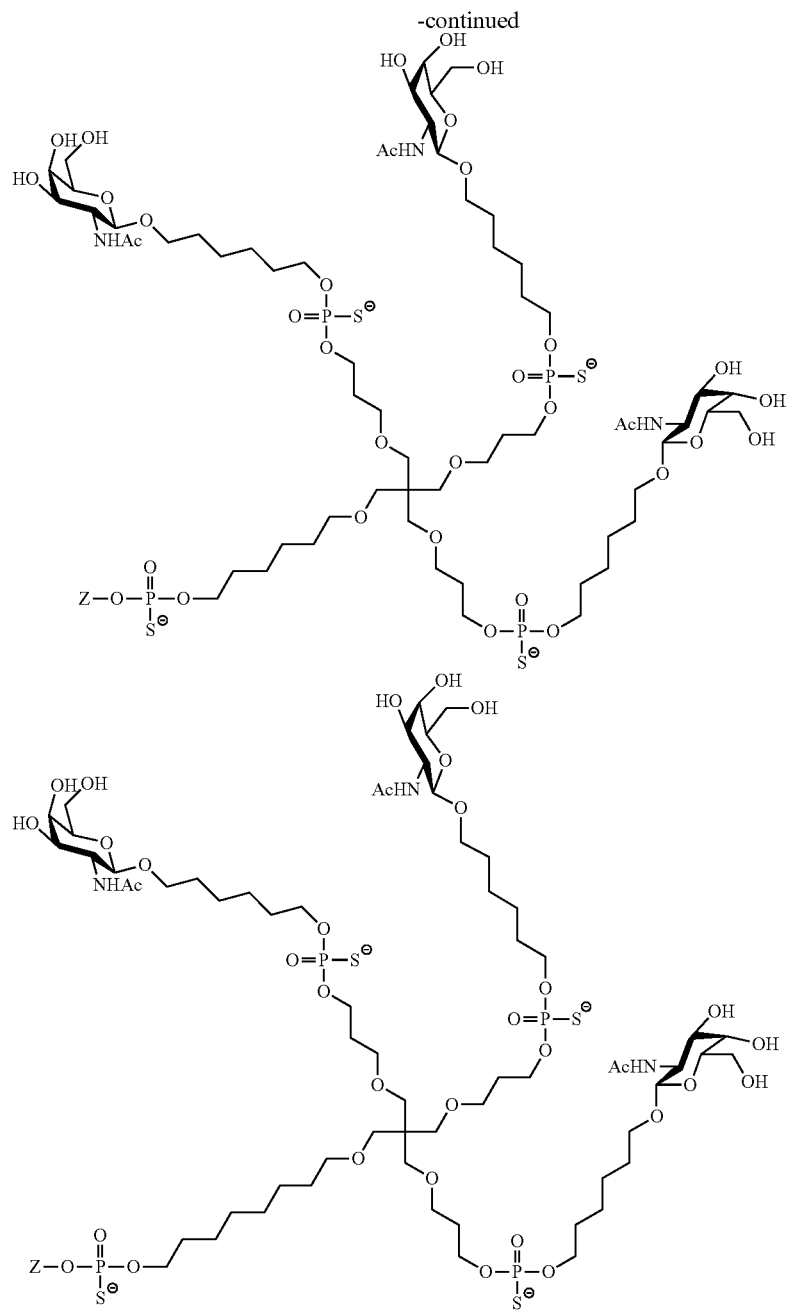

wherein Z is a nucleic acid as described in claim 1.

4. A combination comprising a nucleic acid for inhibiting expression of TMPRSS6 and one or more iron chelators, wherein the nucleic acid comprises at least one duplex region that comprises at least a portion of a first strand and at least a portion of a second strand that is at least partially complementary to the first strand, wherein said first strand is at least partially complementary to at least a portion of RNA transcribed from the TMPRSS6 gene, wherein said first strand comprises the nucleotide sequence of SEQ ID NO: 333, wherein the nucleic acid is stabilised at the 5' and/or 3' end of either or both strands,
optionally wherein the nucleic acid comprises two phosphorothioate linkages between each of the three terminal 3' and between each of the three terminal 5' nucleotides on the first strand, and two phosphorothioate linkages between the three terminal nucleotides of the 3' end of the second strand, having the structure:

(SEQ ID NO: 17)
5'-3' TMPRSS6-hcm-9A 6(ps)2(ps)736462826472845(ps)
4(ps)6

(SEQ ID NO: 18)
5'-3' TMPRSS6-hcm-9B 17273547153517184(ps)5(ps)1 wherein the specific modifications are depicted by the following numbers
1=2'F-dU,
2=2'F-dA,
3=2'F-dC,
4=2'F-dG,
5=2'-OMe-rU;
6=2'-OMe-rA;
7=2'-OMe-rC;
8=2'-OMe-rG
(ps)=phosphorothioate linkage.

5. The combination according to claim 1, wherein the one or more iron chelators are selected from deferoxamine, deferiprone, deferasirox (Exjade) and deferairox (Jadenu).

6. The combination according to claim 4, wherein the one or more iron chelators are selected from deferoxamine, deferiprone, deferasirox (Exjade) and deferairox (Jadenu).

7. The combination according to claim 4, wherein the nucleic acid is conjugated to a ligand, optionally at the 5' end of the second strand, optionally wherein the ligand comprises (i) one or more N-acetyl galactosamine (GalNAc) moieties and derivatives thereof, and (ii) a linker, wherein the linker conjugates the GalNAc moieties to the nucleic acid.

8. The combination according to claim 7, wherein the conjugated nucleic acid has the structure:

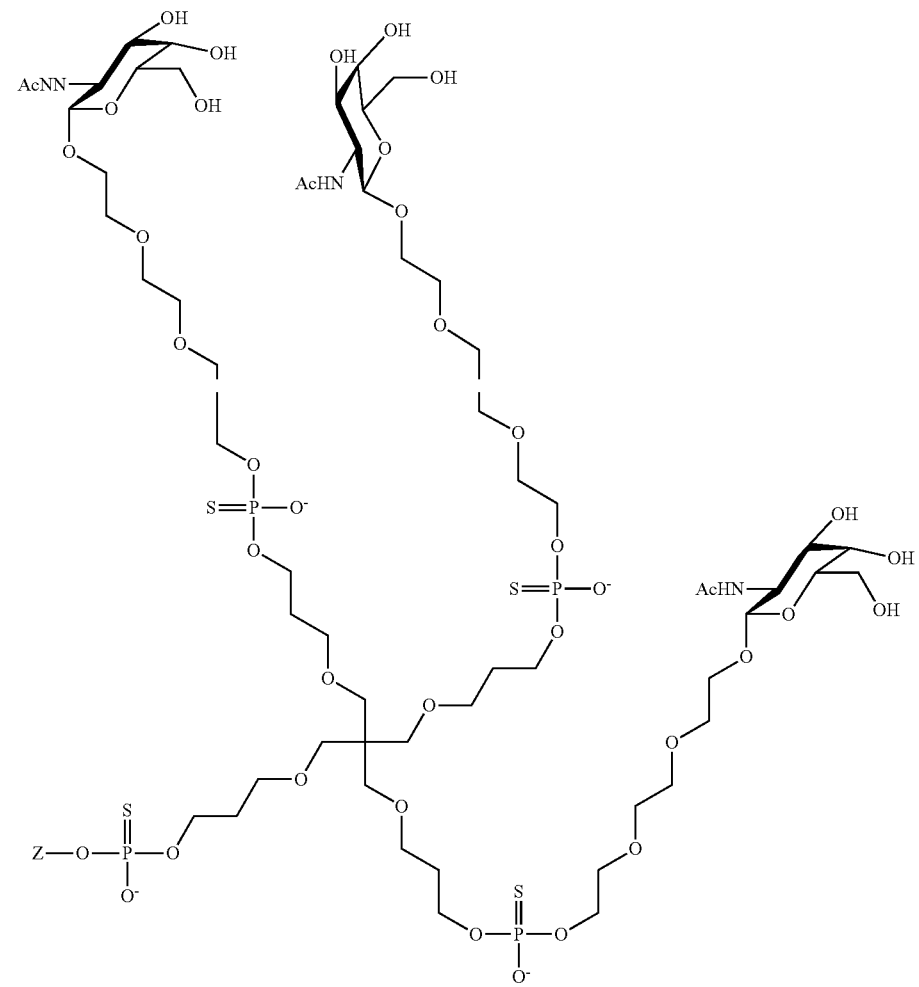

-continued
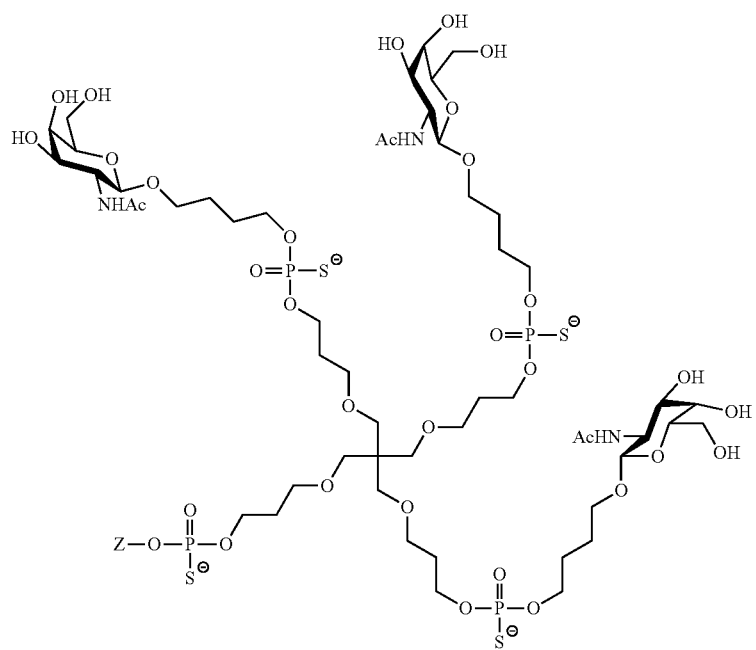
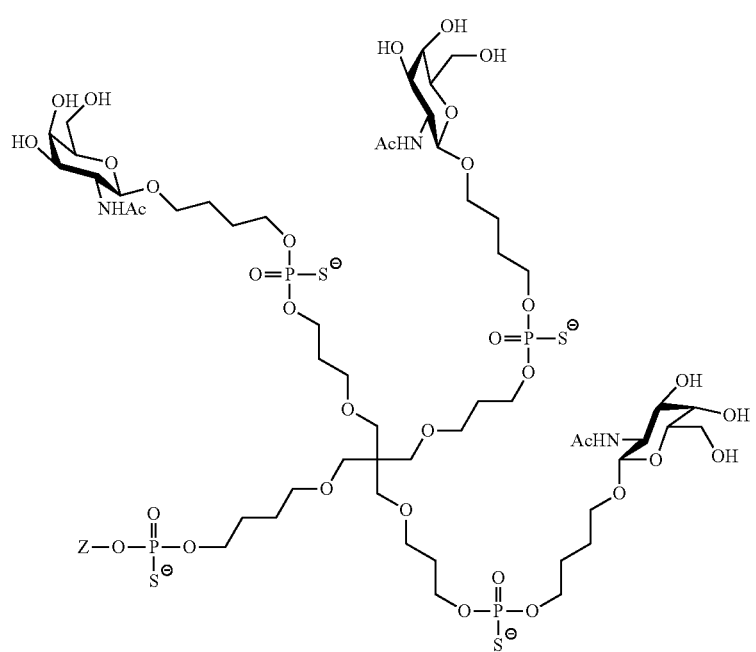

-continued
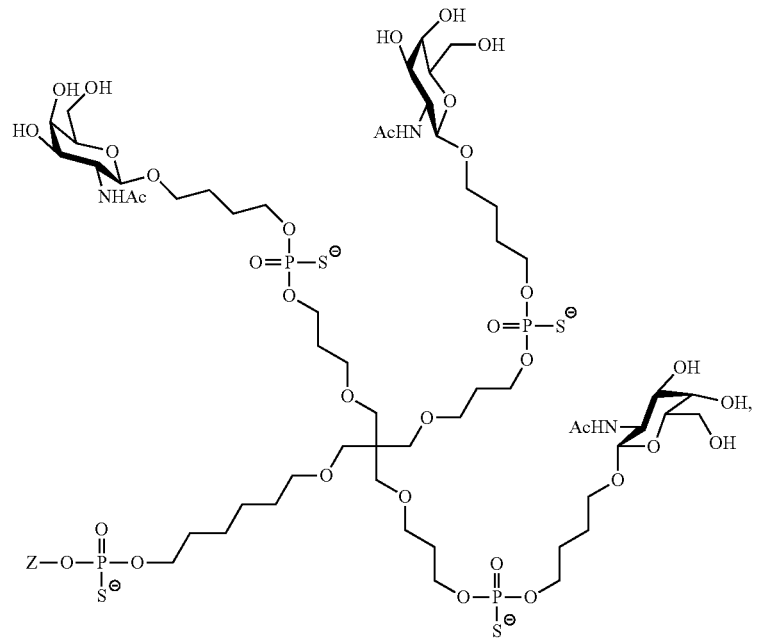
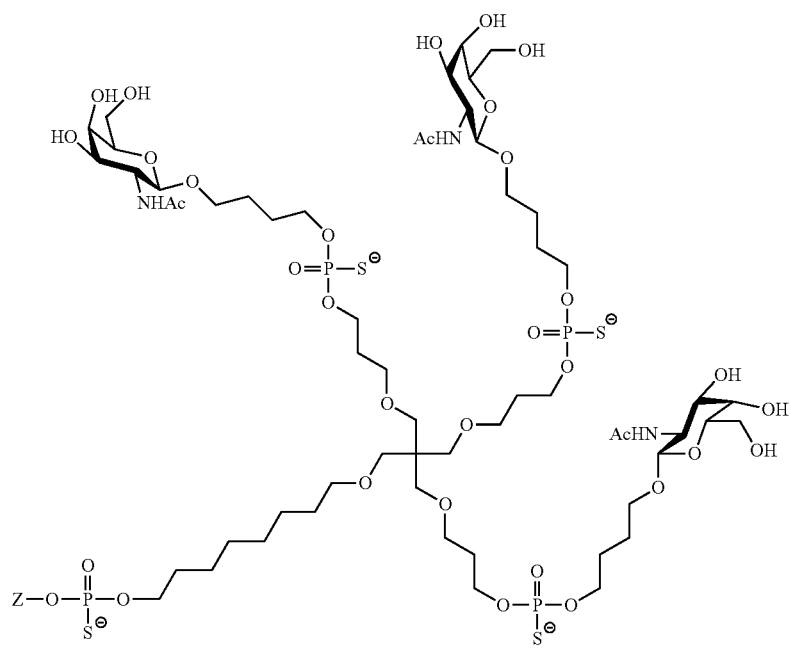

-continued
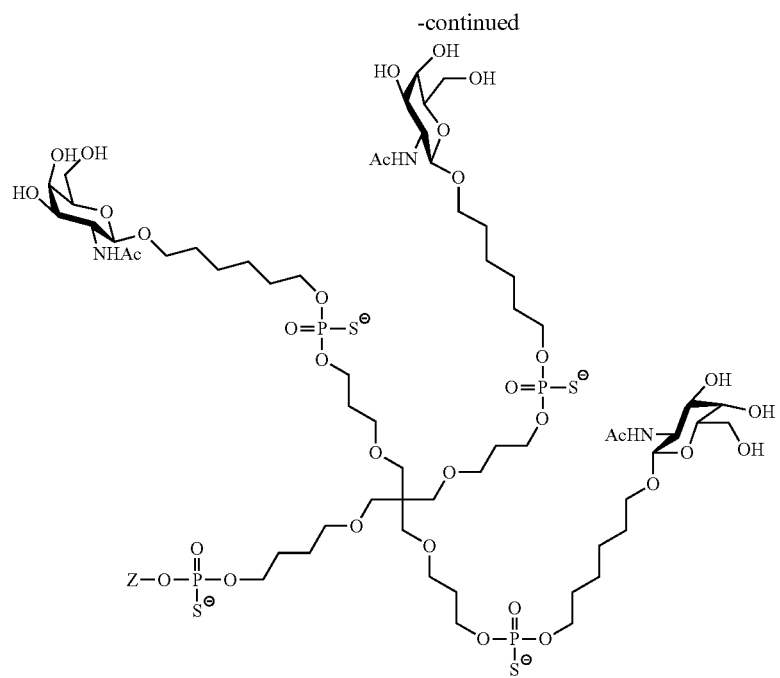
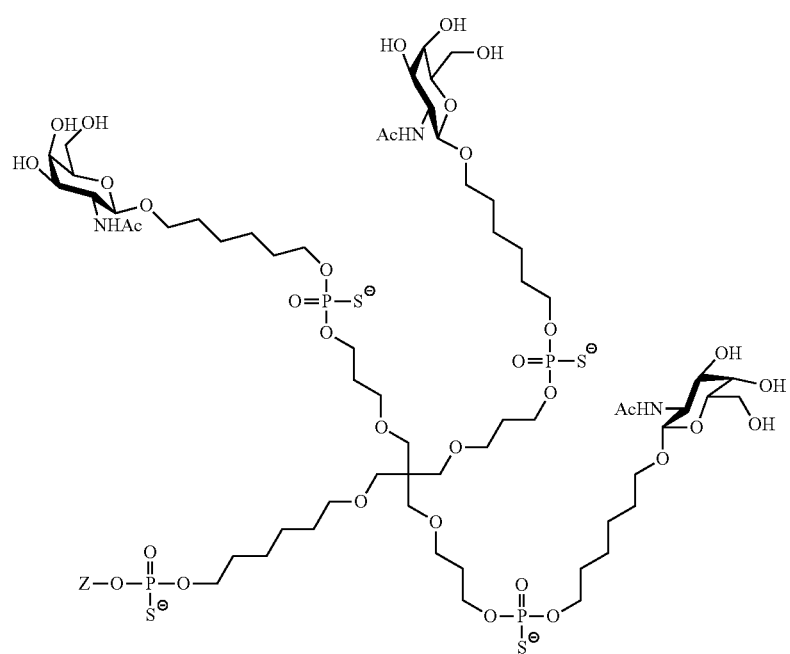

-continued
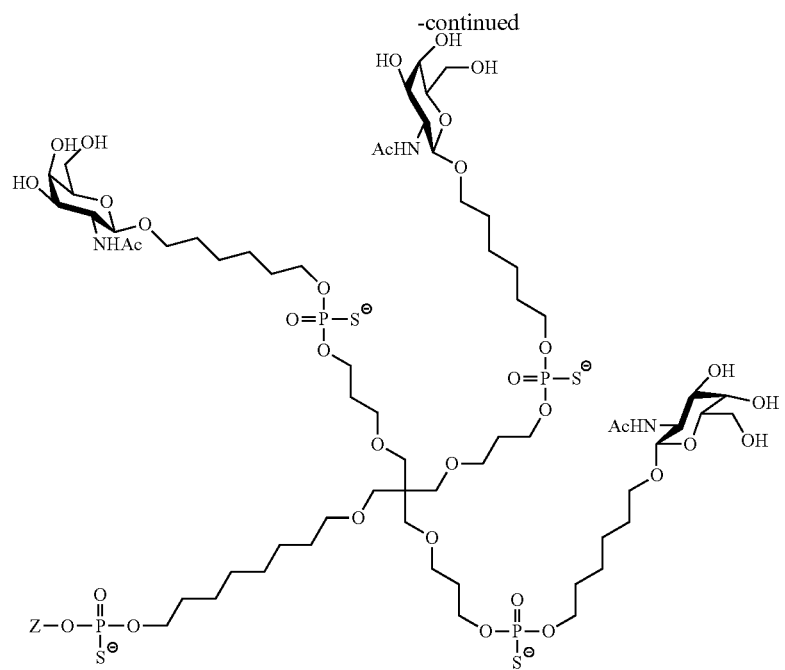
wherein Z is a nucleic acid as described in claim 4.
9. A kit comprising the combination of claim 1.
10. A kit comprising the combination of claim 4.
11. A pharmaceutical composition comprising the combination of claim 1.
12. A pharmaceutical composition comprising the combination of claim 4.
* * * * *

```
                             SEQUENCE LISTING

<160> NUMBER OF SEQ ID NOS: 451

<210> SEQ ID NO 1
<211> LENGTH: 19
<212> TYPE: RNA
<213> ORGANISM: Artificial Sequence
<220> FEATURE:
<223> OTHER INFORMATION: siRNA

<400> SEQUENCE: 1
augucuuuca cacuggcuu                                                    19

<210> SEQ ID NO 2
<211> LENGTH: 19
<212> TYPE: RNA
<213> ORGANISM: Artificial Sequence
<220> FEATURE:
<223> OTHER INFORMATION: siRNA

<400> SEQUENCE: 2
aagccagugu gaaagacau                                                    19

<210> SEQ ID NO 3
<211> LENGTH: 19
<212> TYPE: RNA
<213> ORGANISM: Artificial Sequence
<220> FEATURE:
<223> OTHER INFORMATION: siRNA

<400> SEQUENCE: 3
auugaguaca cgcagacug                                                    19

<210> SEQ ID NO 4
<211> LENGTH: 19
<212> TYPE: RNA
<213> ORGANISM: Artificial Sequence
<220> FEATURE:
<223> OTHER INFORMATION: siRNA

<400> SEQUENCE: 4
cagucugcgu guacucaau                                                    19

<210> SEQ ID NO 5
<211> LENGTH: 19
<212> TYPE: RNA
<213> ORGANISM: Artificial Sequence
<220> FEATURE:
<223> OTHER INFORMATION: siRNA

<400> SEQUENCE: 5
aaguugaugg ugaucccgg                                                    19

<210> SEQ ID NO 6
<211> LENGTH: 19
<212> TYPE: RNA
<213> ORGANISM: Artificial Sequence
```

```
<220> FEATURE:
<223> OTHER INFORMATION: siRNA

<400> SEQUENCE: 6
ccgggaucac caucaacuu                                              19

<210> SEQ ID NO 7
<211> LENGTH: 19
<212> TYPE: RNA
<213> ORGANISM: Artificial Sequence
<220> FEATURE:
<223> OTHER INFORMATION: siRNA

<400> SEQUENCE: 7
uucuggaucg uccacuggc                                              19

<210> SEQ ID NO 8
<211> LENGTH: 19
<212> TYPE: RNA
<213> ORGANISM: Artificial Sequence
<220> FEATURE:
<223> OTHER INFORMATION: siRNA

<400> SEQUENCE: 8
gccaguggac gauccagaa                                              19

<210> SEQ ID NO 9
<211> LENGTH: 19
<212> TYPE: RNA
<213> ORGANISM: Artificial Sequence
<220> FEATURE:
<223> OTHER INFORMATION: siRNA

<400> SEQUENCE: 9
auucacagaa cagaggaac                                              19

<210> SEQ ID NO 10
<211> LENGTH: 19
<212> TYPE: RNA
<213> ORGANISM: Artificial Sequence
<220> FEATURE:
<223> OTHER INFORMATION: siRNA

<400> SEQUENCE: 10
guuccucugu ucugugaau                                              19

<210> SEQ ID NO 11
<211> LENGTH: 19
<212> TYPE: RNA
<213> ORGANISM: Artificial Sequence
<220> FEATURE:
<223> OTHER INFORMATION: siRNA

<400> SEQUENCE: 11
guagucaugg cuguccucu                                              19

<210> SEQ ID NO 12
<211> LENGTH: 19
<212> TYPE: RNA
<213> ORGANISM: Artificial Sequence
<220> FEATURE:
<223> OTHER INFORMATION: siRNA

<400> SEQUENCE: 12
agaggacagc caugacuac                                              19
```

```
<210> SEQ ID NO 13
<211> LENGTH: 19
<212> TYPE: RNA
<213> ORGANISM: Artificial Sequence
<220> FEATURE:
<223> OTHER INFORMATION: siRNA

<400> SEQUENCE: 13
aguuguagua aguucccag                                                   19

<210> SEQ ID NO 14
<211> LENGTH: 19
<212> TYPE: RNA
<213> ORGANISM: Artificial Sequence
<220> FEATURE:
<223> OTHER INFORMATION: siRNA

<400> SEQUENCE: 14
cugggaacuu acuacaacu                                                   19

<210> SEQ ID NO 15
<211> LENGTH: 19
<212> TYPE: RNA
<213> ORGANISM: Artificial Sequence
<220> FEATURE:
<223> OTHER INFORMATION: siRNA

<400> SEQUENCE: 15
uuguacccua ggaaauacc                                                   19

<210> SEQ ID NO 16
<211> LENGTH: 19
<212> TYPE: RNA
<213> ORGANISM: Artificial Sequence
<220> FEATURE:
<223> OTHER INFORMATION: siRNA

<400> SEQUENCE: 16
gguauuuccu aggguacaa                                                   19

<210> SEQ ID NO 17
<211> LENGTH: 19
<212> TYPE: RNA
<213> ORGANISM: Artificial Sequence
<220> FEATURE:
<223> OTHER INFORMATION: siRNA

<400> SEQUENCE: 17
aaccagaaga agcagguga                                                   19

<210> SEQ ID NO 18
<211> LENGTH: 19
<212> TYPE: RNA
<213> ORGANISM: Artificial Sequence
<220> FEATURE:
<223> OTHER INFORMATION: siRNA

<400> SEQUENCE: 18
ucaccugcuu cuucugguu                                                   19

<210> SEQ ID NO 19
<211> LENGTH: 19
<212> TYPE: RNA
<213> ORGANISM: Artificial Sequence
<220> FEATURE:
<223> OTHER INFORMATION: siRNA
```

```
<400> SEQUENCE: 19
uaacaaccca gcguggaau                                              19

<210> SEQ ID NO 20
<211> LENGTH: 19
<212> TYPE: RNA
<213> ORGANISM: Artificial Sequence
<220> FEATURE:
<223> OTHER INFORMATION: siRNA

<400> SEQUENCE: 20
auuccacgcu ggguuguua                                              19

<210> SEQ ID NO 21
<211> LENGTH: 19
<212> TYPE: RNA
<213> ORGANISM: Artificial Sequence
<220> FEATURE:
<223> OTHER INFORMATION: siRNA

<400> SEQUENCE: 21
guuucucuca uccaggccg                                              19

<210> SEQ ID NO 22
<211> LENGTH: 19
<212> TYPE: RNA
<213> ORGANISM: Artificial Sequence
<220> FEATURE:
<223> OTHER INFORMATION: siRNA

<400> SEQUENCE: 22
cggccuggau gagagaaac                                              19

<210> SEQ ID NO 23
<211> LENGTH: 19
<212> TYPE: RNA
<213> ORGANISM: Artificial Sequence
<220> FEATURE:
<223> OTHER INFORMATION: siRNA

<400> SEQUENCE: 23
gcaucuucug ggcuuuggc                                              19

<210> SEQ ID NO 24
<211> LENGTH: 19
<212> TYPE: RNA
<213> ORGANISM: Artificial Sequence
<220> FEATURE:
<223> OTHER INFORMATION: siRNA

<400> SEQUENCE: 24
gccaaagccc agaagaugc                                              19

<210> SEQ ID NO 25
<211> LENGTH: 19
<212> TYPE: RNA
<213> ORGANISM: Artificial Sequence
<220> FEATURE:
<223> OTHER INFORMATION: siRNA

<400> SEQUENCE: 25
ucacacugga aggugaaug                                              19

<210> SEQ ID NO 26
```

```
<211> LENGTH: 19
<212> TYPE: RNA
<213> ORGANISM: Artificial Sequence
<220> FEATURE:
<223> OTHER INFORMATION: siRNA

<400> SEQUENCE: 26
cauucaccuu ccaguguga                                                    19

<210> SEQ ID NO 27
<211> LENGTH: 19
<212> TYPE: RNA
<213> ORGANISM: Artificial Sequence
<220> FEATURE:
<223> OTHER INFORMATION: siRNA

<400> SEQUENCE: 27
cacagaugug ucgaccccg                                                    19

<210> SEQ ID NO 28
<211> LENGTH: 19
<212> TYPE: RNA
<213> ORGANISM: Artificial Sequence
<220> FEATURE:
<223> OTHER INFORMATION: siRNA

<400> SEQUENCE: 28
cggggucgac acaucugug                                                    19

<210> SEQ ID NO 29
<211> LENGTH: 19
<212> TYPE: RNA
<213> ORGANISM: Artificial Sequence
<220> FEATURE:
<223> OTHER INFORMATION: siRNA

<400> SEQUENCE: 29
uguacccuag gaaauacca                                                    19

<210> SEQ ID NO 30
<211> LENGTH: 19
<212> TYPE: RNA
<213> ORGANISM: Artificial Sequence
<220> FEATURE:
<223> OTHER INFORMATION: siRNA

<400> SEQUENCE: 30
ugguauuucc uaggguaca                                                    19

<210> SEQ ID NO 31
<211> LENGTH: 19
<212> TYPE: RNA
<213> ORGANISM: Artificial Sequence
<220> FEATURE:
<223> OTHER INFORMATION: siRNA

<400> SEQUENCE: 31
ucgaaguauu ccgcguacg                                                    19

<210> SEQ ID NO 32
<211> LENGTH: 19
<212> TYPE: RNA
<213> ORGANISM: Artificial Sequence
<220> FEATURE:
<223> OTHER INFORMATION: siRNA

<400> SEQUENCE: 32
```
cguacgcgga auacuucga                                            19

<210> SEQ ID NO 33
<211> LENGTH: 19
<212> TYPE: RNA
<213> ORGANISM: Artificial Sequence
<220> FEATURE:
<223> OTHER INFORMATION: siRNA

<400> SEQUENCE: 33
uaaguucuag cugggugg                                             19

<210> SEQ ID NO 34
<211> LENGTH: 19
<212> TYPE: RNA
<213> ORGANISM: Artificial Sequence
<220> FEATURE:
<223> OTHER INFORMATION: siRNA

<400> SEQUENCE: 34
ccaccacagc uagaacuua                                            19

<210> SEQ ID NO 35
<211> LENGTH: 17
<212> TYPE: DNA
<213> ORGANISM: Artificial Sequence
<220> FEATURE:
<223> OTHER INFORMATION: hTMPRSS6 (upper)

<400> SEQUENCE: 35
ccgccaaagc ccagaag                                              17

<210> SEQ ID NO 36
<211> LENGTH: 21
<212> TYPE: DNA
<213> ORGANISM: Artificial Sequence
<220> FEATURE:
<223> OTHER INFORMATION: hTMPRSS6 (lower)

<400> SEQUENCE: 36
ggtccctccc caaaggaata g                                         21

<210> SEQ ID NO 37
<211> LENGTH: 28
<212> TYPE: DNA
<213> ORGANISM: Artificial Sequence
<220> FEATURE:
<223> OTHER INFORMATION: hTMPRSS6 (probe)

<400> SEQUENCE: 37
cagcacccgc ctgggaactt actacaac                                  28

<210> SEQ ID NO 38
<211> LENGTH: 21
<212> TYPE: DNA
<213> ORGANISM: Artificial Sequence
<220> FEATURE:
<223> OTHER INFORMATION: mTMPRSS6 (upper)

<400> SEQUENCE: 38
cggcacctac cttccactct t                                         21

<210> SEQ ID NO 39
<211> LENGTH: 17
<212> TYPE: DNA

```
<213> ORGANISM: Artificial Sequence
<220> FEATURE:
<223> OTHER INFORMATION: mTMPRSS6 (lower)

<400> SEQUENCE: 39
tcggtggtgg gcatcct                                                          17

<210> SEQ ID NO 40
<211> LENGTH: 28
<212> TYPE: DNA
<213> ORGANISM: Artificial Sequence
<220> FEATURE:
<223> OTHER INFORMATION: mTMPRss6 (probe)

<400> SEQUENCE: 40
ccgagatgtt tccagctccc ctgttcta                                              28

<210> SEQ ID NO 41
<211> LENGTH: 23
<212> TYPE: DNA
<213> ORGANISM: Artificial Sequence
<220> FEATURE:
<223> OTHER INFORMATION: h-Aktin (upper)

<400> SEQUENCE: 41
gcatgggtca aaggattcc tat                                                    23

<210> SEQ ID NO 42
<211> LENGTH: 23
<212> TYPE: DNA
<213> ORGANISM: Artificial Sequence
<220> FEATURE:
<223> OTHER INFORMATION: h-Aktin (lower)

<400> SEQUENCE: 42
tgtagaaggt gtggtgccag att                                                   23

<210> SEQ ID NO 43
<211> LENGTH: 22
<212> TYPE: DNA
<213> ORGANISM: Artificial Sequence
<220> FEATURE:
<223> OTHER INFORMATION: h-Aktin (probe)

<400> SEQUENCE: 43
tcgagcacgg catcgtcacc aa                                                    22

<210> SEQ ID NO 44
<211> LENGTH: 22
<212> TYPE: DNA
<213> ORGANISM: Artificial Sequence
<220> FEATURE:
<223> OTHER INFORMATION: mAktin (upper)

<400> SEQUENCE: 44
gtttgagacc ttcaacaccc ca                                                    22

<210> SEQ ID NO 45
<211> LENGTH: 21
<212> TYPE: DNA
<213> ORGANISM: Artificial Sequence
<220> FEATURE:
<223> OTHER INFORMATION: mAktin (lower)

<400> SEQUENCE: 45
gaccagaggc atacagggac a                                                     21
```

```
<210> SEQ ID NO 46
<211> LENGTH: 26
<212> TYPE: DNA
<213> ORGANISM: Artificial Sequence
<220> FEATURE:
<223> OTHER INFORMATION: mAktin (probe)

<400> SEQUENCE: 46
ccatgtacgt agccatccag gctgtg                                            26

<210> SEQ ID NO 47
<211> LENGTH: 22
<212> TYPE: DNA
<213> ORGANISM: Artificial Sequence
<220> FEATURE:
<223> OTHER INFORMATION: PTEN (upper)

<400> SEQUENCE: 47
caccgccaaa tttaactgca ga                                                22

<210> SEQ ID NO 48
<211> LENGTH: 24
<212> TYPE: DNA
<213> ORGANISM: Artificial Sequence
<220> FEATURE:
<223> OTHER INFORMATION: PTEN (lower)

<400> SEQUENCE: 48
aagggtttga taagttctag ctgt                                              24

<210> SEQ ID NO 49
<211> LENGTH: 31
<212> TYPE: DNA
<213> ORGANISM: Artificial Sequence
<220> FEATURE:
<223> OTHER INFORMATION: PTEN (probe)

<400> SEQUENCE: 49
tgcacagtat cctttgaag accataaccc a                                       31

<210> SEQ ID NO 50
<211> LENGTH: 22
<212> TYPE: DNA
<213> ORGANISM: Artificial Sequence
<220> FEATURE:
<223> OTHER INFORMATION: mHAMP (upper)

<400> SEQUENCE: 50
cctgtctcct gcttctcctc ct                                                22

<210> SEQ ID NO 51
<211> LENGTH: 22
<212> TYPE: DNA
<213> ORGANISM: Artificial Sequence
<220> FEATURE:
<223> OTHER INFORMATION: mHAMP (lower)

<400> SEQUENCE: 51
aatgtctgcc ctgctttctt cc                                                22

<210> SEQ ID NO 52
<211> LENGTH: 28
<212> TYPE: DNA
<213> ORGANISM: Artificial Sequence
<220> FEATURE:
```

```
<223> OTHER INFORMATION: mHAMP (probe)

<400> SEQUENCE: 52
tgagcagcac cacctatctc catcaaca                                          28

<210> SEQ ID NO 53
<211> LENGTH: 19
<212> TYPE: RNA
<213> ORGANISM: Artificial Sequence
<220> FEATURE:
<223> OTHER INFORMATION: siRNA

<400> SEQUENCE: 53
gguauuuccu aggguacaa                                                    19

<210> SEQ ID NO 54
<211> LENGTH: 19
<212> TYPE: RNA
<213> ORGANISM: Artificial Sequence
<220> FEATURE:
<223> OTHER INFORMATION: siRNA

<400> SEQUENCE: 54
cagucugcgu guacucaau                                                    19

<210> SEQ ID NO 55
<211> LENGTH: 19
<212> TYPE: RNA
<213> ORGANISM: Artificial Sequence
<220> FEATURE:
<223> OTHER INFORMATION: siRNA

<400> SEQUENCE: 55
gccaaagccc agaagaugc                                                    19

<210> SEQ ID NO 56
<211> LENGTH: 19
<212> TYPE: RNA
<213> ORGANISM: Artificial Sequence
<220> FEATURE:
<223> OTHER INFORMATION: siRNA

<400> SEQUENCE: 56
cugggaacuu acuacaacu                                                    19

<210> SEQ ID NO 57
<211> LENGTH: 19
<212> TYPE: RNA
<213> ORGANISM: Artificial Sequence
<220> FEATURE:
<223> OTHER INFORMATION: siRNA

<400> SEQUENCE: 57
ucaccugcuu cuucugguu                                                    19

<210> SEQ ID NO 58
<211> LENGTH: 19
<212> TYPE: RNA
<213> ORGANISM: Artificial Sequence
<220> FEATURE:
<223> OTHER INFORMATION: siRNA

<400> SEQUENCE: 58
aagccagugu gaaagacau                                                    19
```

```
<210> SEQ ID NO 59
<211> LENGTH: 19
<212> TYPE: RNA
<213> ORGANISM: Artificial Sequence
<220> FEATURE:
<223> OTHER INFORMATION: siRNA

<400> SEQUENCE: 59
auuccacgcu ggguuguua                                                  19

<210> SEQ ID NO 60
<211> LENGTH: 19
<212> TYPE: RNA
<213> ORGANISM: Artificial Sequence
<220> FEATURE:
<223> OTHER INFORMATION: siRNA

<400> SEQUENCE: 60
gccaguggac gauccagaa                                                  19

<210> SEQ ID NO 61
<211> LENGTH: 19
<212> TYPE: RNA
<213> ORGANISM: Artificial Sequence
<220> FEATURE:
<223> OTHER INFORMATION: siRNA

<400> SEQUENCE: 61
ccgggaucac caucaacuu                                                  19

<210> SEQ ID NO 62
<211> LENGTH: 19
<212> TYPE: RNA
<213> ORGANISM: Artificial Sequence
<220> FEATURE:
<223> OTHER INFORMATION: siRNA

<400> SEQUENCE: 62
guuccucugu ucugugaau                                                  19

<210> SEQ ID NO 63
<211> LENGTH: 19
<212> TYPE: RNA
<213> ORGANISM: Artificial Sequence
<220> FEATURE:
<223> OTHER INFORMATION: siRNA

<400> SEQUENCE: 63
cggccuggau gagagaaac                                                  19

<210> SEQ ID NO 64
<211> LENGTH: 19
<212> TYPE: RNA
<213> ORGANISM: Artificial Sequence
<220> FEATURE:
<223> OTHER INFORMATION: siRNA

<400> SEQUENCE: 64
cauucaccuu ccaguguga                                                  19

<210> SEQ ID NO 65
<211> LENGTH: 19
<212> TYPE: RNA
<213> ORGANISM: Artificial Sequence
<220> FEATURE:
<223> OTHER INFORMATION: siRNA
```

```
<400> SEQUENCE: 65
cggggucgac acaucugug                                                19

<210> SEQ ID NO 66
<211> LENGTH: 19
<212> TYPE: RNA
<213> ORGANISM: Artificial Sequence
<220> FEATURE:
<223> OTHER INFORMATION: siRNA

<400> SEQUENCE: 66
agaggacagc caugacuac                                                19

<210> SEQ ID NO 67
<211> LENGTH: 19
<212> TYPE: RNA
<213> ORGANISM: Artificial Sequence
<220> FEATURE:
<223> OTHER INFORMATION: siRNA

<400> SEQUENCE: 67
aaccagaaga agcagguga                                                19

<210> SEQ ID NO 68
<211> LENGTH: 19
<212> TYPE: RNA
<213> ORGANISM: Artificial Sequence
<220> FEATURE:
<223> OTHER INFORMATION: siRNA

<400> SEQUENCE: 68
ucaccugcuu cuucugguu                                                19

<210> SEQ ID NO 69
<211> LENGTH: 19
<212> TYPE: RNA
<213> ORGANISM: Artificial Sequence
<220> FEATURE:
<223> OTHER INFORMATION: siRNA

<400> SEQUENCE: 69
aaccagaaga agcagguga                                                19

<210> SEQ ID NO 70
<211> LENGTH: 19
<212> TYPE: RNA
<213> ORGANISM: Artificial Sequence
<220> FEATURE:
<223> OTHER INFORMATION: siRNA

<400> SEQUENCE: 70
ucaccugcuu cuucugguu                                                19

<210> SEQ ID NO 71
<211> LENGTH: 19
<212> TYPE: RNA
<213> ORGANISM: Artificial Sequence
<220> FEATURE:
<223> OTHER INFORMATION: siRNA

<400> SEQUENCE: 71
aaccagaaga agcagguga                                                19

<210> SEQ ID NO 72
<211> LENGTH: 19
```

```
<212> TYPE: RNA
<213> ORGANISM: Artificial Sequence
<220> FEATURE:
<223> OTHER INFORMATION: siRNA

<400> SEQUENCE: 72
ucaccugcuu cuucugguu                                                       19

<210> SEQ ID NO 73
<211> LENGTH: 19
<212> TYPE: RNA
<213> ORGANISM: Artificial Sequence
<220> FEATURE:
<223> OTHER INFORMATION: siRNA

<400> SEQUENCE: 73
aaccagaaga agcagguga                                                       19

<210> SEQ ID NO 74
<211> LENGTH: 19
<212> TYPE: RNA
<213> ORGANISM: Artificial Sequence
<220> FEATURE:
<223> OTHER INFORMATION: siRNA

<400> SEQUENCE: 74
aaccagaaga agcagguga                                                       19

<210> SEQ ID NO 75
<211> LENGTH: 19
<212> TYPE: RNA
<213> ORGANISM: Artificial Sequence
<220> FEATURE:
<223> OTHER INFORMATION: siRNA

<400> SEQUENCE: 75
ucaccugcuu cuucugguu                                                       19

<210> SEQ ID NO 76
<211> LENGTH: 19
<212> TYPE: RNA
<213> ORGANISM: Artificial Sequence
<220> FEATURE:
<223> OTHER INFORMATION: siRNA

<400> SEQUENCE: 76
aaccagaaga agcagguga                                                       19

<210> SEQ ID NO 77
<211> LENGTH: 19
<212> TYPE: RNA
<213> ORGANISM: Artificial Sequence
<220> FEATURE:
<223> OTHER INFORMATION: siRNA

<400> SEQUENCE: 77
aaccagaaga agcagguga                                                       19

<210> SEQ ID NO 78
<211> LENGTH: 19
<212> TYPE: RNA
<213> ORGANISM: Artificial Sequence
<220> FEATURE:
<223> OTHER INFORMATION: siRNA

<400> SEQUENCE: 78
```
aaccagaaga agcagguga                                                                    19

<210> SEQ ID NO 79
<211> LENGTH: 19
<212> TYPE: RNA
<213> ORGANISM: Artificial Sequence
<220> FEATURE:
<223> OTHER INFORMATION: siRNA

<400> SEQUENCE: 79
aaccagaaga agcagguga                                                                    19

<210> SEQ ID NO 80
<211> LENGTH: 19
<212> TYPE: RNA
<213> ORGANISM: Artificial Sequence
<220> FEATURE:
<223> OTHER INFORMATION: siRNA

<400> SEQUENCE: 80
aaccagaaga agcagguga                                                                    19

<210> SEQ ID NO 81
<211> LENGTH: 19
<212> TYPE: RNA
<213> ORGANISM: Artificial Sequence
<220> FEATURE:
<223> OTHER INFORMATION: siRNA

<400> SEQUENCE: 81
aaccagaaga agcagguga                                                                    19

<210> SEQ ID NO 82
<211> LENGTH: 19
<212> TYPE: RNA
<213> ORGANISM: Artificial Sequence
<220> FEATURE:
<223> OTHER INFORMATION: siRNA

<400> SEQUENCE: 82
aaccagaaga agcagguga                                                                    19

<210> SEQ ID NO 83
<211> LENGTH: 19
<212> TYPE: RNA
<213> ORGANISM: Artificial Sequence
<220> FEATURE:
<223> OTHER INFORMATION: siRNA

<400> SEQUENCE: 83
aaccagaaga agcagguga                                                                    19

<210> SEQ ID NO 84
<211> LENGTH: 19
<212> TYPE: RNA
<213> ORGANISM: Artificial Sequence
<220> FEATURE:
<223> OTHER INFORMATION: siRNA

<400> SEQUENCE: 84
ucaccugcuu cuucugguu                                                                    19

<210> SEQ ID NO 85
<211> LENGTH: 19
<212> TYPE: RNA
<213> ORGANISM: Artificial Sequence

```
<220> FEATURE:
<223> OTHER INFORMATION: siRNA

<400> SEQUENCE: 85
aaccagaaga agcagguga                                                   19

<210> SEQ ID NO 86
<211> LENGTH: 19
<212> TYPE: RNA
<213> ORGANISM: Artificial Sequence
<220> FEATURE:
<223> OTHER INFORMATION: siRNA

<400> SEQUENCE: 86
ucaccugcuu cuucugguu                                                   19

<210> SEQ ID NO 87
<211> LENGTH: 19
<212> TYPE: RNA
<213> ORGANISM: Artificial Sequence
<220> FEATURE:
<223> OTHER INFORMATION: siRNA

<400> SEQUENCE: 87
aaccagaaga agcagguga                                                   19

<210> SEQ ID NO 88
<211> LENGTH: 19
<212> TYPE: RNA
<213> ORGANISM: Artificial Sequence
<220> FEATURE:
<223> OTHER INFORMATION: siRNA

<400> SEQUENCE: 88
aaccagaaga agcagguga                                                   19

<210> SEQ ID NO 89
<211> LENGTH: 19
<212> TYPE: RNA
<213> ORGANISM: Artificial Sequence
<220> FEATURE:
<223> OTHER INFORMATION: siRNA

<400> SEQUENCE: 89
ucaccugcuu cuucugguu                                                   19

<210> SEQ ID NO 90
<211> LENGTH: 19
<212> TYPE: RNA
<213> ORGANISM: Artificial Sequence
<220> FEATURE:
<223> OTHER INFORMATION: siRNA

<400> SEQUENCE: 90
aaccagaaga agcagguga                                                   19

<210> SEQ ID NO 91
<211> LENGTH: 19
<212> TYPE: RNA
<213> ORGANISM: Artificial Sequence
<220> FEATURE:
<223> OTHER INFORMATION: siRNA

<400> SEQUENCE: 91
aaccagaaga agcagguga                                                   19
```

```
<210> SEQ ID NO 92
<211> LENGTH: 19
<212> TYPE: RNA
<213> ORGANISM: Artificial Sequence
<220> FEATURE:
<223> OTHER INFORMATION: siRNA

<400> SEQUENCE: 92
aaccagaaga agcagguga                                                       19

<210> SEQ ID NO 93
<211> LENGTH: 19
<212> TYPE: RNA
<213> ORGANISM: Artificial Sequence
<220> FEATURE:
<223> OTHER INFORMATION: siRNA

<400> SEQUENCE: 93
aaccagaaga agcagguga                                                       19

<210> SEQ ID NO 94
<211> LENGTH: 19
<212> TYPE: RNA
<213> ORGANISM: Artificial Sequence
<220> FEATURE:
<223> OTHER INFORMATION: siRNA

<400> SEQUENCE: 94
aaccagaaga agcagguga                                                       19

<210> SEQ ID NO 95
<211> LENGTH: 19
<212> TYPE: RNA
<213> ORGANISM: Artificial Sequence
<220> FEATURE:
<223> OTHER INFORMATION: siRNA

<400> SEQUENCE: 95
aaccagaaga agcagguga                                                       19

<210> SEQ ID NO 96
<211> LENGTH: 19
<212> TYPE: RNA
<213> ORGANISM: Artificial Sequence
<220> FEATURE:
<223> OTHER INFORMATION: siRNA

<400> SEQUENCE: 96
aaccagaaga agcagguga                                                       19

<210> SEQ ID NO 97
<211> LENGTH: 19
<212> TYPE: RNA
<213> ORGANISM: Artificial Sequence
<220> FEATURE:
<223> OTHER INFORMATION: siRNA

<400> SEQUENCE: 97
aaccagaaga agcagguga                                                       19

<210> SEQ ID NO 98
<211> LENGTH: 19
<212> TYPE: RNA
<213> ORGANISM: Artificial Sequence
<220> FEATURE:
<223> OTHER INFORMATION: siRNA
```

```
<400> SEQUENCE: 98
aaccagaaga agcagguga                                                19

<210> SEQ ID NO 99
<211> LENGTH: 19
<212> TYPE: RNA
<213> ORGANISM: Artificial Sequence
<220> FEATURE:
<223> OTHER INFORMATION: siRNA

<400> SEQUENCE: 99
aaccagaaga agcagguga                                                19

<210> SEQ ID NO 100
<211> LENGTH: 19
<212> TYPE: RNA
<213> ORGANISM: Artificial Sequence
<220> FEATURE:
<223> OTHER INFORMATION: siRNA

<400> SEQUENCE: 100
ucaccugcuu cuucugguu                                                19

<210> SEQ ID NO 101
<211> LENGTH: 19
<212> TYPE: RNA
<213> ORGANISM: Artificial Sequence
<220> FEATURE:
<223> OTHER INFORMATION: siRNA

<400> SEQUENCE: 101
ucaccugcuu cuucugguu                                                19

<210> SEQ ID NO 102
<211> LENGTH: 19
<212> TYPE: RNA
<213> ORGANISM: Artificial Sequence
<220> FEATURE:
<223> OTHER INFORMATION: siRNA

<400> SEQUENCE: 102
ucaccugcuu cuucugguu                                                19

<210> SEQ ID NO 103
<211> LENGTH: 19
<212> TYPE: RNA
<213> ORGANISM: Artificial Sequence
<220> FEATURE:
<223> OTHER INFORMATION: siRNA

<400> SEQUENCE: 103
ucaccugcuu cuucugguu                                                19

<210> SEQ ID NO 104
<211> LENGTH: 19
<212> TYPE: RNA
<213> ORGANISM: Artificial Sequence
<220> FEATURE:
<223> OTHER INFORMATION: siRNA

<400> SEQUENCE: 104
ucaccugcuu cuucugguu                                                19

<210> SEQ ID NO 105
```

```
<211> LENGTH: 19
<212> TYPE: RNA
<213> ORGANISM: Artificial Sequence
<220> FEATURE:
<223> OTHER INFORMATION: siRNA

<400> SEQUENCE: 105
ucaccugcuu cuucugguu                                                    19

<210> SEQ ID NO 106
<211> LENGTH: 19
<212> TYPE: RNA
<213> ORGANISM: Artificial Sequence
<220> FEATURE:
<223> OTHER INFORMATION: siRNA

<400> SEQUENCE: 106
ucaccugcuu cuucugguu                                                    19

<210> SEQ ID NO 107
<211> LENGTH: 21
<212> TYPE: RNA
<213> ORGANISM: Artificial Sequence
<220> FEATURE:
<223> OTHER INFORMATION: siRNA

<400> SEQUENCE: 107
ucuugguuac augaaauccc a                                                 21

<210> SEQ ID NO 108
<211> LENGTH: 21
<212> TYPE: RNA
<213> ORGANISM: Artificial Sequence
<220> FEATURE:
<223> OTHER INFORMATION: siRNA

<400> SEQUENCE: 108
ugggauuuca uguaaccaag a                                                 21

<210> SEQ ID NO 109
<211> LENGTH: 19
<212> TYPE: RNA
<213> ORGANISM: Artificial Sequence
<220> FEATURE:
<223> OTHER INFORMATION: siRNA

<400> SEQUENCE: 109
ucgaaguauu ccgcguacg                                                    19

<210> SEQ ID NO 110
<211> LENGTH: 19
<212> TYPE: RNA
<213> ORGANISM: Artificial Sequence
<220> FEATURE:
<223> OTHER INFORMATION: siRNA

<400> SEQUENCE: 110
cguacgcgga auacuucga                                                    19

<210> SEQ ID NO 111
<211> LENGTH: 19
<212> TYPE: RNA
<213> ORGANISM: Artificial Sequence
<220> FEATURE:
<223> OTHER INFORMATION: siRNA

<400> SEQUENCE: 111
```

```
aaccagaaga agcagguga                                                19

<210> SEQ ID NO 112
<211> LENGTH: 19
<212> TYPE: RNA
<213> ORGANISM: Artificial Sequence
<220> FEATURE:
<223> OTHER INFORMATION: siRNA

<400> SEQUENCE: 112
ucaccugcuu cuucugguu                                                19

<210> SEQ ID NO 113
<211> LENGTH: 19
<212> TYPE: RNA
<213> ORGANISM: Artificial Sequence
<220> FEATURE:
<223> OTHER INFORMATION: siRNA

<400> SEQUENCE: 113
aaccagaaga agcagguga                                                19

<210> SEQ ID NO 114
<211> LENGTH: 19
<212> TYPE: RNA
<213> ORGANISM: Artificial Sequence
<220> FEATURE:
<223> OTHER INFORMATION: siRNA

<400> SEQUENCE: 114
ucaccugcuu cuucugguu                                                19

<210> SEQ ID NO 115
<211> LENGTH: 19
<212> TYPE: RNA
<213> ORGANISM: Artificial Sequence
<220> FEATURE:
<223> OTHER INFORMATION: siRNA

<400> SEQUENCE: 115
aaccagaaga agcagguga                                                19

<210> SEQ ID NO 116
<211> LENGTH: 19
<212> TYPE: RNA
<213> ORGANISM: Artificial Sequence
<220> FEATURE:
<223> OTHER INFORMATION: siRNA

<400> SEQUENCE: 116
ucaccugcuu cuucugguu                                                19

<210> SEQ ID NO 117
<211> LENGTH: 19
<212> TYPE: RNA
<213> ORGANISM: Artificial Sequence
<220> FEATURE:
<223> OTHER INFORMATION: siRNA

<400> SEQUENCE: 117
aaccagaaga agcagguga                                                19

<210> SEQ ID NO 118
<211> LENGTH: 19
<212> TYPE: DNA
```

<213> ORGANISM: Artificial Sequence
<220> FEATURE:
<223> OTHER INFORMATION: siRNA

<400> SEQUENCE: 118
ucaccugcuu cuucuggut                                              19

<210> SEQ ID NO 119
<211> LENGTH: 19
<212> TYPE: RNA
<213> ORGANISM: Artificial Sequence
<220> FEATURE:
<223> OTHER INFORMATION: siRNA

<400> SEQUENCE: 119
aaccagaaga agcagguga                                              19

<210> SEQ ID NO 120
<211> LENGTH: 19
<212> TYPE: RNA
<213> ORGANISM: Artificial Sequence
<220> FEATURE:
<223> OTHER INFORMATION: siRNA

<400> SEQUENCE: 120
ucaccugcuu cuucugguu                                              19

<210> SEQ ID NO 121
<211> LENGTH: 19
<212> TYPE: RNA
<213> ORGANISM: Artificial Sequence
<220> FEATURE:
<223> OTHER INFORMATION: siRNA

<400> SEQUENCE: 121
aaccagaaga agcagguga                                              19

<210> SEQ ID NO 122
<211> LENGTH: 19
<212> TYPE: RNA
<213> ORGANISM: Artificial Sequence
<220> FEATURE:
<223> OTHER INFORMATION: siRNA

<400> SEQUENCE: 122
ucaccugcuu cuucugguu                                              19

<210> SEQ ID NO 123
<211> LENGTH: 21
<212> TYPE: RNA
<213> ORGANISM: Artificial Sequence
<220> FEATURE:
<223> OTHER INFORMATION: siRNA

<400> SEQUENCE: 123
aaccagaaga agcaggugac c                                           21

<210> SEQ ID NO 124
<211> LENGTH: 19
<212> TYPE: RNA
<213> ORGANISM: Artificial Sequence
<220> FEATURE:
<223> OTHER INFORMATION: siRNA

<400> SEQUENCE: 124
ucaccugcuu cuucugguu                                              19

```
<210> SEQ ID NO 125
<211> LENGTH: 19
<212> TYPE: RNA
<213> ORGANISM: Artificial Sequence
<220> FEATURE:
<223> OTHER INFORMATION: siRNA

<400> SEQUENCE: 125
aaccagaaga agcagguga                                                19

<210> SEQ ID NO 126
<211> LENGTH: 19
<212> TYPE: RNA
<213> ORGANISM: Artificial Sequence
<220> FEATURE:
<223> OTHER INFORMATION: siRNA

<400> SEQUENCE: 126
ucaccugcuu cuucugguu                                                19

<210> SEQ ID NO 127
<211> LENGTH: 19
<212> TYPE: RNA
<213> ORGANISM: Artificial Sequence
<220> FEATURE:
<223> OTHER INFORMATION: siRNA

<400> SEQUENCE: 127
aaccagaaga agcagguga                                                19

<210> SEQ ID NO 128
<211> LENGTH: 19
<212> TYPE: RNA
<213> ORGANISM: Artificial Sequence
<220> FEATURE:
<223> OTHER INFORMATION: siRNA

<400> SEQUENCE: 128
ucaccugcuu cuucugguu                                                19

<210> SEQ ID NO 129
<211> LENGTH: 19
<212> TYPE: RNA
<213> ORGANISM: Artificial Sequence
<220> FEATURE:
<223> OTHER INFORMATION: siRNA

<400> SEQUENCE: 129
aaccagaaga agcagguga                                                19

<210> SEQ ID NO 130
<211> LENGTH: 19
<212> TYPE: RNA
<213> ORGANISM: Artificial Sequence
<220> FEATURE:
<223> OTHER INFORMATION: siRNA

<400> SEQUENCE: 130
ucaccugcuu cuucugguu                                                19

<210> SEQ ID NO 131
<211> LENGTH: 19
<212> TYPE: RNA
<213> ORGANISM: Artificial Sequence
<220> FEATURE:
```

```
<223> OTHER INFORMATION: siRNA

<400> SEQUENCE: 131
uuaguaaacc uuuugagac                                                    19

<210> SEQ ID NO 132
<211> LENGTH: 19
<212> TYPE: RNA
<213> ORGANISM: Artificial Sequence
<220> FEATURE:
<223> OTHER INFORMATION: siRNA

<400> SEQUENCE: 132
gucucaaaag guuuacuaa                                                    19

<210> SEQ ID NO 133
<211> LENGTH: 19
<212> TYPE: RNA
<213> ORGANISM: Artificial Sequence
<220> FEATURE:
<223> OTHER INFORMATION: siRNA

<400> SEQUENCE: 133
cugaggacgc ccugggagu                                                    19

<210> SEQ ID NO 134
<211> LENGTH: 19
<212> TYPE: RNA
<213> ORGANISM: Artificial Sequence
<220> FEATURE:
<223> OTHER INFORMATION: siRNA

<400> SEQUENCE: 134
acucccaggg cguccucag                                                    19

<210> SEQ ID NO 135
<211> LENGTH: 19
<212> TYPE: RNA
<213> ORGANISM: Artificial Sequence
<220> FEATURE:
<223> OTHER INFORMATION: siRNA

<400> SEQUENCE: 135
gcugaggacg cccugggag                                                    19

<210> SEQ ID NO 136
<211> LENGTH: 19
<212> TYPE: RNA
<213> ORGANISM: Artificial Sequence
<220> FEATURE:
<223> OTHER INFORMATION: siRNA

<400> SEQUENCE: 136
cucccagggc guccucagc                                                    19

<210> SEQ ID NO 137
<211> LENGTH: 19
<212> TYPE: RNA
<213> ORGANISM: Artificial Sequence
<220> FEATURE:
<223> OTHER INFORMATION: siRNA

<400> SEQUENCE: 137
ugcugaggac gcccuggga                                                    19
```

```
<210> SEQ ID NO 138
<211> LENGTH: 19
<212> TYPE: RNA
<213> ORGANISM: Artificial Sequence
<220> FEATURE:
<223> OTHER INFORMATION: siRNA

<400> SEQUENCE: 138
ucccagggcg uccucagca                                                        19

<210> SEQ ID NO 139
<211> LENGTH: 19
<212> TYPE: RNA
<213> ORGANISM: Artificial Sequence
<220> FEATURE:
<223> OTHER INFORMATION: siRNA

<400> SEQUENCE: 139
gugcugagga cgcccuggg                                                        19

<210> SEQ ID NO 140
<211> LENGTH: 19
<212> TYPE: RNA
<213> ORGANISM: Artificial Sequence
<220> FEATURE:
<223> OTHER INFORMATION: siRNA

<400> SEQUENCE: 140
cccagggcgu ccucagcac                                                        19

<210> SEQ ID NO 141
<211> LENGTH: 19
<212> TYPE: RNA
<213> ORGANISM: Artificial Sequence
<220> FEATURE:
<223> OTHER INFORMATION: siRNA

<400> SEQUENCE: 141
ggugcugagg acgcccugg                                                        19

<210> SEQ ID NO 142
<211> LENGTH: 19
<212> TYPE: RNA
<213> ORGANISM: Artificial Sequence
<220> FEATURE:
<223> OTHER INFORMATION: siRNA

<400> SEQUENCE: 142
ccagggcguc cucagcacc                                                        19

<210> SEQ ID NO 143
<211> LENGTH: 19
<212> TYPE: RNA
<213> ORGANISM: Artificial Sequence
<220> FEATURE:
<223> OTHER INFORMATION: siRNA

<400> SEQUENCE: 143
gggugcugag gacgcccug                                                        19

<210> SEQ ID NO 144
<211> LENGTH: 19
<212> TYPE: RNA
<213> ORGANISM: Artificial Sequence
<220> FEATURE:
<223> OTHER INFORMATION: siRNA
```

```
<400> SEQUENCE: 144
cagggcgucc ucagcaccc                                              19

<210> SEQ ID NO 145
<211> LENGTH: 19
<212> TYPE: RNA
<213> ORGANISM: Artificial Sequence
<220> FEATURE:
<223> OTHER INFORMATION: siRNA

<400> SEQUENCE: 145
cggggugcug aggacgccc                                              19

<210> SEQ ID NO 146
<211> LENGTH: 19
<212> TYPE: RNA
<213> ORGANISM: Artificial Sequence
<220> FEATURE:
<223> OTHER INFORMATION: siRNA

<400> SEQUENCE: 146
gggcguccuc agcaccccg                                              19

<210> SEQ ID NO 147
<211> LENGTH: 19
<212> TYPE: RNA
<213> ORGANISM: Artificial Sequence
<220> FEATURE:
<223> OTHER INFORMATION: siRNA

<400> SEQUENCE: 147
acggggugcu gaggacgcc                                              19

<210> SEQ ID NO 148
<211> LENGTH: 19
<212> TYPE: RNA
<213> ORGANISM: Artificial Sequence
<220> FEATURE:
<223> OTHER INFORMATION: siRNA

<400> SEQUENCE: 148
ggcguccuca gcaccccgu                                              19

<210> SEQ ID NO 149
<211> LENGTH: 19
<212> TYPE: RNA
<213> ORGANISM: Artificial Sequence
<220> FEATURE:
<223> OTHER INFORMATION: siRNA

<400> SEQUENCE: 149
uacggggugc ugaggacgc                                              19

<210> SEQ ID NO 150
<211> LENGTH: 19
<212> TYPE: RNA
<213> ORGANISM: Artificial Sequence
<220> FEATURE:
<223> OTHER INFORMATION: siRNA

<400> SEQUENCE: 150
gcguccucag caccccgua                                              19

<210> SEQ ID NO 151
<211> LENGTH: 19
```

```
<212> TYPE: RNA
<213> ORGANISM: Artificial Sequence
<220> FEATURE:
<223> OTHER INFORMATION: siRNA

<400> SEQUENCE: 151
guacggggug cugaggacg                                            19

<210> SEQ ID NO 152
<211> LENGTH: 19
<212> TYPE: RNA
<213> ORGANISM: Artificial Sequence
<220> FEATURE:
<223> OTHER INFORMATION: siRNA

<400> SEQUENCE: 152
cguccucagc accccguac                                            19

<210> SEQ ID NO 153
<211> LENGTH: 19
<212> TYPE: RNA
<213> ORGANISM: Artificial Sequence
<220> FEATURE:
<223> OTHER INFORMATION: siRNA

<400> SEQUENCE: 153
aguacggggu gcugaggac                                            19

<210> SEQ ID NO 154
<211> LENGTH: 19
<212> TYPE: RNA
<213> ORGANISM: Artificial Sequence
<220> FEATURE:
<223> OTHER INFORMATION: siRNA

<400> SEQUENCE: 154
guccucagca ccccguacu                                            19

<210> SEQ ID NO 155
<211> LENGTH: 19
<212> TYPE: RNA
<213> ORGANISM: Artificial Sequence
<220> FEATURE:
<223> OTHER INFORMATION: siRNA

<400> SEQUENCE: 155
aaguacgggg ugcugagga                                            19

<210> SEQ ID NO 156
<211> LENGTH: 19
<212> TYPE: RNA
<213> ORGANISM: Artificial Sequence
<220> FEATURE:
<223> OTHER INFORMATION: siRNA

<400> SEQUENCE: 156
uccucagcac cccguacuu                                            19

<210> SEQ ID NO 157
<211> LENGTH: 19
<212> TYPE: RNA
<213> ORGANISM: Artificial Sequence
<220> FEATURE:
<223> OTHER INFORMATION: siRNA

<400> SEQUENCE: 157
```
ggaaguacgg ggugcugag                                                    19

<210> SEQ ID NO 158
<211> LENGTH: 19
<212> TYPE: RNA
<213> ORGANISM: Artificial Sequence
<220> FEATURE:
<223> OTHER INFORMATION: siRNA

<400> SEQUENCE: 158
cucagcaccc cguacuucc                                                    19

<210> SEQ ID NO 159
<211> LENGTH: 19
<212> TYPE: RNA
<213> ORGANISM: Artificial Sequence
<220> FEATURE:
<223> OTHER INFORMATION: siRNA

<400> SEQUENCE: 159
gggaaguacg gggugcuga                                                    19

<210> SEQ ID NO 160
<211> LENGTH: 19
<212> TYPE: RNA
<213> ORGANISM: Artificial Sequence
<220> FEATURE:
<223> OTHER INFORMATION: siRNA

<400> SEQUENCE: 160
ucagcacccc guacuuccc                                                    19

<210> SEQ ID NO 161
<211> LENGTH: 19
<212> TYPE: RNA
<213> ORGANISM: Artificial Sequence
<220> FEATURE:
<223> OTHER INFORMATION: siRNA

<400> SEQUENCE: 161
ggggaaguac ggggugcug                                                    19

<210> SEQ ID NO 162
<211> LENGTH: 19
<212> TYPE: RNA
<213> ORGANISM: Artificial Sequence
<220> FEATURE:
<223> OTHER INFORMATION: siRNA

<400> SEQUENCE: 162
cagcaccccg uacuucccc                                                    19

<210> SEQ ID NO 163
<211> LENGTH: 19
<212> TYPE: RNA
<213> ORGANISM: Artificial Sequence
<220> FEATURE:
<223> OTHER INFORMATION: siRNA

<400> SEQUENCE: 163 ugggaagua cggggugcu                                                     19

<210> SEQ ID NO 164
<211> LENGTH: 19
<212> TYPE: RNA
<213> ORGANISM: Artificial Sequence

```
<220> FEATURE:
<223> OTHER INFORMATION: siRNA

<400> SEQUENCE: 164
agcaccccgu acuuccca                                                      19

<210> SEQ ID NO 165
<211> LENGTH: 19
<212> TYPE: RNA
<213> ORGANISM: Artificial Sequence
<220> FEATURE:
<223> OTHER INFORMATION: siRNA

<400> SEQUENCE: 165
cuggggaagu acggggugc                                                     19

<210> SEQ ID NO 166
<211> LENGTH: 19
<212> TYPE: RNA
<213> ORGANISM: Artificial Sequence
<220> FEATURE:
<223> OTHER INFORMATION: siRNA

<400> SEQUENCE: 166
gcaccccgua cuucccag                                                      19

<210> SEQ ID NO 167
<211> LENGTH: 19
<212> TYPE: RNA
<213> ORGANISM: Artificial Sequence
<220> FEATURE:
<223> OTHER INFORMATION: siRNA

<400> SEQUENCE: 167
agcuggggaa guacggggu                                                     19

<210> SEQ ID NO 168
<211> LENGTH: 19
<212> TYPE: RNA
<213> ORGANISM: Artificial Sequence
<220> FEATURE:
<223> OTHER INFORMATION: siRNA

<400> SEQUENCE: 168
accccguacu uccccagcu                                                     19

<210> SEQ ID NO 169
<211> LENGTH: 19
<212> TYPE: RNA
<213> ORGANISM: Artificial Sequence
<220> FEATURE:
<223> OTHER INFORMATION: siRNA

<400> SEQUENCE: 169
uagcugggga aguacgggg                                                     19

<210> SEQ ID NO 170
<211> LENGTH: 19
<212> TYPE: RNA
<213> ORGANISM: Artificial Sequence
<220> FEATURE:
<223> OTHER INFORMATION: siRNA

<400> SEQUENCE: 170
ccccguacuu ccccagcua                                                     19
```

```
<210> SEQ ID NO 171
<211> LENGTH: 19
<212> TYPE: RNA
<213> ORGANISM: Artificial Sequence
<220> FEATURE:
<223> OTHER INFORMATION: siRNA

<400> SEQUENCE: 171
guagcugggg aaguacggg                                                19

<210> SEQ ID NO 172
<211> LENGTH: 19
<212> TYPE: RNA
<213> ORGANISM: Artificial Sequence
<220> FEATURE:
<223> OTHER INFORMATION: siRNA

<400> SEQUENCE: 172
cccguacuuc cccagcuac                                                19

<210> SEQ ID NO 173
<211> LENGTH: 19
<212> TYPE: RNA
<213> ORGANISM: Artificial Sequence
<220> FEATURE:
<223> OTHER INFORMATION: siRNA

<400> SEQUENCE: 173
aguagcuggg gaaguacgg                                                19

<210> SEQ ID NO 174
<211> LENGTH: 19
<212> TYPE: RNA
<213> ORGANISM: Artificial Sequence
<220> FEATURE:
<223> OTHER INFORMATION: siRNA

<400> SEQUENCE: 174
ccguacuucc ccagcuacu                                                19

<210> SEQ ID NO 175
<211> LENGTH: 19
<212> TYPE: RNA
<213> ORGANISM: Artificial Sequence
<220> FEATURE:
<223> OTHER INFORMATION: siRNA

<400> SEQUENCE: 175
guaguagcug gggaaguac                                                19

<210> SEQ ID NO 176
<211> LENGTH: 19
<212> TYPE: RNA
<213> ORGANISM: Artificial Sequence
<220> FEATURE:
<223> OTHER INFORMATION: siRNA

<400> SEQUENCE: 176
guacuucccc agcuacuac                                                19

<210> SEQ ID NO 177
<211> LENGTH: 19
<212> TYPE: RNA
<213> ORGANISM: Artificial Sequence
<220> FEATURE:
<223> OTHER INFORMATION: siRNA
```

<400> SEQUENCE: 177
aguaguagcu ggggaagua                                                19

<210> SEQ ID NO 178
<211> LENGTH: 19
<212> TYPE: RNA
<213> ORGANISM: Artificial Sequence
<220> FEATURE:
<223> OTHER INFORMATION: siRNA

<400> SEQUENCE: 178
uacuucccca gcuacuacu                                                19

<210> SEQ ID NO 179
<211> LENGTH: 19
<212> TYPE: RNA
<213> ORGANISM: Artificial Sequence
<220> FEATURE:
<223> OTHER INFORMATION: siRNA

<400> SEQUENCE: 179
gaguaguagc ugggaagu                                                 19

<210> SEQ ID NO 180
<211> LENGTH: 19
<212> TYPE: RNA
<213> ORGANISM: Artificial Sequence
<220> FEATURE:
<223> OTHER INFORMATION: siRNA

<400> SEQUENCE: 180
acuuccccag cuacuacuc                                                19

<210> SEQ ID NO 181
<211> LENGTH: 19
<212> TYPE: RNA
<213> ORGANISM: Artificial Sequence
<220> FEATURE:
<223> OTHER INFORMATION: siRNA

<400> SEQUENCE: 181
cgaguaguag cugggaag                                                 19

<210> SEQ ID NO 182
<211> LENGTH: 19
<212> TYPE: RNA
<213> ORGANISM: Artificial Sequence
<220> FEATURE:
<223> OTHER INFORMATION: siRNA

<400> SEQUENCE: 182
cuuccccagc uacuacucg                                                19

<210> SEQ ID NO 183
<211> LENGTH: 19
<212> TYPE: RNA
<213> ORGANISM: Artificial Sequence
<220> FEATURE:
<223> OTHER INFORMATION: siRNA

<400> SEQUENCE: 183
gcgaguagua gcugggaa                                                 19

<210> SEQ ID NO 184

```
<211> LENGTH: 19
<212> TYPE: RNA
<213> ORGANISM: Artificial Sequence
<220> FEATURE:
<223> OTHER INFORMATION: siRNA

<400> SEQUENCE: 184
uuccccagcu acuacucgc                                                      19

<210> SEQ ID NO 185
<211> LENGTH: 19
<212> TYPE: RNA
<213> ORGANISM: Artificial Sequence
<220> FEATURE:
<223> OTHER INFORMATION: siRNA

<400> SEQUENCE: 185
ggcgaguagu agcugggga                                                      19

<210> SEQ ID NO 186
<211> LENGTH: 19
<212> TYPE: RNA
<213> ORGANISM: Artificial Sequence
<220> FEATURE:
<223> OTHER INFORMATION: siRNA

<400> SEQUENCE: 186
uccccagcua cuacucgcc                                                      19

<210> SEQ ID NO 187
<211> LENGTH: 19
<212> TYPE: RNA
<213> ORGANISM: Artificial Sequence
<220> FEATURE:
<223> OTHER INFORMATION: siRNA

<400> SEQUENCE: 187
gggcgaguag uagcugggg                                                      19

<210> SEQ ID NO 188
<211> LENGTH: 19
<212> TYPE: RNA
<213> ORGANISM: Artificial Sequence
<220> FEATURE:
<223> OTHER INFORMATION: siRNA

<400> SEQUENCE: 188
ccccagcuac uacucgccc                                                      19

<210> SEQ ID NO 189
<211> LENGTH: 19
<212> TYPE: RNA
<213> ORGANISM: Artificial Sequence
<220> FEATURE:
<223> OTHER INFORMATION: siRNA

<400> SEQUENCE: 189
ggggcgagua guagcuggg                                                      19

<210> SEQ ID NO 190
<211> LENGTH: 19
<212> TYPE: RNA
<213> ORGANISM: Artificial Sequence
<220> FEATURE:
<223> OTHER INFORMATION: siRNA

<400> SEQUENCE: 190
```
cccagcuacu acucgcccc                                              19

<210> SEQ ID NO 191
<211> LENGTH: 19
<212> TYPE: RNA
<213> ORGANISM: Artificial Sequence
<220> FEATURE:
<223> OTHER INFORMATION: siRNA

<400> SEQUENCE: 191 ugggcgagu aguagcugg                                               19

<210> SEQ ID NO 192
<211> LENGTH: 19
<212> TYPE: RNA
<213> ORGANISM: Artificial Sequence
<220> FEATURE:
<223> OTHER INFORMATION: siRNA

<400> SEQUENCE: 192
ccagcuacua cucgcccca                                              19

<210> SEQ ID NO 193
<211> LENGTH: 19
<212> TYPE: RNA
<213> ORGANISM: Artificial Sequence
<220> FEATURE:
<223> OTHER INFORMATION: siRNA

<400> SEQUENCE: 193
uuggggcgag uaguagcug                                              19

<210> SEQ ID NO 194
<211> LENGTH: 19
<212> TYPE: RNA
<213> ORGANISM: Artificial Sequence
<220> FEATURE:
<223> OTHER INFORMATION: siRNA

<400> SEQUENCE: 194
cagcuacuac ucgccccaa                                              19

<210> SEQ ID NO 195
<211> LENGTH: 19
<212> TYPE: RNA
<213> ORGANISM: Artificial Sequence
<220> FEATURE:
<223> OTHER INFORMATION: siRNA

<400> SEQUENCE: 195
uauuccaaag ggcagcuga                                              19

<210> SEQ ID NO 196
<211> LENGTH: 19
<212> TYPE: RNA
<213> ORGANISM: Artificial Sequence
<220> FEATURE:
<223> OTHER INFORMATION: siRNA

<400> SEQUENCE: 196
ucagcugccc uuuggaaua                                              19

<210> SEQ ID NO 197
<211> LENGTH: 19
<212> TYPE: RNA

```
<213> ORGANISM: Artificial Sequence
<220> FEATURE:
<223> OTHER INFORMATION: siRNA

<400> SEQUENCE: 197
aucuucuggg cuuuggcgg                                                    19

<210> SEQ ID NO 198
<211> LENGTH: 19
<212> TYPE: RNA
<213> ORGANISM: Artificial Sequence
<220> FEATURE:
<223> OTHER INFORMATION: siRNA

<400> SEQUENCE: 198
ccgccaaagc ccagaagau                                                    19

<210> SEQ ID NO 199
<211> LENGTH: 19
<212> TYPE: RNA
<213> ORGANISM: Artificial Sequence
<220> FEATURE:
<223> OTHER INFORMATION: siRNA

<400> SEQUENCE: 199
uuuucucuug gaguccuca                                                    19

<210> SEQ ID NO 200
<211> LENGTH: 19
<212> TYPE: RNA
<213> ORGANISM: Artificial Sequence
<220> FEATURE:
<223> OTHER INFORMATION: siRNA

<400> SEQUENCE: 200
ugaggacucc aagagaaaa                                                    19

<210> SEQ ID NO 201
<211> LENGTH: 19
<212> TYPE: RNA
<213> ORGANISM: Artificial Sequence
<220> FEATURE:
<223> OTHER INFORMATION: siRNA

<400> SEQUENCE: 201
gaauagacgg agcuggagu                                                    19

<210> SEQ ID NO 202
<211> LENGTH: 19
<212> TYPE: RNA
<213> ORGANISM: Artificial Sequence
<220> FEATURE:
<223> OTHER INFORMATION: siRNA

<400> SEQUENCE: 202
acuccagcuc cgucuauuc                                                    19

<210> SEQ ID NO 203
<211> LENGTH: 19
<212> TYPE: RNA
<213> ORGANISM: Artificial Sequence
<220> FEATURE:
<223> OTHER INFORMATION: siRNA

<400> SEQUENCE: 203
uaguagcugg ggaaguacg                                                    19
```

```
<210> SEQ ID NO 204
<211> LENGTH: 19
<212> TYPE: RNA
<213> ORGANISM: Artificial Sequence
<220> FEATURE:
<223> OTHER INFORMATION: siRNA

<400> SEQUENCE: 204
cguacuuccc cagcuacua                                                19

<210> SEQ ID NO 205
<211> LENGTH: 19
<212> TYPE: RNA
<213> ORGANISM: Artificial Sequence
<220> FEATURE:
<223> OTHER INFORMATION: siRNA

<400> SEQUENCE: 205
agauccuggg agaaguggc                                                19

<210> SEQ ID NO 206
<211> LENGTH: 19
<212> TYPE: RNA
<213> ORGANISM: Artificial Sequence
<220> FEATURE:
<223> OTHER INFORMATION: siRNA

<400> SEQUENCE: 206
gccacuucuc ccaggaucu                                                19

<210> SEQ ID NO 207
<211> LENGTH: 19
<212> TYPE: RNA
<213> ORGANISM: Artificial Sequence
<220> FEATURE:
<223> OTHER INFORMATION: siRNA

<400> SEQUENCE: 207 cguucugga ucguccacu                                                 19

<210> SEQ ID NO 208
<211> LENGTH: 19
<212> TYPE: RNA
<213> ORGANISM: Artificial Sequence
<220> FEATURE:
<223> OTHER INFORMATION: siRNA

<400> SEQUENCE: 208
aguggacgau ccagaacag                                                19

<210> SEQ ID NO 209
<211> LENGTH: 19
<212> TYPE: RNA
<213> ORGANISM: Artificial Sequence
<220> FEATURE:
<223> OTHER INFORMATION: siRNA

<400> SEQUENCE: 209
cucaccuuga aggacaccu                                                19

<210> SEQ ID NO 210
<211> LENGTH: 19
<212> TYPE: RNA
<213> ORGANISM: Artificial Sequence
<220> FEATURE:
```

<223> OTHER INFORMATION: siRNA

<400> SEQUENCE: 210 aguguccuu caaggugag                                                    19

<210> SEQ ID NO 211
<211> LENGTH: 19
<212> TYPE: RNA
<213> ORGANISM: Artificial Sequence
<220> FEATURE:
<223> OTHER INFORMATION: siRNA

<400> SEQUENCE: 211
aguuucucuc auccaggcc                                                   19

<210> SEQ ID NO 212
<211> LENGTH: 19
<212> TYPE: RNA
<213> ORGANISM: Artificial Sequence
<220> FEATURE:
<223> OTHER INFORMATION: siRNA

<400> SEQUENCE: 212
ggccuggaug agagaaacu                                                   19

<210> SEQ ID NO 213
<211> LENGTH: 19
<212> TYPE: RNA
<213> ORGANISM: Artificial Sequence
<220> FEATURE:
<223> OTHER INFORMATION: siRNA

<400> SEQUENCE: 213
guacccuagg aaauaccag                                                   19

<210> SEQ ID NO 214
<211> LENGTH: 19
<212> TYPE: RNA
<213> ORGANISM: Artificial Sequence
<220> FEATURE:
<223> OTHER INFORMATION: siRNA

<400> SEQUENCE: 214
cugguauuuc cuaggguac                                                   19

<210> SEQ ID NO 215
<211> LENGTH: 19
<212> TYPE: RNA
<213> ORGANISM: Artificial Sequence
<220> FEATURE:
<223> OTHER INFORMATION: siRNA

<400> SEQUENCE: 215
cuguugacug uggacagca                                                   19

<210> SEQ ID NO 216
<211> LENGTH: 19
<212> TYPE: RNA
<213> ORGANISM: Artificial Sequence
<220> FEATURE:
<223> OTHER INFORMATION: siRNA

<400> SEQUENCE: 216
ugcuguccac agucaacag                                                   19

```
<210> SEQ ID NO 217
<211> LENGTH: 19
<212> TYPE: RNA
<213> ORGANISM: Artificial Sequence
<220> FEATURE:
<223> OTHER INFORMATION: siRNA

<400> SEQUENCE: 217
aaccagaaga agcagguga                                                   19

<210> SEQ ID NO 218
<211> LENGTH: 19
<212> TYPE: RNA
<213> ORGANISM: Artificial Sequence
<220> FEATURE:
<223> OTHER INFORMATION: siRNA

<400> SEQUENCE: 218
ucaccugcuu cuucugguu                                                   19

<210> SEQ ID NO 219
<211> LENGTH: 19
<212> TYPE: RNA
<213> ORGANISM: Artificial Sequence
<220> FEATURE:
<223> OTHER INFORMATION: siRNA

<400> SEQUENCE: 219
aaccagaaga agcagguga                                                   19

<210> SEQ ID NO 220
<211> LENGTH: 19
<212> TYPE: RNA
<213> ORGANISM: Artificial Sequence
<220> FEATURE:
<223> OTHER INFORMATION: siRNA

<400> SEQUENCE: 220
ucaccugcuu cuucugguu                                                   19

<210> SEQ ID NO 221
<211> LENGTH: 19
<212> TYPE: RNA
<213> ORGANISM: Artificial Sequence
<220> FEATURE:
<223> OTHER INFORMATION: siRNA

<400> SEQUENCE: 221
aaccagaaga agcagguga                                                   19

<210> SEQ ID NO 222
<211> LENGTH: 19
<212> TYPE: RNA
<213> ORGANISM: Artificial Sequence
<220> FEATURE:
<223> OTHER INFORMATION: siRNA

<400> SEQUENCE: 222
ucaccugcuu cuucugguu                                                   19

<210> SEQ ID NO 223
<211> LENGTH: 19
<212> TYPE: RNA
<213> ORGANISM: Artificial Sequence
<220> FEATURE:
<223> OTHER INFORMATION: siRNA
```

```
<400> SEQUENCE: 223
ucgaaguauu ccgcguacg                                              19

<210> SEQ ID NO 224
<211> LENGTH: 19
<212> TYPE: RNA
<213> ORGANISM: Artificial Sequence
<220> FEATURE:
<223> OTHER INFORMATION: siRNA

<400> SEQUENCE: 224
cguacgcgga auacuucga                                              19

<210> SEQ ID NO 225
<211> LENGTH: 19
<212> TYPE: RNA
<213> ORGANISM: Artificial Sequence
<220> FEATURE:
<223> OTHER INFORMATION: siRNA

<400> SEQUENCE: 225
aaccagaaga agcagguga                                              19

<210> SEQ ID NO 226
<211> LENGTH: 19
<212> TYPE: RNA
<213> ORGANISM: Artificial Sequence
<220> FEATURE:
<223> OTHER INFORMATION: siRNA

<400> SEQUENCE: 226
ucaccugcuu cuucugguu                                              19

<210> SEQ ID NO 227
<211> LENGTH: 19
<212> TYPE: RNA
<213> ORGANISM: Artificial Sequence
<220> FEATURE:
<223> OTHER INFORMATION: siRNA

<400> SEQUENCE: 227
aaccagaaga agcagguga                                              19

<210> SEQ ID NO 228
<211> LENGTH: 19
<212> TYPE: RNA
<213> ORGANISM: Artificial Sequence
<220> FEATURE:
<223> OTHER INFORMATION: siRNA

<400> SEQUENCE: 228
ucaccugcuu cuucugguu                                              19

<210> SEQ ID NO 229
<211> LENGTH: 19
<212> TYPE: RNA
<213> ORGANISM: Artificial Sequence
<220> FEATURE:
<223> OTHER INFORMATION: siRNA

<400> SEQUENCE: 229
aaccagaaga agcagguga                                              19

<210> SEQ ID NO 230
<211> LENGTH: 19
```

```
<212> TYPE: RNA
<213> ORGANISM: Artificial Sequence
<220> FEATURE:
<223> OTHER INFORMATION: siRNA

<400> SEQUENCE: 230
ucaccugcuu cuucugguu                                                    19

<210> SEQ ID NO 231
<211> LENGTH: 19
<212> TYPE: RNA
<213> ORGANISM: Artificial Sequence
<220> FEATURE:
<223> OTHER INFORMATION: siRNA

<400> SEQUENCE: 231
aaccagaaga agcagguga                                                    19

<210> SEQ ID NO 232
<211> LENGTH: 19
<212> TYPE: RNA
<213> ORGANISM: Artificial Sequence
<220> FEATURE:
<223> OTHER INFORMATION: siRNA

<400> SEQUENCE: 232
ucaccugcuu cuucugguu                                                    19

<210> SEQ ID NO 233
<211> LENGTH: 19
<212> TYPE: RNA
<213> ORGANISM: Artificial Sequence
<220> FEATURE:
<223> OTHER INFORMATION: siRNA

<400> SEQUENCE: 233
aaccagaaga agcagguga                                                    19

<210> SEQ ID NO 234
<211> LENGTH: 19
<212> TYPE: RNA
<213> ORGANISM: Artificial Sequence
<220> FEATURE:
<223> OTHER INFORMATION: siRNA

<400> SEQUENCE: 234
ucaccugcuu cuucugguu                                                    19

<210> SEQ ID NO 235
<211> LENGTH: 19
<212> TYPE: RNA
<213> ORGANISM: Artificial Sequence
<220> FEATURE:
<223> OTHER INFORMATION: siRNA

<400> SEQUENCE: 235
aaccagaaga agcagguga                                                    19

<210> SEQ ID NO 236
<211> LENGTH: 19
<212> TYPE: RNA
<213> ORGANISM: Artificial Sequence
<220> FEATURE:
<223> OTHER INFORMATION: siRNA

<400> SEQUENCE: 236
```
ucaccugcuu cuucugguu                                          19

<210> SEQ ID NO 237
<211> LENGTH: 19
<212> TYPE: RNA
<213> ORGANISM: Artificial Sequence
<220> FEATURE:
<223> OTHER INFORMATION: siRNA

<400> SEQUENCE: 237
aaccagaaga agcagguga                                          19

<210> SEQ ID NO 238
<211> LENGTH: 19
<212> TYPE: RNA
<213> ORGANISM: Artificial Sequence
<220> FEATURE:
<223> OTHER INFORMATION: siRNA

<400> SEQUENCE: 238
ucaccugcuu cuucugguu                                          19

<210> SEQ ID NO 239
<211> LENGTH: 19
<212> TYPE: RNA
<213> ORGANISM: Artificial Sequence
<220> FEATURE:
<223> OTHER INFORMATION: siRNA

<400> SEQUENCE: 239
aaccagaaga agcagguga                                          19

<210> SEQ ID NO 240
<211> LENGTH: 19
<212> TYPE: RNA
<213> ORGANISM: Artificial Sequence
<220> FEATURE:
<223> OTHER INFORMATION: siRNA

<400> SEQUENCE: 240
ucaccugcuu cuucugguu                                          19

<210> SEQ ID NO 241
<211> LENGTH: 19
<212> TYPE: RNA
<213> ORGANISM: Artificial Sequence
<220> FEATURE:
<223> OTHER INFORMATION: siRNA

<400> SEQUENCE: 241
aaccagaaga agcagguga                                          19

<210> SEQ ID NO 242
<211> LENGTH: 19
<212> TYPE: RNA
<213> ORGANISM: Artificial Sequence
<220> FEATURE:
<223> OTHER INFORMATION: siRNA

<400> SEQUENCE: 242
ucaccugcuu cuucugguu                                          19

<210> SEQ ID NO 243
<211> LENGTH: 19
<212> TYPE: RNA
<213> ORGANISM: Artificial Sequence

```
<220> FEATURE:
<223> OTHER INFORMATION: siRNA

<400> SEQUENCE: 243
aaccagaaga agcagguga                                              19

<210> SEQ ID NO 244
<211> LENGTH: 19
<212> TYPE: RNA
<213> ORGANISM: Artificial Sequence
<220> FEATURE:
<223> OTHER INFORMATION: siRNA

<400> SEQUENCE: 244
ucaccugcuu cuucugguu                                              19

<210> SEQ ID NO 245
<211> LENGTH: 19
<212> TYPE: RNA
<213> ORGANISM: Artificial Sequence
<220> FEATURE:
<223> OTHER INFORMATION: siRNA

<400> SEQUENCE: 245
aaccagaaga agcagguga                                              19

<210> SEQ ID NO 246
<211> LENGTH: 19
<212> TYPE: RNA
<213> ORGANISM: Artificial Sequence
<220> FEATURE:
<223> OTHER INFORMATION: siRNA

<400> SEQUENCE: 246
ucaccugcuu cuucugguu                                              19

<210> SEQ ID NO 247
<211> LENGTH: 19
<212> TYPE: RNA
<213> ORGANISM: Artificial Sequence
<220> FEATURE:
<223> OTHER INFORMATION: siRNA

<400> SEQUENCE: 247
aaccagaaga agcagguga                                              19

<210> SEQ ID NO 248
<211> LENGTH: 19
<212> TYPE: RNA
<213> ORGANISM: Artificial Sequence
<220> FEATURE:
<223> OTHER INFORMATION: siRNA

<400> SEQUENCE: 248
ucaccugcuu cuucugguu                                              19

<210> SEQ ID NO 249
<211> LENGTH: 19
<212> TYPE: RNA
<213> ORGANISM: Artificial Sequence
<220> FEATURE:
<223> OTHER INFORMATION: siRNA

<400> SEQUENCE: 249
aaccagaaga agcagguga                                              19
```

```
<210> SEQ ID NO 250
<211> LENGTH: 19
<212> TYPE: RNA
<213> ORGANISM: Artificial Sequence
<220> FEATURE:
<223> OTHER INFORMATION: siRNA

<400> SEQUENCE: 250
ucaccugcuu cuucugguu                                                       19

<210> SEQ ID NO 251
<211> LENGTH: 19
<212> TYPE: RNA
<213> ORGANISM: Artificial Sequence
<220> FEATURE:
<223> OTHER INFORMATION: siRNA

<400> SEQUENCE: 251
aaccagaaga agcagguga                                                       19

<210> SEQ ID NO 252
<211> LENGTH: 19
<212> TYPE: RNA
<213> ORGANISM: Artificial Sequence
<220> FEATURE:
<223> OTHER INFORMATION: siRNA

<400> SEQUENCE: 252
ucaccugcuu cuucugguu                                                       19

<210> SEQ ID NO 253
<211> LENGTH: 19
<212> TYPE: RNA
<213> ORGANISM: Artificial Sequence
<220> FEATURE:
<223> OTHER INFORMATION: siRNA

<400> SEQUENCE: 253
aaccagaaga agcagguga                                                       19

<210> SEQ ID NO 254
<211> LENGTH: 19
<212> TYPE: RNA
<213> ORGANISM: Artificial Sequence
<220> FEATURE:
<223> OTHER INFORMATION: siRNA

<400> SEQUENCE: 254
ucaccugcuu cuucugguu                                                       19

<210> SEQ ID NO 255
<211> LENGTH: 19
<212> TYPE: RNA
<213> ORGANISM: Artificial Sequence
<220> FEATURE:
<223> OTHER INFORMATION: siRNA

<400> SEQUENCE: 255
aaccagaaga agcagguga                                                       19

<210> SEQ ID NO 256
<211> LENGTH: 19
<212> TYPE: RNA
<213> ORGANISM: Artificial Sequence
<220> FEATURE:
<223> OTHER INFORMATION: siRNA
```

```
<400> SEQUENCE: 256
ucaccugcuu cuucugguu                                                    19

<210> SEQ ID NO 257
<211> LENGTH: 19
<212> TYPE: RNA
<213> ORGANISM: Artificial Sequence
<220> FEATURE:
<223> OTHER INFORMATION: siRNA

<400> SEQUENCE: 257
aaccagaaga agcagguga                                                    19

<210> SEQ ID NO 258
<211> LENGTH: 19
<212> TYPE: RNA
<213> ORGANISM: Artificial Sequence
<220> FEATURE:
<223> OTHER INFORMATION: siRNA

<400> SEQUENCE: 258
ucaccugcuu cuucugguu                                                    19

<210> SEQ ID NO 259
<211> LENGTH: 19
<212> TYPE: RNA
<213> ORGANISM: Artificial Sequence
<220> FEATURE:
<223> OTHER INFORMATION: siRNA

<400> SEQUENCE: 259
aaccagaaga agcagguga                                                    19

<210> SEQ ID NO 260
<211> LENGTH: 19
<212> TYPE: RNA
<213> ORGANISM: Artificial Sequence
<220> FEATURE:
<223> OTHER INFORMATION: siRNA

<400> SEQUENCE: 260
ucaccugcuu cuucugguu                                                    19

<210> SEQ ID NO 261
<211> LENGTH: 19
<212> TYPE: RNA
<213> ORGANISM: Artificial Sequence
<220> FEATURE:
<223> OTHER INFORMATION: siRNA

<400> SEQUENCE: 261
aaccagaaga agcagguga                                                    19

<210> SEQ ID NO 262
<211> LENGTH: 19
<212> TYPE: RNA
<213> ORGANISM: Artificial Sequence
<220> FEATURE:
<223> OTHER INFORMATION: siRNA

<400> SEQUENCE: 262
ucaccugcuu cuucugguu                                                    19

<210> SEQ ID NO 263
```

```
<211> LENGTH: 19
<212> TYPE: RNA
<213> ORGANISM: Artificial Sequence
<220> FEATURE:
<223> OTHER INFORMATION: siRNA

<400> SEQUENCE: 263
aaccagaaga agcagguga                                                  19

<210> SEQ ID NO 264
<211> LENGTH: 19
<212> TYPE: RNA
<213> ORGANISM: Artificial Sequence
<220> FEATURE:
<223> OTHER INFORMATION: siRNA

<400> SEQUENCE: 264
ucaccugcuu cuucugguu                                                  19

<210> SEQ ID NO 265
<211> LENGTH: 19
<212> TYPE: RNA
<213> ORGANISM: Artificial Sequence
<220> FEATURE:
<223> OTHER INFORMATION: siRNA

<400> SEQUENCE: 265
aaccagaaga agcagguga                                                  19

<210> SEQ ID NO 266
<211> LENGTH: 19
<212> TYPE: RNA
<213> ORGANISM: Artificial Sequence
<220> FEATURE:
<223> OTHER INFORMATION: siRNA

<400> SEQUENCE: 266
ucaccugcuu cuucugguu                                                  19

<210> SEQ ID NO 267
<211> LENGTH: 19
<212> TYPE: RNA
<213> ORGANISM: Artificial Sequence
<220> FEATURE:
<223> OTHER INFORMATION: siRNA

<400> SEQUENCE: 267
aaccagaaga agcagguga                                                  19

<210> SEQ ID NO 268
<211> LENGTH: 19
<212> TYPE: RNA
<213> ORGANISM: Artificial Sequence
<220> FEATURE:
<223> OTHER INFORMATION: siRNA

<400> SEQUENCE: 268
ucaccugcuu cuucugguu                                                  19

<210> SEQ ID NO 269
<211> LENGTH: 19
<212> TYPE: RNA
<213> ORGANISM: Artificial Sequence
<220> FEATURE:
<223> OTHER INFORMATION: siRNA

<400> SEQUENCE: 269
```

```
aaccagaaga agcagguga                                                    19

<210> SEQ ID NO 270
<211> LENGTH: 19
<212> TYPE: RNA
<213> ORGANISM: Artificial Sequence
<220> FEATURE:
<223> OTHER INFORMATION: siRNA

<400> SEQUENCE: 270
ucaccugcuu cuucugguu                                                    19

<210> SEQ ID NO 271
<211> LENGTH: 19
<212> TYPE: RNA
<213> ORGANISM: Artificial Sequence
<220> FEATURE:
<223> OTHER INFORMATION: siRNA

<400> SEQUENCE: 271
aaccagaaga agcagguga                                                    19

<210> SEQ ID NO 272
<211> LENGTH: 19
<212> TYPE: RNA
<213> ORGANISM: Artificial Sequence
<220> FEATURE:
<223> OTHER INFORMATION: siRNA

<400> SEQUENCE: 272
ucaccugcuu cuucugguu                                                    19

<210> SEQ ID NO 273
<211> LENGTH: 19
<212> TYPE: RNA
<213> ORGANISM: Artificial Sequence
<220> FEATURE:
<223> OTHER INFORMATION: siRNA

<400> SEQUENCE: 273
aaccagaaga agcagguga                                                    19

<210> SEQ ID NO 274
<211> LENGTH: 19
<212> TYPE: RNA
<213> ORGANISM: Artificial Sequence
<220> FEATURE:
<223> OTHER INFORMATION: siRNA

<400> SEQUENCE: 274
ucaccugcuu cuucugguu                                                    19

<210> SEQ ID NO 275
<211> LENGTH: 19
<212> TYPE: RNA
<213> ORGANISM: Artificial Sequence
<220> FEATURE:
<223> OTHER INFORMATION: siRNA

<400> SEQUENCE: 275
aaccagaaga agcagguga                                                    19

<210> SEQ ID NO 276
<211> LENGTH: 19
<212> TYPE: RNA
```

```
<213> ORGANISM: Artificial Sequence
<220> FEATURE:
<223> OTHER INFORMATION: siRNA

<400> SEQUENCE: 276
ucaccugcuu cuucugguu                                                        19

<210> SEQ ID NO 277
<211> LENGTH: 19
<212> TYPE: RNA
<213> ORGANISM: Artificial Sequence
<220> FEATURE:
<223> OTHER INFORMATION: siRNA

<400> SEQUENCE: 277
aaccagaaga agcagguga                                                        19

<210> SEQ ID NO 278
<211> LENGTH: 19
<212> TYPE: RNA
<213> ORGANISM: Artificial Sequence
<220> FEATURE:
<223> OTHER INFORMATION: siRNA

<400> SEQUENCE: 278
ucaccugcuu cuucugguu                                                        19

<210> SEQ ID NO 279
<211> LENGTH: 19
<212> TYPE: RNA
<213> ORGANISM: Artificial Sequence
<220> FEATURE:
<223> OTHER INFORMATION: siRNA

<400> SEQUENCE: 279
aaccagaaga agcagguga                                                        19

<210> SEQ ID NO 280
<211> LENGTH: 19
<212> TYPE: RNA
<213> ORGANISM: Artificial Sequence
<220> FEATURE:
<223> OTHER INFORMATION: siRNA

<400> SEQUENCE: 280
ucaccugcuu cuucugguu                                                        19

<210> SEQ ID NO 281
<211> LENGTH: 19
<212> TYPE: RNA
<213> ORGANISM: Artificial Sequence
<220> FEATURE:
<223> OTHER INFORMATION: siRNA

<400> SEQUENCE: 281
aaccagaaga agcagguga                                                        19

<210> SEQ ID NO 282
<211> LENGTH: 19
<212> TYPE: RNA
<213> ORGANISM: Artificial Sequence
<220> FEATURE:
<223> OTHER INFORMATION: siRNA

<400> SEQUENCE: 282
ucaccugcuu cuucugguu                                                        19
```

<210> SEQ ID NO 283
<211> LENGTH: 19
<212> TYPE: RNA
<213> ORGANISM: Artificial Sequence
<220> FEATURE:
<223> OTHER INFORMATION: siRNA

<400> SEQUENCE: 283
aaccagaaga agcagguga                                                  19

<210> SEQ ID NO 284
<211> LENGTH: 19
<212> TYPE: RNA
<213> ORGANISM: Artificial Sequence
<220> FEATURE:
<223> OTHER INFORMATION: siRNA

<400> SEQUENCE: 284
ucaccugcuu cuucugguu                                                  19

<210> SEQ ID NO 285
<211> LENGTH: 19
<212> TYPE: RNA
<213> ORGANISM: Artificial Sequence
<220> FEATURE:
<223> OTHER INFORMATION: siRNA

<400> SEQUENCE: 285
aaccagaaga agcagguga                                                  19

<210> SEQ ID NO 286
<211> LENGTH: 19
<212> TYPE: RNA
<213> ORGANISM: Artificial Sequence
<220> FEATURE:
<223> OTHER INFORMATION: siRNA

<400> SEQUENCE: 286
ucaccugcuu cuucugguu                                                  19

<210> SEQ ID NO 287
<211> LENGTH: 19
<212> TYPE: RNA
<213> ORGANISM: Artificial Sequence
<220> FEATURE:
<223> OTHER INFORMATION: siRNA

<400> SEQUENCE: 287
aaccagaaga agcagguga                                                  19

<210> SEQ ID NO 288
<211> LENGTH: 19
<212> TYPE: RNA
<213> ORGANISM: Artificial Sequence
<220> FEATURE:
<223> OTHER INFORMATION: siRNA

<400> SEQUENCE: 288
ucaccugcuu cuucugguu                                                  19

<210> SEQ ID NO 289
<211> LENGTH: 19
<212> TYPE: RNA
<213> ORGANISM: Artificial Sequence
<220> FEATURE:

<223> OTHER INFORMATION: siRNA

<400> SEQUENCE: 289
aaccagaaga agcaggug a                                                    19

<210> SEQ ID NO 290
<211> LENGTH: 19
<212> TYPE: RNA
<213> ORGANISM: Artificial Sequence
<220> FEATURE:
<223> OTHER INFORMATION: siRNA

<400> SEQUENCE: 290
ucaccugcuu cuucugguu                                                     19

<210> SEQ ID NO 291
<211> LENGTH: 19
<212> TYPE: RNA
<213> ORGANISM: Artificial Sequence
<220> FEATURE:
<223> OTHER INFORMATION: siRNA

<400> SEQUENCE: 291
aaccagaaga agcaggug a                                                    19

<210> SEQ ID NO 292
<211> LENGTH: 19
<212> TYPE: RNA
<213> ORGANISM: Artificial Sequence
<220> FEATURE:
<223> OTHER INFORMATION: siRNA

<400> SEQUENCE: 292
ucaccugcuu cuucugguu                                                     19

<210> SEQ ID NO 293
<211> LENGTH: 19
<212> TYPE: RNA
<213> ORGANISM: Artificial Sequence
<220> FEATURE:
<223> OTHER INFORMATION: siRNA

<400> SEQUENCE: 293
uaccagaaga agcaggug a                                                    19

<210> SEQ ID NO 294
<211> LENGTH: 19
<212> TYPE: RNA
<213> ORGANISM: Artificial Sequence
<220> FEATURE:
<223> OTHER INFORMATION: siRNA

<400> SEQUENCE: 294
ucaccugcuu cuucuggua                                                     19

<210> SEQ ID NO 295
<211> LENGTH: 19
<212> TYPE: RNA
<213> ORGANISM: Artificial Sequence
<220> FEATURE:
<223> OTHER INFORMATION: siRNA

<400> SEQUENCE: 295
uaccagaaga agcaggug a                                                    19

```
<210> SEQ ID NO 296
<211> LENGTH: 19
<212> TYPE: RNA
<213> ORGANISM: Artificial Sequence
<220> FEATURE:
<223> OTHER INFORMATION: siRNA

<400> SEQUENCE: 296
ucaccugcuu cuucuggua                                                    19

<210> SEQ ID NO 297
<211> LENGTH: 19
<212> TYPE: RNA
<213> ORGANISM: Artificial Sequence
<220> FEATURE:
<223> OTHER INFORMATION: siRNA

<400> SEQUENCE: 297
uaccagaaga agcagguga                                                    19

<210> SEQ ID NO 298
<211> LENGTH: 19
<212> TYPE: RNA
<213> ORGANISM: Artificial Sequence
<220> FEATURE:
<223> OTHER INFORMATION: siRNA

<400> SEQUENCE: 298
ucaccugcuu cuucuggua                                                    19

<210> SEQ ID NO 299
<211> LENGTH: 19
<212> TYPE: RNA
<213> ORGANISM: Artificial Sequence
<220> FEATURE:
<223> OTHER INFORMATION: siRNA

<400> SEQUENCE: 299
uaccagaaga agcagguga                                                    19

<210> SEQ ID NO 300
<211> LENGTH: 19
<212> TYPE: RNA
<213> ORGANISM: Artificial Sequence
<220> FEATURE:
<223> OTHER INFORMATION: siRNA

<400> SEQUENCE: 300
ucaccugcuu cuucuggua                                                    19

<210> SEQ ID NO 301
<211> LENGTH: 19
<212> TYPE: RNA
<213> ORGANISM: Artificial Sequence
<220> FEATURE:
<223> OTHER INFORMATION: siRNA

<400> SEQUENCE: 301
ucgaaguauu ccgcguacg                                                    19

<210> SEQ ID NO 302
<211> LENGTH: 19
<212> TYPE: RNA
<213> ORGANISM: Artificial Sequence
<220> FEATURE:
<223> OTHER INFORMATION: siRNA
```

```
<400> SEQUENCE: 302
cguacgcgga auacuucga                                           19

<210> SEQ ID NO 303
<211> LENGTH: 22
<212> TYPE: DNA
<213> ORGANISM: Artificial Sequence
<220> FEATURE:
<223> OTHER INFORMATION: PTEN-2-A

<400> SEQUENCE: 303
caccgccaaa tttaactgca ga                                       22

<210> SEQ ID NO 304
<211> LENGTH: 24
<212> TYPE: DNA
<213> ORGANISM: Artificial Sequence
<220> FEATURE:
<223> OTHER INFORMATION: PTEN-2-B

<400> SEQUENCE: 304
aagggtttga taagttctag ctgt                                     24

<210> SEQ ID NO 305
<211> LENGTH: 31
<212> TYPE: DNA
<213> ORGANISM: Artificial Sequence
<220> FEATURE:
<223> OTHER INFORMATION: PTEN-2-C

<400> SEQUENCE: 305
tgcacagtat cctttttgaag accataaccc a                            31

<210> SEQ ID NO 306
<211> LENGTH: 17
<212> TYPE: DNA
<213> ORGANISM: Artificial Sequence
<220> FEATURE:
<223> OTHER INFORMATION: hTMSS6:379U17

<400> SEQUENCE: 306
ccgccaaagc ccagaag                                             17

<210> SEQ ID NO 307
<211> LENGTH: 21
<212> TYPE: DNA
<213> ORGANISM: Artificial Sequence
<220> FEATURE:
<223> OTHER INFORMATION: hTMSS6:475L21

<400> SEQUENCE: 307
ggtccctccc caaaggaata g                                        21

<210> SEQ ID NO 308
<211> LENGTH: 28
<212> TYPE: DNA
<213> ORGANISM: Artificial Sequence
<220> FEATURE:
<223> OTHER INFORMATION: hTMSS6:416U28FL

<400> SEQUENCE: 308
cagcacccgc ctgggaactt actacaac                                 28

<210> SEQ ID NO 309
<211> LENGTH: 19
```

```
<212> TYPE: RNA
<213> ORGANISM: Artificial Sequence
<220> FEATURE:
<223> OTHER INFORMATION: siRNA

<400> SEQUENCE: 309
aaccagaaga agcagguga                                                        19

<210> SEQ ID NO 310
<211> LENGTH: 19
<212> TYPE: RNA
<213> ORGANISM: Artificial Sequence
<220> FEATURE:
<223> OTHER INFORMATION: siRNA

<400> SEQUENCE: 310
ucaccugcuu cuucugguu                                                        19

<210> SEQ ID NO 311
<211> LENGTH: 19
<212> TYPE: RNA
<213> ORGANISM: Artificial Sequence
<220> FEATURE:
<223> OTHER INFORMATION: siRNA

<400> SEQUENCE: 311
aaccagaaga agcagguga                                                        19

<210> SEQ ID NO 312
<211> LENGTH: 19
<212> TYPE: RNA
<213> ORGANISM: Artificial Sequence
<220> FEATURE:
<223> OTHER INFORMATION: siRNA

<400> SEQUENCE: 312
ucaccugcuu cuucugguu                                                        19

<210> SEQ ID NO 313
<211> LENGTH: 19
<212> TYPE: RNA
<213> ORGANISM: Artificial Sequence
<220> FEATURE:
<223> OTHER INFORMATION: siRNA

<400> SEQUENCE: 313
aaccagaaga agcagguga                                                        19

<210> SEQ ID NO 314
<211> LENGTH: 19
<212> TYPE: RNA
<213> ORGANISM: Artificial Sequence
<220> FEATURE:
<223> OTHER INFORMATION: siRNA

<400> SEQUENCE: 314
ucaccugcuu cuucugguu                                                        19

<210> SEQ ID NO 315
<211> LENGTH: 19
<212> TYPE: RNA
<213> ORGANISM: Artificial Sequence
<220> FEATURE:
<223> OTHER INFORMATION: siRNA

<400> SEQUENCE: 315
```
aaccagaaga agcagguga                                            19

<210> SEQ ID NO 316
<211> LENGTH: 19
<212> TYPE: RNA
<213> ORGANISM: Artificial Sequence
<220> FEATURE:
<223> OTHER INFORMATION: siRNA

<400> SEQUENCE: 316
ucaccugcuu cuucugguu                                            19

<210> SEQ ID NO 317
<211> LENGTH: 19
<212> TYPE: RNA
<213> ORGANISM: Artificial Sequence
<220> FEATURE:
<223> OTHER INFORMATION: siRNA

<400> SEQUENCE: 317
augucuuuca cacuggcuu                                            19

<210> SEQ ID NO 318
<211> LENGTH: 19
<212> TYPE: RNA
<213> ORGANISM: Artificial Sequence
<220> FEATURE:
<223> OTHER INFORMATION: siRNA

<400> SEQUENCE: 318
aagccagugu gaaagacau                                            19

<210> SEQ ID NO 319
<211> LENGTH: 19
<212> TYPE: RNA
<213> ORGANISM: Artificial Sequence
<220> FEATURE:
<223> OTHER INFORMATION: siRNA

<400> SEQUENCE: 319
auugaguaca cgcagacug                                            19

<210> SEQ ID NO 320
<211> LENGTH: 19
<212> TYPE: RNA
<213> ORGANISM: Artificial Sequence
<220> FEATURE:
<223> OTHER INFORMATION: siRNA

<400> SEQUENCE: 320
cagucugcgu guacucaau                                            19

<210> SEQ ID NO 321
<211> LENGTH: 19
<212> TYPE: RNA
<213> ORGANISM: Artificial Sequence
<220> FEATURE:
<223> OTHER INFORMATION: siRNA

<400> SEQUENCE: 321
aaguugaugg ugaucccgg                                            19

<210> SEQ ID NO 322
<211> LENGTH: 19
<212> TYPE: RNA
<213> ORGANISM: Artificial Sequence

```
<220> FEATURE:
<223> OTHER INFORMATION: siRNA

<400> SEQUENCE: 322
ccgggaucac caucaacuu                                                    19

<210> SEQ ID NO 323
<211> LENGTH: 19
<212> TYPE: RNA
<213> ORGANISM: Artificial Sequence
<220> FEATURE:
<223> OTHER INFORMATION: siRNA

<400> SEQUENCE: 323
uucuggaucg uccacuggc                                                    19

<210> SEQ ID NO 324
<211> LENGTH: 19
<212> TYPE: RNA
<213> ORGANISM: Artificial Sequence
<220> FEATURE:
<223> OTHER INFORMATION: siRNA

<400> SEQUENCE: 324
gccaguggac gauccagaa                                                    19

<210> SEQ ID NO 325
<211> LENGTH: 19
<212> TYPE: RNA
<213> ORGANISM: Artificial Sequence
<220> FEATURE:
<223> OTHER INFORMATION: siRNA

<400> SEQUENCE: 325
auucacagaa cagaggaac                                                    19

<210> SEQ ID NO 326
<211> LENGTH: 19
<212> TYPE: RNA
<213> ORGANISM: Artificial Sequence
<220> FEATURE:
<223> OTHER INFORMATION: siRNA

<400> SEQUENCE: 326
guuccucugu ucugugaau                                                    19

<210> SEQ ID NO 327
<211> LENGTH: 19
<212> TYPE: RNA
<213> ORGANISM: Artificial Sequence
<220> FEATURE:
<223> OTHER INFORMATION: siRNA

<400> SEQUENCE: 327
guagucaugg cuguccucu                                                    19

<210> SEQ ID NO 328
<211> LENGTH: 19
<212> TYPE: RNA
<213> ORGANISM: Artificial Sequence
<220> FEATURE:
<223> OTHER INFORMATION: siRNA

<400> SEQUENCE: 328
agaggacagc caugacuac                                                    19
```

<210> SEQ ID NO 329
<211> LENGTH: 19
<212> TYPE: RNA
<213> ORGANISM: Artificial Sequence
<220> FEATURE:
<223> OTHER INFORMATION: siRNA

<400> SEQUENCE: 329
aguuguagua aguucccag                                                  19

<210> SEQ ID NO 330
<211> LENGTH: 19
<212> TYPE: RNA
<213> ORGANISM: Artificial Sequence
<220> FEATURE:
<223> OTHER INFORMATION: siRNA

<400> SEQUENCE: 330
cugggaacuu acuacaacu                                                  19

<210> SEQ ID NO 331
<211> LENGTH: 19
<212> TYPE: RNA
<213> ORGANISM: Artificial Sequence
<220> FEATURE:
<223> OTHER INFORMATION: siRNA

<400> SEQUENCE: 331
uuguacccua ggaaauacc                                                  19

<210> SEQ ID NO 332
<211> LENGTH: 19
<212> TYPE: RNA
<213> ORGANISM: Artificial Sequence
<220> FEATURE:
<223> OTHER INFORMATION: siRNA

<400> SEQUENCE: 332
gguauuuccu aggguacaa                                                  19

<210> SEQ ID NO 333
<211> LENGTH: 19
<212> TYPE: RNA
<213> ORGANISM: Artificial Sequence
<220> FEATURE:
<223> OTHER INFORMATION: siRNA

<400> SEQUENCE: 333
aaccagaaga agcagguga                                                  19

<210> SEQ ID NO 334
<211> LENGTH: 19
<212> TYPE: RNA
<213> ORGANISM: Artificial Sequence
<220> FEATURE:
<223> OTHER INFORMATION: siRNA

<400> SEQUENCE: 334
ucaccugcuu cuucugguu                                                  19

<210> SEQ ID NO 335
<211> LENGTH: 19
<212> TYPE: RNA
<213> ORGANISM: Artificial Sequence
<220> FEATURE:
<223> OTHER INFORMATION: siRNA

```
<400> SEQUENCE: 335
uaacaaccca gcguggaau                                                        19

<210> SEQ ID NO 336
<211> LENGTH: 19
<212> TYPE: RNA
<213> ORGANISM: Artificial Sequence
<220> FEATURE:
<223> OTHER INFORMATION: siRNA

<400> SEQUENCE: 336
auuccacgcu ggguuguua                                                        19

<210> SEQ ID NO 337
<211> LENGTH: 19
<212> TYPE: RNA
<213> ORGANISM: Artificial Sequence
<220> FEATURE:
<223> OTHER INFORMATION: siRNA

<400> SEQUENCE: 337
guuucucuca uccaggccg                                                        19

<210> SEQ ID NO 338
<211> LENGTH: 19
<212> TYPE: RNA
<213> ORGANISM: Artificial Sequence
<220> FEATURE:
<223> OTHER INFORMATION: siRNA

<400> SEQUENCE: 338
cggccuggau gagagaaac                                                        19

<210> SEQ ID NO 339
<211> LENGTH: 19
<212> TYPE: RNA
<213> ORGANISM: Artificial Sequence
<220> FEATURE:
<223> OTHER INFORMATION: siRNA

<400> SEQUENCE: 339
gcaucuucug ggcuuuggc                                                        19

<210> SEQ ID NO 340
<211> LENGTH: 19
<212> TYPE: RNA
<213> ORGANISM: Artificial Sequence
<220> FEATURE:
<223> OTHER INFORMATION: siRNA

<400> SEQUENCE: 340
gccaaagccc agaagaugc                                                        19

<210> SEQ ID NO 341
<211> LENGTH: 19
<212> TYPE: RNA
<213> ORGANISM: Artificial Sequence
<220> FEATURE:
<223> OTHER INFORMATION: siRNA

<400> SEQUENCE: 341
ucacacugga aggugaaug                                                        19

<210> SEQ ID NO 342
```

```
<211> LENGTH: 19
<212> TYPE: RNA
<213> ORGANISM: Artificial Sequence
<220> FEATURE:
<223> OTHER INFORMATION: siRNA

<400> SEQUENCE: 342
cauucaccuu ccaguguga                                                        19

<210> SEQ ID NO 343
<211> LENGTH: 19
<212> TYPE: RNA
<213> ORGANISM: Artificial Sequence
<220> FEATURE:
<223> OTHER INFORMATION: siRNA

<400> SEQUENCE: 343
cacagaugug ucgaccccg                                                        19

<210> SEQ ID NO 344
<211> LENGTH: 19
<212> TYPE: RNA
<213> ORGANISM: Artificial Sequence
<220> FEATURE:
<223> OTHER INFORMATION: siRNA

<400> SEQUENCE: 344
cggggucgac acaucugug                                                        19

<210> SEQ ID NO 345
<211> LENGTH: 19
<212> TYPE: RNA
<213> ORGANISM: Artificial Sequence
<220> FEATURE:
<223> OTHER INFORMATION: siRNA

<400> SEQUENCE: 345
uguacccuag gaaauacca                                                        19

<210> SEQ ID NO 346
<211> LENGTH: 19
<212> TYPE: RNA
<213> ORGANISM: Artificial Sequence
<220> FEATURE:
<223> OTHER INFORMATION: siRNA

<400> SEQUENCE: 346
ugguauuucc uaggguaca                                                        19

<210> SEQ ID NO 347
<211> LENGTH: 19
<212> TYPE: RNA
<213> ORGANISM: Artificial Sequence
<220> FEATURE:
<223> OTHER INFORMATION: siRNA

<400> SEQUENCE: 347
ucgaaguauu ccgcguacg                                                        19

<210> SEQ ID NO 348
<211> LENGTH: 19
<212> TYPE: RNA
<213> ORGANISM: Artificial Sequence
<220> FEATURE:
<223> OTHER INFORMATION: siRNA

<400> SEQUENCE: 348
```
cguacgcgga auacuucga      19

<210> SEQ ID NO 349
<211> LENGTH: 19
<212> TYPE: RNA
<213> ORGANISM: Artificial Sequence
<220> FEATURE:
<223> OTHER INFORMATION: siRNA

<400> SEQUENCE: 349
uaaguucuag cuguggugg      19

<210> SEQ ID NO 350
<211> LENGTH: 19
<212> TYPE: RNA
<213> ORGANISM: Artificial Sequence
<220> FEATURE:
<223> OTHER INFORMATION: siRNA

<400> SEQUENCE: 350
ccaccacagc uagaacuua      19

<210> SEQ ID NO 351
<211> LENGTH: 21
<212> TYPE: RNA
<213> ORGANISM: Artificial Sequence
<220> FEATURE:
<223> OTHER INFORMATION: siRNA

<400> SEQUENCE: 351
ucuugguuac augaaauccc a      21

<210> SEQ ID NO 352
<211> LENGTH: 21
<212> TYPE: RNA
<213> ORGANISM: Artificial Sequence
<220> FEATURE:
<223> OTHER INFORMATION: siRNA

<400> SEQUENCE: 352
ugggauuuca uguaaccaag a      21

<210> SEQ ID NO 353
<211> LENGTH: 21
<212> TYPE: RNA
<213> ORGANISM: Artificial Sequence
<220> FEATURE:
<223> OTHER INFORMATION: siRNA

<400> SEQUENCE: 353
aaccagaaga agcaggugac c      21

<210> SEQ ID NO 354
<211> LENGTH: 19
<212> TYPE: RNA
<213> ORGANISM: Artificial Sequence
<220> FEATURE:
<223> OTHER INFORMATION: siRNA

<400> SEQUENCE: 354
uuaguaaacc uuuugagac      19

<210> SEQ ID NO 355
<211> LENGTH: 19
<212> TYPE: RNA

```
<213> ORGANISM: Artificial Sequence
<220> FEATURE:
<223> OTHER INFORMATION: siRNA

<400> SEQUENCE: 355
gucucaaaag guuuacuaa                                                  19

<210> SEQ ID NO 356
<211> LENGTH: 19
<212> TYPE: RNA
<213> ORGANISM: Artificial Sequence
<220> FEATURE:
<223> OTHER INFORMATION: siRNA

<400> SEQUENCE: 356
cugaggacgc ccugggagu                                                  19

<210> SEQ ID NO 357
<211> LENGTH: 19
<212> TYPE: RNA
<213> ORGANISM: Artificial Sequence
<220> FEATURE:
<223> OTHER INFORMATION: siRNA

<400> SEQUENCE: 357
acucccaggg cguccucag                                                  19

<210> SEQ ID NO 358
<211> LENGTH: 19
<212> TYPE: RNA
<213> ORGANISM: Artificial Sequence
<220> FEATURE:
<223> OTHER INFORMATION: siRNA

<400> SEQUENCE: 358
gcugaggacg cccugggag                                                  19

<210> SEQ ID NO 359
<211> LENGTH: 19
<212> TYPE: RNA
<213> ORGANISM: Artificial Sequence
<220> FEATURE:
<223> OTHER INFORMATION: siRNA

<400> SEQUENCE: 359
cucccagggc guccucagc                                                  19

<210> SEQ ID NO 360
<211> LENGTH: 19
<212> TYPE: RNA
<213> ORGANISM: Artificial Sequence
<220> FEATURE:
<223> OTHER INFORMATION: siRNA

<400> SEQUENCE: 360
ugcugaggac gcccuggga                                                  19

<210> SEQ ID NO 361
<211> LENGTH: 19
<212> TYPE: RNA
<213> ORGANISM: Artificial Sequence
<220> FEATURE:
<223> OTHER INFORMATION: siRNA

<400> SEQUENCE: 361
ucccagggcg uccucagca                                                  19
```

<210> SEQ ID NO 362
<211> LENGTH: 19
<212> TYPE: RNA
<213> ORGANISM: Artificial Sequence
<220> FEATURE:
<223> OTHER INFORMATION: siRNA

<400> SEQUENCE: 362
gugcugagga cgcccuggg                                                19

<210> SEQ ID NO 363
<211> LENGTH: 19
<212> TYPE: RNA
<213> ORGANISM: Artificial Sequence
<220> FEATURE:
<223> OTHER INFORMATION: siRNA

<400> SEQUENCE: 363
cccagggcgu ccucagcac                                                19

<210> SEQ ID NO 364
<211> LENGTH: 19
<212> TYPE: RNA
<213> ORGANISM: Artificial Sequence
<220> FEATURE:
<223> OTHER INFORMATION: siRNA

<400> SEQUENCE: 364
ggugcugagg acgcccugg                                                19

<210> SEQ ID NO 365
<211> LENGTH: 19
<212> TYPE: RNA
<213> ORGANISM: Artificial Sequence
<220> FEATURE:
<223> OTHER INFORMATION: siRNA

<400> SEQUENCE: 365
ccagggcguc cucagcacc                                                19

<210> SEQ ID NO 366
<211> LENGTH: 19
<212> TYPE: RNA
<213> ORGANISM: Artificial Sequence
<220> FEATURE:
<223> OTHER INFORMATION: siRNA

<400> SEQUENCE: 366
gggugcugag gacgcccug                                                19

<210> SEQ ID NO 367
<211> LENGTH: 19
<212> TYPE: RNA
<213> ORGANISM: Artificial Sequence
<220> FEATURE:
<223> OTHER INFORMATION: siRNA

<400> SEQUENCE: 367
cagggcgucc ucagcaccc                                                19

<210> SEQ ID NO 368
<211> LENGTH: 19
<212> TYPE: RNA
<213> ORGANISM: Artificial Sequence
<220> FEATURE:

<223> OTHER INFORMATION: siRNA

<400> SEQUENCE: 368
cggggugcug aggacgccc					19

<210> SEQ ID NO 369
<211> LENGTH: 19
<212> TYPE: RNA
<213> ORGANISM: Artificial Sequence
<220> FEATURE:
<223> OTHER INFORMATION: siRNA

<400> SEQUENCE: 369
gggcguccuc agcaccccg					19

<210> SEQ ID NO 370
<211> LENGTH: 19
<212> TYPE: RNA
<213> ORGANISM: Artificial Sequence
<220> FEATURE:
<223> OTHER INFORMATION: siRNA

<400> SEQUENCE: 370
acggggugcu gaggacgcc					19

<210> SEQ ID NO 371
<211> LENGTH: 19
<212> TYPE: RNA
<213> ORGANISM: Artificial Sequence
<220> FEATURE:
<223> OTHER INFORMATION: siRNA

<400> SEQUENCE: 371
ggcguccuca gcaccccgu					19

<210> SEQ ID NO 372
<211> LENGTH: 19
<212> TYPE: RNA
<213> ORGANISM: Artificial Sequence
<220> FEATURE:
<223> OTHER INFORMATION: siRNA

<400> SEQUENCE: 372
uacggggugc ugaggacgc					19

<210> SEQ ID NO 373
<211> LENGTH: 19
<212> TYPE: RNA
<213> ORGANISM: Artificial Sequence
<220> FEATURE:
<223> OTHER INFORMATION: siRNA

<400> SEQUENCE: 373
gcguccucag caccccgua					19

<210> SEQ ID NO 374
<211> LENGTH: 19
<212> TYPE: RNA
<213> ORGANISM: Artificial Sequence
<220> FEATURE:
<223> OTHER INFORMATION: siRNA

<400> SEQUENCE: 374
guacggggug cugaggacg					19

```
<210> SEQ ID NO 375
<211> LENGTH: 19
<212> TYPE: RNA
<213> ORGANISM: Artificial Sequence
<220> FEATURE:
<223> OTHER INFORMATION: siRNA

<400> SEQUENCE: 375
cguccucagc accccguac                                              19

<210> SEQ ID NO 376
<211> LENGTH: 19
<212> TYPE: RNA
<213> ORGANISM: Artificial Sequence
<220> FEATURE:
<223> OTHER INFORMATION: siRNA

<400> SEQUENCE: 376
aguacggggu gcugaggac                                              19

<210> SEQ ID NO 377
<211> LENGTH: 19
<212> TYPE: RNA
<213> ORGANISM: Artificial Sequence
<220> FEATURE:
<223> OTHER INFORMATION: siRNA

<400> SEQUENCE: 377
guccucagca ccccguacu                                              19

<210> SEQ ID NO 378
<211> LENGTH: 19
<212> TYPE: RNA
<213> ORGANISM: Artificial Sequence
<220> FEATURE:
<223> OTHER INFORMATION: siRNA

<400> SEQUENCE: 378
aaguacgggg ugcugagga                                              19

<210> SEQ ID NO 379
<211> LENGTH: 19
<212> TYPE: RNA
<213> ORGANISM: Artificial Sequence
<220> FEATURE:
<223> OTHER INFORMATION: siRNA

<400> SEQUENCE: 379
uccucagcac cccguacuu                                              19

<210> SEQ ID NO 380
<211> LENGTH: 19
<212> TYPE: RNA
<213> ORGANISM: Artificial Sequence
<220> FEATURE:
<223> OTHER INFORMATION: siRNA

<400> SEQUENCE: 380
ggaaguacgg ggugcugag                                              19

<210> SEQ ID NO 381
<211> LENGTH: 19
<212> TYPE: RNA
<213> ORGANISM: Artificial Sequence
<220> FEATURE:
<223> OTHER INFORMATION: siRNA
```

```
<400> SEQUENCE: 381
cucagcaccc cguacuucc                                                    19

<210> SEQ ID NO 382
<211> LENGTH: 19
<212> TYPE: RNA
<213> ORGANISM: Artificial Sequence
<220> FEATURE:
<223> OTHER INFORMATION: siRNA

<400> SEQUENCE: 382
gggaaguacg gggugcuga                                                    19

<210> SEQ ID NO 383
<211> LENGTH: 19
<212> TYPE: RNA
<213> ORGANISM: Artificial Sequence
<220> FEATURE:
<223> OTHER INFORMATION: siRNA

<400> SEQUENCE: 383
ucagcacccc guacuuccc                                                    19

<210> SEQ ID NO 384
<211> LENGTH: 19
<212> TYPE: RNA
<213> ORGANISM: Artificial Sequence
<220> FEATURE:
<223> OTHER INFORMATION: siRNA

<400> SEQUENCE: 384
ggggaaguac ggggugcug                                                    19

<210> SEQ ID NO 385
<211> LENGTH: 19
<212> TYPE: RNA
<213> ORGANISM: Artificial Sequence
<220> FEATURE:
<223> OTHER INFORMATION: siRNA

<400> SEQUENCE: 385
cagcaccccg uacuuuccc                                                    19

<210> SEQ ID NO 386
<211> LENGTH: 19
<212> TYPE: RNA
<213> ORGANISM: Artificial Sequence
<220> FEATURE:
<223> OTHER INFORMATION: siRNA

<400> SEQUENCE: 386
uggggaagua cggggugcu                                                    19

<210> SEQ ID NO 387
<211> LENGTH: 19
<212> TYPE: RNA
<213> ORGANISM: Artificial Sequence
<220> FEATURE:
<223> OTHER INFORMATION: siRNA

<400> SEQUENCE: 387
agcaccccgu acuucccca                                                    19

<210> SEQ ID NO 388
<211> LENGTH: 19
```

```
<212> TYPE: RNA
<213> ORGANISM: Artificial Sequence
<220> FEATURE:
<223> OTHER INFORMATION: siRNA

<400> SEQUENCE: 388
cuggggaagu acgggugc                                                 19

<210> SEQ ID NO 389
<211> LENGTH: 19
<212> TYPE: RNA
<213> ORGANISM: Artificial Sequence
<220> FEATURE:
<223> OTHER INFORMATION: siRNA

<400> SEQUENCE: 389
gcaccccgua cuuccccag                                                19

<210> SEQ ID NO 390
<211> LENGTH: 19
<212> TYPE: RNA
<213> ORGANISM: Artificial Sequence
<220> FEATURE:
<223> OTHER INFORMATION: siRNA

<400> SEQUENCE: 390
agcuggggaa guacggggu                                                19

<210> SEQ ID NO 391
<211> LENGTH: 19
<212> TYPE: RNA
<213> ORGANISM: Artificial Sequence
<220> FEATURE:
<223> OTHER INFORMATION: siRNA

<400> SEQUENCE: 391
accccguacu uccccagcu                                                19

<210> SEQ ID NO 392
<211> LENGTH: 19
<212> TYPE: RNA
<213> ORGANISM: Artificial Sequence
<220> FEATURE:
<223> OTHER INFORMATION: siRNA

<400> SEQUENCE: 392
uagcugggga aguacgggg                                                19

<210> SEQ ID NO 393
<211> LENGTH: 19
<212> TYPE: RNA
<213> ORGANISM: Artificial Sequence
<220> FEATURE:
<223> OTHER INFORMATION: siRNA

<400> SEQUENCE: 393
ccccguacuu ccccagcua                                                19

<210> SEQ ID NO 394
<211> LENGTH: 19
<212> TYPE: RNA
<213> ORGANISM: Artificial Sequence
<220> FEATURE:
<223> OTHER INFORMATION: siRNA

<400> SEQUENCE: 394
```
guagcugggg aaguacggg                                        19

<210> SEQ ID NO 395
<211> LENGTH: 19
<212> TYPE: RNA
<213> ORGANISM: Artificial Sequence
<220> FEATURE:
<223> OTHER INFORMATION: siRNA

<400> SEQUENCE: 395
cccguacuuc cccagcuac                                        19

<210> SEQ ID NO 396
<211> LENGTH: 19
<212> TYPE: RNA
<213> ORGANISM: Artificial Sequence
<220> FEATURE:
<223> OTHER INFORMATION: siRNA

<400> SEQUENCE: 396
aguagcuggg gaaguacgg                                        19

<210> SEQ ID NO 397
<211> LENGTH: 19
<212> TYPE: RNA
<213> ORGANISM: Artificial Sequence
<220> FEATURE:
<223> OTHER INFORMATION: siRNA

<400> SEQUENCE: 397
ccguacuucc ccagcuacu                                        19

<210> SEQ ID NO 398
<211> LENGTH: 19
<212> TYPE: RNA
<213> ORGANISM: Artificial Sequence
<220> FEATURE:
<223> OTHER INFORMATION: siRNA

<400> SEQUENCE: 398
guaguagcug gggaaguac                                        19

<210> SEQ ID NO 399
<211> LENGTH: 19
<212> TYPE: RNA
<213> ORGANISM: Artificial Sequence
<220> FEATURE:
<223> OTHER INFORMATION: siRNA

<400> SEQUENCE: 399
guacuucccc agcuacuac                                        19

<210> SEQ ID NO 400
<211> LENGTH: 19
<212> TYPE: RNA
<213> ORGANISM: Artificial Sequence
<220> FEATURE:
<223> OTHER INFORMATION: siRNA

<400> SEQUENCE: 400
aguaguagcu ggggaagua                                        19

<210> SEQ ID NO 401
<211> LENGTH: 19
<212> TYPE: RNA
<213> ORGANISM: Artificial Sequence

```
<220> FEATURE:
<223> OTHER INFORMATION: siRNA

<400> SEQUENCE: 401
uacuucccca gcuacuacu                                                    19

<210> SEQ ID NO 402
<211> LENGTH: 19
<212> TYPE: RNA
<213> ORGANISM: Artificial Sequence
<220> FEATURE:
<223> OTHER INFORMATION: siRNA

<400> SEQUENCE: 402
gaguaguagc ugggaagu                                                     19

<210> SEQ ID NO 403
<211> LENGTH: 19
<212> TYPE: RNA
<213> ORGANISM: Artificial Sequence
<220> FEATURE:
<223> OTHER INFORMATION: siRNA

<400> SEQUENCE: 403
acuuccccag cuacuacuc                                                    19

<210> SEQ ID NO 404
<211> LENGTH: 19
<212> TYPE: RNA
<213> ORGANISM: Artificial Sequence
<220> FEATURE:
<223> OTHER INFORMATION: siRNA

<400> SEQUENCE: 404
cgaguaguag cuggggaag                                                    19

<210> SEQ ID NO 405
<211> LENGTH: 19
<212> TYPE: RNA
<213> ORGANISM: Artificial Sequence
<220> FEATURE:
<223> OTHER INFORMATION: siRNA

<400> SEQUENCE: 405 cuucccagc uacuacucg                                                     19

<210> SEQ ID NO 406
<211> LENGTH: 19
<212> TYPE: RNA
<213> ORGANISM: Artificial Sequence
<220> FEATURE:
<223> OTHER INFORMATION: siRNA

<400> SEQUENCE: 406
gcgaguagua gcuggggaa                                                    19

<210> SEQ ID NO 407
<211> LENGTH: 19
<212> TYPE: RNA
<213> ORGANISM: Artificial Sequence
<220> FEATURE:
<223> OTHER INFORMATION: siRNA

<400> SEQUENCE: 407
uuccccagcu acuacucgc                                                    19
```

<210> SEQ ID NO 408
<211> LENGTH: 19
<212> TYPE: RNA
<213> ORGANISM: Artificial Sequence
<220> FEATURE:
<223> OTHER INFORMATION: siRNA

<400> SEQUENCE: 408
ggcgaguagu agcuggga                                                   19

<210> SEQ ID NO 409
<211> LENGTH: 19
<212> TYPE: RNA
<213> ORGANISM: Artificial Sequence
<220> FEATURE:
<223> OTHER INFORMATION: siRNA

<400> SEQUENCE: 409
uccccagcua cuacucgcc                                                  19

<210> SEQ ID NO 410
<211> LENGTH: 19
<212> TYPE: RNA
<213> ORGANISM: Artificial Sequence
<220> FEATURE:
<223> OTHER INFORMATION: siRNA

<400> SEQUENCE: 410
gggcgaguag uagcugggg                                                  19

<210> SEQ ID NO 411
<211> LENGTH: 19
<212> TYPE: RNA
<213> ORGANISM: Artificial Sequence
<220> FEATURE:
<223> OTHER INFORMATION: siRNA

<400> SEQUENCE: 411
ccccagcuac uacucgccc                                                  19

<210> SEQ ID NO 412
<211> LENGTH: 19
<212> TYPE: RNA
<213> ORGANISM: Artificial Sequence
<220> FEATURE:
<223> OTHER INFORMATION: siRNA

<400> SEQUENCE: 412
ggggcgagua guagcuggg                                                  19

<210> SEQ ID NO 413
<211> LENGTH: 19
<212> TYPE: RNA
<213> ORGANISM: Artificial Sequence
<220> FEATURE:
<223> OTHER INFORMATION: siRNA

<400> SEQUENCE: 413
cccagcuacu acucgcccc                                                  19

<210> SEQ ID NO 414
<211> LENGTH: 19
<212> TYPE: RNA
<213> ORGANISM: Artificial Sequence
<220> FEATURE:
<223> OTHER INFORMATION: siRNA

```
<400> SEQUENCE: 414 ugggggcgagu aguagcugg                                              19

<210> SEQ ID NO 415
<211> LENGTH: 19
<212> TYPE: RNA
<213> ORGANISM: Artificial Sequence
<220> FEATURE:
<223> OTHER INFORMATION: siRNA

<400> SEQUENCE: 415
ccagcuacua cucgcccca                                               19

<210> SEQ ID NO 416
<211> LENGTH: 19
<212> TYPE: RNA
<213> ORGANISM: Artificial Sequence
<220> FEATURE:
<223> OTHER INFORMATION: siRNA

<400> SEQUENCE: 416
uuggggcgag uaguagcug                                               19

<210> SEQ ID NO 417
<211> LENGTH: 19
<212> TYPE: RNA
<213> ORGANISM: Artificial Sequence
<220> FEATURE:
<223> OTHER INFORMATION: siRNA

<400> SEQUENCE: 417
cagcuacuac ucgcccaa                                                19

<210> SEQ ID NO 418
<211> LENGTH: 19
<212> TYPE: RNA
<213> ORGANISM: Artificial Sequence
<220> FEATURE:
<223> OTHER INFORMATION: siRNA

<400> SEQUENCE: 418
uauuccaaag ggcagcuga                                               19

<210> SEQ ID NO 419
<211> LENGTH: 19
<212> TYPE: RNA
<213> ORGANISM: Artificial Sequence
<220> FEATURE:
<223> OTHER INFORMATION: siRNA

<400> SEQUENCE: 419
ucagcugccc uuuggaaua                                               19

<210> SEQ ID NO 420
<211> LENGTH: 19
<212> TYPE: RNA
<213> ORGANISM: Artificial Sequence
<220> FEATURE:
<223> OTHER INFORMATION: siRNA

<400> SEQUENCE: 420
aucuucuggg cuuuggcgg                                               19

<210> SEQ ID NO 421
```

```
<211> LENGTH: 19
<212> TYPE: RNA
<213> ORGANISM: Artificial Sequence
<220> FEATURE:
<223> OTHER INFORMATION: siRNA

<400> SEQUENCE: 421
ccgccaaagc ccagaagau                                                    19

<210> SEQ ID NO 422
<211> LENGTH: 19
<212> TYPE: RNA
<213> ORGANISM: Artificial Sequence
<220> FEATURE:
<223> OTHER INFORMATION: siRNA

<400> SEQUENCE: 422
uuuucucuug gaguccuca                                                    19

<210> SEQ ID NO 423
<211> LENGTH: 19
<212> TYPE: RNA
<213> ORGANISM: Artificial Sequence
<220> FEATURE:
<223> OTHER INFORMATION: siRNA

<400> SEQUENCE: 423
ugaggacucc aagagaaaa                                                    19

<210> SEQ ID NO 424
<211> LENGTH: 19
<212> TYPE: RNA
<213> ORGANISM: Artificial Sequence
<220> FEATURE:
<223> OTHER INFORMATION: siRNA

<400> SEQUENCE: 424
gaauagacgg agcuggagu                                                    19

<210> SEQ ID NO 425
<211> LENGTH: 19
<212> TYPE: RNA
<213> ORGANISM: Artificial Sequence
<220> FEATURE:
<223> OTHER INFORMATION: siRNA

<400> SEQUENCE: 425
acuccagcuc cgucuauuc                                                    19

<210> SEQ ID NO 426
<211> LENGTH: 19
<212> TYPE: RNA
<213> ORGANISM: Artificial Sequence
<220> FEATURE:
<223> OTHER INFORMATION: siRNA

<400> SEQUENCE: 426
uaguagcugg ggaaguacg                                                    19

<210> SEQ ID NO 427
<211> LENGTH: 19
<212> TYPE: RNA
<213> ORGANISM: Artificial Sequence
<220> FEATURE:
<223> OTHER INFORMATION: siRNA

<400> SEQUENCE: 427
```
cguacuuccc cagcuacua                                          19

<210> SEQ ID NO 428
<211> LENGTH: 19
<212> TYPE: RNA
<213> ORGANISM: Artificial Sequence
<220> FEATURE:
<223> OTHER INFORMATION: siRNA

<400> SEQUENCE: 428
agauccuggg agaaguggc                                          19

<210> SEQ ID NO 429
<211> LENGTH: 19
<212> TYPE: RNA
<213> ORGANISM: Artificial Sequence
<220> FEATURE:
<223> OTHER INFORMATION: siRNA

<400> SEQUENCE: 429
gccacuucuc ccaggaucu                                          19

<210> SEQ ID NO 430
<211> LENGTH: 19
<212> TYPE: RNA
<213> ORGANISM: Artificial Sequence
<220> FEATURE:
<223> OTHER INFORMATION: siRNA

<400> SEQUENCE: 430
cuguucugga ucguccacu                                          19

<210> SEQ ID NO 431
<211> LENGTH: 19
<212> TYPE: RNA
<213> ORGANISM: Artificial Sequence
<220> FEATURE:
<223> OTHER INFORMATION: siRNA

<400> SEQUENCE: 431
aguggacgau ccagaacag                                          19

<210> SEQ ID NO 432
<211> LENGTH: 19
<212> TYPE: RNA
<213> ORGANISM: Artificial Sequence
<220> FEATURE:
<223> OTHER INFORMATION: siRNA

<400> SEQUENCE: 432
cucaccuuga aggacaccu                                          19

<210> SEQ ID NO 433
<211> LENGTH: 19
<212> TYPE: RNA
<213> ORGANISM: Artificial Sequence
<220> FEATURE:
<223> OTHER INFORMATION: siRNA

<400> SEQUENCE: 433
agguguccuu caaggugag                                          19

<210> SEQ ID NO 434
<211> LENGTH: 19
<212> TYPE: RNA

```
<213> ORGANISM: Artificial Sequence
<220> FEATURE:
<223> OTHER INFORMATION: siRNA

<400> SEQUENCE: 434
aguuucucuc auccaggcc                                          19

<210> SEQ ID NO 435
<211> LENGTH: 19
<212> TYPE: RNA
<213> ORGANISM: Artificial Sequence
<220> FEATURE:
<223> OTHER INFORMATION: siRNA

<400> SEQUENCE: 435
ggccuggaug agagaaacu                                          19

<210> SEQ ID NO 436
<211> LENGTH: 19
<212> TYPE: RNA
<213> ORGANISM: Artificial Sequence
<220> FEATURE:
<223> OTHER INFORMATION: siRNA

<400> SEQUENCE: 436
guacccuagg aaauaccag                                          19

<210> SEQ ID NO 437
<211> LENGTH: 19
<212> TYPE: RNA
<213> ORGANISM: Artificial Sequence
<220> FEATURE:
<223> OTHER INFORMATION: siRNA

<400> SEQUENCE: 437
cugguauuuc cuaggguac                                          19

<210> SEQ ID NO 438
<211> LENGTH: 19
<212> TYPE: RNA
<213> ORGANISM: Artificial Sequence
<220> FEATURE:
<223> OTHER INFORMATION: siRNA

<400> SEQUENCE: 438
cuguugacug uggacagca                                          19

<210> SEQ ID NO 439
<211> LENGTH: 19
<212> TYPE: RNA
<213> ORGANISM: Artificial Sequence
<220> FEATURE:
<223> OTHER INFORMATION: siRNA

<400> SEQUENCE: 439
ugcuguccac agucaacag                                          19

<210> SEQ ID NO 440
<211> LENGTH: 19
<212> TYPE: RNA
<213> ORGANISM: Artificial Sequence
<220> FEATURE:
<223> OTHER INFORMATION: siRNA

<400> SEQUENCE: 440
uaccagaaga agcagguga                                          19
```

<210> SEQ ID NO 441
<211> LENGTH: 19
<212> TYPE: RNA
<213> ORGANISM: Artificial Sequence
<220> FEATURE:
<223> OTHER INFORMATION: siRNA

<400> SEQUENCE: 441
ucaccugcuu cuucuggua                                              19

<210> SEQ ID NO 442
<211> LENGTH: 19
<212> TYPE: RNA
<213> ORGANISM: Artificial Sequence
<220> FEATURE:
<223> OTHER INFORMATION: siRNA

<400> SEQUENCE: 442
ucgaaguauu ccgcguacg                                              19

<210> SEQ ID NO 443
<211> LENGTH: 19
<212> TYPE: RNA
<213> ORGANISM: Artificial Sequence
<220> FEATURE:
<223> OTHER INFORMATION: siRNA

<400> SEQUENCE: 443
cguacgcgga auacuucga                                              19

<210> SEQ ID NO 444
<211> LENGTH: 22
<212> TYPE: DNA
<213> ORGANISM: Artificial Sequence
<220> FEATURE:
<223> OTHER INFORMATION: PTEN-2-A

<400> SEQUENCE: 444
caccgccaaa tttaactgca ga                                          22

<210> SEQ ID NO 445
<211> LENGTH: 24
<212> TYPE: DNA
<213> ORGANISM: Artificial Sequence
<220> FEATURE:
<223> OTHER INFORMATION: PTEN-2-B

<400> SEQUENCE: 445
aagggtttga taagttctag ctgt                                        24

<210> SEQ ID NO 446
<211> LENGTH: 31
<212> TYPE: DNA
<213> ORGANISM: Artificial Sequence
<220> FEATURE:
<223> OTHER INFORMATION: PTEN-2-C

<400> SEQUENCE: 446
tgcacagtat cctttgaag accataaccc a                                 31

```
<210> SEQ ID NO 447
<211> LENGTH: 17
<212> TYPE: DNA
<213> ORGANISM: Artificial Sequence
<220> FEATURE:
<223> OTHER INFORMATION: hTMSS6:379U17

<400> SEQUENCE: 447
ccgccaaagc ccagaag                                                  17

<210> SEQ ID NO 448
<211> LENGTH: 21
<212> TYPE: DNA
<213> ORGANISM: Artificial Sequence
<220> FEATURE:
<223> OTHER INFORMATION: hTMSS6:475L21

<400> SEQUENCE: 448
ggtccctccc caaaggaata g                                             21

<210> SEQ ID NO 449
<211> LENGTH: 28
<212> TYPE: DNA
<213> ORGANISM: Artificial Sequence
<220> FEATURE:
<223> OTHER INFORMATION: hTMSS6:416U28FL

<400> SEQUENCE: 449
cagcacccgc ctgggaactt actacaac                                      28

<210> SEQ ID NO 450
<211> LENGTH: 13
<212> TYPE: PRT
<213> ORGANISM: Human immunodeficiency virus

<400> SEQUENCE: 450

Gly Arg Lys Lys Arg Arg Gln Arg Arg Arg Pro Pro Gln
1               5                   10

<210> SEQ ID NO 451
<211> LENGTH: 16
<212> TYPE: PRT
<213> ORGANISM: Drosophila sp.

<400> SEQUENCE: 451

Arg Gln Ile Lys Ile Trp Phe Gln Asn Arg Arg Met Lys Trp Lys Lys
1               5                   10                  15
```